US007635699B2

(12) United States Patent
Meng et al.

(10) Patent No.: US 7,635,699 B2
(45) Date of Patent: Dec. 22, 2009

(54) AZOLOPYRIMIDINE-BASED INHIBITORS OF DIPEPTIDYL PEPTIDASE IV AND METHODS

(75) Inventors: Wei Meng, Pennington, NJ (US); Lawrence G. Hamann, Cherry Hill, NJ (US); Robert Brigance, Levittown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 316 days.

(21) Appl. No.: 11/314,470

(22) Filed: Dec. 21, 2005

(65) Prior Publication Data

US 2006/0178377 A1    Aug. 10, 2006

Related U.S. Application Data

(60) Provisional application No. 60/640,135, filed on Dec. 29, 2004.

(51) Int. Cl.
*A01N 43/90* (2006.01)
*A61K 31/519* (2006.01)
*C07D 487/00* (2006.01)

(52) U.S. Cl. .................... 514/259.1; 544/281; 544/280; 544/256; 514/259.3; 514/259.31

(58) Field of Classification Search ........................ None
See application file for complete search history.

(56) References Cited

U.S. PATENT DOCUMENTS

| | | | |
|---|---|---|---|
| 3,674,836 A | 7/1972 | Creger |
| 3,983,140 A | 9/1976 | Endo et al. |
| 4,027,009 A | 5/1977 | Grier et al. |
| 4,231,938 A | 11/1980 | Monaghan et al. |
| 4,346,227 A | 8/1982 | Terahara et al. |
| 4,448,784 A | 5/1984 | Glamkowski et al. |
| 4,450,171 A | 5/1984 | Hoffman et al. |
| 4,499,289 A | 2/1985 | Baran et al. |
| 4,613,610 A | 9/1986 | Wareing |
| 4,647,576 A | 3/1987 | Hoefle et al. |
| 4,681,893 A | 7/1987 | Roth |
| 4,686,237 A | 8/1987 | Anderson |
| 4,759,923 A | 7/1988 | Buntin et al. |
| 4,871,721 A | 10/1989 | Biller |
| 4,924,024 A | 5/1990 | Biller |
| 5,006,530 A | 4/1991 | Angerbauer et al. |
| 5,011,930 A | 4/1991 | Fujikawa et al. |
| 5,177,080 A | 1/1993 | Angerbauer et al. |
| 5,260,440 A | 11/1993 | Hirai et al. |
| 5,273,995 A | 12/1993 | Roth |
| 5,346,701 A | 9/1994 | Heiber et al. |
| 5,354,772 A | 10/1994 | Kathawala |
| 5,385,929 A | 1/1995 | Bjorge et al. |
| 5,488,064 A | 1/1996 | Sher |
| 5,491,134 A | 2/1996 | Sher et al. |
| 5,506,219 A | 4/1996 | Robl |
| 5,541,204 A | 7/1996 | Sher et al. |
| 5,594,016 A | 1/1997 | Ueno et al. |
| 5,595,872 A | 1/1997 | Wetterau, II et al. |
| 5,612,359 A | 3/1997 | Murugesan |
| 5,614,492 A | 3/1997 | Habener |
| 5,631,224 A | 5/1997 | Efendic et al. |
| 5,686,104 A | 11/1997 | Mills et al. |
| 5,691,322 A | 11/1997 | Robl |
| 5,712,279 A | 1/1998 | Biller et al. |
| 5,712,396 A | 1/1998 | Magnin et al. |
| 5,739,135 A | 4/1998 | Biller et al. |
| 5,753,675 A | 5/1998 | Wattanasin |
| 5,760,246 A | 6/1998 | Biller et al. |
| 5,770,615 A | 6/1998 | Cheng et al. |
| 5,776,983 A | 7/1998 | Washburn et al. |
| 5,827,875 A | 10/1998 | Dickson, Jr. et al. |
| 5,885,983 A | 3/1999 | Biller et al. |
| 5,962,440 A | 10/1999 | Sulsky |
| 6,395,767 B2 | 5/2002 | Robl et al. |
| 6,548,529 B1 | 4/2003 | Robl et al. |
| 6,653,314 B2 | 11/2003 | Cheng et al. |
| 6,995,183 B2 | 2/2006 | Hamann et al. |

FOREIGN PATENT DOCUMENTS

DE    102 56 264    6/2004

(Continued)

OTHER PUBLICATIONS

Dipeptidyl peptidase IV (DPP-IV) inhibitors for type 2 diabetes mellitus; 2007; http://limaye.ecri.org/summary/detail.aspx?doc_id=10028.*

(Continued)

*Primary Examiner*—James O Wilson
*Assistant Examiner*—Jeffrey H Murray
(74) *Attorney, Agent, or Firm*—Maureen S. Gibbons

(57) ABSTRACT

Compounds are provided having the formula (I)

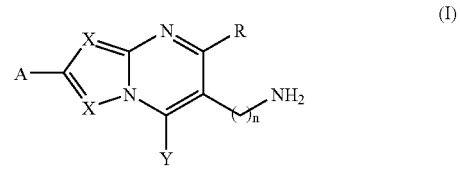

wherein X for each occurrence is N or C-A, and R, Y, A and n are as defined herein, which compounds are dipeptidyl peptidase IV inhibitors and as such are useful in treating diabetes and micro- and macrovascular complications of diabetes, such as retinopathy, neuropathy, and nephropathy.

A method for treating diabetes and related diseases employing the above compounds is also provided.

3 Claims, No Drawings

FOREIGN PATENT DOCUMENTS

| | | |
|---|---|---|
| EP | 0 142 146 | 11/1984 |
| EP | 0 221 025 | 10/1986 |
| FR | 2 596 393 | 5/1986 |
| GB | 2 205 837 A | 12/1988 |
| WO | WO86/03488 | 6/1986 |
| WO | WO86/07054 | 12/1986 |
| WO | WO96/38144 | 12/1996 |
| WO | WO97/12613 | 4/1997 |
| WO | WO97/12615 | 4/1997 |
| WO | WO97/21993 | 6/1997 |
| WO | WO99/00353 | 1/1999 |
| WO | WO99/38501 | 8/1999 |
| WO | WO99/46272 | 9/1999 |
| WO | WO99/61431 | 12/1999 |
| WO | WO99/67278 | 12/1999 |
| WO | WO99/67279 | 12/1999 |
| WO | WO00/01389 | 1/2000 |
| WO | WO01/21602 | 3/2001 |
| WO | WO01/68603 | 9/2001 |
| WO | WO03/033671 | 4/2003 |
| WO | WO 2004/043940 | 5/2004 |

OTHER PUBLICATIONS

Attaby, et. al., Archives of Pharmacal Research (1997), 20(4), 330-337.*

Borisy, et. al., Proceedings of the National Academy of Sciences of the United States of America, 100(13) 7977-7982.*

Ashworth, D. et al., "4-Cyanothiazolidides as very potent, stable inhibitors of Dipeptidyl Peptidase IV", Bioorganic & Medicinal Chem. Letters, vol. 6(22), pp. 2745-2748 (1996).

Ashworth, D. et al., "2-Cyanopyrrolidides as potent, stable inhibitors of Dipeptidyl Peptidase IV", Bioorganic & Medicinal Chem. Letters, vol. 6(10), pp. 1163-1166 (1996).

Biller, S. et al., "Isoprenoid (Phosphinylmethyl) phosphonates as Inhibitors of Squalene Synthetase", J. Medicinal Chemistry, vol. 31(10), pp. 1869-1871 (1988).

Biller, S. et al., "Squalene Synthase Inhibitors", Current Pharmaceutical Design, vol. 2, pp. 1-40 (1996).

Corey, E.J. et al., "Application of Unreactive Analogs of Terpenoid Pyrophosphates to Studies of Multistep Biosynthesis. Demonstration that "Presqualene Pyrophosphate" Is an Essential Intermediate on the Path to Squalene", J. Amer. Chem. Soc., vol. 98(5) pp. 1291-1293 (1976).

Cornicelli, J.A. et al., "15-Lipoxygenase and Its Inhibition: A Novel Therapeutic Target for Vascular Disease", Current Pharmaceutical Design, vol. 5, pp. 11-20 (1999).

Hart, D. et al., "Preparation of Primary Amines and 2-Azetidinones via N-Trimethylsiyl Imines", J. Org. Chem., vol. 48(3), pp. 289-294 (1983).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Design Reviews, vol. 16(1), pp. 16-30 (1998).

Hara, S., "Ileal Na+/bile acid cotransporter inhibitors", Drugs of the Future, vol. 24(4), pp. 425-430 (1999).

Johannsson. G. et al., "Growth Hormone Treatment of Abdominally Obese Men Reduces Abdominal Fat Mass, Improves Glucose and Lipoprotein Metabolism, and Reduces Diastolic Blood Pressure*", J. of Clin. Endocrinology and Metabolism, vol. 82(3), pp. 727-734 (1997).

Krause, B. et al., "ACAT Inhibitors: Physiologic mechanisms for Hypolipidemic and Anti-Atherosclerotic Activities in Experimental Animals", Inflammation: Mediators and Pathways, pp. 173-198 (1995).

McClard, R. et al., "Novel Phosphonylphosphinyl (P-C-P-C-) Analogues of Biochemically Interesting Diphosphates. Syntheses and Properties of P-C-P-C- Analogues of Isopentenyl Diphosphate and Dimethylallyl Diphosphate", J. Am. Chem. Soc., vol. 109, pp. 5544-5545 (1987).

Murakami, K. et al., "A Novel Insulin Sensitizer Acts as a Coligand for Peroxisome Proliferator-Activated Receptor-α (PPAR-α) and PPAR-γ", Diabetes, vol. 47, pp. 1841-1847 (1998).

Nicolosi, R. et al., "The ACAT inhibitor, CI-1011 is effective in the prevention and regression of aortic fatty streak area in hamsters", Atherosclerosis, vol. 137, pp. 77-85 (1998).

Ortiz de Montellano, P. et al., "Inhibition of Squalene Synthetase by Farnesyl Pyrophosphate Analogues[1]", J. of Medicinal Chemistry, vol. 20(2), pp. 243-249 (1977).

Rosenblum, S. et al., "Discovery of 1-(4-Flurophenyl)-(3R)-[3-(4-flurophenyl)-(3S)-hydrozypropyl]-(4S)-(4-hydroxyphenyl)-2-azetidinone (SCH 58235): A Designed, Potent, Orally Active Inhibitor of Cholesterol Absorption", J. Med. Chem., vol. 41, pp. 973-980 (1998).

Salisbury, B. et al., "Hypocholesterolemic activity of a novel inhibitor of cholesterol absorption, SCH 48461", Atherosclerosis, vol. 115, pp. 45-63 (1995).

Sendobry, S. et al., "Attenuation of diet-induced atherosclerosis in rabbits with a highly selective 15-lipoxygenase inhibitor lacking significant antioxidant properties", British J. of Pharmacology, vol. 120, pp. 1199-1206 (1997).

Sliskovic, D. et al., "ACAT Inhibitors: Potential Anti-atherosclerotic Agents", Current Medicinal Chemistry, vol. 1, pp. 204-225 (1994).

Smith, C. et al., "RP 73163: A Bioavailable Alkylsulphinyl-Diphenylimidazole ACAT Inhibitor", Bioorganic & Medicinal Chemistry Letters, vol. 6(1), pp. 47-50 (1996).

Sorbera, L. et al., "Treatment of Lipoprotein Disorders ACAT Inhibitor", Drugs of the Future, vol. 24(1), pp. 9-15 (1999).

Yamada, M. et al., "A Potent Dipeptide Inhibitor of Depeptidyl Peptidase IV", Bioorganic & Medicinal Chemistry Letters, vol. 8, pp. 1537-1540 (1998).

Morrison J. et al., "The Behavior and Significance of Slow-Binding Enzyme Inhibitors", Advances in Enzymology, vol. 61, pp. 201-301 1988.

* cited by examiner

SEQUENCE LISTING

<160> NUMBER OF SEQ ID NOS: 4

<210> SEQ ID NO 1
<211> LENGTH: 18
<212> TYPE: DNA
<213> ORGANISM: Artificial
<220> FEATURE:
<223> OTHER INFORMATION: primer

<400> SEQUENCE: 1
acgccgacga tgaagaca                                                 18

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
aggtaaagag aaacattgtt                                               20

<210> SEQ ID NO 3
<211> LENGTH: 19
<212> TYPE: DNA

-continued
```
<213> ORGANISM: Artificial
<220> FEATURE:
<223> OTHER INFORMATION: primer
<400> SEQUENCE: 3
ggtaccagcg cagaggctt                                         19
<210> SEQ ID NO 4
<211> LENGTH: 27
<212> TYPE: DNA
<213> ORGANISM: Artificial
<220> FEATURE:
<223> OTHER INFORMATION: primer
<400> SEQUENCE: 4
ctcgagctaa ggtaaagaga aacattg                                27
```

AZOLOPYRIMIDINE-BASED INHIBITORS OF DIPEPTIDYL PEPTIDASE IV AND METHODS

RELATED APPLICATION

This application claims priority benefit under Title 35 § 119(e) of U.S. Provisional Application No. 60/640,135, filed Dec. 29, 2004, the contents of which are herein incorporated by reference.

FIELD OF THE INVENTION

The present invention relates to azolopyrimidine-based inhibitors of dipeptidyl peptidase IV (DPP-4), and to a method for treating multiple diseases or disorders by employing such azolopyrimidine-based inhibitors alone, or in combination with another type of therapeutic agent.

BACKGROUND OF THE INVENTION

Dipeptidyl peptidase IV (DPP-4) is a membrane bound non-classical serine aminodipeptidase which is located in a variety of tissues (intestine, liver, lung, kidney) as well as on circulating T-lymphocytes (where the enzyme is known as CD-26). It is responsible for the metabolic cleavage of certain endogenous peptides (GLP-1(7-36), glucagon) in vivo and has demonstrated proteolytic activity against a variety of other peptides (GHRH, NPY, GLP-2, VIP) in vitro.

GLP-1(7-36) is a 29 amino-acid peptide derived by post-translational processing of proglucagon in the small intestine. GLP-1(7-36) has multiple actions in vivo including the stimulation of insulin secretion, inhibition of glucagon secretion, the promotion of satiety, and the slowing of gastric emptying. Based on its physiological profile, the actions of GLP-1(7-36) are expected to be beneficial in the prevention and treatment of type II diabetes and potentially obesity. To support this claim, exogenous administration of GLP-1(7-36) (continuous infusion) in diabetic patients has demonstrated efficacy in this patient population. Unfortunately GLP-1(7-36) is degraded rapidly in vivo and has been shown to have a short half-life in vivo ($t_{1/2} \approx 1.5$ min). Based on a study of genetically bred DPP-4 KO mice and on in vivo/in vitro studies with selective DPP-4 inhibitors, DPP-4 has been shown to be the primary degrading enzyme of GLP-1(7-36) in vivo. GLP-1 (7-36) is degraded by DPP-4 efficiently to GLP-1(9-36), which has been speculated to act as a physiological antagonist to GLP-1(7-36). Thus, inhibition of DPP-4 in vivo should potentiate endogenous levels of GLP-1(7-36) and attenuate formation of its antagonist GLP-1(9-36) and thus serve to ameliorate the diabetic condition.

DESCRIPTION OF THE INVENTION

In accordance with the present invention, compounds of formula (I) are provided

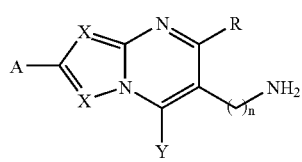

(I)

wherein:

n is 1 or 2;

R is a functional group selected from the group consisting of hydrogen (H), halogen, $CF_3$, cyano (CN), amino, substituted amino, alkyl, alkenyl, alkynyl, cycloalkyl, cycloalkylalkyl, bicycloalkyl, bicycloalkylalkyl, alkylthioalkyl, arylalkylthioalkyl, cycloalkenyl, aryl, arylalkyl, heteroaryl, heteroarylalkyl, cycloheteroalkyl and cycloheteroalkylalkyl, wherein any such functional group may optionally be substituted through available carbon atoms with 1, 2, 3, 4 or 5 groups selected from the group consisting of hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamide and sulfonyl;

X for each occurrence, is selected from nitrogen (N) or C-A, wherein at least one occurrence of X is nitrogen;

A is a functional group selected from the group consisting of hydrogen (H), alkyl, alkenyl, alkynyl, cycloalkyl, cycloalkylalkyl, bicycloalkyl, bicycloalkylalkyl, alkylthioalkyl, arylalkylthioalkyl, cycloalkenyl, aryl, arylalkyl, heteroaryl, heteroarylalkyl, cycloheteroalkyl, cycloheteroalkylalkyl, O—$R_1$, cyano, amino, halo, —C(O)—OH, —C(O)—$NR_1R_2$, —C(O)—$OR_1$, $S(O)_m$—$R_1$, —$S(O)_2NR_1R_2$, —$NR_1R_2$, —$NR_1$—C(O)$R_2$, —$NR_1$—$SO_2R_2$, wherein any such functional group may optionally be substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido or sulfonyl;

m is 0, 1 or 2;

$R_1$ and $R_2$ are (i) each independently a functional group selected from the group consisting of hydrogen (H), alkyl, alkenyl, alkynyl, cycloalkyl, cycloalkylalkyl, bicycloalkyl, bicycloalkylalkyl, alkylthioalkyl, arylalkylthioalkyl, cycloalkenyl, aryl, arylalkyl, heteroaryl, heteroarylalkyl, cycloheteroalkyl and cycloheteroalkylalkyl, wherein either functional group may optionally be substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl; or (ii) $R_1$ and $R_2$ in $NR_1R_2$ may be taken together to form a 5- and 6-membered saturated or partially unsaturated ring system selected from the group consisting of heterocycloalkyl, heterobicycloalkyl, heteroaryl and bicycloheteroaryl, wherein any such ring system may optionally be substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl; and Y is aryl or heteroaryl, wherein said aryl or heteraryl group may optionally be substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl.

The definition of formula I above includes all pharmaceutically acceptable salts, stereoisomers, and prodrug esters of formula I.

The compounds of formula I possess activity as inhibitors of DPP-4 in vivo and are useful in the treatment of diabetes and the micro- and macrovascular complications of diabetes such as retinopathy, neuropathy, nephropathy, and wound healing. Such diseases and maladies are also sometimes referred to as "diabetic complications".

The present invention provides for compounds of formula I, pharmaceutical compositions employing such compounds and for methods of using such compounds. In particular, the present invention provides a pharmaceutical composition comprising a therapeutically effective amount of a compound of formula I, alone or in combination with a pharmaceutically acceptable carrier.

Further provided is a method for treating or delaying the progression or onset of diabetes, especially type II diabetes, including complications of diabetes, including retinopathy, neuropathy, nephropathy and delayed wound healing, and related diseases such as insulin resistance (impaired glucose homeostasis), hyperglycemia, hyperinsulinemia, elevated blood levels of fatty acids or glycerol, obesity, hyperlipidemia including hypertriglyceridemia, Syndrome X, atherosclerosis and hypertension, and for increasing high density lipoprotein levels, wherein a therapeutically effective amount of a compound of formula I, is administered to a mammalian, e.g., human, patient in need of treatment.

The compounds of the invention can be used alone, in combination with other compounds of the present invention, or in combination with one or more other agent(s) active in the therapeutic areas described herein.

In addition, a method is provided for treating diabetes and related diseases as defined above and hereinafter, wherein a therapeutically effective amount of a combination of a compound of formula I and at least one other type of therapeutic agent, such as an antidiabetic agent and/or a hypolipidemic agent, is administered to a human patient in need of treatment.

Specific embodiments of the invention include compounds of formula I having the structure

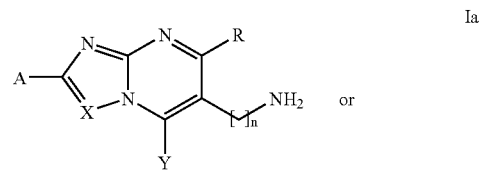

Ia

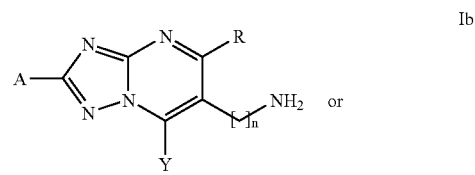

Ib

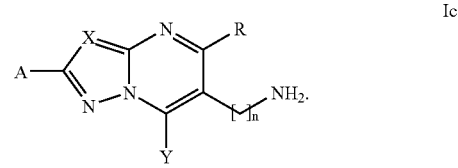

Ic

Further embodiments of the invention include compounds of formula I having the structure:

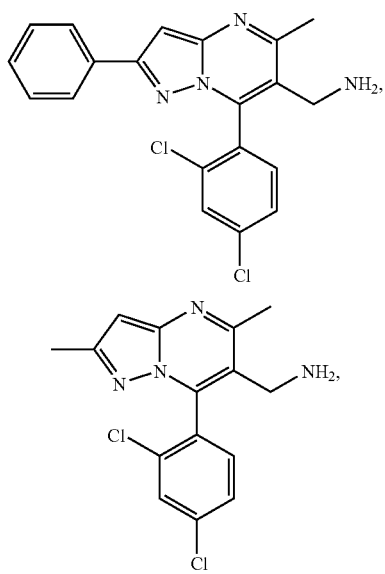

-continued
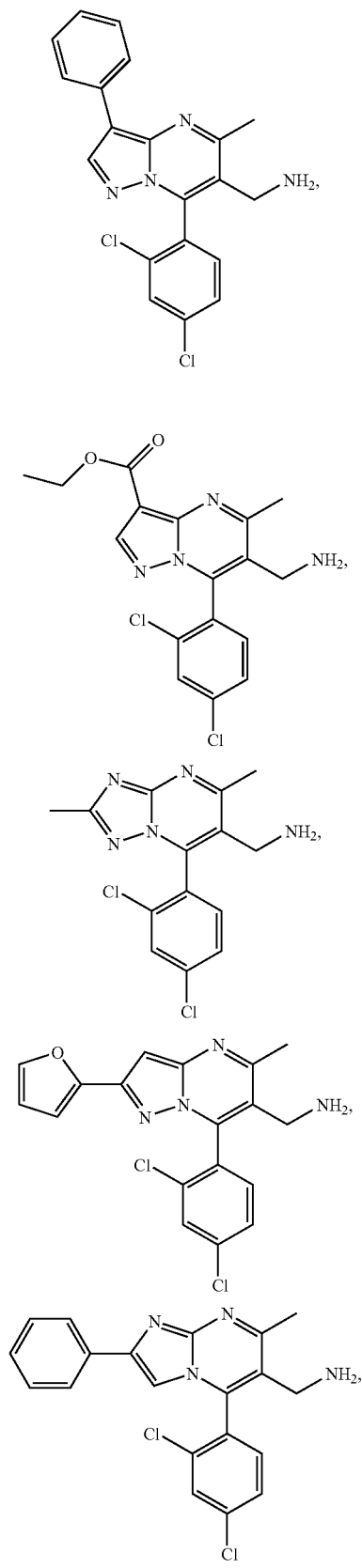
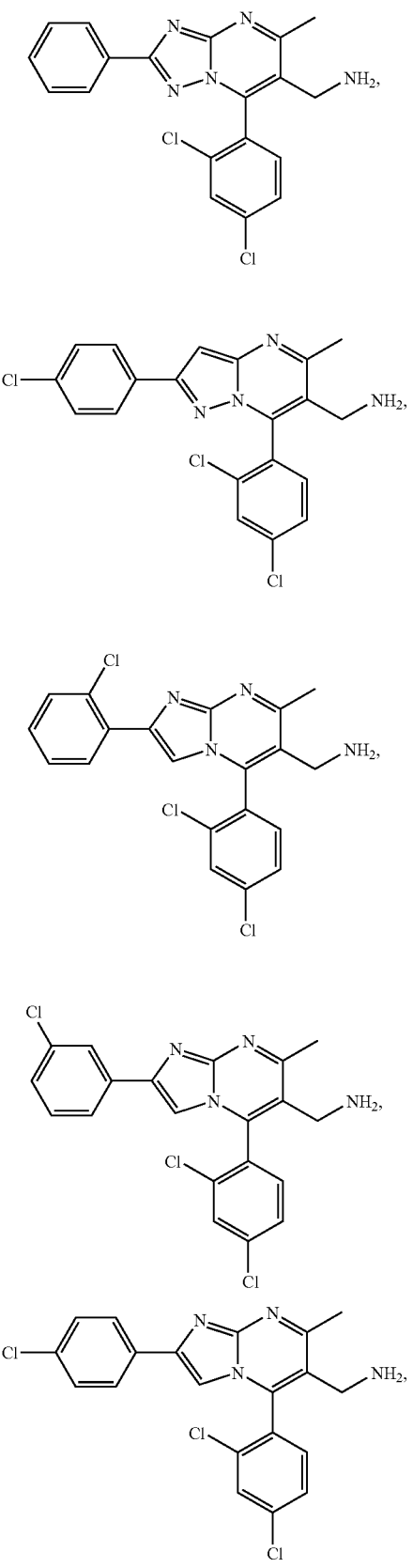

-continued
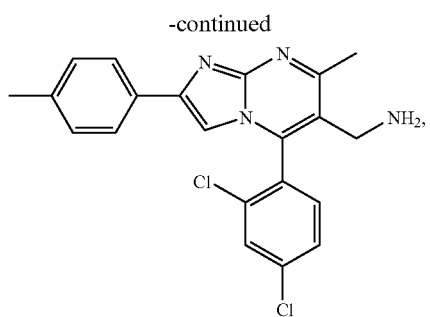
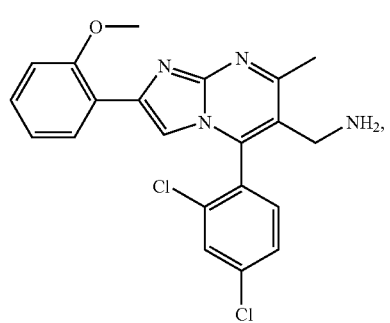
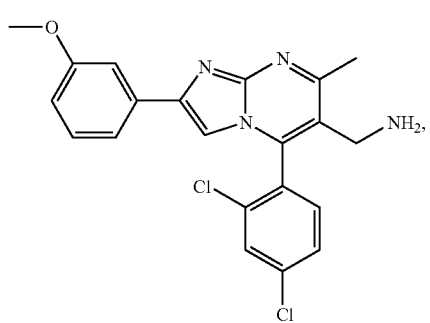
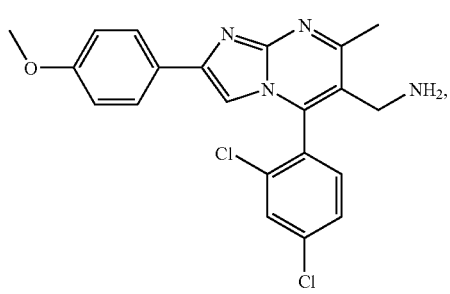
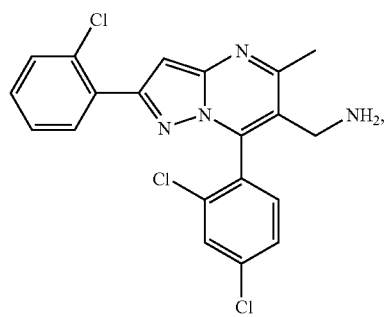
-continued
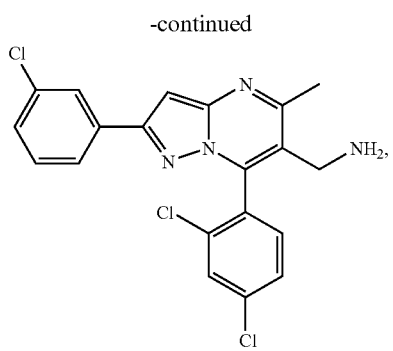
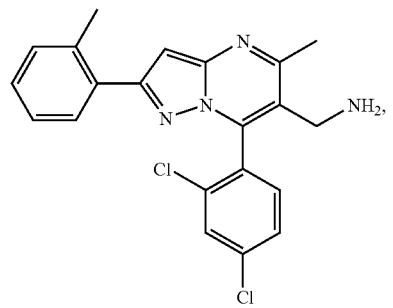
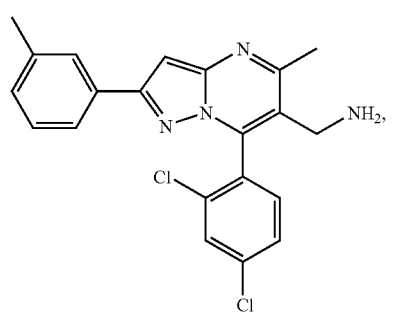
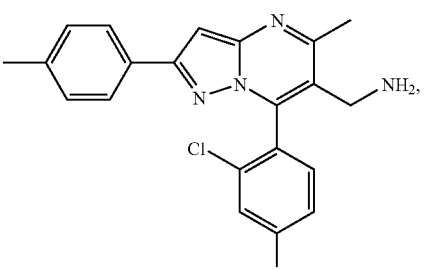
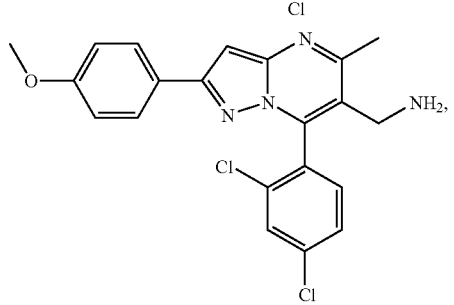

-continued
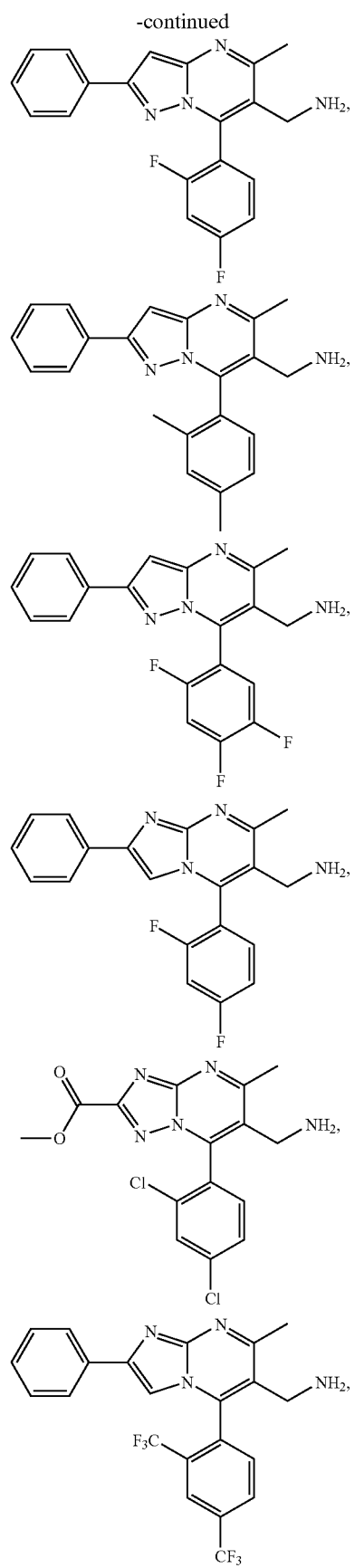
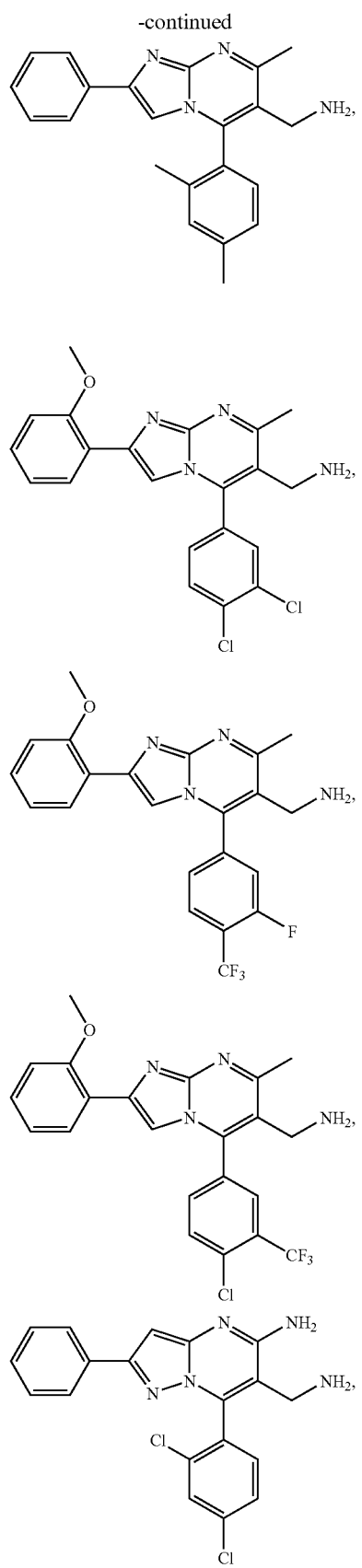

-continued
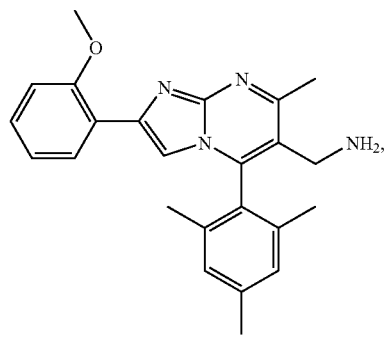
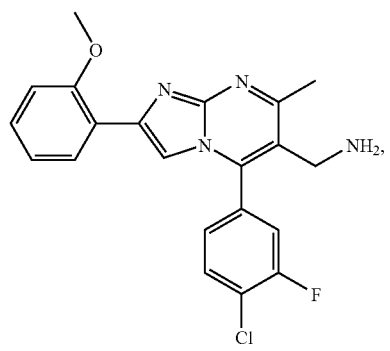
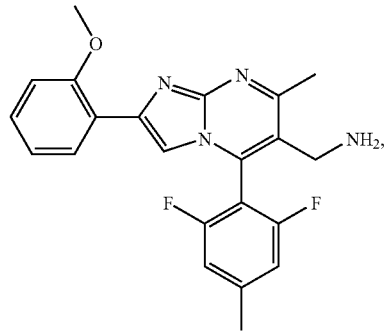
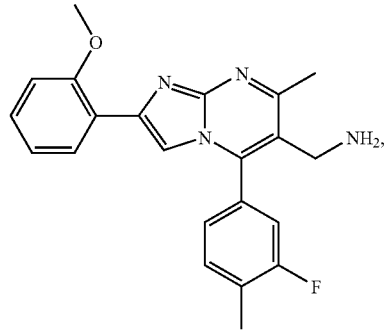
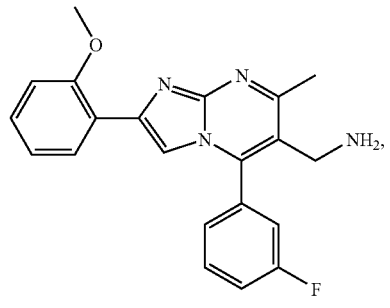
-continued
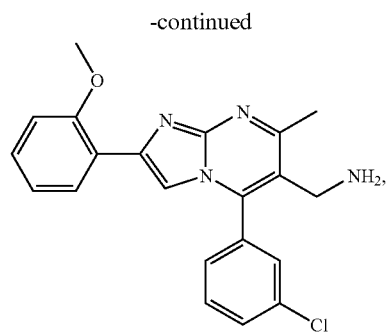
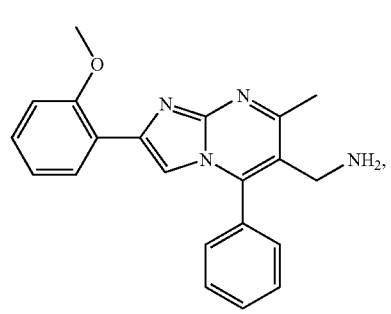
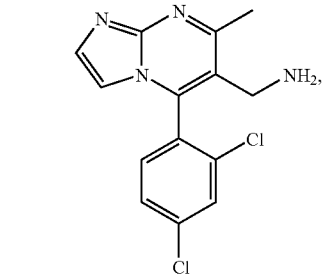
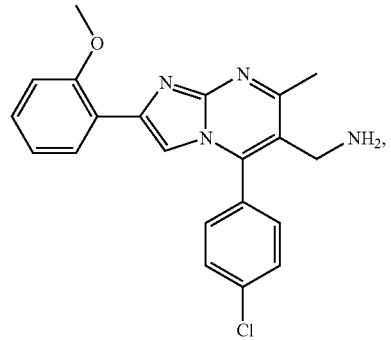
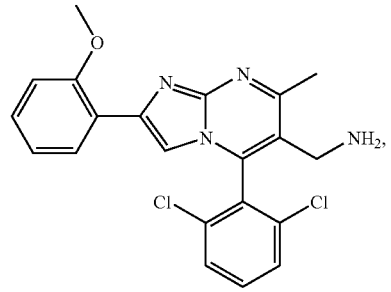

-continued
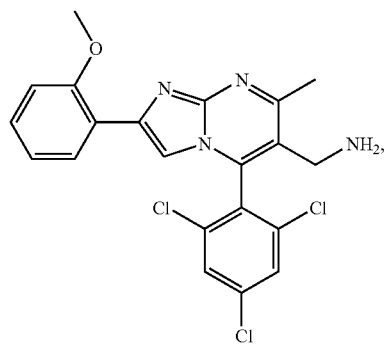
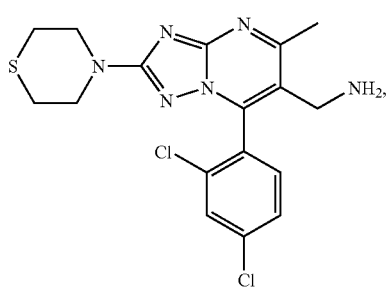
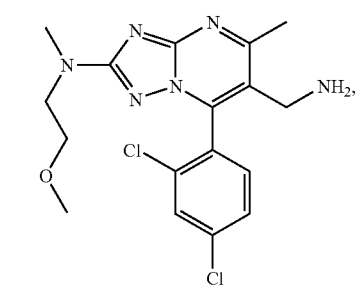
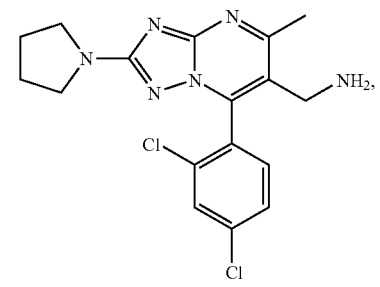
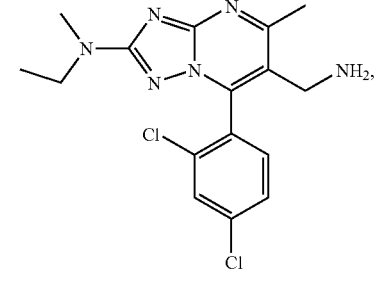
-continued
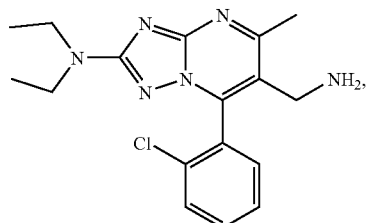
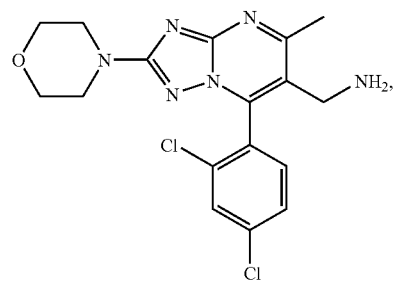
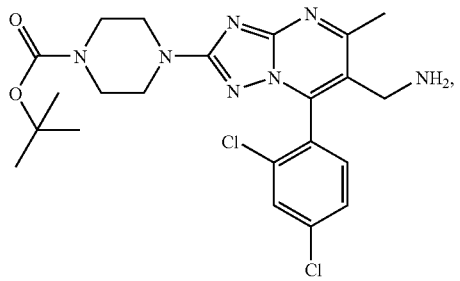
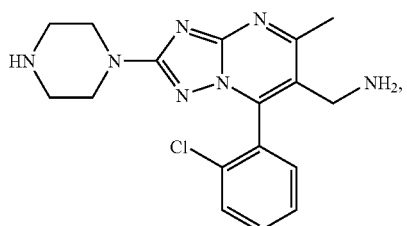
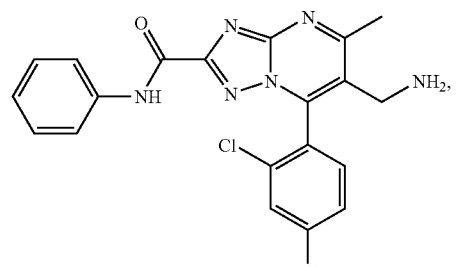
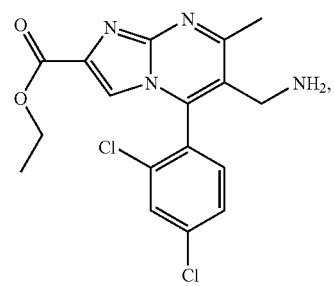

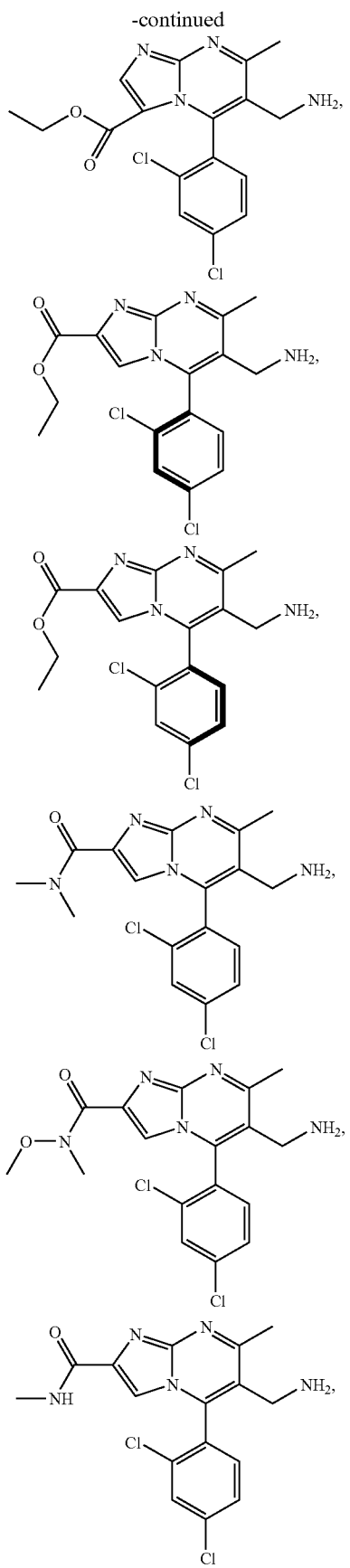
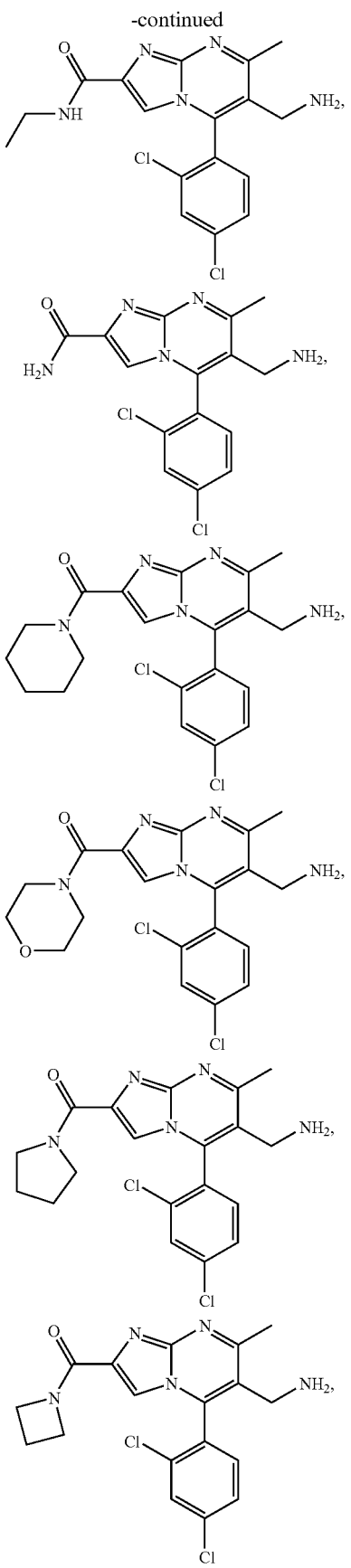

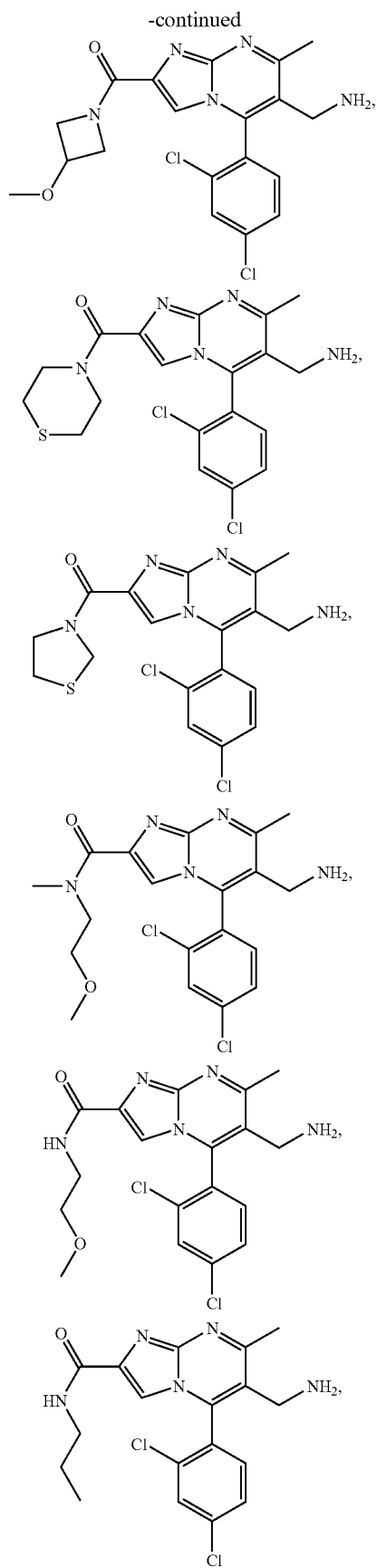
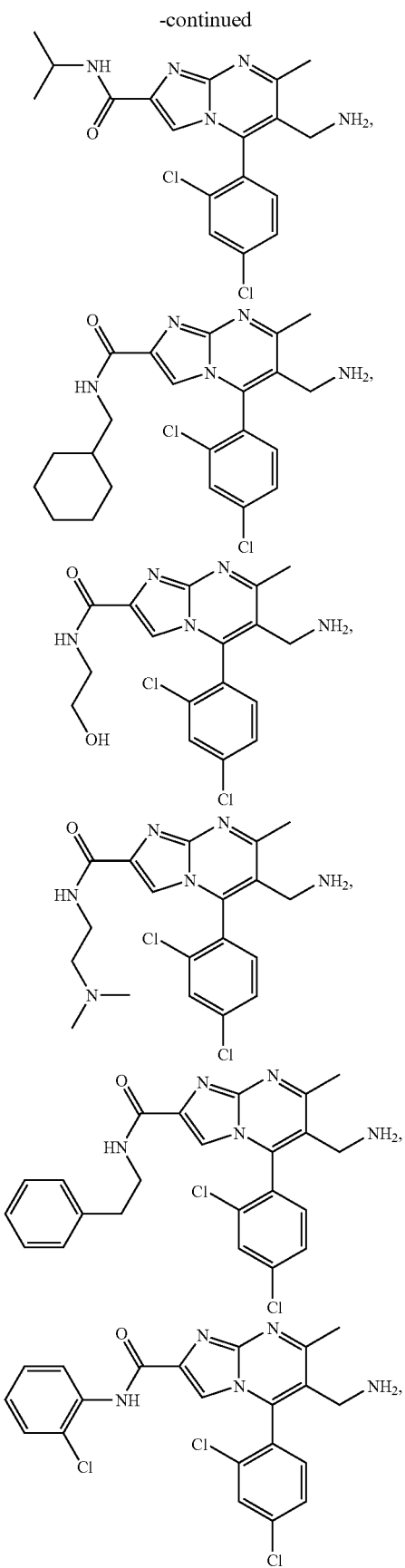

-continued
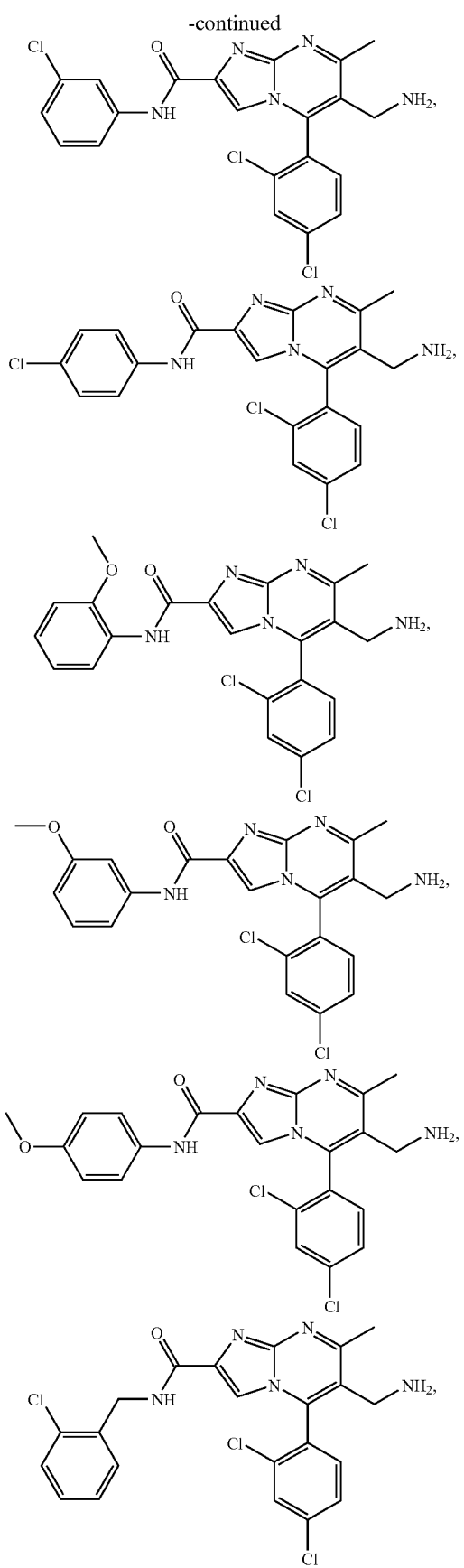
-continued
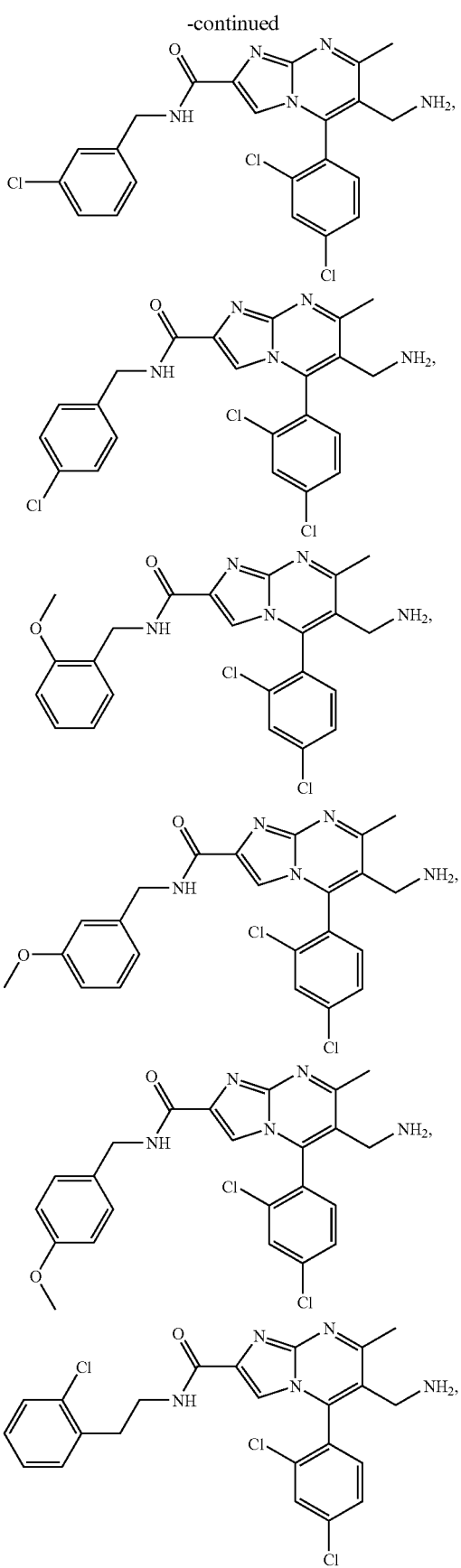

21
-continued
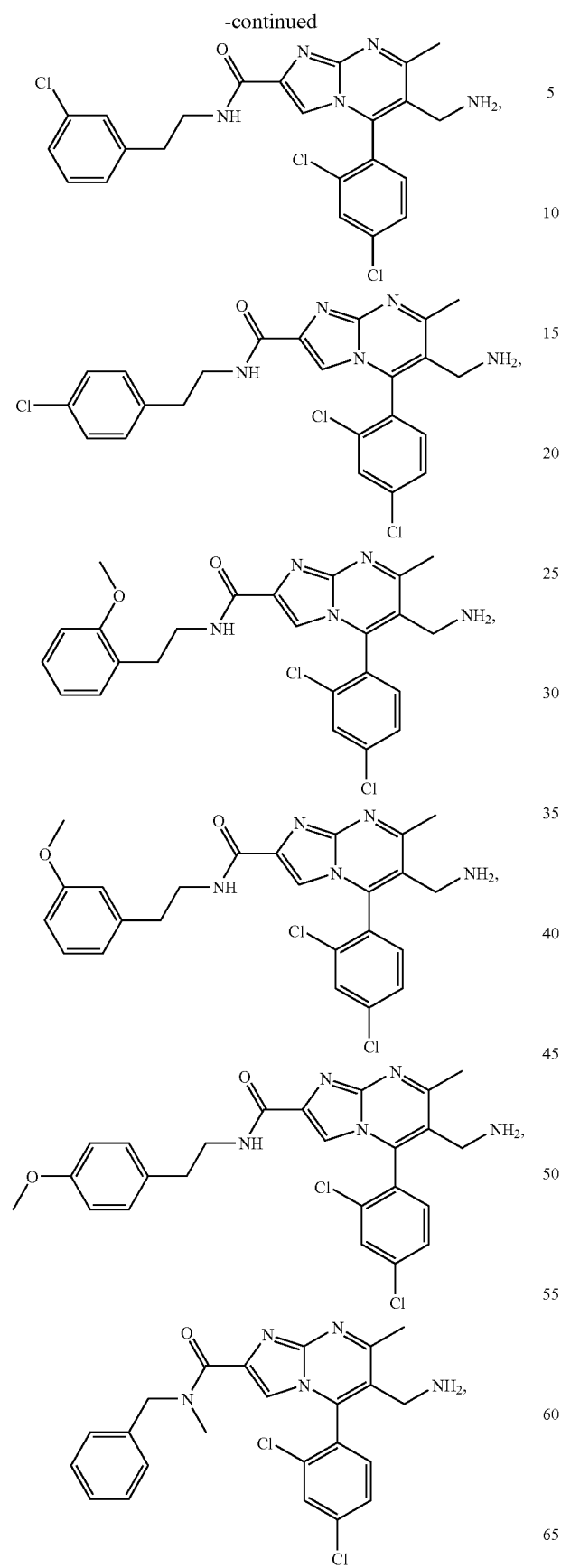
22
-continued
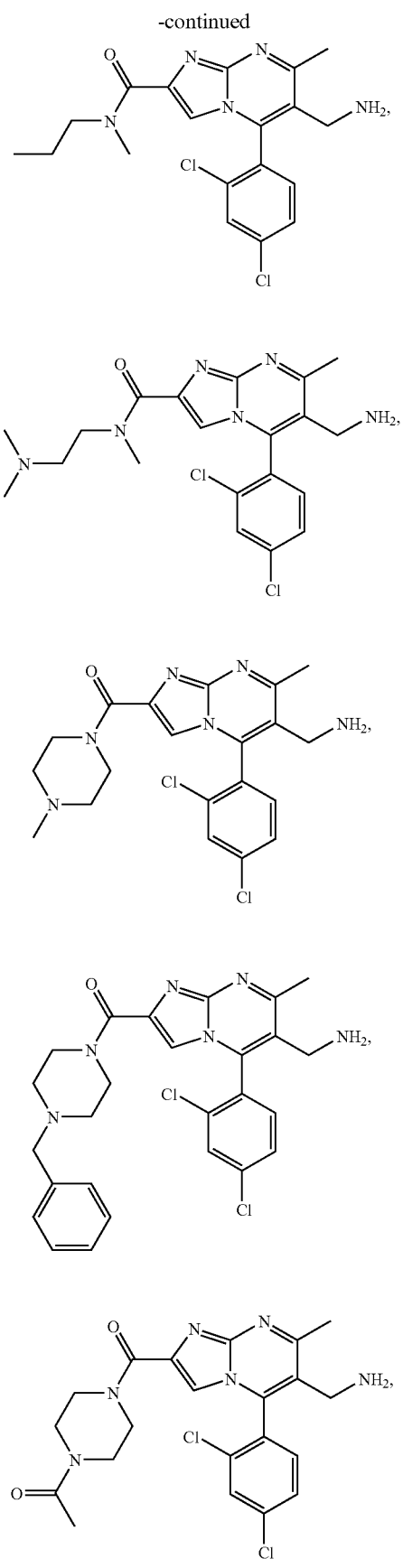

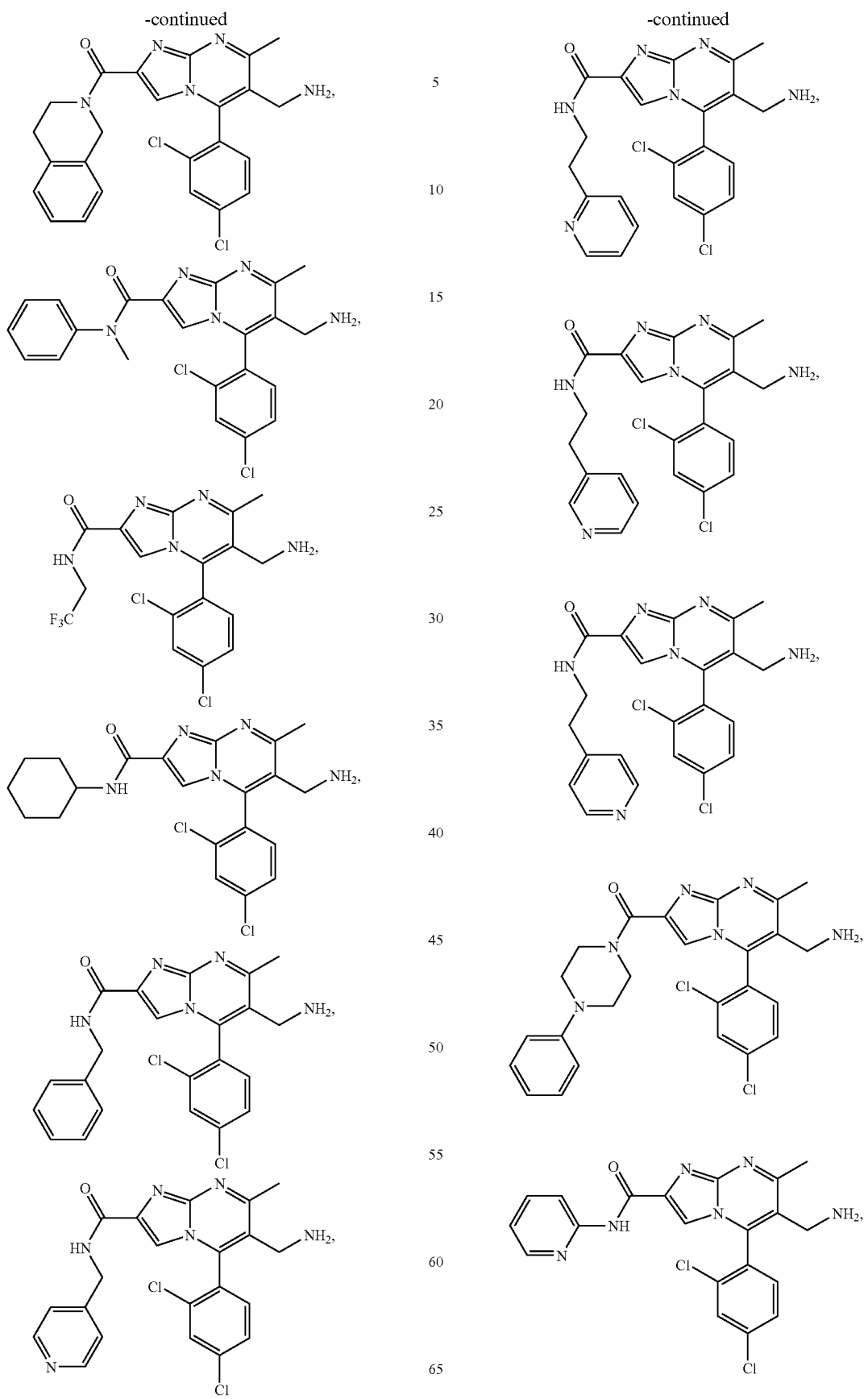

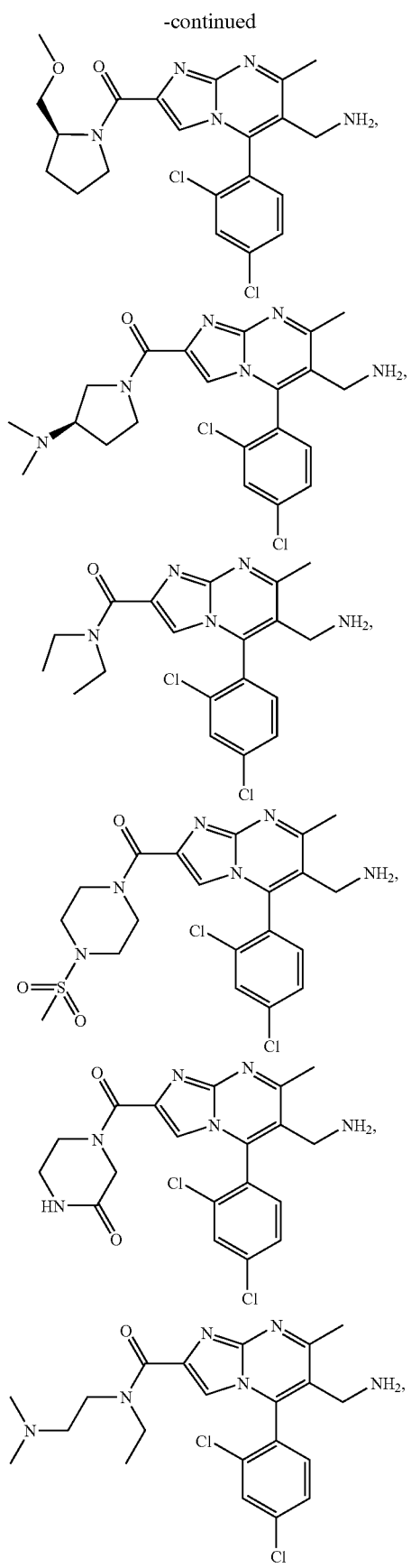

-continued
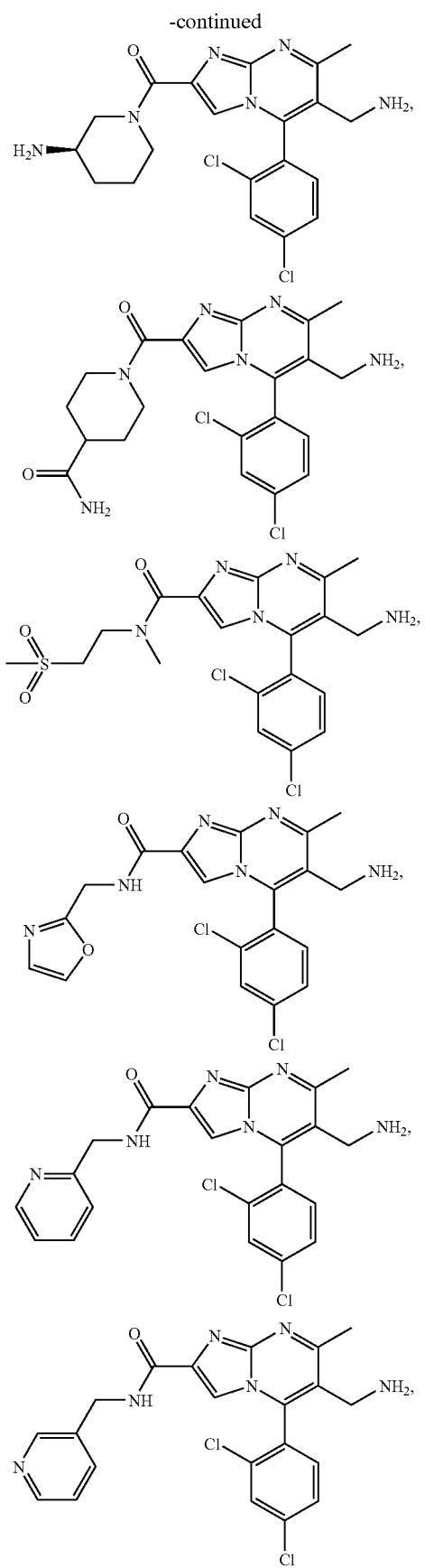
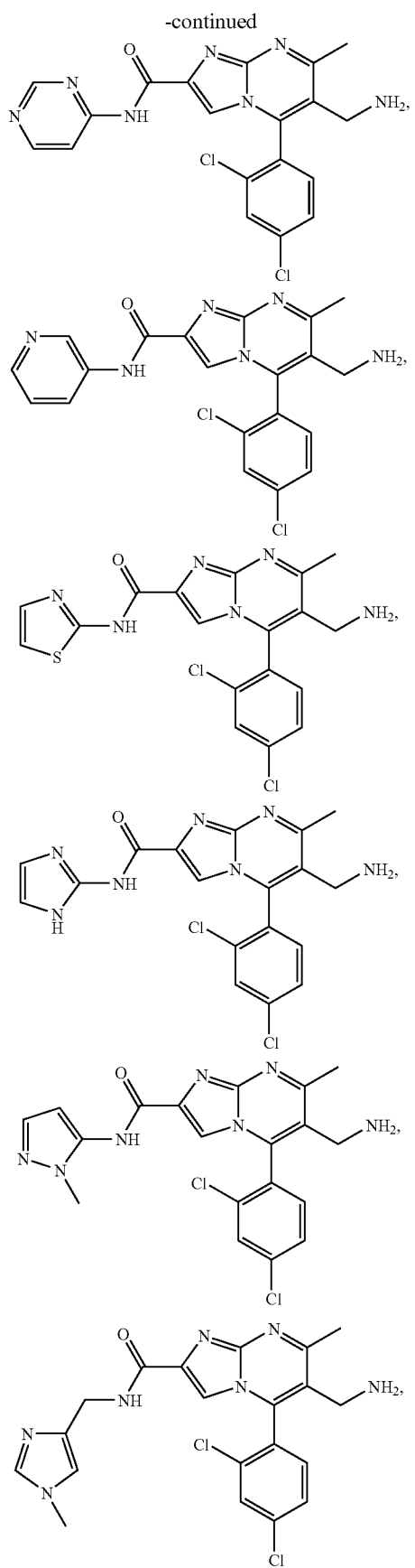

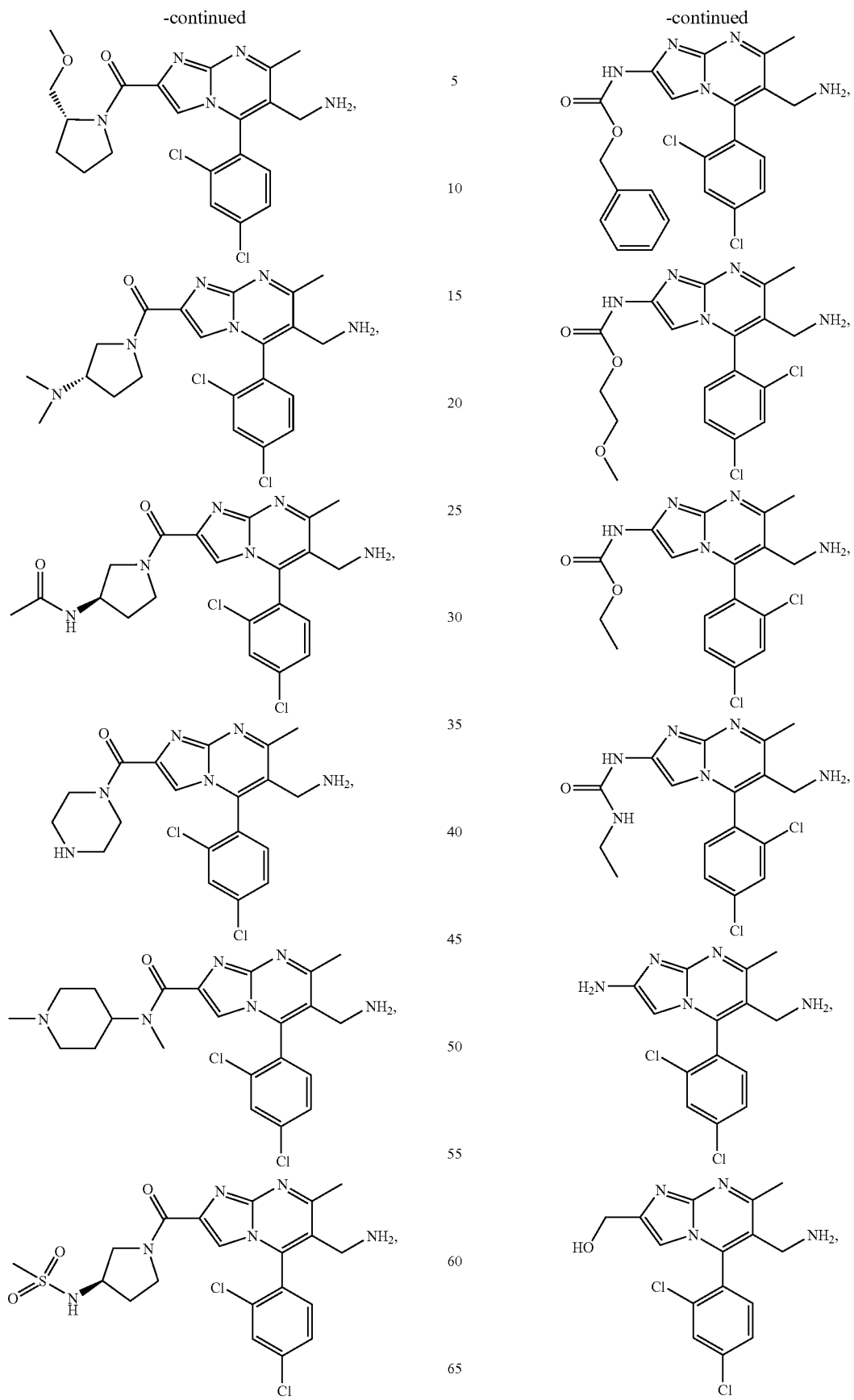

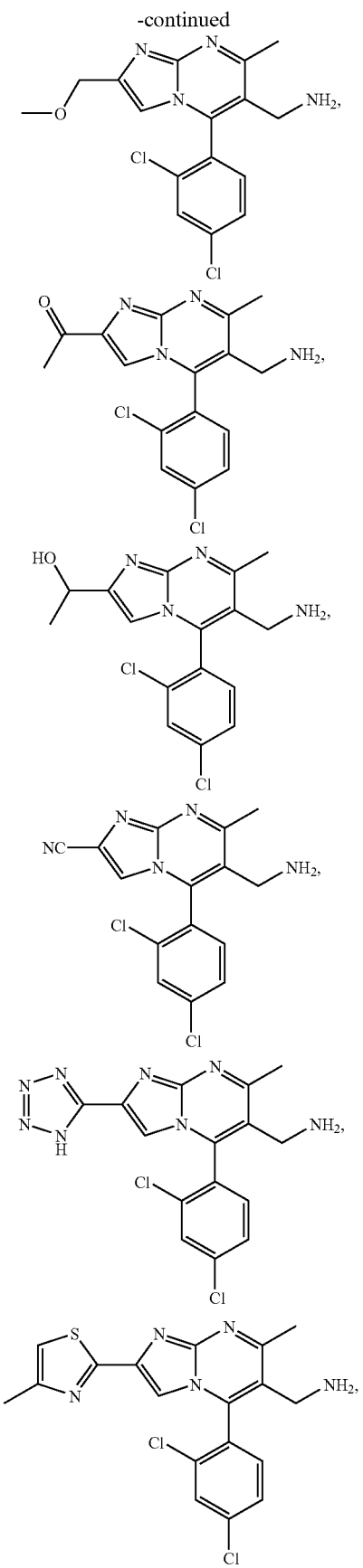
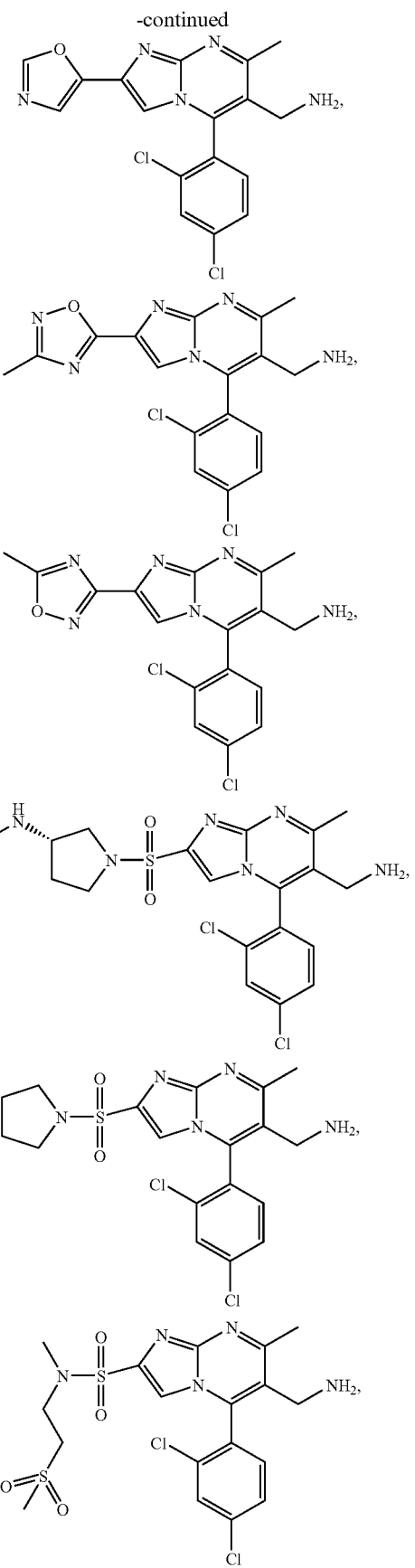

-continued
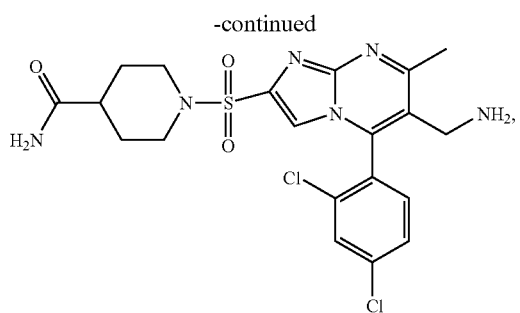
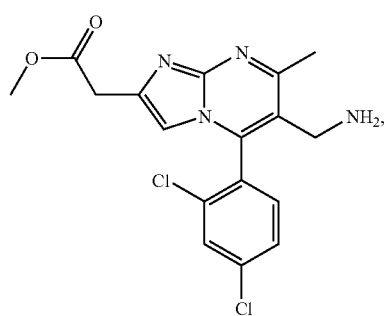
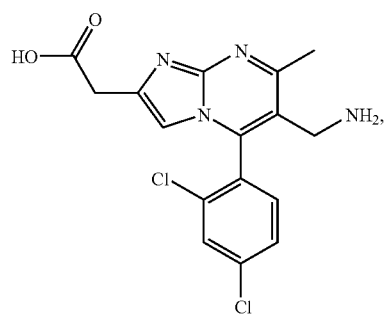
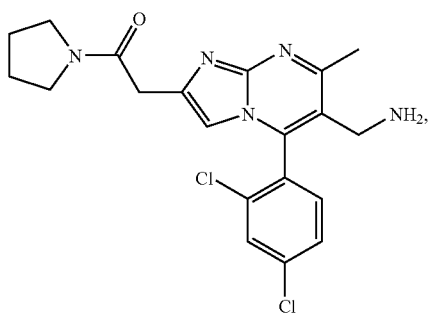
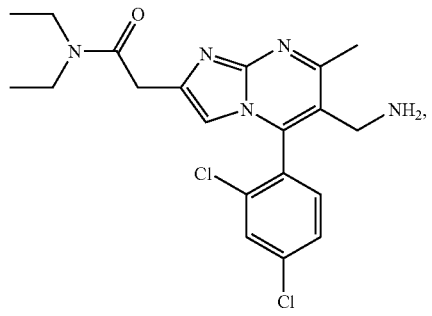
-continued
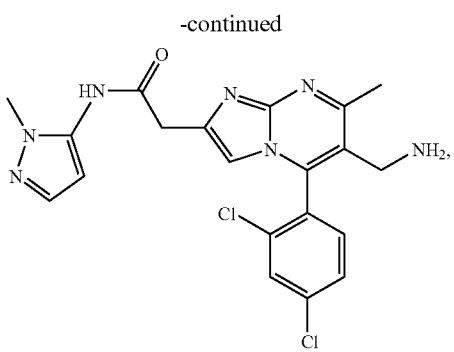
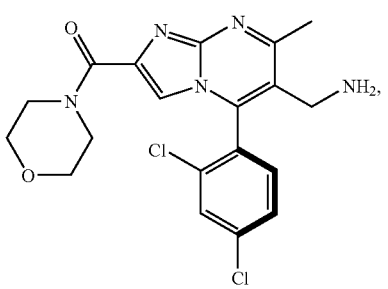
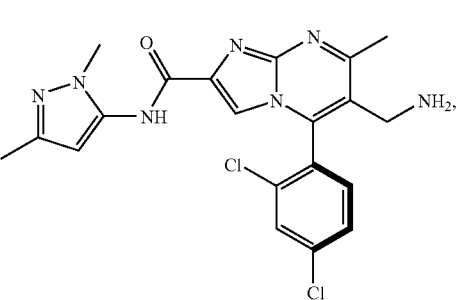
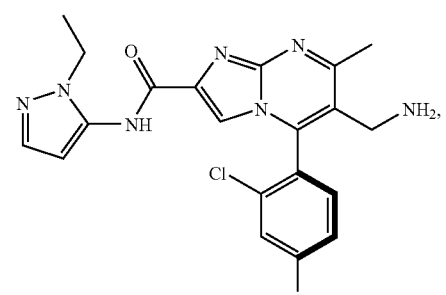
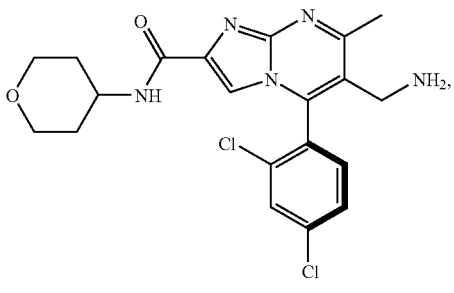

-continued
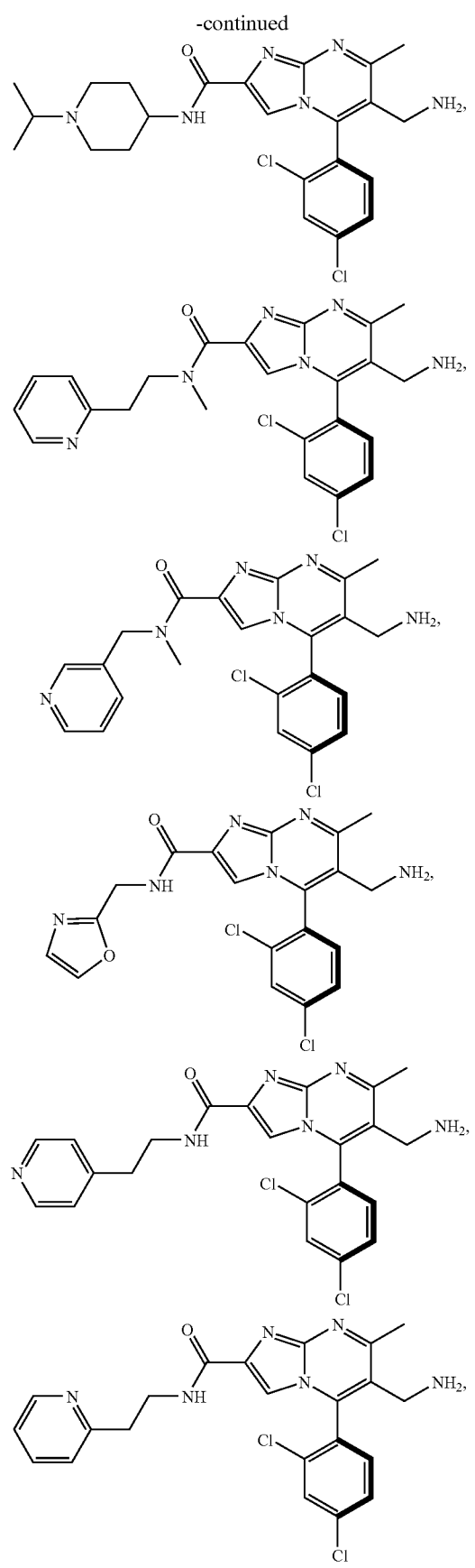
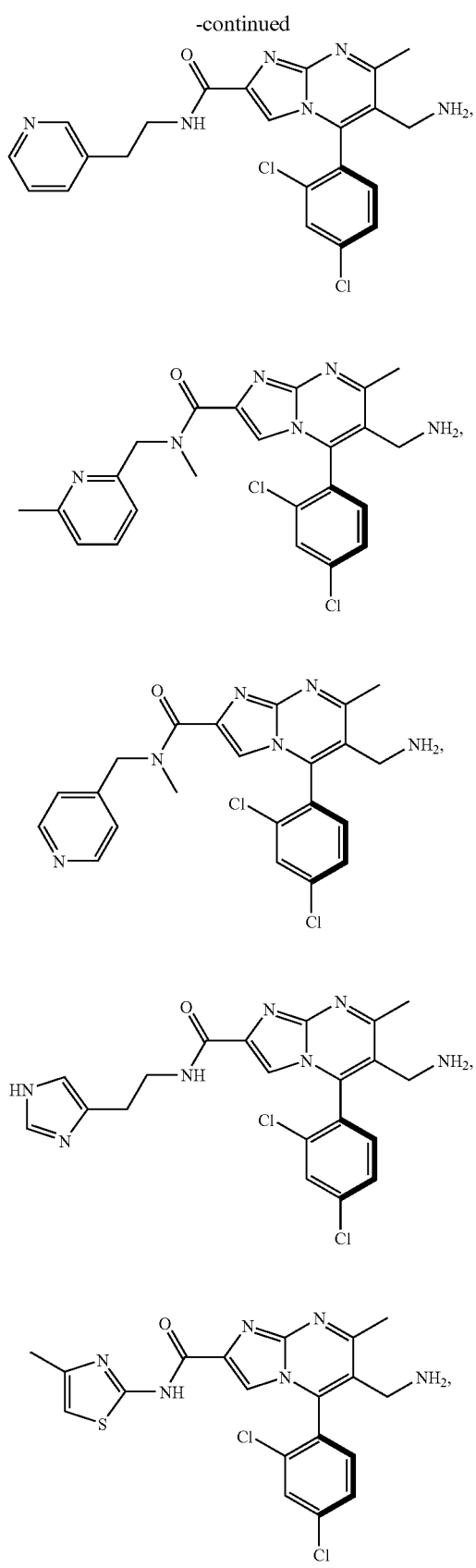

37
-continued
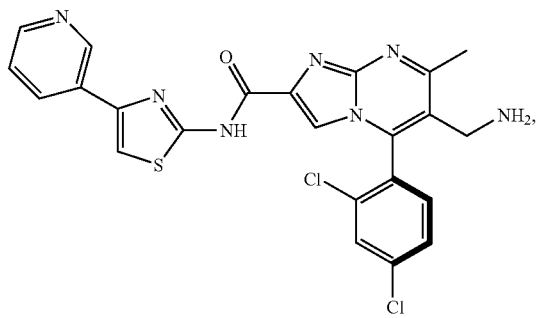
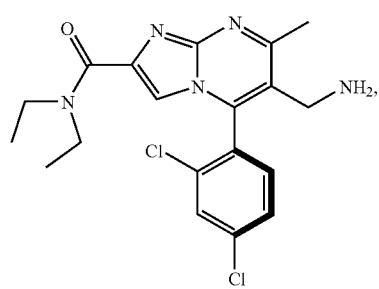
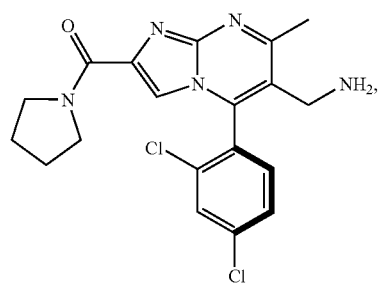
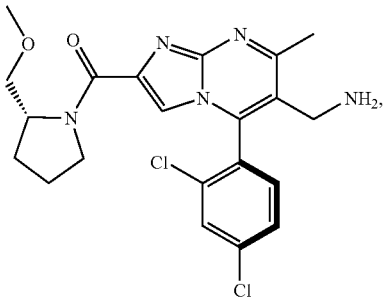
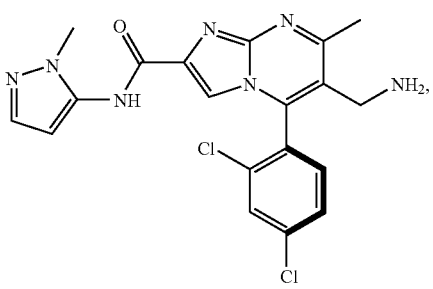
38
-continued
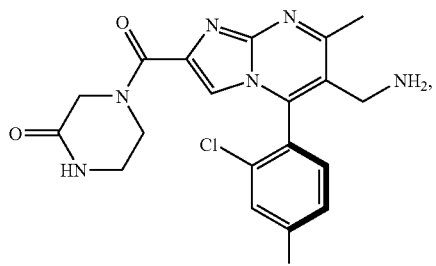
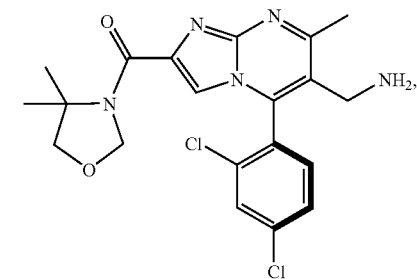
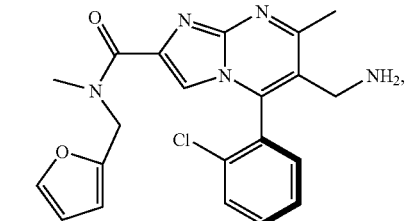
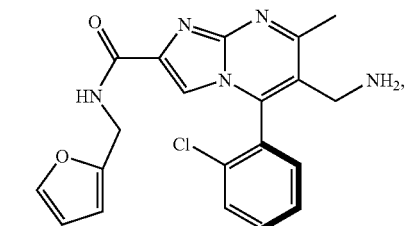
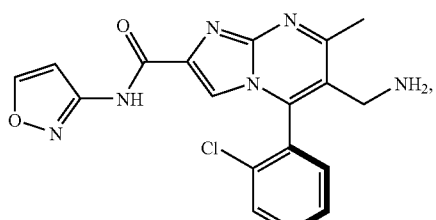
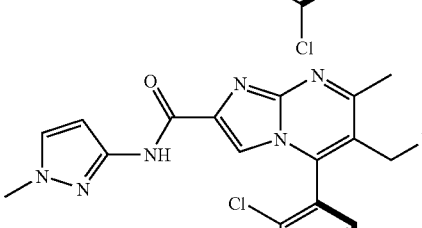

-continued

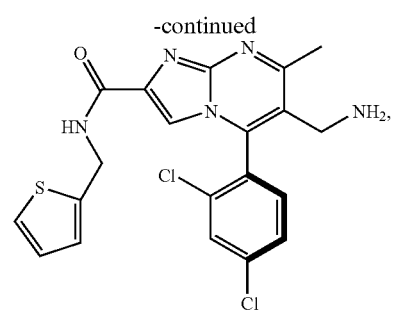

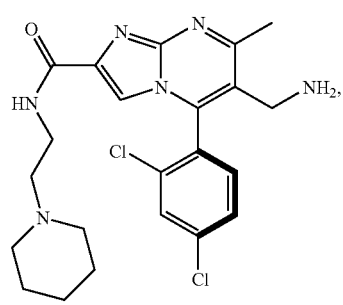

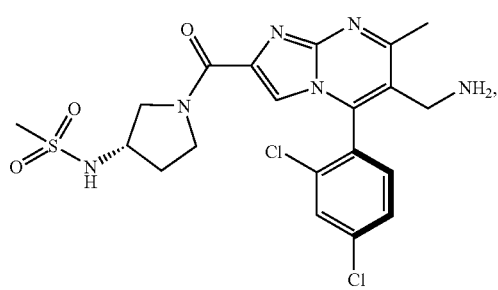

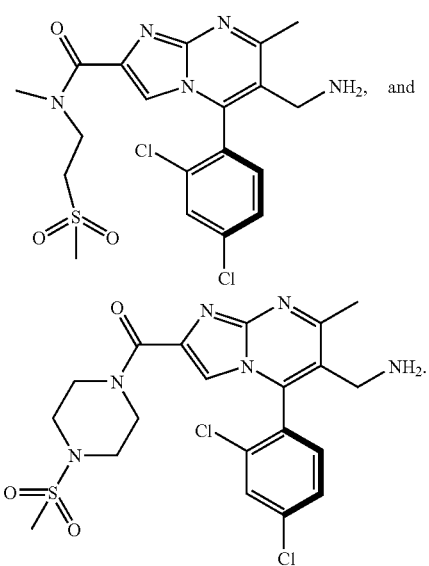
and

In the above method of the invention, the compound of formula (I) will be employed in a weight ratio to the antidiabetic agent or other type therapeutic agent (depending upon its mode of operation) within the range from about 0.01:1 to about 500:1, preferably from about 0.1:1 to about 100:1, more preferably from about 0.2:1 to about 10:1.

DETAILED DESCRIPTION OF THE INVENTION

Compounds of formula (I) may be generated by the methods as shown in the following reaction schemes and the description thereof.

SCHEME 1

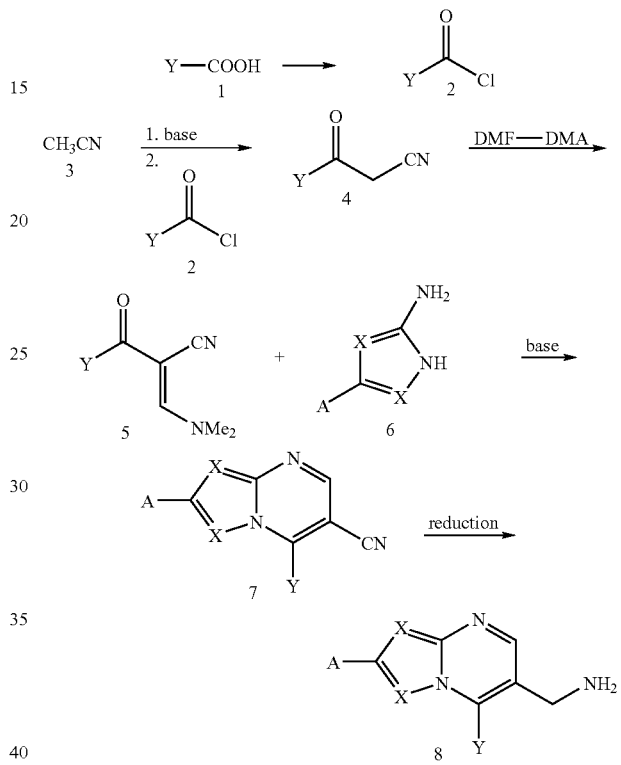

Scheme 1 provides a general route to prepare aminomethyl azolopyrimidine of formula (8). An acid chloride of formula (2) may be obtained from commercial sources, or alternatively generated by methods as described herein from the corresponding carboxylic acid of formula (1). For example, the acid chloride (2) can be formed by treating carboxylic acid (1) with $(COCl)_2$ or $SOCl_2$ in an inert solvent such as methylene chloride or THF at 0 to 60° C. for 2-48 hours.

A ketonitrile of formula (4) can be prepared by combining the lithium anion of acetonitrile (3) with acid chloride of formula (2). Acetonitrile can be deprotonated by a strong base such as n-BuLi in an anhydrous solvent such as THF or diethyl ether at low temperature to give the lithium anion of acetonitrile.

An acrylnitrile of formula (5) can be prepared by methods known in the art such as heating a ketonitrile of formula (4) with dimethylformamide dimethylacetal in an inert solvent such as toluene at elevated temperature for 2-48 hours.

Aminopyrazole, aminotriazole or aminoimidazole of formula (6) can be either obtained through commercial sources, or conveniently prepared by methods known to those skilled in the art (see Schemes 9 to 12). An azolopyrimidine of formula (7) can be prepared by combining an acrylonitrile (5) and an azole (6) by methods known in the art. For example, the process can be performed by heating an acrylonitrile (5)

and an azole (6) with a base such as NaOMe in methanol at room temperature to reflux for 2-48 hours.

An aminomethyl azolopyrimidine of formula (8) can be prepared from a nitrile (7) through a reductive process. The reducing agents which may be used for this process include, but are not limited to LAH, $CoCl_2/NaBH_4$, $BH_3$, Raney $Ni/H_2$, $Rh-Al_2O_3/H_2$, $LiBH_4$, $Pt/H_2$, $PtO_2/H_2$, Na, $SmI_2$, $Pd/H_2$.

Scheme 2 describes an alternative route to prepare an aminomethyl pyrimidine of formula (8).

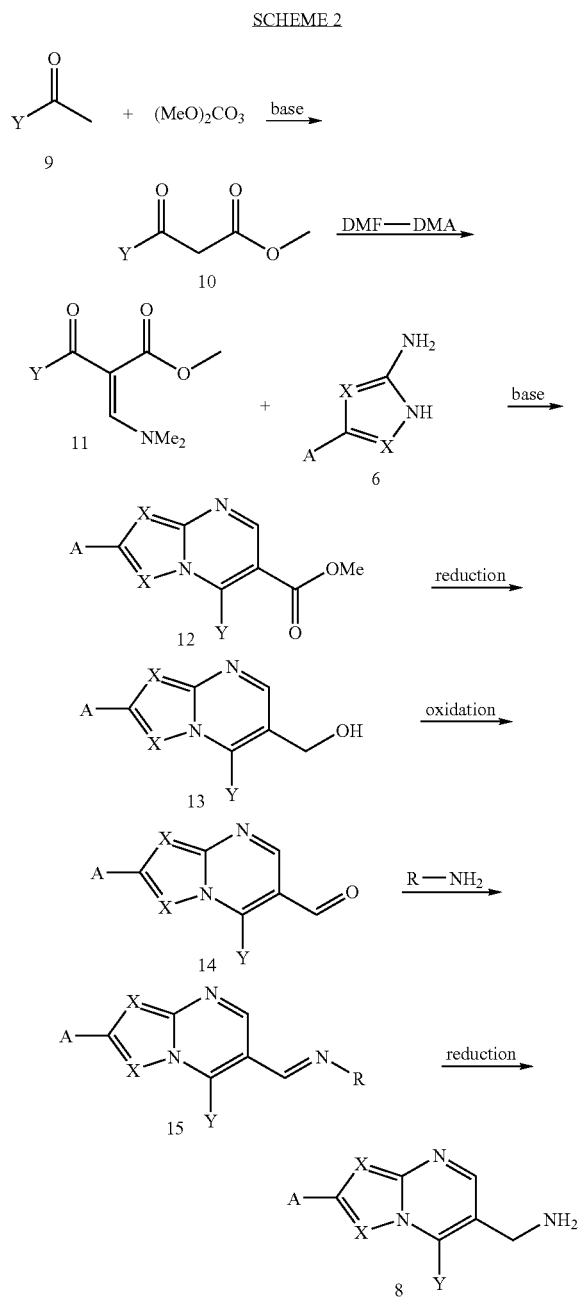

Ketoesters of formula (10) are known in the art or can be conveniently prepared by the methods known in the art. An example of one suitable method to prepare ketoester (10) is to combine a ketone (9) with a methylcarbonate and a base such as NaH in an inert solvent such as THF at ambient temperature for 2-24 hours.

An acryloester of formula (11) can be prepared by the same methods as described in Scheme 1 for acrylonitriles (5).

An ester azolopyrimidine of formula (12) can be prepared by combining an acryloester (11) and an azole (6) using the same methods as described in Scheme 1 for pyrimidines (7).

An aminomethyl azolopyrimidine of formula (8) can then be prepared by one skilled in the art through a reduction, oxidation, reduction sequence on an azolopyrimidine ester of formula (12) as described in Scheme 2. The reducing agents that may be used to convert the ester of formula (12) to an alcohol of formula (13) include, but are not limited to DIBAL, LAH, Red-Al. The oxidizing agents that can be used to convert an alcohol of formula (13) to an aldehyde of formula (14) include, but are not limited to Dess-Martin periodinane, Swern, PCC, $MnO_2$, TPAP/NMO. As understood by those skilled in the art, a compound of formula (15) can be either an oxime or an imine, which can be conveniently prepared by combining an aldehyde of formula (14) with an amine or hydroxylamine. The reduction of a compound of formula (15) to an aminomethyl azolopyrimidine of formula (8) can be performed by using reducing agents such as Zn/HOAc, $Pd/H_2$, Raney $Ni/H_2$, or other suitable reagents.

Scheme 3 provides an alternative route of converting an alcohol of formula (13) to an aminomethyl azolopyrimidine of formula (8).

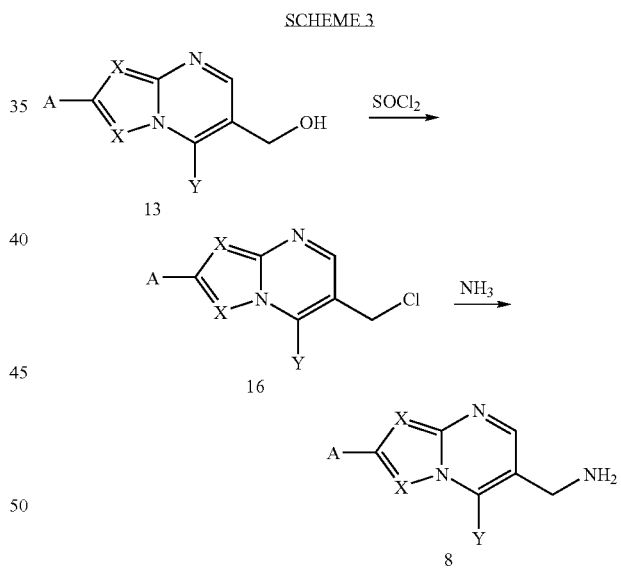

A chloroazolopyrimidine of formula (16) can be formed from an alcohol of formula (13) by methods known to one skilled in the art. An example of a suitable method for such a transformation is to treat an alcohol of formula (13) with $SOCl_2$ in an inert solvent such as $CH_2Cl_2$ at elevated temperature for 2-24 hours. The resulting chloroazolopyrimidine of formula (16) can then be converted to an aminomethyl azolopyrimidine of formula (8) by bubbling $NH_3$ gas through a solution of a chloroazolopyrimidine of formula (16) in an inert solvent such as methanol.

Scheme 4 provides an alternative route of converting an alcohol of formula (13) to an aminomethyl azolopyrimidine of formula (8).

SCHEME 4

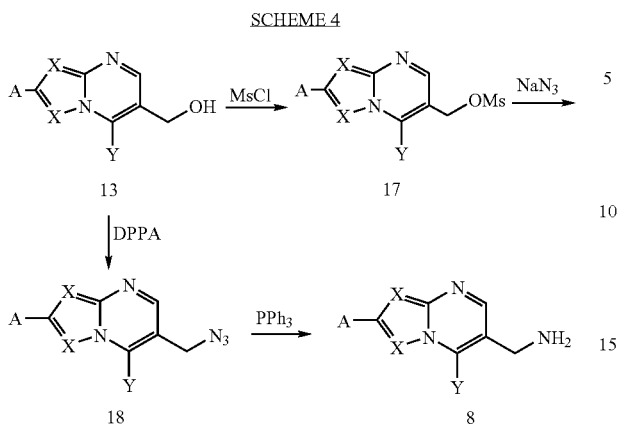

An alcohol of formula (13) can be converted to a suitable leaving group such as a mesylate by treating the alcohol of formula (13) with methanesulfonyl chloride and a base such as triethylamine or pyridine in an inert solvent such as tetrahydrofuran or methylene chloride at 0 to 60° C. for 1 to 24 hours. A mesylate compound of formula (17) can then be converted to an azide of formula (18) by methods known to one skilled in the art. One such set of conditions is to treat a mesylate compound of formula (17) with sodium azide in an inert solvent such as DMF at room temperature to 100° C. for 1 to 24 hours. Alternatively, the azide of formula (18) can be prepared directly from alcohol of formula (13) as described in Thompson, A. S.; Humphrey, G. R.; DeMarco, A. M.; Mathre, D. J.; Grabowski, E. J. J. J. Org. Chem. 1993, 58, 5886-5888. The resultant azide of formula (18) can then be reduced to form an aminomethyl azolopyrimidine of formula (8). The reducing agents that may be used for this transformation include, but are not limited to triphenylphosphine, trialkyl phosphine (including polymer supported phosphines), lithium aluminum hydride, hydrogen with palladium, and platinum containing catalysts.

Alkylated aminomethyl azolopyrimidines of formula (19) can be prepared from aldehydes of formula (14) as described in Scheme 5. One example of such a transformation can be found in: Hart, David J.; Kanai, Kenichi; Thomas, Dudley G.; Yang, Teng Kuei. Journal of Organic Chemistry (1983), 48(3), 289-94. Another example of such a transformation is to add R—MgBr to the aldehyde, followed by oxidation, imine/oxime formation and reduction as described in Scheme 2.

SCHEME 5

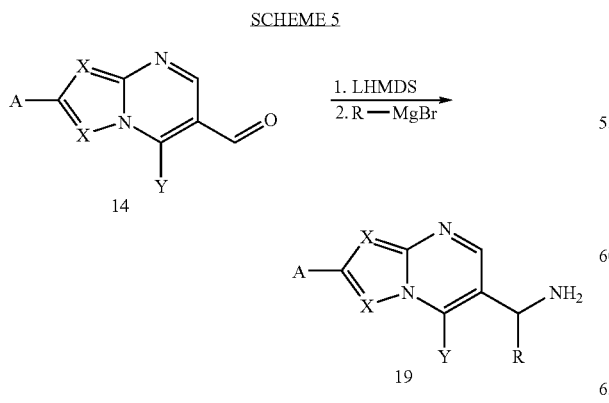

Scheme 6 and Scheme 7 describes a route to prepare 6-substituted aminomethyl pyrimidines of formula (24).

SCHEME 6

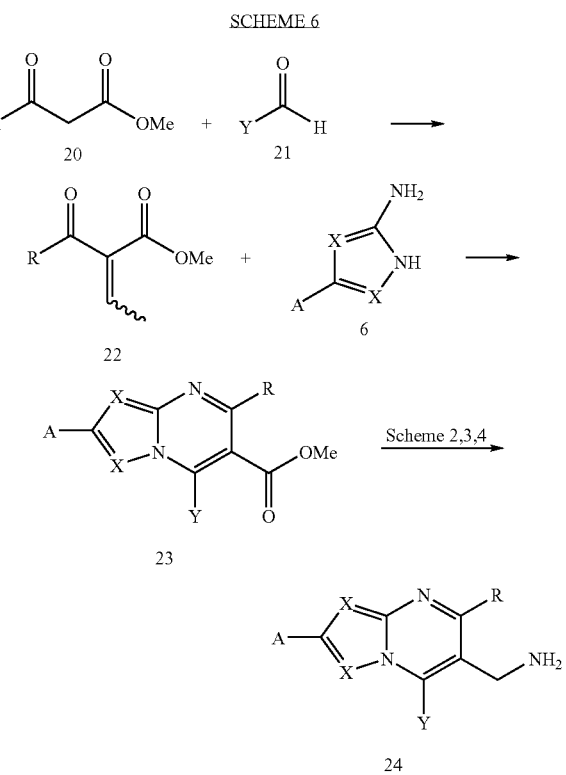

SCHEME 7

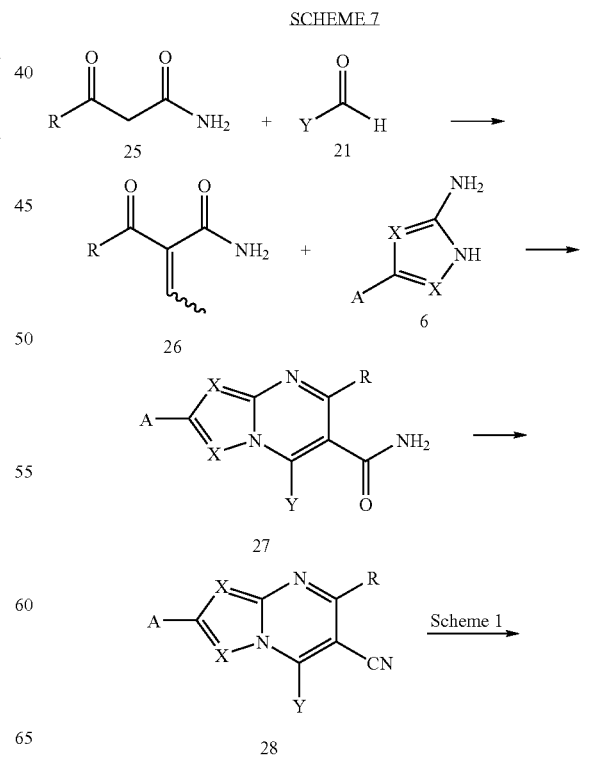

-continued

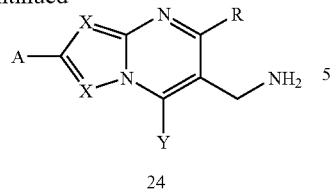

24

A keto ester of formula (20) or (25) can be either obtained from commercial sources or conveniently prepared by the methods described in Scheme 2.

An acryloester of formula (22) or (26) can be prepared by methods known to one skilled in the art by combining ketoester of formula (20) or (21) and an aldehyde of formula (21). One such example to prepare acryloesters of formula (22) or (26) is through a Knovenagel reaction.

Pyrimidines esters of formula (23) or (27) can be prepared by methods known to one skilled in the art by combining an acryloester of formula (22) or (26) and an azole of formula (6). For example, mixing an acryloester of formula (22) or (26) and an azole of formula (6) with a base such as triethylamine, pyridine, NaOMe or KOAc in an inert solvent such as tolene, chloroform, benzene or DMF at elevated temperature can provide an azolopyrimidine ester of formula (23) or (27).

The conversion of an azolopyrimidine ester of formula (23) to an aminomethyl azolopyrimidine of formula (24) following the same procedures as described in Scheme 2, 3 and 4.

Alternatively, formula (27) can be dehydrated to form formular (28) by one skilled in the art. The dehydrating agents that may be used for this transformation include, but are not limited to phosphorous oxychloride, thionyl chloride, formic acid, trifluoroacetic anhydride/pyridine or triethyl amine, oxaly chloride/pyridine or triethyl amine, cyanuric chloride, methanesulfonyl chloride/triethyl amine, triphenylphosphine, polyphosphoric acid, acetic anhydride/triethyl amine, tosyl chloride/pyridine, phosgene, titanium tetrachloride.

The cyano group of formula (28) can be reduced to an aminomethyl azolopyrimidine of formula (24) following the same procedures as described in Scheme 1.

A one pot procedure to form an azolopyrimidine of formula (23) is described in Scheme 8.

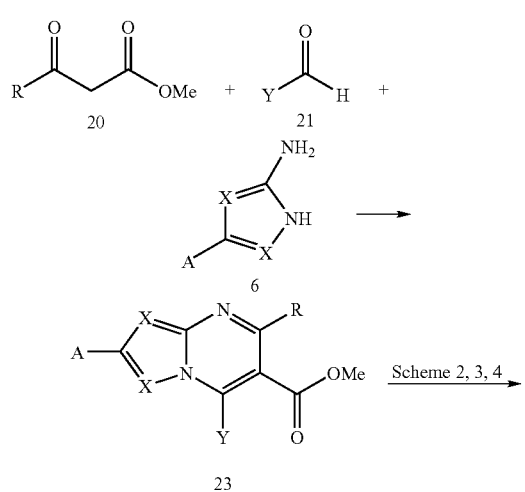

-continued

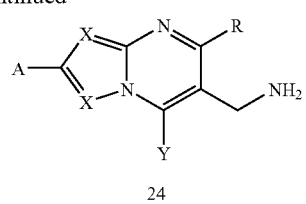

24

A keto ester of formula (20), an aldehyde of formula (21) and an azole of formula (6) can be mixed in an inert solvent such as THF, toluene, or heptane at elevated temperature for 2 hours to 7 days to form an azolopyrimidine of formula (23). The conversion of ester azolopyrimidines (23) to aminomethyl azolopyrimidines (24) follows the same procedures as described in Scheme 2, 3, and 4.

The aminopyrazoles, aminotriazoles and aminoimidazoles used for the above Schemes are commercially available, or can alternatively be prepared by one skilled in the art. These procedures are well documented in the literature and additional examples are described in Schemes 9 through 12.

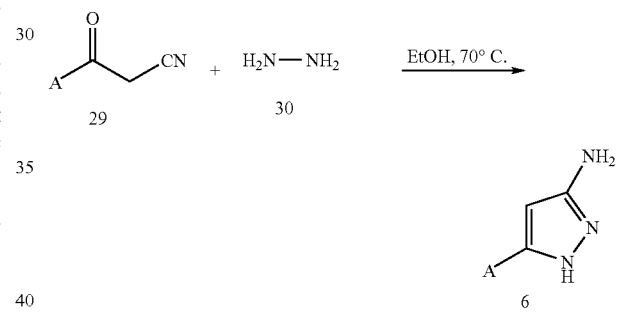

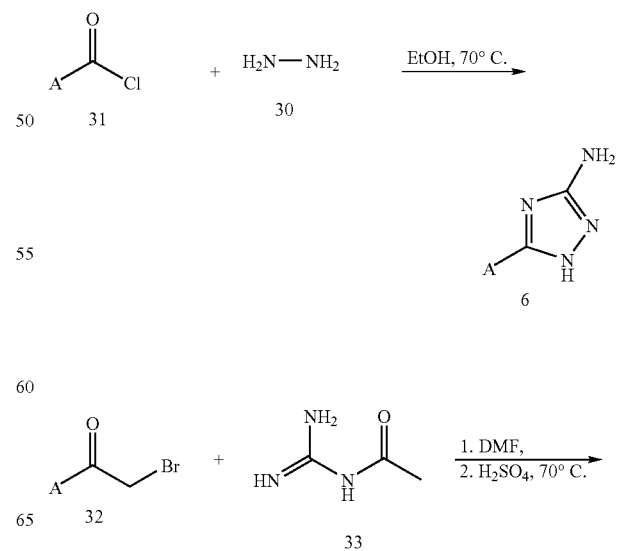

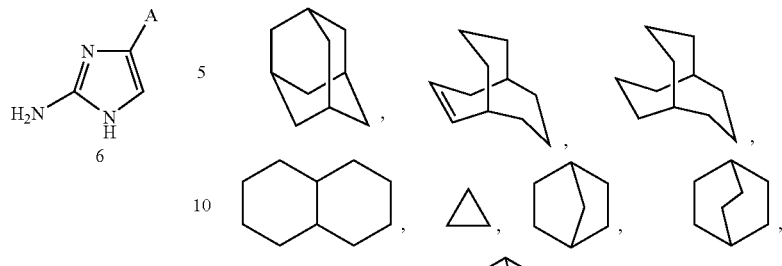

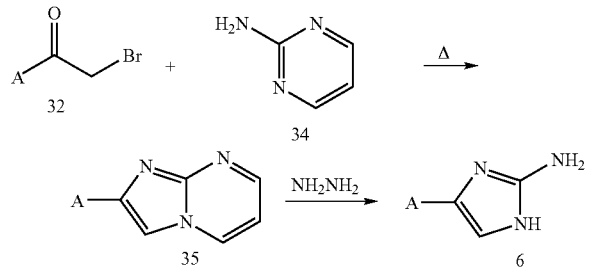

SCHEME 12

Definitions

The following definitions apply to the terms as used throughout this specification, unless otherwise limited in specific instances.

Unless otherwise indicated, the term "alkyl" or "alk" as used herein alone or as part of another group includes both branched and straight-chain saturated aliphatic hydrocarbon radicals/groups having the specified number of carbon atoms. In particular, "Alkyl" refers to a monoradical branched or unbranched saturated hydrocarbon chain, preferably having from 1 to 40 carbon atoms, more preferably 1 to 10 carbon atoms, even more preferably 1 to 6 carbon atoms, such as methyl, ethyl, n-propyl, isopropyl, n-butyl, secondary butyl, tert-butyl, n-hexyl, n-octyl, n-decyl, n-dodecyl, 2-ethyldodecyl, tetradecyl, and the like, unless otherwise indicated. Unless otherwise constrained by the definition for the alkyl substituent, such alkyl groups can optionally be substituted with one or more substituents selected from a member of the group consisting of such as halo, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl", "carbocycle" or "carbocyclic" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl, which includes, for example cyclopropyl, cyclobutyl, cyclopentyl, cyclohexyl, cycloheptyl, cyclooctyl, cyclodecyl and cyclododecyl, cyclohexenyl, any of which groups may be optionally substituted with 1 or more substituents such as of the substituents for described herein for alkyl or aryl.

The term "Aryl" or "Ar" as used herein alone or as part of another group refers to an unsaturated aromatic carbocyclic group of from 5 to 20 carbon atoms having a single ring (e.g., phenyl) or multiple condensed (fused) rings (e.g., naphthyl or anthryl). Representative examples include, but are not limited to, aromatic radicals such as phenyl, naphthyl, tetrahydronaphthyl, indane and biphenyl. Unless otherwise constrained by the definition for the aryl substituent, such aryl groups can optionally be substituted with one or more substituents selected from a member of the group consisting of hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, any of the alkyl substituents described herein, or substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "cycloheteroalkyl", "heterocyclo", "heterocyclic group" or "heterocyclyl" as used herein alone or as part of another group refers to a saturated or unsaturated group having a single ring, multiple condensed rings or multiple covalently joined rings, from 1 to 40 carbon atoms and from 1 to 10 hetero ring atoms, preferably 1 to 4 hetero ring atoms, selected from nitrogen, sulfur, phosphorus, and/or oxygen. Preferably, "Heterocycle" or "Heterocyclic group" means a stable 5 to 7 membered monocyclic or bicyclic or 7 to 10 membered bicyclic heterocyclic ring that may be saturated, partially unsaturated, or aromatic, and that comprises carbon atoms and from 1 to 4 heteroatoms independently selected from a member of the group consisting of nitrogen, oxygen and sulfur and wherein the nitrogen and sulfur heteroatoms are optionally be oxidized and the nitrogen heteroatom may optionally be quaternized, and including any bicyclic group in which any of the above-defined heterocyclic rings is fused to a benzene ring. The heterocyclic groups may be substituted on carbon or on a nitrogen, sulfur, phosphorus, and/or oxygen heteroatom, such as, but not limited to, the substituents described for alkyl or aryl herein, so long as the resulting compound is stable. For example:

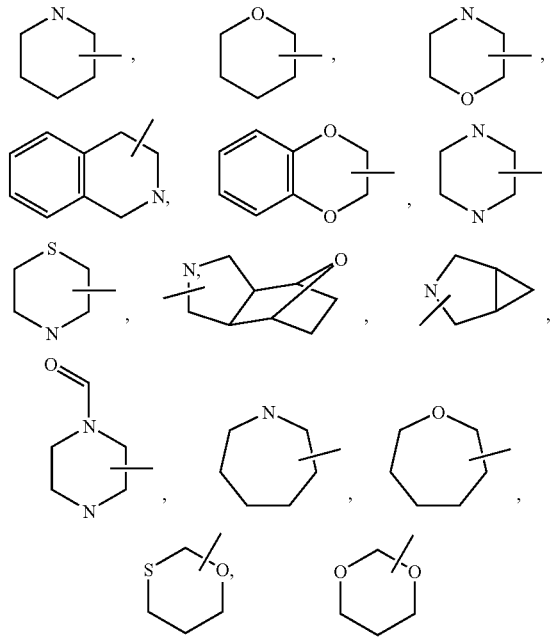

and the like.

"Heteroaryl" as used herein alone or as part of another group embraces unsaturated heterocyclic radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like. Further, examples of heteroaryl groups include the following:

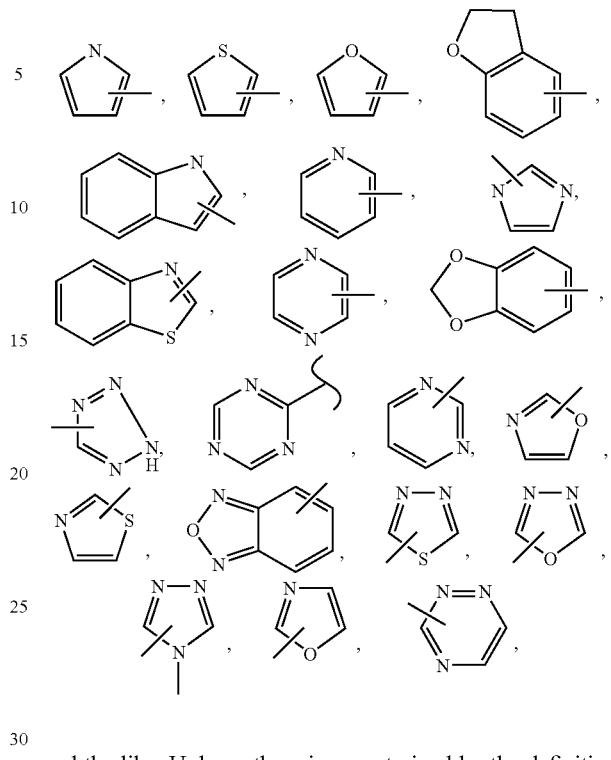

and the like. Unless otherwise constrained by the definition for the heteroaryl substituent, such heteroaryl groups can optionally be substituted with one or more substituents, such as those described for alkyl or aryl herein.

Unless otherwise indicated, the term "alkenyl" as used herein alone or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. Optionally, said alkenyl group may be substituted with one or substituents, such as those substituents disclosed for alkyl.

Unless otherwise indicated, the term "alkynyl" as used herein alone or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. Optionally, said alkynyl group may be substituted with one or substituents, such as those substituents disclosed for alkyl.

The term "cycloalkenyl" as employed herein alone or as part of another group refers to partially unsaturated cyclic hydrocarbons containing 3 to 12 carbons, preferably 5 to 10 carbons and 1 or 2 double bonds. Exemplary cycloalkenyl groups include cyclobutenyl, cyclopentenyl, cyclohexenyl, cycloheptenyl, cyclooctenyl, cyclohexadienyl, and cycloheptadienyl. Optionally, said cycloalkenyl group may be substituted with one or substituents, such as those substituents disclosed for alkyl.

The term "bicycloalkyl" as employed herein alone or as part of another group includes saturated bicyclic ring groups such as, without limitation, [3.3.0]bicyclooctane, [4.3.0]bicyclononane, [4.4.0]bicyclodecane(decalin), [2.2.2]bicyclooctane, and so forth.

The term "cycloalkenyl" as employed herein alone or as part of another group includes partially unsaturated carbocyclic radicals having three to twelve carbon atoms. Examples include, without limitation, cyclobutenyl, cyclopentenyl and cyclohexenyl.

The term "polycycloalkyl" as employed herein alone or as part of another group includes two or more cycloalkyl ring systems, as defined herein, wherein at least one carbon atom is a part of at least two separately identifiable ring systems. The polycycloalkyl group may contain bridging between two carbon atoms, for example, bicyclo[1.1.0]butyl, bicyclo[3.2.1]octyl, bicyclo[5.2.0]nonyl, tricycl[2.2.1.0.sup.1]heptyl, norbornyl and pinanyl. The polycycloalkyl group may contain one or more fused ring systems, for example, decalinyl (radical from decalin) and perhydroanthracenyl. The polycycloalkyl group may contain a spiro union, in which a single atom is the only common member of two rings, for example, spiro[3.4]octyl, spiro[3.3]heptyl and spiro[4.5]decyl.

The term "halogen" or "halo" as used herein alone or as part of another group refers to chlorine, bromine, fluorine, and iodine as well as $CF_3$.

The term "alkoxy" or "alkyloxy" as used herein alone or as part of another group, refers to an alkyl group, as defined herein, appended to a parent molecular moiety through an alkyl group, as defined herein.

The term "haloalkoxy" as used herein alone or as part of another group refers to alkoxy radicals, as defined herein, further substituted with one or more halo atoms, such as fluoro, chloro or bromo, to provide haloalkoxy radicals. Examples include, without limitation, fluoromethoxy, chloromethoxy, trifluoromethoxy, trifluoromethoxy, fluoroethoxy and fluoropropoxy.

The term "acyl" as employed herein by itself or part of another group, as defined herein, refers to an organic radical linked to a carbonyl

group; examples of acyl groups include a substituent group attached to a carbonyl, such as alkanoyl, alkenoyl, aroyl, aralkanoyl, heteroaroyl, cycloalkanoyl, cycloheteroalkanoyl and the like.

The term "cycloalkylalkyl", "arylalkyl", "cycloheteroalkyl", "bicycloalkylalkyl" or "heteroarylalkyl" as used herein alone or as part of another group, refers to a cycloalkyl, an aryl, a cyclohetero, a bicycloalkyl or heteroaryl group, as defined herein, appended to a parent molecular moiety through an alkyl group, as defined herein. Representative examples of arylalkyl include, but are not limited to, benzyl, 2-phenylethyl, 3-phenylpropyl, and the like.

The term "cycloheteroalkylalkyl" as used herein alone or as part of another group refers to a cycloheteroalkyl group as defined herein linked through a C atom or heteroatom to a $(CH_2)_r$ chain, where "r" can be 1 to 10.

The term "polyhaloalkyl" as used herein alone or as part of another group refers to an "alkyl" group as defined above, having 2 to 9, preferably from 2 to 5, halo substituents, such as $CF_3CH_2$, $CF_3$ or $CF_3CF_2CH_2$.

The term "polyhaloalkoxy" as used herein refers to an "alkoxy" or "alkyloxy" group as defined above having 2 to 9, preferably from 2 to 5, halo substituents, such as $CF_3CH_2O$—, $CF_3O$— or $CF_3CF_2CH_2O$—.

The term "thiol" or "thio" as used herein alone or as part of another group, refers to (—S) or (—S—).

The term "alkylthio" or "arylalkylthio" refers to an alkyl group or and arylalkyl group, as defined herein, linked to a parent molecular moiety through a thiol group.

The term "alkylthioalkyl" or "arylalkylthioalkyl" refers to an alkylthio group or and arylalkylthio group, as defined herein, linked to a parent molecular moiety through an alkyl group.

The term "hydroxy" as used herein alone or as part of another group, refers to a —OH group.

The term "hydroxyalkyl" as used herein alone or as part of another group, refers to a hydroxyl group, as defined herein, appended to a parent molecular moiety through a alkyl group, as defined herein.

The term "cyano" as used herein alone or as part of another group, refers to a —CN group.

The term "nitro" as used herein, refers to a —$NO_2$ group.

The term "sulfinyl", whether used alone or linked to other terms such as alkylsulfinyl, denotes respectively divalent radicals —S(O)—.

The term "alkylsulfinyl" as used herein alone or as part of another group, refers to an alkyl group, as defined herein, appended to a parent molecular moiety through a sulfinyl group, as defined herein.

The term "sulfonyl" as used herein alone or as part of another group, refers to an $SO_2$ group.

The term "alkylsulfonyl" or "aminosulfonyl", as used herein, refer to an alkyl or amino group, as defined herein, appended to a parent molecular moiety through a sulfonyl group, as defined herein.

The term "amino" as employed herein, refers to an —$NH_3$ group or an amine linkage: —$NR_a$—, wherein Ra may be as described below in the definition for "substituted amino".

The term "substituted amino" as employed herein alone or as part of another group refers to amino substituted with one or two substituents. For example, $NR_aR_b$, wherein $R_a$ and $R_b$ may be the same or different and are, for example chosen from hydrogen, alkyl, cycloalkyl, alkenyl, cycloalkenyl, alkynyl, aryl, heteroaryl, heterocyclic, arylalkyl, heteroarylalkyl, cycloheteroalkyl, cycloheteroalkylalkyl, cycloalkylalkyl, haloalklyl, hydrooxyalkyl, alkoxyalkyl or thioalkyl. These substituents may optionally be further substituted with any of the alkyl substituents as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolindinyl, 1-piperidinyl, or 1-azepinyl, optionally substituted with alkyl, alkoxy, alkylthio, halo, triflouromethyl or hydroxyl.

The term "dialkylamino" as employed herein alone, or as part of another group, refers to a substituted amino group having two alkyl substituents. For example, $NR_aR_b$, wherein $R_a$ and $R_b$ are each an alkyl group, as defined herein.

The term "carbonyl" as used herein, refers to a —C(O)— group.

The term "aminocarbonyl", "alkylcarbonyl", "alkoxycarbonyl", "arylcarbonyl", "alkynylaminocarbonyl", "alkylaminocarbonyl" and "alkenylaminocarbonyl" as used herein, refer to an amino group, alkyl group, alkoxy group, aryl group, alkynylamino group, alkylamino group or an alkenylamino group, as defined herein, appended to a parent molecular moiety through a carbonyl group, as defined herein.

The term "heteroarylamino", "arylamino", "alkylamino", "alkylcarbonylamino", "arylcarbonylamino", "alkylsulfonylamino", "alkylaminocarbonylamino" or "alkoxycarbonylamino" as used herein, refers to a heteroaryl, aryl, alkyl, alkylcarbonyl, arylcarbonyl, alkylsulfonyl, alkylaminocarbonyl or alkoxycarbonyl group as defined herein, appended to a parent molecular moiety through an amino group, as defined herein.

The term "sulfonamido" refers to $—S(O)_2—NR_aR_b$, wherein Ra and Rb are as defined above for "substituted amino".

The term "alkylcarbonyloxy" as used herein, refers to an "alkyl-CO—O—" group, wherein alkyl is as defined above.

"Optional" or "optionally" means that the subsequently described event or circumstance may or may not occur, and that the description includes, without limitation, instances where said event or circumstance occurs and instances in which it does not. For example, optionally substituted alkyl means that alkyl may or may not be substituted by those groups enumerated in the definition of substituted alkyl.

"Substituted," as used herein, whether express or implied and whether preceded by "optionally" or not, means that any one or more hydrogen on the designated atom (C, N, etc.) is replaced with a selection from the indicated group, provided that the designated atom's normal valency is not exceeded, and that the substitution results in a stable compound. For instance, when a $CH_2$ is substituted by a keto substituent (=O), then 2 hydrogens on the atom are replaced. Combinations of substituents and/or variables are permissible only if such combinations result in stable compounds. Further, when more than one position in a given structure may be substituted with a substituent selected from a specified group, the substituents may be either the same or different at every position.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Various forms of prodrugs are well known in the art. A comprehensive description of prodrugs and prodrug derivatives are described in:

a) *The Practice of Medicinal Chemistry*, Camille G. Wermuth et al., Ch. 31, (Academic Press, 1996);

b) *Design of Prodrugs*, edited by H. Bundgaard, (Elsevier, 1985); and c) *A Textbook of Drug Design and Development*, P. Krogsgaard-Larson and H. Bundgaard, eds. Ch. 5, pp. 113-191 (Harwood Academic Publishers, 1991). Said references are incorporated herein by reference.

The conditions, diseases and maladies collectively referred to as "diabetic complications" include retinopathy, neuropathy and nephropathy, erectile dysfunction, and other known complications of diabetes.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

The term "other type of therapeutic agents" as employed herein includes, but is not limited to one or more antidiabetic agents (other than DPP-IV inhibitors of formula I), one or more anti-obesity agents, one or more anti-hypertensive agents, one or more anti-platelet agents, one or more anti-atherosclerotic agents and/or one or more lipid-lowering agents (including anti-atherosclerosis agents).

Utilities and Combinations

A. Utilities

The compounds of the present invention possess activity as inhibitors of the dipeptidyl peptidase IV which is found in a variety of tissues, such as the intestine, liver, lung and kidney of mammals. Via the inhibition of dipeptidyl peptidase IV in vivo, the compounds of the present invention possess the ability to potentiate endogenous levels of GLP-1(7-36) and attenuate formation of its antagonist GLP-1(9-36).

Accordingly, the compounds of the present invention can be administered to mammals, preferably humans, for the treatment of a variety of conditions and disorders, including, but not limited to, treating or delaying the progression or onset of diabetes(preferably Type II, impaired glucose tolerance, insulin resistance, and diabetic complications, such as nephropathy, retinopathy, neuropathy and cataracts), hyperglycemia, hyperinsulinemia, hypercholesterolemia, elevated blood levels of free fatty acids or glycerol, hyperlipidemia, hypertriglyceridemia, obesity, wound healing, tissue ischemia, atherosclerosis and hypertension. The compounds of the present invention may also be utilized to increase the blood levels of high density lipoprotein (HDL).

In addition, the conditions, diseases, and maladies collectively referenced to as "Syndrome X" or Metabolic Syndrome as detailed in Johannsson, *J. Clin. Endocrinol. Metab.*, 82, 727-34 (1997), may be treated employing the compounds of the invention.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

Other "therapeutic agent(s)" suitable for combination with the compound of the present invention include, but are not limited to, known therapeutic agents useful in the treatment of the aforementioned disorders including: anti-diabetic agents; anti-hyperglycemic agents; hypolipidemic/lipid lowering agents; anti-obesity agents; anti-hypertensive agents, and appetite suppressants. Additional therapeutic agents suitable for combination with the compound of the present invention include agents for treating infertility, agents for treating polycystic ovary syndrome, agents for treating a growth disorder and/or frailty, an anti-arthritis agent, agents for preventing inhibiting allograft rejection in transplantation, agents for treating autoimmune disease, an anti-AIDS agent, agents for treating inflammatory bowel disease/syndrome, agents for treating anorexia nervosa and an anti-osteoporosis agent.

Examples of suitable anti-diabetic agents for use in combination with the compound of the present invention include biguanides (e.g., metformin or phenformin), glucosidase inhibitors (e.g., acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., GLUCOVANCE®), thiazolidinediones (e.g., troglitazone, rosiglitazone and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, SGLT2 inhibitors and other dipeptidyl peptidase IV (DPP4) inhibitors.

Other suitable thiazolidinediones include Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi).

Examples of PPAR-alpha agonists, PPAR-gamma agonists and PPAR alpha/gamma dual agonists include muraglitizar, peliglitazar, AR-HO39242 (Astra/Zeneca), GW-409544 (Glaxo-Wellcome), GW-501516 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998), WO 01/21602 and in U.S. Pat. No. 6,653,314, the disclosure of which is incorporated herein by reference, employing dosages as set out therein, which compounds designated as preferred are preferred for use herein.

Suitable aP2 inhibitors include those disclosed in U.S. application Ser. No. 09/391,053, filed Sep. 7, 1999, and in U.S. application Ser. No. 09/519,079, filed Mar. 6, 2000, employing dosages as set out herein.

Suitable other DPP4 inhibitors include saxagliptin, those disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al, Biochemistry, 38(36), 11597-11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537-1540), 2-cyanopyrrolidides and 4-cyanopyrrolidides, as disclosed by Ashworth et al, Bioorg. & Med. Chem. Lett., Vol. 6, No. 22, pp 1163-1166 and 2745-2748 (1996), the compounds disclosed in U.S. application Ser. No. 10/899, 641, WO 01/868603 and U.S. Pat. No. 6,395,767, employing dosages as set out in the above references.

Other suitable meglitinides include nateglinide (Novartis) or KAD1229 (PF/Kissei).

Examples of suitable anti-hyperglycemic agents for use in combination with the compound of the present invention include glucagon-like peptide-1 (GLP-1,) such as GLP-1(1-36) amide, GLP-1(7-36) amide, GLP-1(7-37) (as disclosed in U.S. Pat. No. 5,614,492), as well as exenatide (Amylin/Lilly), LY-315902 (Lilly), MK-0431 (Merck), liraglutide (NovoNordisk), ZP-10 (Zealand Pharmaceuticals A/S), CJC-1131 (Conjuchem Inc), and the compounds disclosed in WO 03/033671.

Examples of suitable hypolipidemic/lipid lowering agents for use in combination with the compound of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid co-transporter inhibitors, up-regulators of LDL receptor activity, bile acid sequestrants, cholesterol ester transfer protein (e.g., CETP inhibitors, such as CP-529414 (Pfizer) and JTT-705 (Akros Pharma)), PPAR agonists (as described above) and/or nicotinic acid and derivatives thereof.

MTP inhibitors which may be employed as described above include those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885, 983 and U.S. Pat. No. 5,962,440.

The HMG CoA reductase inhibitors which may be employed in combination with one or more compound of formula I include mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686, 104, atavastatin (Nissan/Sankyo's nisvastatin (NK-104)), as disclosed in U.S. Pat. No. 5,011,930, visastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphoric acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No.0142146 A2, and quinoline and pyridine derivatives, as disclosed in U.S. Pat. No. 5,506,219 and 5,691,322.

Preferred hypolipidemic agents are pravastatin, lovastatin, simvastatin, atorvastatin, fluvastatin, cerivastatin, atavastatin and ZD-4522.

In addition, phosphinic acid compounds useful in inhibiting HMG CoA reductase, such as those disclosed in GB 2205837, are suitable for use in combination with the compound of the present invention.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869-1871, including isoprenoid (phosphinyl-methyl)phosphonates, as well as other known squalene synthetase inhibitors, for example, as disclosed in U.S. Pat. Nos. 4,871,721 and 4,924, 024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40-43, 48-51, Summary.

The fibric acid derivatives which may be employed in combination with the compound of formula I include fenofibrate, gemfibrozil, clofibrate, bezafibrate, ciprofibrate, clinofibrate and the like, probucol, and related compounds, as disclosed in U.S. Pat. No. 3,674,836, probucol and gemfibrozil being preferred, bile acid sequestrants, such as cholestyramine, colestipol and DEAE- Sephadex (SEC-HOLEX®, mixture of polidexide and gum acacia), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283, 546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination the compound of formula I include those disclosed in Drugs of the Future 24, 9-15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962 (Taisho Pharmaceutical Co. Ltd).

The hypolipidemic agent may be an up-regulator of LD2 receptor activity, such as MD-700 (Taisho Pharmaceutical Co. Ltd) and LY295427 (Eli Lilly).

Examples of suitable cholesterol absorption inhibitor for use in combination with the compound of the invention include SCH48461 (Schering-Plough), as well as those disclosed in Atherosclerosis 115, 45-63 (1995) and J. Med. Chem. 41, 973 (1998).

Examples of suitable ileal $Na^+$/bile acid co-transporter inhibitors for use in combination with the compound of the invention include compounds as disclosed in Drugs of the Future, 24, 425-430 (1999).

The lipoxygenase inhibitors which may be employed in combination the compound of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

Examples of suitable anti-hypertensive agents for use in combination with the compound of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compound of the present invention include a beta 3 adrenergic agonist, a lipase inhibitor, a serotonin (and dopamine) reuptake inhibitor, a thyroid receptor beta drug, 5HT2C agonists, (such as Arena APD-356); MCHR1 antagonists such as Synaptic SNAP-7941 and Takeda T-226926, melanocortin receptor (MC4R) agonists, melanin-concentrating hormone receptor (MCHR) antagonists (such as Synaptic SNAP-7941 and Takeda T-226926), galanin receptor modulators, orexin antagonists, CCK agonists, NPY1 or NPY5 antagonist, NPY2 and NPY4 modulators, corticotropin releasing factor agonists, histamine receptor-3 (H3) modulators, 11-beta-HSD-1 inhibitors, adinopectin receptor modulators, monoamine reuptake inhibitors or releasing agents, a ciliary neurotrophic factor (CNTF, such as AXOKINE® by Regeneron), BDNF (brain-derived neurotrophic factor), leptin and leptin receptor modulators, cannabinoid-1 receptor antagonists (such as SR-141716 (Sanofi) or SLV-319 (Solvay)), and/or an anorectic agent.

The beta 3 adrenergic agonists which may be optionally employed in combination with compound of the present invention include AJ9677 (Takeda/Dainippon), L750355 (Merck), or CP331648 (Pfizer,) or other known beta 3 agonists, as disclosed in U.S. Pat. Nos. 5,541,204, 5,770,615, 5,491,134, 5,776,983 and 5,488,064.

Examples of lipase inhibitors which may be optionally employed in combination with compound of the present invention include orlistat or ATL-962 (Alizyme).

The serotonin (and dopoamine) reuptake inhibitor (or serotonin receptor agonists) which may be optionally employed in combination with a compound of the present invention may be BVT-933 (Biovitrum), sibutramine, topiramate (Johnson & Johnson) or axokine (Regeneron).

Examples of thyroid receptor beta compounds which may be optionally employed in combination with the compound of the present invention include thyroid receptor ligands, such as those disclosed in WO97/21993 (U. Cal SF) and WO99/00353 (KaroBio).

The monoamine reuptake inhibitors which may be optionally employed in combination with compound of the present invention include fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol.

The anorectic agent which may be optionally employed in combination with the compound of the present invention include topiramate (Johnson & Johnson), dexamphetamine, phentermine, phenylpropanolamine or mazindol.

The aforementioned patents and patent applications are incorporated herein by reference.

The above other therapeutic agents, when employed in combination with the compound of the present invention may be used, for example, in those amounts indicated in the Physician's Desk Reference, as in the patents set out above or as otherwise determined by one of ordinary skill in the art.

Where the compound of the invention are utilized in combination with one or more other therapeutic agent(s), either concurrently or sequentially, the following combination ratios and dosage ranges are preferred.

Where the compound of the invention of formula I is utilized in combination with an antidiabetic agent, the compound of formula I will be employed in a weight ratio to the antidiabetic agent in the range from about 0.01:1 to about 300:1.

Where the other antidiabetic agent is a biguanide, the compound of formula I will be employed in a weight ratio to biguanide within the range from about 0.01:1 to about 100:1, preferably from about 0.1:1 to about 5:1.

The compound of formula I will be employed in a weight ratio to the glucosidase inhibitor within the range from about 0.01:1 to about 100:1, preferably from about 0.5:1 to about 50:1.

The compound of formula I will be employed in a weight ratio to the sulfonyl urea in the range from about 0.01:1 to about 100:1, preferably from about 0.2:1 to about 10:1.

The compound of formula I will be employed in a weight ratio to the thiazolidinedione in an amount within the range from about 0.01:1 to about 100:1, preferably from about 0.2:1 to about 10:1.

Where present, the thiazolidinedione anti-diabetic agent may be employed in amounts within the range from about 0.01 to about 2000 mg/day which may be administered in single or divided doses one to four times per day.

Optionally, the sulfonyl urea and thiazolidinedione may be incorporated in a single tablet with the compound of formula I in amounts of less than about 150 mg.

Where present, metformin or salt thereof may be employed in amounts within the range from about 500 to about 2000 mg per day which may be administered in single or divided doses one to four times daily.

Where present GLP-1 peptides may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The compound of formula I will be employed in a weight ratio to the meglitinide, PPAR-gamma agonist, PPAR-alpha/gamma dual agonist, aP2 inhibitor or other DPP4 inhibitor within the range from about 0.01:1 to about 100:1, preferably from about 0.2:1 to about 10:1.

The compound of formula I of the invention will be generally be employed in a weight ratio to the hypolipidemic agent (were present), within the range from about 500:1 to about 1:500, preferably from about 100:1 to about 1:100.

For oral administration, a satisfactory result may be obtained employing the MTP inhibitor in an amount within the range of from about 0.01 mg/kg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor in an amount within the range of from about 1 to 2000 mg, and preferably from about 4 to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

The squalene synthetase inhibitor may be employed in dosages in an amount within the range of from about 10 mg to about 2000 mg and preferably from about 25 mg to about 200 mg.

A preferred oral dosage form, such as tablets or capsules will contain the squalene synthetase inhibitor in an amount of from about 10 to about 500 mg, preferably from about 25 to about 200 mg.

The compound of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out a preferred method of the invention for treating any of the diseases disclosed herein, such as diabetes and related diseases, a pharmaceutical composition will be employed containing one or more of the compound of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders and the like. The compound can be administered to mammalian species including humans, monkeys, dogs, etc. by an oral route, for example, in the form of tablets, capsules, beads, granules or powders, or they can be administered by a parenteral route in the form of injectable preparations, or they can be administered intranasally or in transdermal patches. Typical solid formulations will contain from about 10 to about 500 mg of a compound of formula I. The dose for adults is preferably between 10 and 2,000 mg per day, which can be administered in a single dose or in the form of individual doses from 1-4 times per day.

A typical injectable preparation may be produced by aseptically placing 250 mg of compound of formula I into a vial, aseptically freeze-drying and sealing. For use, the contents of the vial are mixed with 2 mL of physiological saline, to produce an injectable preparation.

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

DPP-4 inhibitory activity of the compounds of the present invention may be determined by use of an in vitro assay system which measures the degree in inhibition of DPP-4-mediated cleavage of an appropriate substrate or pseudosubstrate. Inhibition constants (Ki values) for the DPP-4 inhibitors of the invention may be determined by the method described in the experimental section below.

Cloning, Expression and Purification of Human DPP4

To generate human DPP-4, PCR (Red-tag polymerase, Sigma) was performed on Human cDNA from placenta (Clontech) using two primers, ACGCCGACGATGAAGACA (SEQ ID NO:1) and AGGTAAAGAGAAACATTGTT (SEQ ID NO:2) based on the nucleotide sequence of the human clone (accession number M74777). PCR products were cloned into the pcDN4/HisMax TOPO vector (Invitrogene). For stable transfection of CHO-DG44 cells, DPP4 was rePCRed using primers GGTACCAGCGCAGAGGCTT (SEQ ID NO:3) and CTCGAGCTAAGGTAAAGAGAAACATTG (SEQ ID NO:4) to generate KpnI and XhoI sites. The KpnI and XhoI sites were used to extract the N-terminal His tagged gene. The His tag, which could be cleaved and removed by Enterokinase, was included to allow purification using the TALON affinity column. The gene was then ligated into the KpnI and XhoI sites of the pD16 vector for stable transfection. Stable cell lines were generated by transfecting the expression vector into Chinese hamster ovary (CHO-DG44) cells using electroporation. The CHO-DG44 cell line was grown in PFCHO media supplemented with HT (glycine, hypoxanthine and thymidine, Invitrogene), glutamine and Recombulin (ICN). Then $1 \times 10^7$ cells/ml were collected, transfected with 60 µg of DNA using electroporation at 300V, and then transferred to a T75 flask. On the third day following transfection, the HT supplement was removed and selection was initiated with methotrexate (MTX, 10 nM, ICN). After a further 10 days the cells were plated into individual wells of 96 well plates. Every 10 days the concentration of MTX was increased two to three fold, up to a maximum of 400 nM. Final stable cell line selection was based on yield and activity of the expressed protein.

An attempt to purify recombinant DPP-4 using Talon resin was not efficient, resulting in small yields, with most of the DPP activity passing through the column. Therefore, protein was further purified using conventional anion exchange (Sepharose Q), gel filtration (S-200) and high resolution MonoQ columns. The final protein yielded a single band on SDS-PAGE gels. Amino acid sequence analysis indicated two populations of DPP-4 in the sample. One portion of the protein had 27 amino acids truncated from the N-terminus, while the other was lacking the N-terminal 37 amino acids. This suggests that during isolation the entire transmembrane domain (including His tag) is removed by proteases present in the CHO cells. Total protein concentration was measured using the Bradford dye method and the amount of the active DPP-4 was determined by titrating the enzyme with a previously characterized inhibitor (Ki=0.4 nM). No biphasic behavior was observed during inhibition or catalysis, suggesting that both protein populations are functionally identical.

DPP-4 Inhibition Assays

Inhibition of human DPP-4 activity was measured under steady-state conditions by following the absorbance increase at 405 nm upon the cleavage of the pseudosubstrate, Gly-Pro-pNA. Assays were performed in 96-well plates using a Thermomax plate reader. Typically reactions contained 100 µl of ATE buffer (100 mM Aces, 52 mM Tris, 52 mM ethanolamine, pH 7.4), 0.45 nM enzyme, either 120 or 1000 µM of substrate (S<Km and S>Km, Km=180 µM) and variable concentration of the inhibitor. To ensure steady-state conditions for slow-binding inhibitors, enzyme was preincubated with the compound for 40 minutes prior to substrate addition, to initiate the reaction. All serial inhibitor dilutions were in DMSO and final solvent concentration did not exceed 1%.

Inhibitor potency was evaluated by fitting inhibition data to the binding isotherm:

$$\frac{vi}{v} = \frac{\text{Range}}{1 + \left(\frac{I}{IC_{50}}\right)^n} + \text{Background} \qquad (1)$$

where vi is the initial reaction velocity at different concentrations of inhibitor I; v is the control velocity in the absence of inhibitor, range is the difference between the uninhibited velocity and background; background is the rate of spontaneous substrate hydrolysis in the absent of enzyme, n is the Hill coefficient.

Calculated $IC_{50}$s at each substrate concentration were converted to Ki assuming competitive inhibition according to:

$$Ki = \frac{IC_{50}}{\left(1 + \frac{S}{Km}\right)} \qquad (2)$$

All inhibitors were competitive as judged by a very good agreement of Ki values obtained from the assays at high and low substrate concentrations. In cases where $IC_{50}$ at the low substrate concentration was close to the enzyme concentration used in the assay, the data were fit to the Morrison equation[1], to account for the depletion of the free inhibitor:

[1] Morrison, J F, Walsh, Conn. Advances in Enzymology. 61 (1988), 201-206.

$$\frac{vi}{v0} = 1 - \frac{(E + I + IC_{50}) - \sqrt{(E + I + IC_{50})^2 - 4EI}}{2E} \qquad (3)$$

where vi and v0 are the steady state velocities measured in the presence and absence of inhibitor, E enzyme concentration.

Each $IC_{50}$ was further refined to Ki, to account for the substrate concentration in the assay using equation (2).

Abbreviations

The following abbreviations are employed in the Examples and elsewhere herein:
Ph=phenyl
Bn=benzyl
i-Bu=iso-butyl
Me=methyl
Et=ethyl
Pr=propyl
Bu=butyl
TMS=trimethylsilyl
FMOC=fluorenylmethoxycarbonyl
Boc or BOC=tert-butoxycarbonyl
Cbz=carbobenzyloxy or carbobenzoxy or benzyloxycarbonyl
HOAc or AcOH=acetic acid
DMF=N,N-dimethylformamide
DMSO=dimethylsulfoxide
EtOAc=ethyl acetate
THF=tetrahydrofuran
TFA=trifluoroacetic acid
Et$_2$NH=diethylamine
NMM=N-methyl morpholine
n-BuLi=n-butyllithium
Pd/C=palladium on carbon
PtO$_2$=platinum oxide
TEA=triethylamine
min=minute(s)
h or hr=hour(s)
L=liter
mL=milliliter
μL=microliter
g=gram(s)
mg=milligram(s)
mol=mole(s)
mmol=millimole(s)
meq=milliequivalent
rt=room temperature
sat or sat'd=saturated
aq.=aqueous
TLC=thin layer chromatography
t$_R$=retention time
mp=melting point
HPLC=high performance liquid chromatography
LC/MS=high performance liquid chromatography/mass spectrometry
MS or Mass Spec=mass spectrometry
NMR=nuclear magnetic resonance
EDCI or EDAC=3-ethyl-3'-(dimethylamino)propyl-carbodiimide hydrochloride (or 1-[(3-(dimethyl)amino)propyl])-3-ethylcarbodiimide hydrochloride)
HOBT or HOBT•H$_2$O=1-hydroxybenzotriazole hydrate
HOAT=1-hydroxy-7-azabenzotriazole
PyBOP reagent=benzotriazol-1-yloxy-tripyrrolidino phosphonium hexafluorophosphate
equiv=equivalent(s)
UCT=United Chemical Technologies, Inc.; Bristol, Pa.

EXAMPLES

The following examples are provided to describe the invention in further detail. These examples, which set forth the best mode presently contemplated for carrying out the invention, are intended to illustrate and not to limit the invention.

In general, preferred compounds of the present invention, such as the compounds disclosed in the following examples, have been identified to inhibit the catalytic activity of dipeptidyl peptidase IV at concentrations equivalent to, or more potently than, 10 μM, preferably 5 μM, more preferably 3 μM, thereby corroborating the utility of the compounds of the present invention as effective inhibitors dipeptidyl peptidase IV. Potencies can be calculated and expressed as either inhibition constants (Ki values) or as IC$_{50}$ (inhibitory concentration 50%) values, and refer to activity measured employing the in vitro assay system described herein.

Preparation of Selected Common Intermediates

Intermediate 1. 5-o-tolyl-1H-pyrazol-3-amine

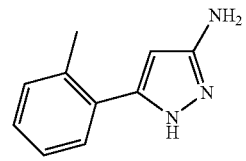

To a stirred solution of 3-oxo-3-o-tolylpropanenitrile (100 mg, 0.63 mmol) in EtOH (2 mL) was added NH$_2$NH$_2$H$_2$O (46 μL, 0.95 mmol). After heating to 70° C. for 16 h, the reaction was concentrated under reduced pressure to provide 5-o-tolyl-1H-pyrazol-3-amine (100 mg, 92% crude yield) as yellow oil. The product was used for the next step without further purification.

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=1.68 min, 93% homogeneity index.

LCMS: Anal. Calcd. for C$_{10}$H$_{11}$N$_3$ 173.10 found: 174.30 (M+H)$^+$.

These same procedures were followed to prepare related 5-substituted phenyl-1H-pyrazol-3-amine.

Intermediate 2.
4-(2-methoxyphenyl)-1H-imidazol-2-amine

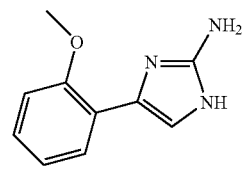

Intermediate 2, Step 1.
2-(2-methoxyphenyl)imidazo[1,2-a]pyrimidine

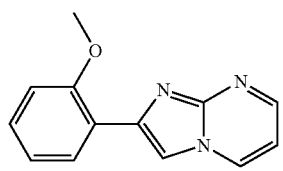

A stirred solution of 2-bromo-1-(2-methoxyphenyl)ethanone (1.5 g, 6.6 mmol) and 2-aminopyrimidine (0.62 g, 6.6 mmol) in EtOH (10 mL) was heated to 75° C. for 24 h. White precipitate formation was observed. The reaction was concentrated under reduced pressure to a volume of 3 mL and was filtered to collect 2-(2-methoxyphenyl)imidazo[1,2-+]pyrimidine (1.54 g, 100%) as a white solid.

$^1$H NMR (400 MHz, CDCl$_3$) δ 9.44 (d, J=6.6 Hz, 1H), 8.82 (m, 1H), 8.72 (s, 1H), 7.75 (dd, J=1.8, 7.9 Hz, 1H), 7.37-7.51 (m, 2H), 7.03 (m, 2H), 3.96 (s, 3H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=1.19 min, 97% homogeneity index.

Intermediate 2, Step 2.
4-(2-methoxyphenyl)-1H-imidazol-2-amine

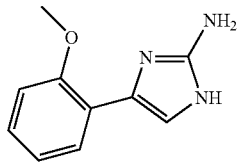

To a stirred solution of 2-(2-methoxyphenyl)imidazo[1,2-α]pyrimidine (1.24 g, 5.5 mmol) in EtOH (8 mL) was added NH$_2$NH$_2$.H$_2$O (0.3 mL, 6.1 mmol). After heating to 75° C. for 24 h, the reaction was concentrated under reduced pressure. The residue was suspended in Et$_2$O and filtered to collect 4-(2-methoxyphenyl)-1H-imidazol-2-amine (1 g, 96%) as a light yellow solid.

$^1$H NMR (400 MHz, CD$_3$OD) δ 9.44 (dd, J=1.7, 7.9 Hz, 1H), 7.32 (dt, J=1.9, 7.6 Hz, 1H), 7.16 (s, 1H), 7.11 (d, J=7.9 Hz, 1H), 7.02 (dt, J=1.6, 7.6 Hz, 1H), 3.95 (s, 3H). $^{13}$C NMR (400 MHz, CD$_3$OD) δ 155.3, 147.3, 129.0, 125.9, 124.8, 121.1, 116.5, 111.4, 111.1, 55.6.

These same procedures were followed to prepare related 4-substituted phenyl-1H-imidazol-2-amine.

Intermediate 3. E/Z-tert-butyl 2-(2,4-dichlorobenzylidene)-3-oxobutanoate

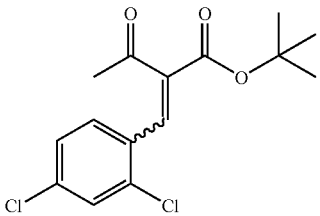

To a stirred solution of tert-butyl 3-oxobutanoate (1.5 g, 9.5 mmol) and 2,4-dichlorobenzaldehyde (1.7 g, 9.5 mmol) in 2-propanol (10 mL) was added acetic acid (23 mg, 0.4 mmol) and dimethyl amine (2 M solution in THF, 0.2 mL, 0.4 mmol). The reaction was kept at room temperature for 3 days and was concentrated under reduced pressure. The resulting yellow oil was purified by silica gel chromatography to obtain a 1:1 mixture of (E) and (Z)-tert-butyl 2-(2,4-dichlorobenzylidene)-3-oxobutanoate (2 g, 67%).

Based on NOE experiments, the Z isomer is the slower moving compound on thin layer chromatography (100% hexanes, r$_f$=0.60) and the E isomer is the faster moving isomer on thin layer chromatography (100% hexanes, r$_f$=0.70).

For Z isomer: $^1$H NMR (400 MHz, CDCl$_3$) δ 7.68 (s, 1H), 7.49 (d, J=8.4 Hz, 1H), 7.47 (d, J=2.2 Hz, 1H), 7.24 (dd, J=2.2, 7.3 Hz, 1H), 2.44 (s, 3H), 1.45 (s, 9H). Anal. Calcd for C$_{15}$H$_{16}$Cl$_2$O$_3$: C, 57.16; H, 5.11. Found: C, 57.26; H, 4.93.

These same procedures were followed to prepare related E/Z-2-substituted benzylidene)-3-oxobutanoate.

Example 1

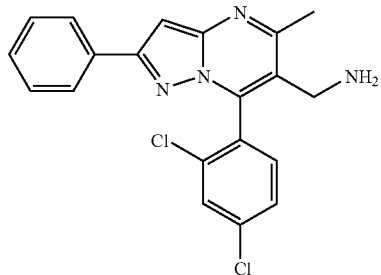

Example 1

Step 1-2. Methyl 7-(2,4-dichlorophenyl)-5-methyl-2-phenylpyrazolo[1,5-a]pyrimidine-6-carboxylate

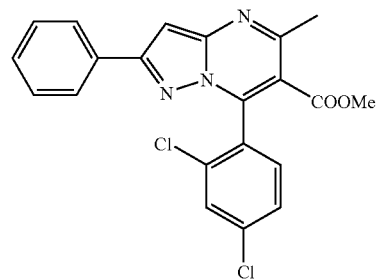

To a stirred solution of 2,4-dichlorobenzaldehyde (500 mg, 3.73 mmol), 5-phenyl-1H-pyrazol-3-amine (539 mg, 3.73 mmol), and methyl acetoacetate (433 mg, 4.10 mmol) in THF (8 mL) and heptane (2 mL) was added piperidine (10 μL, 0.1 mmol). The reaction was heated to reflux for 24 h and was concentrated under reduced pressure. The crude reaction product was moved onto next step without further purification (purity ~85%).

The crude dihydropyrimidine from above was dissolved in CH$_2$Cl$_2$ (10 mL) and DDQ (750 mg, 3.3 mmol) was added. After 1 h, the reaction was diluted with cyclohexane/EtOAc (4:1, 50 mL) and the organic layer was extracted with NaHCO$_3$ (2×50 mL), brine, dried (MgSO$_4$), filtered and concentrated under reduced pressure. The crude reaction product was purified by flash chromatography (silica gel, 25% EtOAc/hexane) to give methyl 7-(2,4-dichlorophenyl)-5-methyl-2-phenylpyrazolo[1,5-a]pyrimidine-6-carboxylate (700 mg, 46% for two steps).

$^1$H NMR (400 MHz, CDCl$_3$) δ 7.87 (dd, J=1.6, 7.6 Hz, 1H), 7.61 (d, J=1.6 Hz, 1H), 7.40 (m, 6H), 6.96 (s, 1H), 3.65 (s, 3H), 2.74 (s, 3H).

HPLC Phenomenex LUNA C-18 4.6×50 mm, 0 to 100% B over 4 minutes, 1 minutes hold time, A=90% water, 10% methanol, 0.2% phosphoric acid, B=10% water, 90% methanol, 0.2% phosphoric acid, RT=2.73 min, 95.5% homogeneity index.

LCMS: Anal. Calcd. for $C_9H_5Cl_2NO$ 212.97; found: 211.89 (M−H)⁻.

Example 1

Step 3. 7-(2,4-Dichlorophenyl)-5-methyl-2-phenylpyrazolo[1,5-a]pyrimidine-6-carboxylic acid

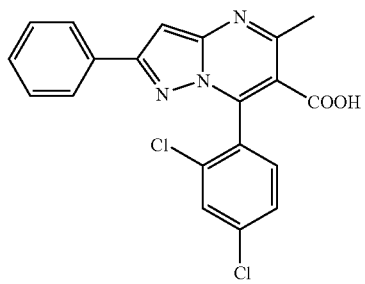

To a stirred solution of 7-(2,4-dichlorophenyl)-5-methyl-2-phenylpyrazolo[1,5-a]pyrimidine-6-carboxylate (27.5 mg, 0.07 mmol) in THF (2 mL) and $H_2O$ (0.5 mL) was added LiOH·$H_2O$ (4.2 mg, 0.1 mmol). After 5 h at 50° C., the reaction was concentrated under reduced pressure and diluted with EtOAc (10 mL). The organic layer was extracted with 1N HCl (6 mL), saturated $NH_4Cl$ (10 mL) and brine, dried ($MgSO_4$), filtered and concentrated. The crude reaction product, 7-(2,4-dichlorophenyl)-5-methyl-2-phenylpyrazolo[1,5-a]pyrimidine-6-carboxylic acid, was moved onto next step without further purification (purity ~90%).

Example 1

Step 4-5. (7-(2,4-Dichlorophenyl)-5-methyl-2-phenylpyrazolo[1,5-a]pyrimidin-6-yl)methanol

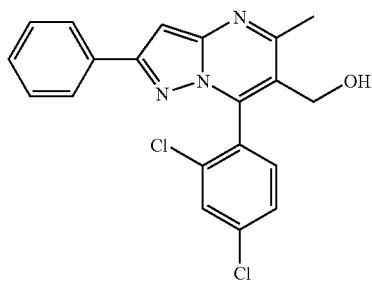

To a stirred solution of crude 7-(2,4-dichlorophenyl)-5-methyl-2-phenylpyrazolo[1,5-a]pyrimidine-6-carboxylic acid (~0.07 mmol) in THF (2 mL) was added chloroethylformate (12.4 µL, 0.13 mmol). The reaction turned cloudy after 5 minutes and after 1 h, the reaction was filtered through cotton and concentrated under reduced pressure. The crude reaction product was moved onto next step without further purification (purity ~90%).

To a stirred solution of crude mixed anhydride (~0.07 mmol) from above in THF (2 mL) was added $NaBH_4$ (5 mg, 0.13 mmol) in $H_2O$ (0.5 mL). After 4 h at room temperature, the reaction was quenched by addition of 1N HCl (5 mL). The reaction was diluted with EtOAc (10 mL) and the organic layer was extracted with 1N HCl (6 mL), saturated $NH_4Cl$ (10 mL) and brine, dried ($MgSO_4$), filtered and concentrated. The crude reaction product was purified by flash chromatography (silica gel, 40% EtOAc/hexane) to give (7-(2,4-dichlorophenyl)-5-methyl-2-phenylpyrazolo[1,5-a]pyrimidin-6-yl)methanol (17.5 mg, 68% for three steps).

Example 1

Step 6-8. (7-(2,4-Dichlorophenyl)-5-methyl-2-phenylpyrazolo[1,5-a]pyrimidin-6-yl)methanamine

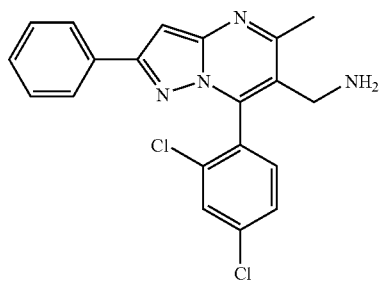

To a stirred solution of (7-(2,4-dichlorophenyl)-5-methyl-2-phenylpyrazolo[1,5-a]pyrimidin-6-yl)methanol (17.5 mg, 0.046 mmol) in $CH_2Cl_2$ (2 mL) was added MsCl (7 µL, 0.09 mmol) and $Et_3N$ (32 µL, 0.23 mmol). The reaction was kept at ambient temperature for 16 h and was quenched by addition of $H_2O$ (5 mL). The organic layer was extracted with $H_2O$ and brine, dried ($MgSO_4$), filtered and concentrated under reduced pressure to afford the desired mesylate. The crude reaction product was dissolve in DMF (2 mL) and $NaN_3$ (4 mg, 0.055 mmol) was added. The reaction was heated to 50° C. for 1 h and was quenched by $H_2O$ (5 mL). The aqueous layer was extracted with EtOAc (2×10 mL) and the combined organic layers were washed with brine, dried ($MgSO_4$), filtered and concentrated under reduced pressure to give the desired azide. The azide was dissolved in THF (1 mL) and $H_2O$ (0.2 mL) and $PPh_3$ (polymer supported, 3 mmol/g, 33 mg, 0.09 mmol) was added. The reaction was heated to 50° C. for 1 h and filtered to remove polymer support. The filtrated was concentrated under reduced pressure and purified by reverse-phase preparative HPLC to provide (7-(2,4-dichlorophenyl)-5-methyl-2-phenylpyrazolo[1,5-a]pyrimidin-6-yl)methanamine, TFA salt (15 mg, 65% for 3 steps) as a white solid.

$^1$H NMR (400 MHz, $CD_3OD$) δ 7.85 (m, 3H), 7.67 (dd, J=1.6, 7.6 Hz, 1H), 7.61 (d, J=7.5 Hz, 1H), 7.38 (m, 3H), 7.04 (s, 1H), 4.18 (d, J=14.9 Hz, 1H), 3.96 (d, J=14.9 Hz, 1H), 2.78 (s, 3H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=2.79 min, 99% homogeneity index.

LCMS: Anal. Calcd. for $C_{20}H_{16}Cl_2N_4$ 382.08; found: 383.13 (M+H)⁺.

HRMS: Anal. Calcd. for $C_{20}H_{17}Cl_2N_4$ 383.0830; found: 383.0833 (M+H)⁺.

Examples 2 to 34

Using the same methods for preparation of Example 1 the following compounds were prepared as TFA or di-TFA salts:

| Example 2 | 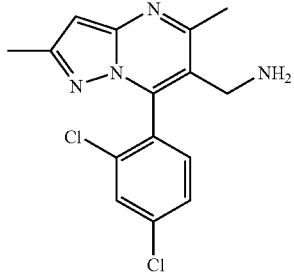 | $t_R$ = =2.13 min (99%)<br>LCMS: Anal. Calcd. for $C_{15}H_{14}Cl_2N_4$<br>320.06 found: 321.00 $(M + H)^+$<br>HRMS: Anal. Calcd. for $C_{15}H_{15}Cl_2N_4$<br>321.0674 found: 321.0685 $(M + H)^+$ |
|---|---|---|
| Example 3 | 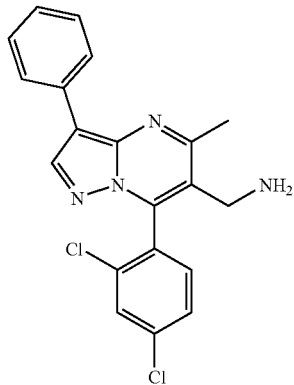 | $t_R$ = 3.60 min (99%)<br>LCMS: Anal. Calcd. for $C_{20}H_{16}Cl_2N_4$<br>382.08 found: 383.04 $(M + H)^+$<br>HRMS: Anal. Calcd. for $C_{20}H_{17}Cl_2N_4$<br>383.0830 found: 383.0823 $(M + H)^+$ |
| Example 4 | 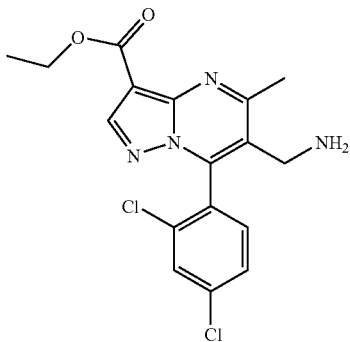 | $t_R$ = 2.56 min (98%)<br>LCMS: Anal. Calcd. for $C_{17}H_{16}Cl_2N_4O_2$<br>378.07 found: 379.16 $(M + H)^+$<br>HRMS: Anal. Calcd. for $C_{17}H_{16}Cl_2N_4O_2Na$<br>401.0548 found: 401.0568 $(M + Na)^+$ |
| Example 5 | 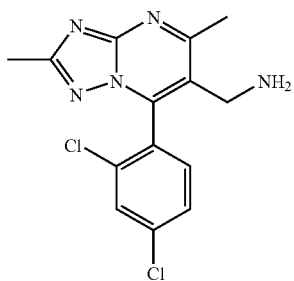 | $t_R$ = 1.83 min (100%)<br>LCMS: Anal. Calcd. for $C_{14}H_{13}Cl_2N_5$<br>321.05 found: 322.20 $(M + H)^+$<br>HRMS: Anal. Calcd. for $C_{14}H_{14}Cl_2N_5$<br>322.0626 found: 322.0630 $(M + H)^+$ |
| Example 6 | 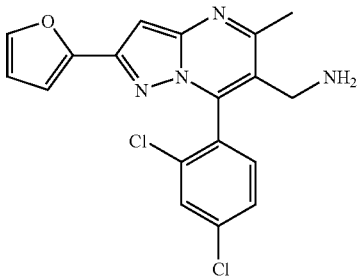 | $t_R$ = 2.35 min (98%)<br>LCMS: Anal. Calcd. for $C_{18}H_{14}Cl_2N_4O$<br>372.05 found: 373.20 $(M + H)^+$<br>HRMS: Anal. Calcd. for $C_{18}H_{15}Cl_2N_4O$<br>373.0623 found: 373.0634 $(M + H)^+$ |

-continued

| | | |
|---|---|---|
| Example 7 | 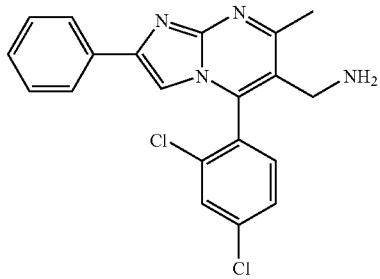 | $t_R$ = 2.31 min (96%)<br>LCMS: Anal. Calcd. for $C_{20}H_{16}Cl_2N_4$<br>382.08 found: 383.19 $(M + H)^+$<br>HRMS: Anal. Calcd. for $C_{20}H_{17}Cl_2N_4$<br>383.0830 found: 383.0839 $(M + H)^+$ |
| Example 8 | 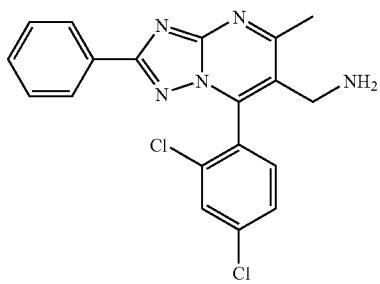 | $t_R$ = 2.69 min (99%)<br>LCMS: Anal. Calcd. for $C_{19}H_{15}Cl_2N_5$<br>383.07 found: 384.00 $(M + H)^+$<br>HRMS: Anal. Calcd. for $C_{19}H_{16}Cl_2N_5$<br>384.0783 found: 384.0797 $(M + H)^+$ |
| Example 9 | 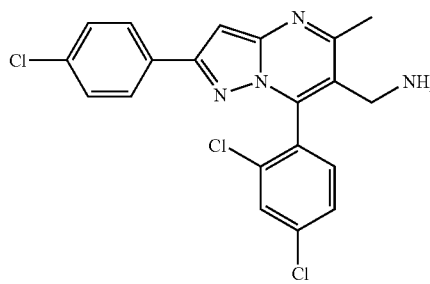 | $t_R$ = 3.37 min (98%)<br>LCMS: Anal. Calcd. for $C_{20}H_{15}Cl_3N_4$<br>416.04 found: 417.21 $(M + H)^+$<br>HRMS: Anal. Calcd. for $C_{20}H_{16}Cl_3N_4$<br>417.0441 found: 417.0447 $(M + H)^+$ |
| Example 10 | 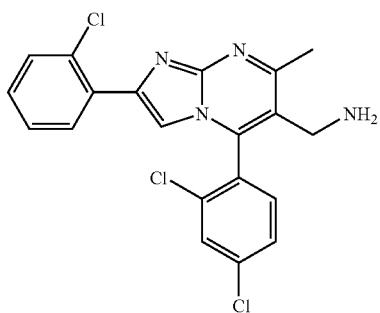 | $t_R$ = 2.77 min (97%)<br>LCMS: Anal. Calcd. for $C_{20}H_{15}Cl_3N_4$<br>416.04 found: 417.21 $(M + H)^+$<br>HRMS: Anal. Calcd. for $C_{20}H_{16}Cl_3N_4$<br>417.0441 found: 417.0443 $(M + H)^+$ |
| Example 11 | 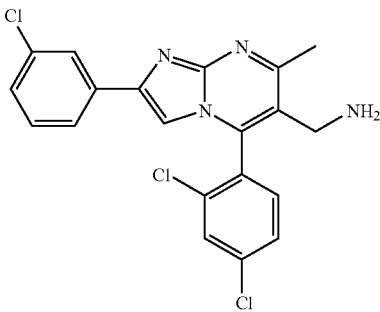 | $t_R$ = 2.85 min (100%)<br>LCMS: Anal. Calcd. for $C_{20}H_{15}Cl_3N_4$<br>416.04 found: 417.22 $(M + H)^+$<br>HRMS: Anal. Calcd. for $C_{20}H_{16}Cl_3N_4$<br>417.0441 found: 417.0450 $(M + H)^+$ |

-continued

| | | |
|---|---|---|
| Example 12 | 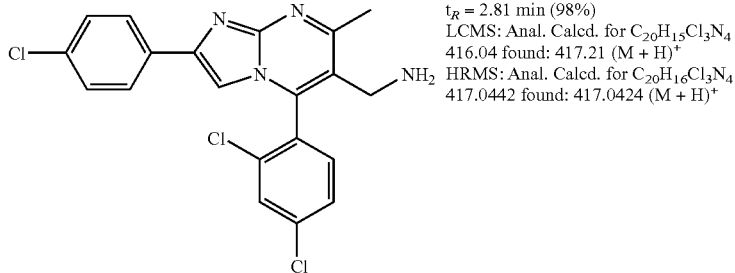 | $t_R$ = 2.81 min (98%)<br>LCMS: Anal. Calcd. for $C_{20}H_{15}Cl_3N_4$<br>416.04 found: 417.21 $(M + H)^+$<br>HRMS: Anal. Calcd. for $C_{20}H_{16}Cl_3N_4$<br>417.0442 found: 417.0424 $(M + H)^+$ |
| Example 13 | 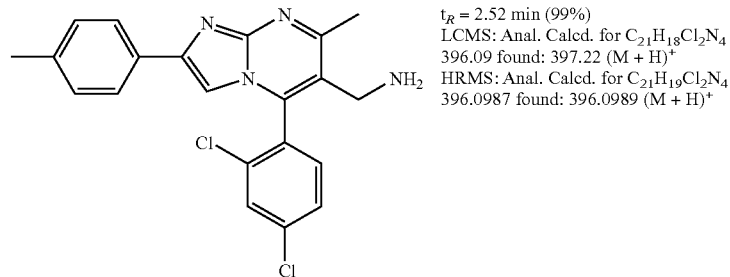 | $t_R$ = 2.52 min (99%)<br>LCMS: Anal. Calcd. for $C_{21}H_{18}Cl_2N_4$<br>396.09 found: 397.22 $(M + H)^+$<br>HRMS: Anal. Calcd. for $C_{21}H_{19}Cl_2N_4$<br>396.0987 found: 396.0989 $(M + H)^+$ |
| Example 14 | 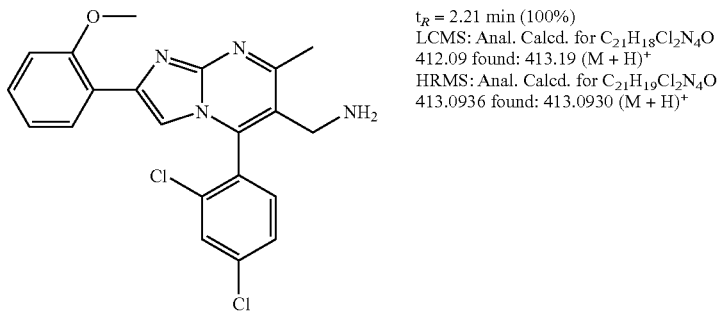 | $t_R$ = 2.21 min (100%)<br>LCMS: Anal. Calcd. for $C_{21}H_{18}Cl_2N_4O$<br>412.09 found: 413.19 $(M + H)^+$<br>HRMS: Anal. Calcd. for $C_{21}H_{19}Cl_2N_4O$<br>413.0936 found: 413.0930 $(M + H)^+$ |
| Example 15 | 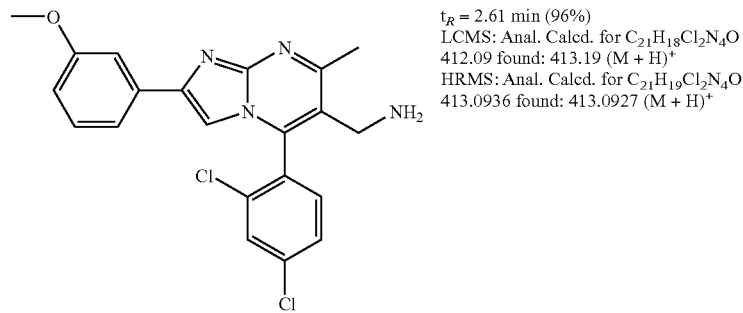 | $t_R$ = 2.61 min (96%)<br>LCMS: Anal. Calcd. for $C_{21}H_{18}Cl_2N_4O$<br>412.09 found: 413.19 $(M + H)^+$<br>HRMS: Anal. Calcd. for $C_{21}H_{19}Cl_2N_4O$<br>413.0936 found: 413.0927 $(M + H)^+$ |
| Example 16 | 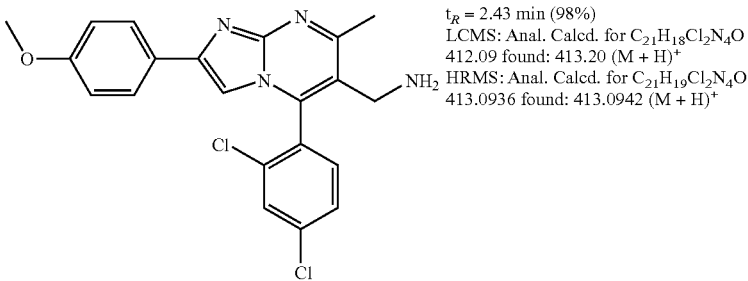 | $t_R$ = 2.43 min (98%)<br>LCMS: Anal. Calcd. for $C_{21}H_{18}Cl_2N_4O$<br>412.09 found: 413.20 $(M + H)^+$<br>HRMS: Anal. Calcd. for $C_{21}H_{19}Cl_2N_4O$<br>413.0936 found: 413.0942 $(M + H)^+$ |

-continued

| | | |
|---|---|---|
| Example 17 | 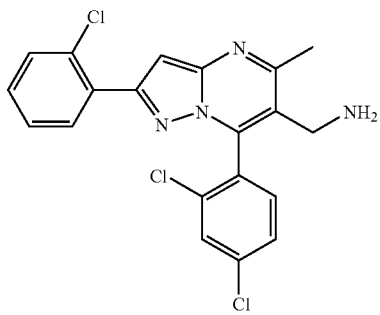 | $t_R$ = 3.14 min (96%)<br>LCMS: Anal. Calcd. for $C_{20}H_{15}Cl_3N_4$<br>416.04 found: 417.19 $(M + H)^+$<br>HRMS: Anal. Calcd. for $C_{20}H_{16}Cl_3N_4$<br>417.0441 found: 417.0444 $(M + H)^+$ |
| Example 18 | 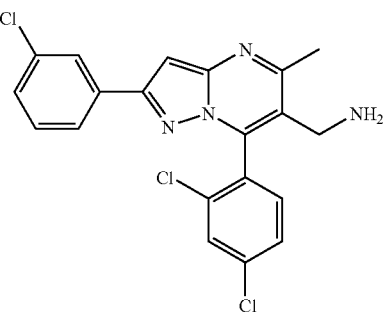 | $t_R$ = 3.30 min (100%)<br>LCMS: Anal. Calcd. for $C_{20}H_{15}Cl_3N_4$<br>416.04 found: 416.92 $(M + H)^+$<br>HRMS: Anal. Calcd. for $C_{20}H_{16}Cl_3N_4$<br>417.0441 found: 417.0431 $(M + H)^+$ |
| Example 19 | 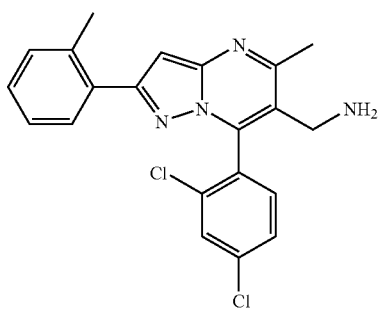 | $t_R$ = 2.96 min (99%)<br>LCMS: Anal. Calcd. for $C_{21}H_{18}Cl_2N_4$<br>396.09 found: 397.20 $(M + H)^+$<br>HRMS: Anal. Calcd. for $C_{21}H_{19}Cl_2N_4$<br>397.0987 found: 397.0981 $(M + H)^+$ |
| Example 20 | 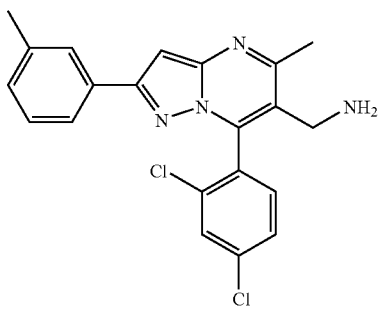 | $t_R$ = 3.00 min (100%)<br>LCMS: Anal. Calcd. for $C_{21}H_{18}Cl_2N_4$<br>396.09 found: 396.99 $(M + H)^+$<br>HRMS: Anal. Calcd. for $C_{21}H_{19}Cl_2N_4$<br>397.0987 found: 397.0981 $(M + H)^+$ |
| Example 21 | 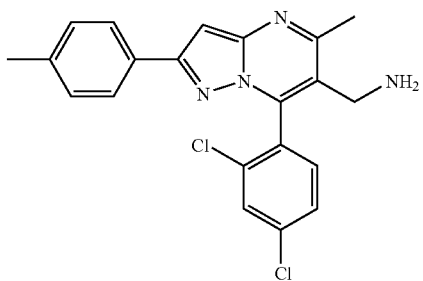 | $t_R$ = 3.34 min (97%)<br>LCMS: Anal. Calcd. for $C_{21}H_{18}Cl_2N_4$<br>396.09 found: 396.96 $(M + H)^+$<br>HRMS: Anal. Calcd. for $C_{21}H_{19}Cl_2N_4$<br>397.0987 found: 397.1001 $(M + H)^+$ |

-continued

| Example 22 | 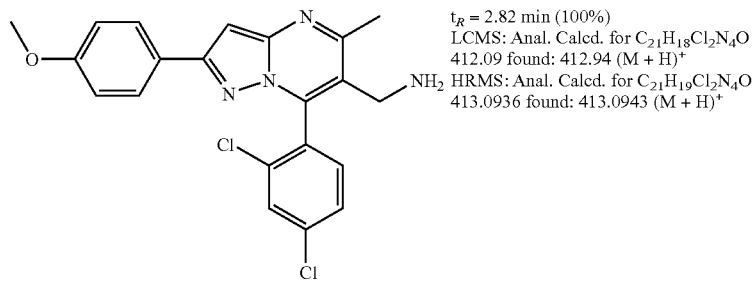 | $t_R$ = 2.82 min (100%)<br>LCMS: Anal. Calcd. for $C_{21}H_{18}Cl_2N_4O$<br>412.09 found: 412.94 $(M + H)^+$<br>HRMS: Anal. Calcd. for $C_{21}H_{19}Cl_2N_4O$<br>413.0936 found: 413.0943 $(M + H)^+$ |

| Example 23 | 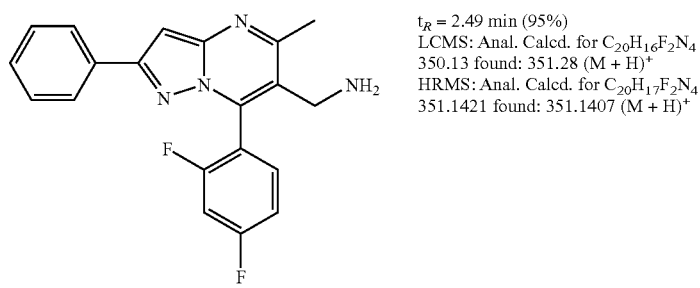 | $t_R$ = 2.49 min (95%)<br>LCMS: Anal. Calcd. for $C_{20}H_{16}F_2N_4$<br>350.13 found: 351.28 $(M + H)^+$<br>HRMS: Anal. Calcd. for $C_{20}H_{17}F_2N_4$<br>351.1421 found: 351.1407 $(M + H)^+$ |

| Example 24 | 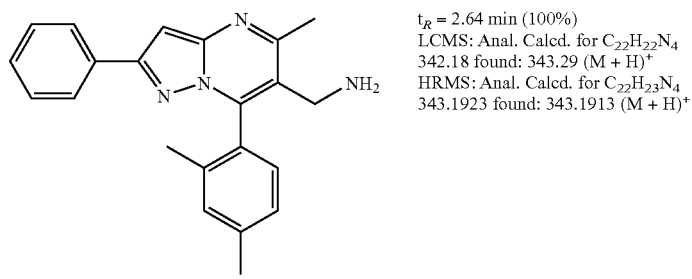 | $t_R$ = 2.64 min (100%)<br>LCMS: Anal. Calcd. for $C_{22}H_{22}N_4$<br>342.18 found: 343.29 $(M + H)^+$<br>HRMS: Anal. Calcd. for $C_{22}H_{23}N_4$<br>343.1923 found: 343.1913 $(M + H)^+$ |

| Example 25 | 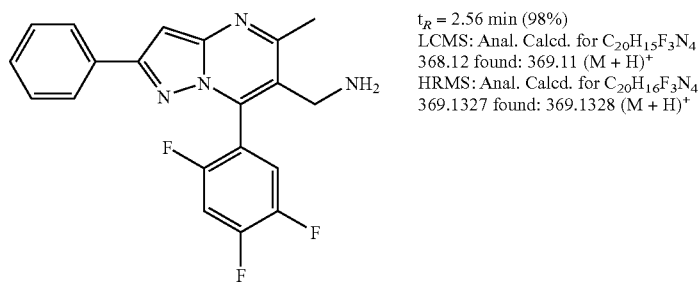 | $t_R$ = 2.56 min (98%)<br>LCMS: Anal. Calcd. for $C_{20}H_{15}F_3N_4$<br>368.12 found: 369.11 $(M + H)^+$<br>HRMS: Anal. Calcd. for $C_{20}H_{16}F_3N_4$<br>369.1327 found: 369.1328 $(M + H)^+$ |

| Example 26 | 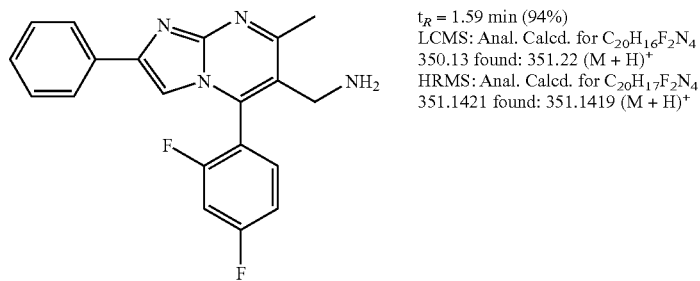 | $t_R$ = 1.59 min (94%)<br>LCMS: Anal. Calcd. for $C_{20}H_{16}F_2N_4$<br>350.13 found: 351.22 $(M + H)^+$<br>HRMS: Anal. Calcd. for $C_{20}H_{17}F_2N_4$<br>351.1421 found: 351.1419 $(M + H)^+$ |

-continued

| Example 27 | 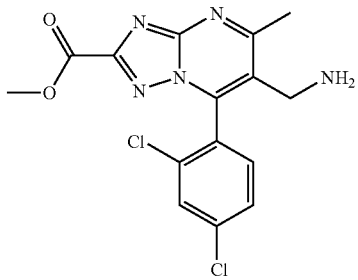 | $t_R$ = 1.54 min (94%)<br>LCMS: Anal. Calcd. for $C_{15}H_{13}Cl_2N_5O_2$<br>365.04 found: 365.99 $(M + H)^+$<br>HRMS: Anal. Calcd. for $C_{15}H_{14}Cl_2N_5O_2$<br>366.0525 found: 366.0517 $(M + H)^+$ |
|---|---|---|
| Example 28 | 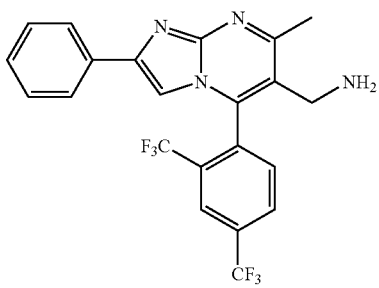 | $t_R$ = 2.83 min (99%)<br>LCMS: Anal. Calcd. for $C_{22}H_{16}F_6N_4$<br>450.13 found: 451.04 $(M + H)^+$<br>HRMS: Anal. Calcd. for $C_{22}H_{17}F_6N_4$<br>451.1357 found: 451.1366 $(M + H)^+$ |
| Example 29 | 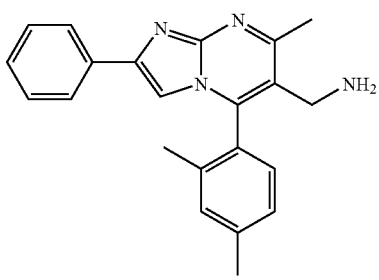 | $t_R$ = 2.34 min (95%)<br>LCMS: Anal. Calcd. for $C_{22}H_{22}N_4$<br>342.18 found: 343.13 $(M + H)^+$<br>HRMS: Anal. Calcd. for $C_{22}H_{23}N_4$<br>343.1924 found: 343.1911 $(M + H)^+$ |
| Example 30 | 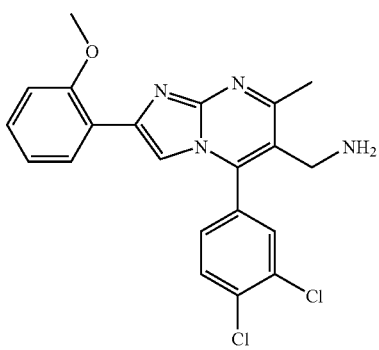 | $t_R$ = 1.86 min (99%)<br>LCMS: Anal. Calcd. for $C_{21}H_{18}Cl_2N_4O$<br>412.09 found: 412.97 $(M + H)^+$<br>HRMS: Anal. Calcd. for $C_{21}H_{19}Cl_2N_4O$<br>413.0936 found: 413.0924 $(M + H)^+$ |
| Example 31 | 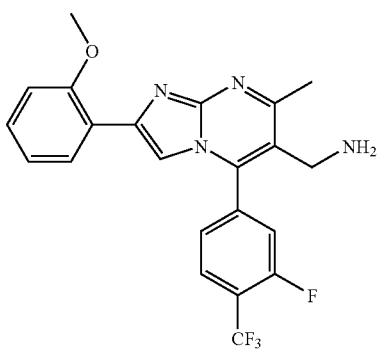 | $t_R$ = 1.74 min (100%)<br>LCMS: Anal. Calcd. for $C_{22}H_{18}F_4N_4O$<br>430.14 found: 431.11 $(M + H)^+$<br>HRMS: Anal. Calcd. for $C_{22}H_{19}F_4N_4O$<br>431.1495 found: 413.1487 $(M + H)^+$ |

-continued

| Example 32 | 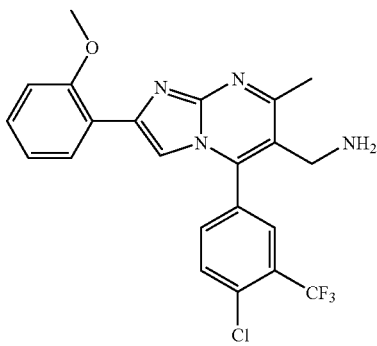 | $t_R$ = 1.79 min (100%)<br>LCMS: Anal. Calcd. for $C_{22}H_{18}ClF_3N_4O$<br>446.11 found: 447.05 $(M + H)^+$<br>HRMS: Anal. Calcd. for $C_{22}H_{19}ClF_3N_4O$<br>447.1199 found: 447.1208 $(M + H)^+$ |
|---|---|---|
| Example 33 | 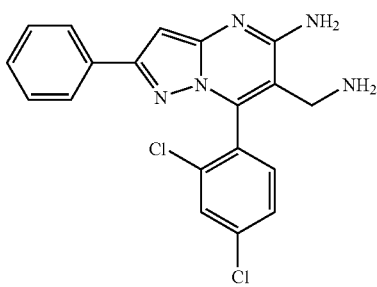 | $t_R$ = 2.61 min (97%)<br>LCMS: Anal. Calcd. for $C_{19}H_{15}Cl_2N_5$<br>383.07 found: 384.17 $(M + H)^+$<br>HRMS: Anal. Calcd. for $C_{19}H_{16}Cl_2N_5$<br>384.0783 found: 384.0783 $(M + H)^+$ |
| Example 34 | 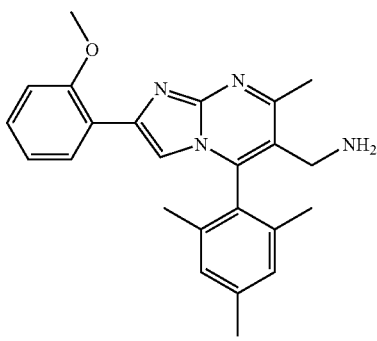 | tR = 2.05 min (98%)<br>LCMS: Anal. Calcd. for C24H26N4O<br>386.21 found: 387.40 $(M + H)+$ |

Example 35

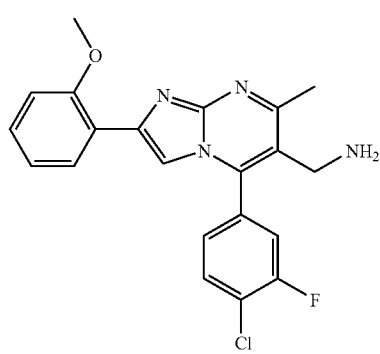

Example 35

Step 1.
2-(4-Chloro-3-fluorobenzylidene)-3-oxobutanamide

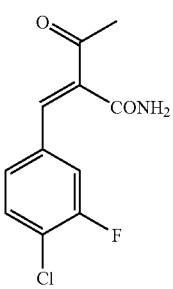

A mixture of 4-chloro-3-fluorobenzaldehyde (2.47 g, 15.5 mmol), acetoacetamide (1.57 g, 15.5 mmol), AcOH (35 μL, 0.62 mmol) and piperidine (61 μL, 0.62 mmol) in isopropyl alcohol (30 mL) was stirred at room temperature for 2.5 days and evaporated under reduced pressure. The crude product was purified by a silica gel column (120 g) eluting from 50% to 80% EtOAc in hexanes to afford 2-(4-chloro-3-fluorobenzylidene)-3-oxobutanamide (2.54 g, 67.6%) as an off-white solid.

$^1$H NMR (400 MHz, d$^6$-DMSO) δ 7.89 (s, br, 1H), 7.67 (m, 3H), 7.54 (dd, J=2.2, 8.35 Hz, 1H), 7.50 (s, 1H), 2.43 (s, 3H).

HPLC Phenomenex Luna, 5 u, 4.6×50 mm, detection at 220 nm, flow rate 4 mL/min, 0 to 100% B over 4 minutes, 1 minute hold time, A=90% water, 10% methanol, 0.2% H$_3$PO$_4$, B=10% water, 90% methanol, 0.2% H$_3$PO$_4$, 94% purity.

Example 35

Step 2. 5-(4-Chloro-3-fluorophenyl)-2-(2-methoxyphenyl)-7-methyl-5,8-dihydroimidazo[1,2-a]pyrimidine-6-carboxamide

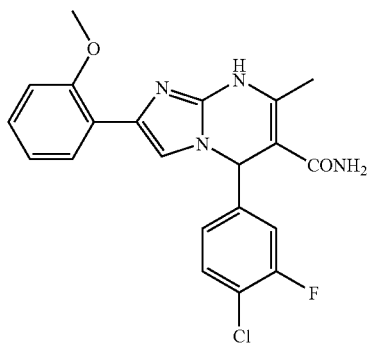

A mixture of 4-(2-methoxyphenyl)-1H-imidazol-2-amine (0.85 g, 4.5 mmol) and NaOAc (267.3 mg, 4.95 mmol) in THF (5 mL) and MeOH (1.5 mL) was stirred at room temperature for 20 min and followed by addition of 2-(4-chloro-3-fluorobenzylidene)-3-oxobutanamide (1.09 g, 4.5 mmol). The reaction mixture was then heated to 70° C. for 2 h and evaporated under reduced pressure. The residue was suspended in THF, and the slurry mixture was filtered to give 5-(4-chloro-3-fluorophenyl)-2-(2-methoxyphenyl)-7-methyl-5,8-dihydroimidazo[1,2-a]pyrimidine-6-carboxamide (1.01 g, 54.4%) as a yellow solid.

$^1$H NMR (500 MHz, d$^6$-DMSO) δ 7.91 (dd, J=1.7, 7.7 Hz, 1H), 7.56 (t, J=8.0 Hz, 1H), 7.29 (d, J=9.4 Hz, 1H), 7.14 (m, 2H), 7.05 (s, 1H), 6.97 (d, J=8.3 Hz, 1H), 6.93 (t, J=8.0 Hz, 1H), 6.33 (s, 1H), 3.80 (s, 3H), 2.19 (s, 3H).

HPLC Phenomenex Luna, 5 u, 4.6×50 mm, detection at 220 nm, flow rate 4 mL/min, 0 to 100% B over 4 minutes, 1 minute hold time, A=90% water, 10% methanol, 0.2% H$_3$PO$_4$, B=10% water, 90% methanol, 0.2% H$_3$PO$_4$, 98% purity.

LCMS: Anal. Calcd. for C$_{21}$H$_{18}$ClFN$_4$O$_2$: 412.11; found: 413.20 (M+H)$^+$.

Example 35

Step 3. 5-(4-Chloro-3-fluorophenyl)-2-(2-methoxyphenyl)-7-methyl-5,8-dihydroimidazo[1,2-a]pyrimidine-6-carbonitrile

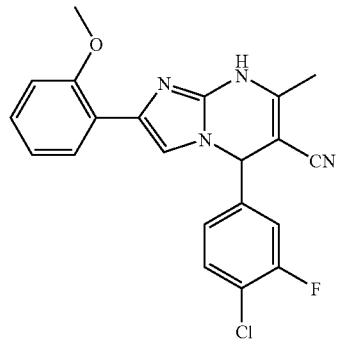

To a suspension of 5-(4-chloro-3-fluorophenyl)-2-(2-methoxyphenyl)-7-methyl-5,8-dihydroimidazo[1,2-a]pyrimidine-6-carboxamide (351 mg, 0.85 mmol) in CH$_2$Cl$_2$ (10 mL) at 0° C. was added Et$_3$N (0.73 mL, 5.27 mmol) followed by trifluoroacetic anhydride (0.38 mL, 2.72 mmol) over a period of 10 min. The reaction mixture was stirred at 0° C. for an additional 40 min and quenched with 10% Na$_2$CO$_3$ (5 mL) and H$_2$O (10 mL). The organic layer was separated and the aqueous layer was extracted with CH$_2$Cl$_2$ (2×). The combined organic extracts were washed with brine, dried (Na$_2$SO$_4$) and evaporated under reduced pressure. The residue was triturated with ether and purified by column chromatography on silica gel eluting from 30% to 50% EtOAc in hexanes to give 5-(4-chloro-3-fluorophenyl)-2-(2-methoxyphenyl)-7-methyl-5,8-dihydroimidazo[1,2-a]pyrimidine-6-carbonitrile (120 mg, 36%) as a yellow solid.

$^1$H NMR (500 MHz, d$^6$-DMSO) δ 7.93 (dd, J=1.7, 7.7 Hz, 1H), 7.65 (t, J=8.0 Hz, 1H), 7.43 (dd, J=1.7, 9.9 Hz, 1H), 7.20 (dd, J=1.7, 8.3 Hz, 1H), 7.17 (t, J=8.5 Hz, 1H), 6.99 (d, J=7.7 Hz, 1H), 6.98 (s, 1H), 6.95 (t, J=7.7 Hz, 1H), 6.22 (s, 1H), 3.79 (s, 3H), 2.17 (s, 3H).

HPLC Phenomenex Luna, 5 u, 4.6×50 mm, detection at 220 nm, flow rate 4 mL/min, 0 to 100% B over 4 minutes, 1 minute hold time, A=90% water, 10% methanol, 0.2% H$_3$PO$_4$, B=10% water, 90% methanol, 0.2% H$_3$PO$_4$, 98% purity.

LCMS: Anal. Calcd. for C$_{21}$H$_{16}$ClFN$_4$O: 394.1; found: 395.1 (M+H)$^+$.

Example 35

Step 4. 5-(4-Chloro-3-fluorophenyl)-2-(2-methoxyphenyl)-7-methylimidazo[1,2-a]pyrimidine-6-carbonitrile

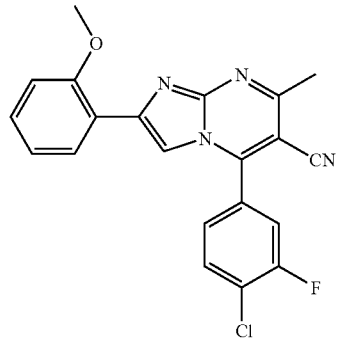

To a stirred suspension of 5-(4-chloro-3-fluorophenyl)-2-(2-methoxyphenyl)-7-methyl-5,8-dihydroimidazo[1,2-a]pyrimidine-6-carbonitrile (180 mg, 0.46 mmol) in CH$_2$Cl$_2$ (5 mL) was added 2,3-dichloro-5,6-dicyano-1,4-benzoquinone (103 mg, 0.46 mmol) in one portion. The reaction was kept at ambient temperature for 2.5 h, diluted with CH$_2$Cl$_2$ and washed with satd aq NaHCO$_3$ (5×). The organic layer was washed again with brine, dried (Na$_2$SO$_4$) and concentrated under reduced pressure to afford 5-(4-chloro-3-fluorophenyl)-2-(2-methoxyphenyl)-7-methylimidazo[1,2-a]pyrimidine-6-carbonitrile (168 mg, 94%) as a light orange solid.

Example 35

Step 5. (5-(4-Chloro-3-fluorophenyl)-2-(2-methoxyphenyl)-7-methylimidazo[1,2-a]pyrimidin-6-yl)methanamine

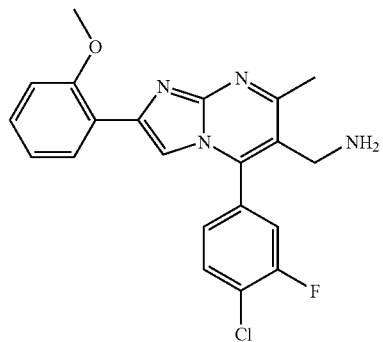

A stirred suspension of 5-(4-chloro-3-fluorophenyl)-2-(2-methoxyphenyl)-7-methylimidazo[1,2-a]pyrimidine-6-carbonitrile (75 mg, 0.19 mmol) in 2M NH$_3$/MeOH (6 mL) was hydrogenated under H$_2$ (40 psi) in the presence of Raney-Nickel (3-5 equiv.) for 70 min. The reaction mixture was filtered through a pad of Celite. The filtrate was evaporated under reduced pressure, and the residue was purified by reverse-phase preparative HPLC (Phenomenex Luna, 21.2× 100 mm, detection at 220 nm, flow rate 20 mL/min, 5 to 60% B over 18 min; A=90% water, 10% methanol, 0.1% TFA, B=10% water, 90% methanol, 0.1% TFA) to provide (5-(4-chloro-3-fluorophenyl)-2-(2-methoxyphenyl)-7-methylimidazo[1,2-a]pyrimidin-6-yl)methanamine, TFA salt (31 mg, 41%) as a light yellow solid.

$^1$H NMR (500 MHz, CD$_3$OD) δ 8.94 (t, J=7.7 Hz, 1H), 7.81 (m, 1H), 7.78 (s, 1H), 7.71 (m, 1H), 7.53 (m, 1H), 7.20 (d, J=8.8 Hz, 1H), 7.09 (t, J=7.7 Hz, 1H), 4.22 (s, 2H), 3.91 (s, 3H), 2.95 (s, 3H).

HPLC Phenomenex Luna, 5 u, 4.6×50 mm, detection at 220 nm, flow rate 4 mL/min, 0 to 100% B over 4 minutes, 1 minute hold time, A=90% water, 10% methanol, 0.2% H$_3$PO$_4$, B=10% water, 90% methanol, 0.2% H$_3$PO$_4$, 97% purity.

LCMS: Anal. Calcd. for C$_{21}$H$_{18}$ClFN$_4$O: 396.12; found: 397.20 (M+H)$^+$.

Examples 36 to 44

Using the same methods for preparation of Example 35, the following compounds were prepared as TFA salts:

Example 36

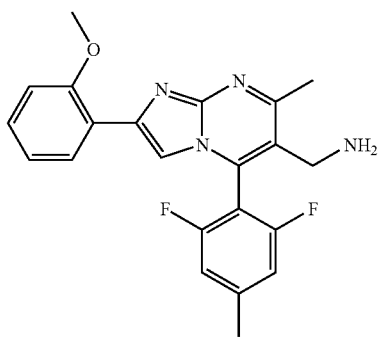

t$_R$ = 1.91 min (98%)
LCMS: Anal. Calcd. for C$_{22}$H$_{20}$F$_2$N$_4$O
394.16 found: 395.23 (M + H)$^+$ Example 37

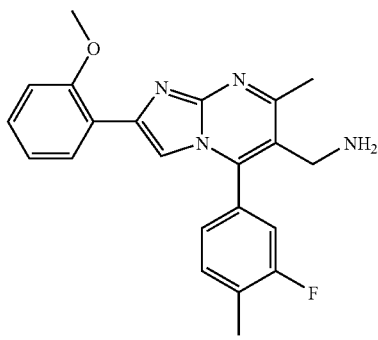

t$_R$ = 1.78 min (99%)
LCMS: Anal. Calcd. for C$_{22}$H$_{21}$FN$_4$O
37617 found: 377.30 (M + H)

-continued
| Example 38 | 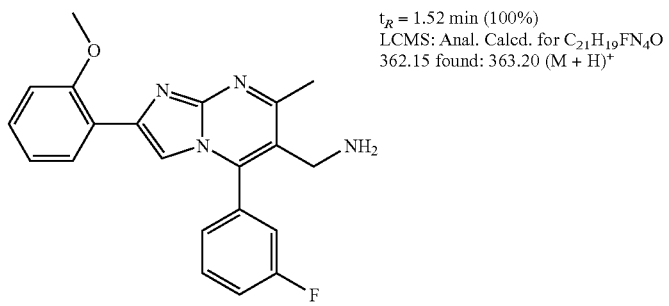 | $t_R$ = 1.52 min (100%)<br>LCMS: Anal. Calcd. for $C_{21}H_{19}FN_4O$<br>362.15 found: 363.20 $(M + H)^+$ |
| Example 39 | 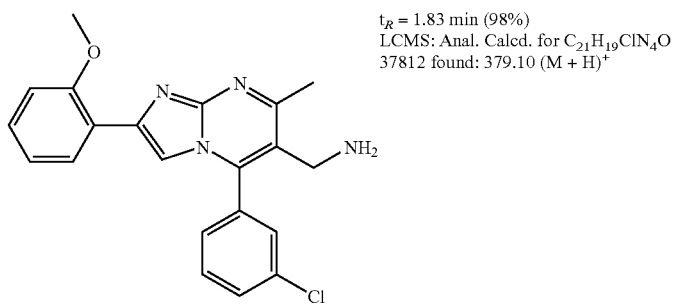 | $t_R$ = 1.83 min (98%)<br>LCMS: Anal. Calcd. for $C_{21}H_{19}ClN_4O$<br>37812 found: 379.10 $(M + H)^+$ |
| Example 40 | 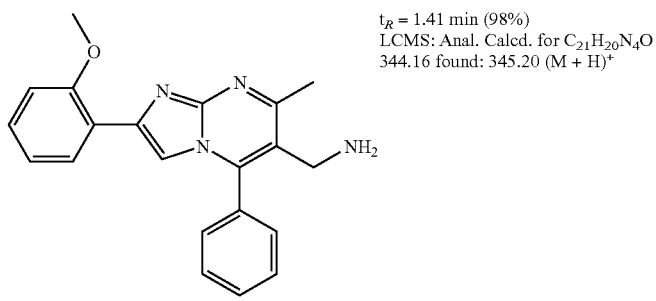 | $t_R$ = 1.41 min (98%)<br>LCMS: Anal. Calcd. for $C_{21}H_{20}N_4O$<br>344.16 found: 345.20 $(M + H)^+$ |
| Example 41 | 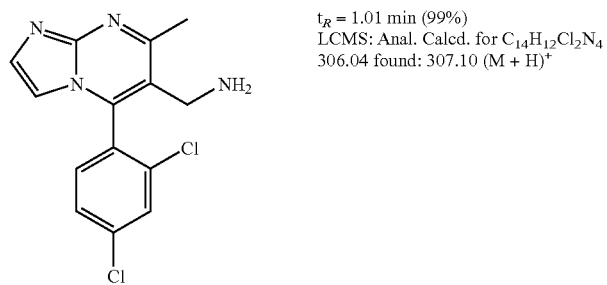 | $t_R$ = 1.01 min (99%)<br>LCMS: Anal. Calcd. for $C_{14}H_{12}Cl_2N_4$<br>306.04 found: 307.10 $(M + H)^+$ |
| Example 42 | 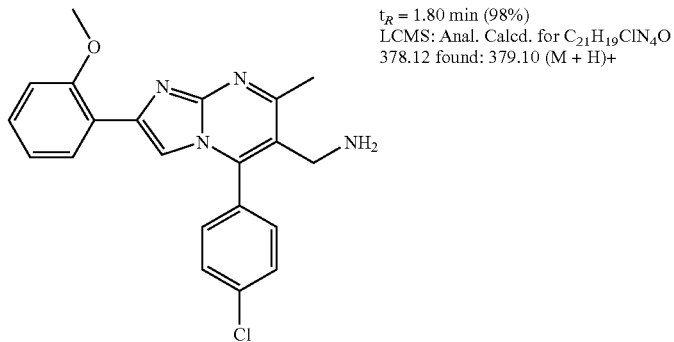 | $t_R$ = 1.80 min (98%)<br>LCMS: Anal. Calcd. for $C_{21}H_{19}ClN_4O$<br>378.12 found: 379.10 $(M + H)+$ |

-continued

| | | |
|---|---|---|
| Example 43 | 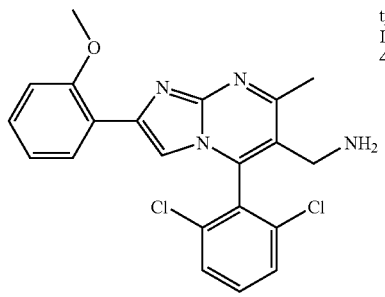 | $t_R$ = 2.00 min (94%)<br>LCMS: Anal. Calcd. for $C_{21}H_{18}Cl_2N_4O$<br>412.09 found: 413.00 (M + H)+ |
| Example 44 | 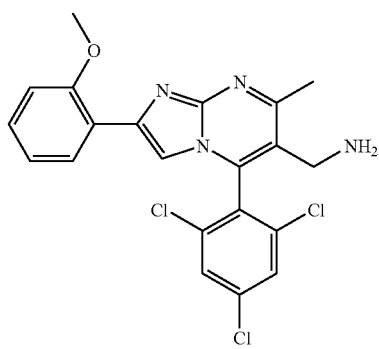 | $t_R$ = 2.38 min (100%)<br>LCMS: Anal. Calcd. for $C_{21}H_{17}Cl_3N_4O$<br>446.05 found: 449.10 (M + H)+<br>HRMS: Anal. Calcd. for C21H18Cl3N4O<br>447.0546 found: (M + H)+ |

Example 45

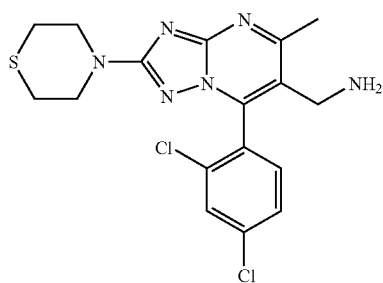

Example 45

Step 1-2. Methyl 2-amino-7-(2,4-dichlorophenyl)-5-methyl-[1,2,4]-triazolo[1,5-a]pyrimidine-6-carboxylate

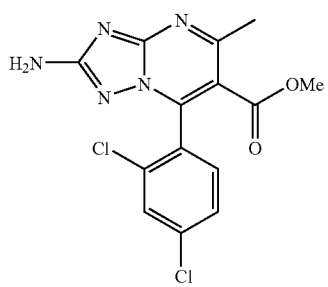

To a stirred solution of 1H-1,2,4-triazole-3,5-diamine (1.0 g, 10.1 mmol), methyl 3-oxobutanoate (1.17 g, 10.1 mmol), and 2,4-dichlorobenzaldehyde (1.35 g, 10.1 mmol) in THF (30 mL) and heptane (8 mL) was added piperidine (30 mg, 0.3 mmol) and the reaction was heated to 70° C. for 2 days. The reaction was concentrated to afford crude methyl 2-amino-7-(2,4-dichlorophenyl)-5-methyl-4,7-dihydro-[1,2,4]-triazolo[1,5-a]pyrimidine-6-carboxylate as a light yellow solid.

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.03 min, 97% homogeneity index.

To a stirred solution of crude methyl 2-amino-7-(2,4-dichlorophenyl)-5-methyl-4,7-dihydro-[1,2,4]-triazolo[1,5-a]pyrimidine-6-carboxylate (10.1 mmol) in $CH_2Cl_2$ (100 mL) was added DDQ (2.75 g, 12.1 mmol). The reaction was kept at room temperature for 1 h and was quenched by satd aq $NaHCO_3$ solution. The organic layer was washed with satd aq $NaHCO_3$ and brine prior to drying over anhydrous $MgSO_4$. Filtration, concentration under reduced pressure and purification by silica gel chromatography afforded methyl 2-amino-7-(2,4-dichlorophenyl)-5-methyl-[1,2,4]-triazolo[1,5-a]pyrimidine-6-carboxylate (2.0 g, 56%) as a light yellow solid.

$^1$H NMR (400 MHz, $CDCl_3$) δ 7.59 (d, J=1.8 Hz, 1H), 7.43 (dd, J=1.8, 7.9 Hz, 1H), 7.29 (d, J=7.9 Hz, 1H), 4.72 (s, 2H), 3.64 (s, 3H), 2.77 (s, 3H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=2.85 min, 100% homogeneity index.

LCMS: Anal. Calcd. for $C_{14}H_{11}Cl_2N_5O_2$ 351.03; found: 352.11 (M+H)+.

Example 45

Step 3. Methyl 2-bromo-7-(2,4-dichlorophenyl)-5-methyl-[1,2,4]-triazolo[1,5-a]pyrimidine-6-carboxylate

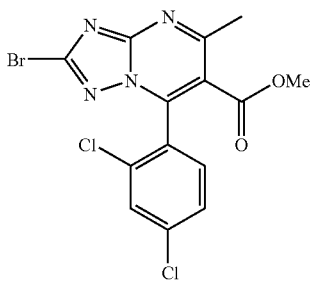

CuBr$_2$ (38 mg, 0.17 mmol) and $^t$BuONO (25 mL, 0.21 mmol) were mixed in CH$_3$CN (2 mL) and heated to 65° C. To this, a solution of methyl 2-amino-7-(2,4-dichlorophenyl)-5-methyl-[1,2,4]triazolo[1,5-a]pyrimidine-6-carboxylate (50 mg, 0.14 mmol) in CH$_3$CN (1 mL) was added dropwise to allow a slow evolution of N$_2$ gas. After 20 min, the reaction was concentrated under reduced pressure and diluted with EtOAc. The organic layer was washed with 1N HCl, satd aq NH$_4$Cl and brine prior to drying over anhydrous MgSO$_4$. Filtration, concentration under reduced pressure and purification by silica gel chromatography afforded methyl 2-bromo-7-(2,4-dichlorophenyl)-5-methyl-[1,2,4]-triazolo[1,5-a]pyrimidine-6-carboxylate (66 mg, 100%) as a yellow solid.

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.52 mim, 99% homogeneity index.

$^1$H NMR (400 MHz, CDCl$_3$) δ 7.61 (d, J=1.8 Hz, 1H), 7.46 (dd, J=1.8, 8.4 Hz, 1H), 7.32 (d, J=8.4 Hz, 1H), 3.70 (s, 3H), 2.84 (s, 3H).

LCMS: Anal. Calcd. for C$_{14}$H$_9$BrCl$_2$N$_4$O$_2$ 413.93; found: 415.02 (M+H)$^+$.

Example 45

Step 4. Methyl 7-(2,4-dichlorophenyl)-5-methyl-2-thiomorpholino-[1,2,4]-triazolo[1,5-a]pyrimidine-6-carboxylate

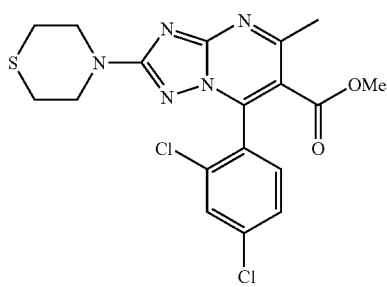

To a stirred solution of methyl 2-bromo-7-(2,4-dichlorophenyl)-5-methyl-[1,2,4]-triazolo[1,5-a]pyrimidine-6-carboxylate (30 mg, 0.07 mmol) in dioxane (2 mL) was added thiomorpholine (15 µL, 0.14 mmol). After heating to 75° C. for 16 h, the reaction was concentrated under reduced pressure and diluted with EtOAc. The organic layer was washed with satd aq NH$_4$Cl and brine prior to drying over anhydrous MgSO$_4$. Filtration, concentration under reduced pressure and purification by silica gel chromatography afforded methyl 7-(2,4-dichlorophenyl)-5-methyl-2-thiomorpholino-[1,2,4]-triazolo[1,5-a]pyrimidine-6-carboxylate (28 mg, 90%) as a yellow solid.

$^1$H NMR (400 MHz, CDCl$_3$) δ 7.57 (d, J=1.8 Hz, 1H), 7.42 (dd, J=1.8, 8.4 Hz, 1H), 7.27 (d, J=8.4 Hz, 1H), 3.91 (m, 4H), 3.63 (s, 3H), 2.75 (s, 3H), 2.64 (m, 4H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.90 min, 95% homogeneity index.

LCMS: Anal. Calcd. for C$_{18}$H$_{17}$Cl$_2$N$_5$O$_2$S 437.05; found: 438.18 (M+H)$^+$.

Example 45

Step 5-10. (7-(2,4-dichlorophenyl)-5-methyl-2-thiomorpholino-[1,2,4]-triazolo[1,5-a]pyrimidin-6-yl)methanamine

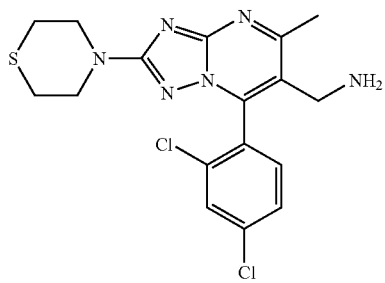

Starting from methyl 7-(2,4-dichlorophenyl)-5-methyl-2-thiomorpholino-[1,2,4]triazolo[1,5-a]pyrimidine-6-carboxylate, (7-(2,4-dichlorophenyl)-5-methyl-2-thiomorpholino-[1,2,4]-triazolo[1,5-a]pyrimidin-6-yl)methanamine, TFA salt was prepared using the same methods described in Example 1.

$^1$H NMR (400 MHz, CDCl$_3$) δ 7.83 (d, J=1.8 Hz, 1H), 7.67 (dd, J=1.8, 8.4 Hz, 1H), 7.54 (d, J=8.4 Hz, 1H), 4.17 (d, J=15.0 Hz, 1H), 3.96 (d, J=15.0 Hz, 1H), 3.83 (m, 4H), 2.77 (s, 3H), 2.61 (m, 4H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=2.75 min, 95% homogeneity index.

LCMS: Anal. Calcd. for C$_{17}$H$_{18}$Cl$_2$N$_6$S 408.07; found: 409.23 (M+H)$^+$.

HRMS: Anal. Calcd. for C$_{17}$H$_{19}$Cl$_2$N$_6$S 409.0769; found: 409.0763 (M+H)$^+$.

Examples 46 to 52

Using the same methods for preparation of Example 45, the following compounds were prepared as TFA or di-TFA salts:

| | | |
|---|---|---|
| Example 46 | 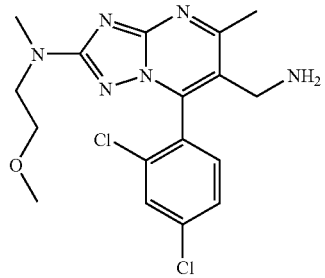 | $t_R$ = 2.10 min (96%)<br>LCMS: Anal. Calcd. for $C_{17}H_{20}Cl_2N_6O$<br>394.11 found: 395.26 $(M + H)^+$<br>HRMS: Anal. Calcd. for $C_{17}H_{21}Cl_2N_6O$<br>395.1154 found: 395.1148 $(M + H)^+$ |
| Example 47 | 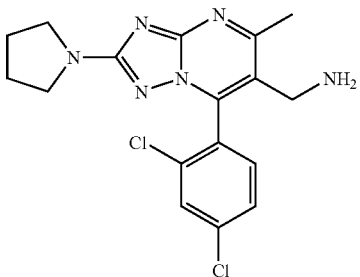 | $t_R$ = 2.24 min (98%)<br>LCMS: Anal. Calcd. for $C_{17}H_{18}Cl_2N_6$<br>376.10 found: 377.10 $(M + H)^+$<br>HRMS: Anal. Calcd. for $C_{17}H_{19}Cl_2N_6$<br>377.1048 found: 377.1042 $(M + H)^+$ |
| Example 48 | 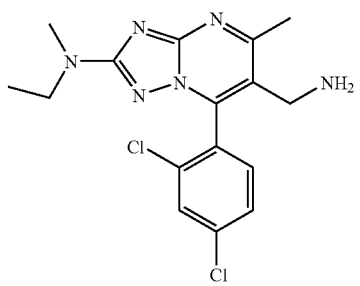 | $t_R$ = 2.27 min (99%)<br>LCMS: Anal. Calcd. for $C_{16}H_{18}Cl_2N_6$<br>364.10 found: 365.09 $(M + H)^+$<br>HRMS: Anal. Calcd. for $C_{16}H_{19}Cl_2N_6$<br>365.1048 found: 365.1042 $(M + H)^+$ |
| Example 49 | 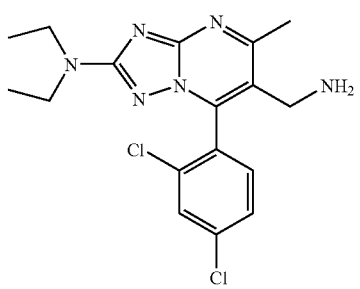 | $t_R$ = 2.54 min (99%)<br>LCMS: Anal. Calcd. for $C_{17}H_{20}Cl_2N_6$<br>378.11 found: 379.12 $(M + H)^+$<br>HRMS: Anal. Calcd. for $C_{17}H_{21}Cl_2N_6$<br>379.1205 found: 379.1192 $(M + H)^+$ |
| Example 50 | 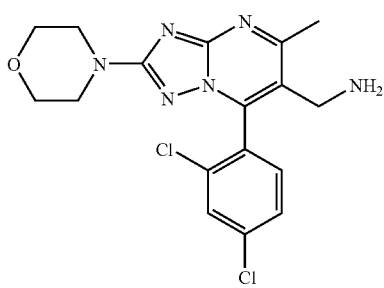 | $t_R$ = 1.98 min (98%)<br>LCMS: Anal. Calcd. for $C_{17}H_{18}Cl_2N_6O$<br>392.09 found: 393.07 $(M + H)^+$<br>HRMS: Anal. Calcd. for $C_{22}H_{29}Cl_2N_7O$<br>393.0997 found: 393.0987 $(M + H)^+$ |

-continued

Example 51
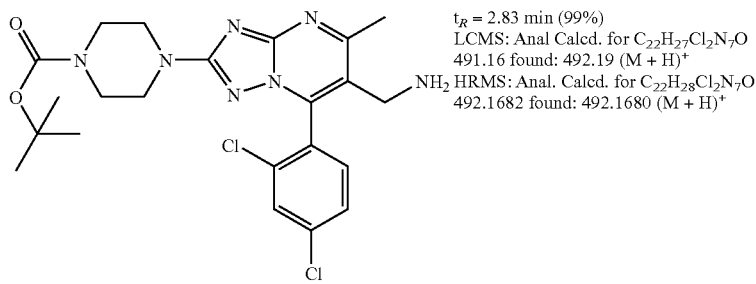

$t_R$ = 2.83 min (99%)
LCMS: Anal Calcd. for $C_{22}H_{27}Cl_2N_7O$ 491.16 found: 492.19 (M + H)$^+$
HRMS: Anal. Calcd. for $C_{22}H_{28}Cl_2N_7O$ 492.1682 found: 492.1680 (M + H)$^+$ Example 52
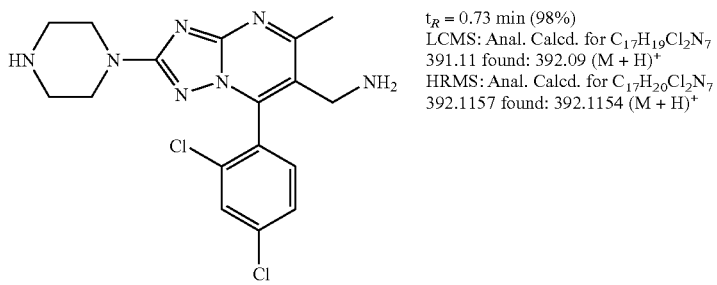

$t_R$ = 0.73 min (98%)
LCMS: Anal. Calcd. for $C_{17}H_{19}Cl_2N_7$ 391.11 found: 392.09 (M + H)$^+$
HRMS: Anal. Calcd. for $C_{17}H_{20}Cl_2N_7$ 392.1157 found: 392.1154 (M + H)$^+$ Example 53

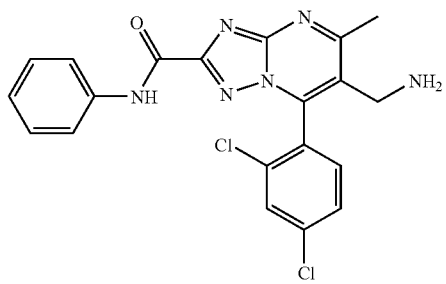

Example 53

Step 1-2. 6-((tert-butoxycarbonyl)methyl)-7-(2,4-dichlorophenyl)-5-methyl-[1,2,4]triazolo[1,5-a]pyrimidine-2-carboxylic acid

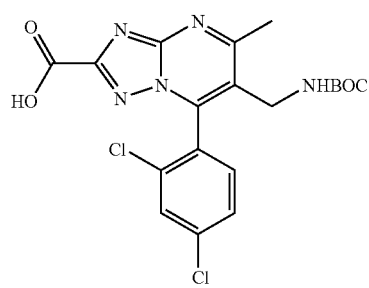

To a stirred solution of methyl 6-(aminomethyl)-7-(2,4-dichlorophenyl)-5-methyl-[1,2,4]triazolo[1,5-a]pyrimidine-2-carboxylate (Example 27, 50 mg, 0.14 mmol) in THF (3 mL) was added (BOC)$_2$O (75 µL, 0.34 mmol) and Et$_3$N (100 µl, 0.70 mmol). After 2 h, the reaction was concentrated under reduced pressure and diluted with EtOAc. The organic layer was washed with satd aq NH$_4$Cl and brine prior to drying over anhydrous MgSO$_4$. Filtration, concentration under reduced pressure and purification by silica gel chromatography (50% EtOAc in hexanes) afforded methyl 6-((tert-butoxycarbonyl)methyl)-7-(2,4-dichlorophenyl)-5-methyl-[1,2,4]triazolo[1,5-a]pyrimidine-2-carboxylate (13 mg, 20%) as a white solid.

$^1$H NMR (400 MHz, CDCl$_3$) δ 7.64 (d, J=1.8 Hz, 1H), 7.48 (dd, J=1.8, 8.4 Hz, 1H), 7.37 (d, J=8.4 Hz, 1H), 4.61 (br s, 1H), 4.17-4.38 (m, 2H), 4.00 (s, 3H), 2.87 (s, 3H), 1.41 (s, 9H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.47 min, 90% homogeneity index.

LCMS: Anal. Calcd. for $C_{20}H_{21}Cl_2N_5O_4$ 465.10; found: 465.96 (M+H)$^+$.

To a stirred solution of 6-((tert-butoxycarbonyl)methyl)-7-(2,4-dichlorophenyl)-5-methyl-[1,2,4]triazolo[1,5-a]pyrimidine-2-carboxylate (13 mg, 0.03 mmol) in THF (1 mL) was added LiOH-H$_2$O (9 mg, 0.21 mmol) in H$_2$O (0.1 mL). After heating to 40° C. for 1 h, the reaction was concentrated under reduced pressure and diluted with EtOAc. The organic layer was washed with 1N HCl and brine prior to drying over anhydrous MgSO$_4$. Filtration, concentration under reduced pressure afforded 6-((tert-butoxycarbonyl)methyl)-7-(2,4-dichlorophenyl)-5-methyl-[1,2,4]triazolo[1,5-a]pyrimidine-2-carboxylic acid (13 mg, 100%) as a white solid.

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.25 min, 90% homogeneity index.

LCMS: Anal. Calcd. for $C_{19}H_{19}Cl_2N_5O_4$ 451.08; found: 451.92 (M+H)$^+$.

Example 53

Step 3-4. 6-(aminomethyl)-7-(2,4-dichlorophenyl)-5-methyl-N-phenyl-[1,2,4]triazolo[1,5-a]pyrimidine-2-carboxamide

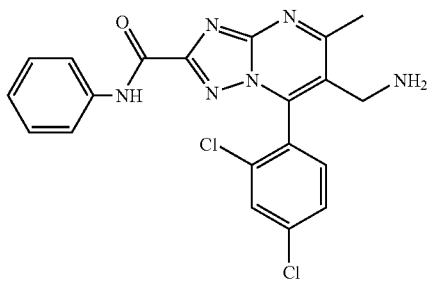

To a stirred solution of 6-((tert-butoxycarbonyl)methyl)-7-(2,4-dichlorophenyl)-5-methyl-[1,2,4]triazolo[1,5-a]pyrimidine-2-carboxylic acid (13 mg, 0.03 mmol) in $CH_2Cl_2$ (3 mL) was added aniline (4 µL, 0.05 mmol), HOAt (8 mg, 0.06 mmol), EDC (12 mg, 0.06 mmol) and $Pr_2NEt$ (11 µL, 0.06 mmol). The reaction was kept at room temperature for 2 h and was concentrated under reduced pressure. The residue was diluted with EtOAc and the organic layer was washed with 1N HCl, 1N NaOH and brine prior to drying over anhydrous $MgSO_4$. Filtration and concentration under reduced pressure afforded tert-butyl (7-(2,4-dichlorophenyl)-5-methyl-2-(phenylcarbamoyl)-[1,2,4]triazolo[1,5-a]pyrimidin-6-yl)methylcarbamate (10 mg, 63% crude yield).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.80 min, 93% homogeneity index.

LCMS: Anal. Calcd. for $C_{25}H_{24}Cl_2N_6O_3$ 526.13; found: 527.16 $(M+H)^+$.

To a stirred solution of tert-butyl (7-(2,4-dichlorophenyl)-5-methyl-2-(phenylcarbamoyl)-[1,2,4]triazolo[1,5-a]pyrimidin-6-yl)methylcarbamate (10 mg, 0.02 mmol) in $CH_2Cl_2$ (2 mL) was added TFA (0.5 mL). After 16 h, the reaction was concentrated and purified by reverse phase HPLC to provide 6-(aminomethyl)-7-(2,4-dichlorophenyl)-5-methyl-N-phenyl-[1,2,4]triazolo[1,5-a]pyrimidine-2-carboxamide, TFA salt (5 mg, 27% for two steps) as a white solid.

$^1H$ NMR (400 MHz, $CD_3OD$) δ 7.89 (d, J=2.2 Hz, 1H), 7.74 (dd, J=0.9, 8.4 Hz, 2H), 7.71 (dd, J=2.2, 8.4 Hz, 1H), 7.62 (d, J=8.4 Hz, 1H), 7.37 (dd, J=6.6, 8.4 Hz, 2H), 7.18 (d, J=7.3 Hz, 1H), 4.27 (d, J=15.0 Hz, 1H), 4.11 (d, J=15.0 Hz, 1H), 2.93 (s, 3H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=2.29 min, 90% homogeneity index.

LCMS: Anal. Calcd. for $C_{20}H_{12}Cl_2N_6O$ 426.08; found: 427.07 $(M+H)^+$.

HRMS: Anal. Calcd. for $C_{20}H_{13}Cl_2N_6O$ 427.0842; found: 427.0836 $(M+H)^+$.

Examples 54 and 55

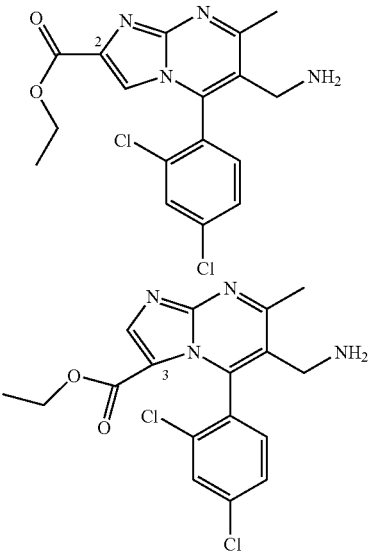

Example 54-55

Step 1. Ethyl imidazo[1,2-a]pyrimidine-2-carboxylate and Ethyl imidazo[1,2-a]pyrimidine-3-carboxylate

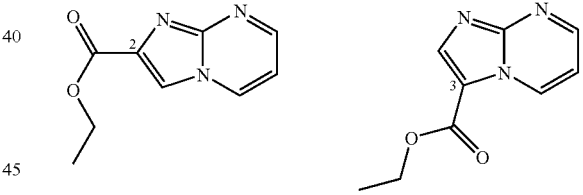

2-Aminopyrimidine (5 g, 52.6 mmol) and bromoethyl pyruvate (90%, 7.35 mL, 52.6 mmol) were dissolved in ethanol (80 mL) and the reaction was heated to 75° C. for 16 h. The reaction was concentrated under reduced pressure and diluted with $CH_2Cl_2$ and sat aq $NaHCO_3$. The organic layer was washed with sat aq $NaHCO_3$ (2×) and the aq layers were extracted with $CH_2Cl_2$ (3×). The combined organic layers were dried over $MgSO_4$ and concentrated under reduced pressure. The resulting brown oil was suspended in cold $CH_2Cl_2$ and filtered. The filter cake was washed with cold $CH_2Cl_2$ to obtain ethyl imidazo[1,2-a]pyrimidine-2-carboxylate (3 g, 30%) as a light yellow oil. The mother liquor contains a mixture of ethyl imidazo[1,2-a]pyrimidine-2-carboxylate and ethyl imidazo[1,2-a]pyrimidine-3-carboxylate (6 g, 60%) in the form of thick, black oil. This black oil was first purified by silica gel chromatography followed by recrystallization from EtOAc to obtain ethyl imidazo[1,2-a]pyrimidine-3-carboxylate (2 g, 20%).

For 2-isomer: $^1H$ NMR (500 MHz, $CDCl_3$) δ 8.69 (dd, J=2.2, 6.6 Hz, 1H), 8.67 (dd, J=2.2, 4.4 Hz, 1H), 8.22 (s, 1H), 7.01 (dd, J=3.9, 6.6 Hz, 1H), 4.46 (q, J=7.2 Hz, 2H), 1.43 (t, J=7.2 Hz, 3H). $^{13}$C NMR (500 MHz, CDCl$_3$) δ 162.8, 152.2, 147.8, 137.7, 134.4, 115.3, 110.0, 61.2, 14.2.

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=0.99 min, 95% homogeneity index.

LCMS: Anal. Calcd. for C$_9$H$_9$N$_3$O$_2$ 191.07 found: 192.13 (M+H)$^+$. For 3-isomer: HPLC Phenomenex LUNA C-18 4.6×50 mm, 0 to 100% B=over 4 minutes, 1 minutes hold time, A=90% water, 10% methanol, 0.1% TFA, B=10% water, 90% methanol, 0.1% TFA, RT=1.39 min, 100% homogeneity index.

LCMS: Anal. Calcd. for C$_9$H$_9$N$_3$O$_2$ 191.07 found: 192.19 (M+H)$^+$.

Example 54-55

Step 2. Ethyl 2-amino-1H-imidazole-4-carboxylate

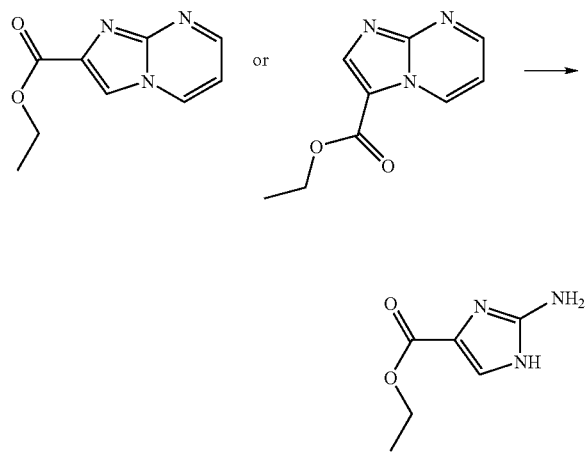

To a stirred solution of ethyl imidazo[1,2-a]pyrimidine-2-carboxylate or ethyl imidazo[1,2-a]pyrimidine-3-carboxylate (1 g, 5.2 mmol) in ethanol (40 mL) was added hydrazine monohydrate (0.28 mL, 5.7 mmol). The reaction was heated to 75° C. for 16 h and was concentrated under reduced pressure. The resulting light yellow solid was suspended in diethyl ether and filtered to collect ethyl 2-amino-1H-imidazole-4-carboxylate (800 mg, 100%) as a white solid.

$^1$H NMR (400 MHz, CD$_3$OD) δ 7.27 (s, 1H), 4.24 (q, J=7.0 Hz, 2H), 1.31 (t, J=7.0 Hz, 3H).

$^{13}$C NMR (500 MHz, CD$_3$OD) δ 165.5, 156.1, 131.8, 125.7, 63.8, 17.3.

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=0.46 min, 100% homogeneity index.

Anal. Calcd for C$_6$H$_9$N$_3$O$_2$: C, 46.44; H, 5.84; N, 27.08. Found: C, 46.17; H, 5.65; N, 27.28.

HRMS: Anal. Calcd. for C$_6$H$_{10}$N$_3$O$_2$ 156.0773 found: 156.0779 (M+H)$^+$.

Example 54-55

Step 3-4. 6-tert-Butyl 2-ethyl 5-(2,4-dichlorophenyl)-7-methyl-5,8-dihydroimidazo[1,2-a]pyrimidine-2,6-dicarboxylate and 6-tert-Butyl 3-ethyl 5-(2,4-dichlorophenyl)-7-methyl-5,8-dihydroimidazo[1,2-a]pyrimidine-3,6-dicarboxylate

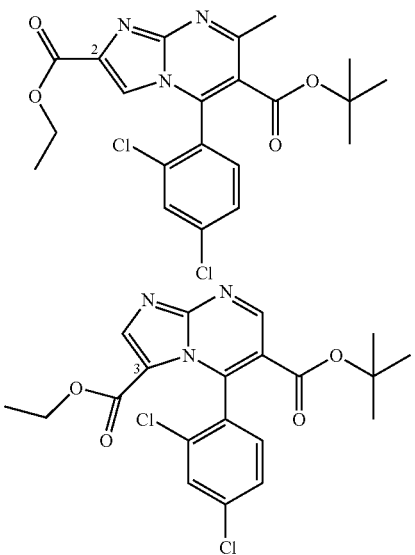

Ethyl 2-amino-1H-imidazole-4-carboxylate (980 mg, 6.8 mmol) and tert-butyl 2-(2,4-dichlorobenzylidene)-3-oxobutanoate (2.03 g, 6.4 mmol) were dissolved in ethanol (15 mL) and the reaction was heated to 75° C. for 16 h. The reaction was concentrated under reduced pressure to obtain a 10:1 mixture (by HPLC) of 6-tert-butyl 2-ethyl 5-(2,4-dichlorophenyl)-7-methyl-5,8-dihydroimidazo[1,2-a]pyrimidine-2,6-dicarboxylate and 6-tert-butyl 3-ethyl 5-(2,4-dichlorophenyl)-7-methyl-5,8-dihydroimidazo[1,2-a]pyrimidine-3,6-dicarboxylate (3.07 g, 100% crude yield) as a yellow foam. A small amount of this mixture (350 mg) was purified by silica gel chromatography to obtain 6-tert-butyl 2-ethyl 5-(2,4-dichlorophenyl)-7-methyl-5,8-dihydroimidazo[1,2-a]pyrimidine-2,6-dicarboxylate (190 mg, 54%) and 6-tert-butyl 3-ethyl 5-(2,4-dichlorophenyl)-7-methyl-5,8-dihydroimidazo[1,2-a]pyrimidine-3,6-dicarboxylate (19 mg, 5.4%) as white solids.

For 2-isomer: $^1$H NMR (400 MHz, CDCl$_3$) δ 10.19 (br s, 1H), 7.43 (d, J=2.2 Hz, 1H), 7.38 (s, 1H), 7.34 (d, J=7.2 Hz, 1H), 7.21 (dd, J=2.2, 7.2 Hz, 1H), 6.67 (s, 1H), 4.29 (m, 2H), 2.57 (s, 3H), 1.34 (t, J=7.0 Hz, 3H), 1.26 (s, 9H).

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=4.13 min, 98% homogeneity index.

LCMS: Anal. Calcd. for C$_{21}$H$_{23}$Cl$_2$N$_3$O$_4$ 451.11 found: 452.24 (M+H)$^+$. For 3-isomer: $^1$H NMR (400 MHz, CDCl$_3$) δ 11.72 (br s, 1H), 7.59 (d, J=8.4 Hz, 1H), 7.50 (br s, 1H), 7.27 (d, J=3.5 Hz, 1H), 7.18 (dd, J=3.0, 8.4 Hz, 1H), 6.91 (s, 1H), 4.16 (m, 2H), 2.44 (s, 3H), 1.41 (s, 9H), 1.26 (t, J=7.0 Hz, 3H).

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=4.24 min, 99% homogeneity index.

LCMS: Anal. Calcd. for $C_{21}H_{23}Cl_2N_3O_4$ 451.11 found: 452.24 $(M+H)^+$.

To a stirred solution of 6-tert-butyl 2-ethyl 5-(2,4-dichlorophenyl)-7-methyl-5,8-dihydroimidazo[1,2-a]pyrimidine-2,6-dicarboxylate (191 mg, 0.42 mmol) in acetone (5 mL) was added $KMnO_4$ (66 mg, 0.42 mmol). After 1 h, the reaction was filtered through celite and concentrated under reduced pressure. The resulting residue was diluted with $CH_2Cl_2$ and extracted with $H_2O$ (2×). The organic layer was dried over $MgSO_4$, concentrated under reduced pressure and recrystallized from EtOAc to obtain 6-tert-butyl 2-ethyl 5-(2,4-dichlorophenyl)-7-methylimidazo[1,2-a]pyrimidine-2,6-dicarboxylate (107 mg, 57%) as white crystals.

To a stirred solution of 6-tert-butyl 3-ethyl 5-(2,4-dichlorophenyl)-7-methyl-5,8-dihydroimidazo[1,2-a]pyrimidine-3,6-dicarboxylate (19 mg, 0.04 mmol) in acetone (2 mL) was added $KMnO_4$ (7 mg, 0.04 mmol). After 1 h, the reaction was filtered through celite and concentrated under reduced pressure. The resulting residue was diluted with $CH_2Cl_2$ and extracted with $H_2O$ (2×). The organic layer was dried over $MgSO_4$, concentrated under reduced pressure and purified by silica gel chromatography to obtain 6-tert-butyl 3-ethyl 5-(2,4-dichlorophenyl)-7-methylimidazo[1,2-a]pyrimidine-2,6-dicarboxylate (14 mg, 74%) as white solid.

For 2-isomer: $^1$H NMR (400 MHz, $CDCl_3$) δ 7.68 (d, J=1.8 Hz, 1H), 7.53 (s, 1H), 7.50 (dd, J=1.8, 7.6 Hz, 1H), 7.35 (d, J=7.6 Hz, 1H), 4.43 (m, 2H), 2.77 (s, 3H), 1.41 (t, J=7.2 Hz, 3H), 1.29 (s, 9H). $^{13}$C NMR (500 MHz, $CDCl_3$) δ 163.7, 162.7, 159.8, 147.0, 141.1, 138.5, 138.2, 134.5, 131.4, 130.3, 128.1, 127.8, 119.0, 114.1, 83.8, 61.4, 27.7, 24.3, 14.3.

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.89 min, 99% homogeneity index.

LCMS: Anal. Calcd. for $C_{21}H_{21}Cl_2N_3O_4$ 449.09 found: 450.11 $(M+H)^+$.

HRMS: Anal. Calcd. for $C_{21}H_{22}Cl_2N_3O_4$ 450.0987 found: 450.0981 $(M+H)^+$.

For 3-isomer: $^1$H NMR (400 MHz, $CDCl_3$) δ 8.38 (s, 1H), 7.41 (d, J=1.7 Hz, 1H), 7.41 (m, 2H), 3.98-4.17 (m, 2H), 2.77 (s, 3H), 1.27 (s, 9H), 1.22 (t, J=7.0 Hz, 3H).

$^{13}$C NMR (400 MHz, $CDCl_3$) δ 164.0, 159.1, 158.3, 150.5, 144.4, 142.4, 137.0, 134.8, 131.7, 129.9, 128.9, 126.9, 121.1, 117.6, 83.9, 61.0, 27.5, 23.5, 14.3.

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.89 min, 99% homogeneity index.

LCMS: Anal. Calcd. for $C_{21}H_{21}Cl_2N_3O_4$ 449.09 found: 450.20 $(M+H)^+$.

The regiochemistry for the 2- and 3-isomers were unequivocally established by single crystal X-ray analysis for both compounds.

Example 54-55

Step 5-7. Ethyl 5-(2,4-dichlorophenyl)-6-(hydroxymethyl)-7-methylimidazo[1,2-a]pyrimidine-2-carboxylate and Ethyl 5-(2,4-dichlorophenyl)-6-(hydroxymethyl)-7-methylimidazo[1,2-a]pyrimidine-3-carboxylate

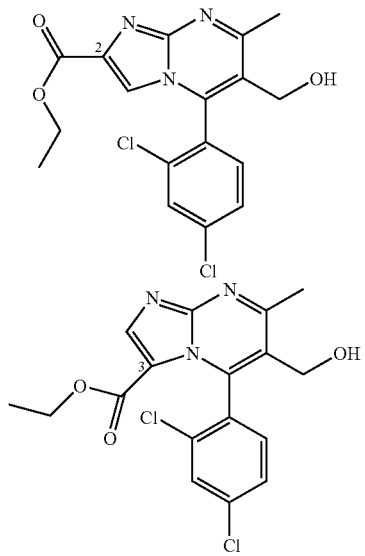

To a stirred solution of 6-tert-butyl 2-ethyl 5-(2,4-dichlorophenyl)-7-methylimidazo[1,2-a]pyrimidine-2,6-dicarboxylate (1.14 g, 2.53 mmol) in $CH_2Cl_2$ (5 mL) was added TFA (5 mL). The reaction was heated to 60° C. for 30 h and concentrated under reduced pressure to obtain 5-(2,4-dichlorophenyl)-2-(ethoxycarbonyl)-7-methylimidazo[1,2-a]pyrimidine-6-carboxylic acid (1 g, 100% crude yield) as a yellow oil.

$^1$H NMR (400 MHz, $CD_3OD$) δ 7.80 (d, J=1.3 Hz, 1H), 7.65 (s, 1H), 7.59 (d, J=1.3 Hz, 2H), 4.36 (q, J=7.0 Hz, 2H), 2.78 (s, 3H), 1.36 (t, J=7.0 Hz, 3H).

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.14 min, 99% homogeneity index.

LCMS: Anal. Calcd. for $C_{17}H_{14}Cl_2N_3O_4$ 393.03 found: 394.01 $(M+H)^+$.

HRMS: Anal. Calcd. for $C_{17}H_{15}Cl_2N_3O_4$ 394.0361 found: 394.0370 $(M+H)^+$.

The structure of the acid was confirmed by single crystal X-ray analysis.

To a stirred solution of crude 5-(2,4-dichlorophenyl)-2-(ethoxycarbonyl)-7-methylimidazo[1,2-a]pyrimidine-6-carboxylic acid (1 g, 2.53 mmol) in THF (10 mL) was added ClCOOEt (0.3 mL, 3.03 mmol) and $Et_3N$ (0.53 mL, 3.8 mmol). After 2 h, the reaction was filtered and concentrated under reduced pressure to obtain the mixed anhydride (1.18 g, 100% crude yield) as brown oil.

To a stirred solution of crude mixed anhydride (1.18 g, 2.53 mmol) in THF (10 mL) at 0° C. was added $NaBH_4$ (144 mg, 3.8 mmol) in $H_2O$ (0.1 mL). After 1 h, the reaction was quenched by 1N HCl and diluted with EtOAc. The organic layer was extracted with 1N HCl, sat aq $NH_4Cl$ and brine before drying over $MgSO_4$. Filtration, concentration under reduced pressure and purification by silica gel chromatography gave ethyl 5-(2,4-dichlorophenyl)-6-(hydroxymethyl)-7-methylimidazo[1,2-a]pyrimidine-2-carboxylate (430 mg, 45% for 3 steps) as a light yellow oil.

$^1$H NMR (400 MHz, CDCl$_3$) δ 7.70 (d, J=7.9 Hz, 1H), 7.63 (d, J=1.8 Hz, 1H), 7.49 (dd, J=1.8, 7.9 Hz, 1H), 7.36 (s, 1H), 4.68 (d, J=12.3 Hz, 1H), 4.36 (m, 3H), 2.75 (s, 3H), 1.35 (t, J=7.0 Hz, 3H). Anal. Calcd for C$_{17}$H$_{15}$Cl$_2$N$_3$O$_3$: C, 53.70; H, 3.97; N, 11.05. Found: C, 52.56; H, 4.01; N, 10.78.

HRMS: Anal. Calcd. for C$_{17}$H$_{16}$Cl$_2$N$_3$O$_3$ 380.0569 found: 380.0571 (M+H)$^+$.

These same procedures were followed to provide ethyl 5-(2,4-dichlorophenyl)-6-(hydroxymethyl)-7-methylimidazo[1,2-a]pyrimidine-3-carboxylate Example 54-55

Step 8-9. Ethyl 6-(azidomethyl)-5-(2,4-dichlorophenyl)-7-methylimidazo[1,2-a]pyrimidine-2-carboxylate and Ethyl 6-(azidomethyl)-5-(2,4-dichlorophenyl)-7-methylimidazo [1,2-a]pyrimidine-3-carboxylate

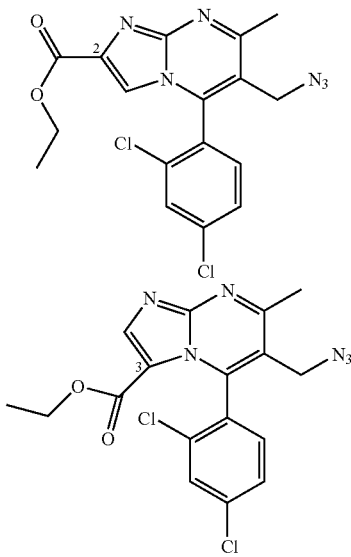

To a stirred solution of ethyl 5-(2,4-dichlorophenyl)-6-(hydroxymethyl)-7-methylimidazo[1,2-a]pyrimidine-2-carboxylate (430 mg, 1.12 mmol) in CH$_2$Cl$_2$ (10 mL) was added MsCl (0.1 mL, 1.35 mmol) and Et$_3$N (0.24 mL, 1.69 mmol). After 10 h, the reaction was concentrated under reduced pressure and diluted with EtOAc. The mixture was extracted with H$_2$O and brine before drying over MgSO$_4$. Filtration and concentration under reduced pressure gave ethyl 6-(chloromethyl)-5-(2,4-dichlorophenyl)-7-methylimidazo[1,2-a]pyrimidine-2-carboxylate (448 mg, 100% crude yield) as a yellow oil.

$^1$H NMR (400 MHz, CDCl$_3$) δ 7.72 (d, J=2.2 Hz, 1H), 7.57 (dd, J=2.2, 8.4 Hz, 1H), 7.46 (d, J=8.4 Hz, 1H), 7.45 (s, 1H), 4.53 (d, J=12.3 Hz, 1H), 4.43 (m, 2H), 4.23 (d, J=12.3 Hz, 1H), 2.86 (s, 3H), 1.40 (t, J=7.5 Hz, 3H).

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.57 min, 99% homogeneity index.

LCMS: Anal. Calcd. for C$_{17}$H$_{14}$Cl$_3$N$_3$O$_2$ 397.02 found: 397.92 (M+H)$^+$.

To a stirred solution of crude ethyl 6-(chloromethyl)-5-(2,4-dichlorophenyl)-7-methylimidazo[1,2-a]pyrimidine-2-carboxylate (448 mg, 1.12 mmol) in DMF (5 mL) was added NaN$_3$ (110 mg, 1.69 mmol). The reaction was heated to 50° C. for 1 h. After cooling, the reaction was diluted with EtOAc and extracted with H$_2$O and brine before drying over MgSO$_4$. Filtration and concentration under reduced pressure gave ethyl 6-(azidomethyl)-5-(2,4-dichlorophenyl)-7-methylimidazo[1,2-a]pyrimidine-2-carboxylate (450 mg, 100% crude yield) as a yellow oil.

$^1$H NMR (400 MHz, CDCl$_3$) δ 7.72 (d, J=2.2 Hz, 1H), 7.59 (dd, J=2.2, 7.2 Hz, 1H), 7.43 (s, 1H), 7.43 (d, J=7.0 Hz, 1H), 4.41 (m, 2H), 4.31 (d, J=14.0 Hz, 1H), 4.18 (d, J=14.0 Hz, 1H), 2.79 (s, 3H), 1.40 (t, J=7.04 Hz, 3H).

$^{13}$C NMR (125 MHz, CDCl$_3$) δ 162.7, 162.3, 147.1, 141.5, 138.6, 137.7, 134.3, 132.0, 130.7, 128.7, 126.5, 116.5, 113.9, 61.2, 48.1, 23.6, 14.2.

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.70 min, 97% homogeneity index.

LCMS: Anal. Calcd. for C$_{17}$H$_{14}$Cl$_2$N$_6$O$_2$ 404.06 found: 405.15 (M+H)$^+$.

These same procedures were followed to prepare ethyl 6-(azidomethyl)-5-(2,4-dichlorophenyl)-7-methylimidazo[1,2-a]pyrimidine-3-carboxylate.

$^1$H NMR (400 MHz, CDCl$_3$) δ 8.33 (s, 1H), 7.59 (d, J=2.2 Hz, 1H), 7.46 (dd, J=2.2, 8.4 Hz, 1H), 7.30 (d, J=8.4 Hz, 1H), 4.33 (d, J=13.6 Hz, 1H), 4.19 (d, J=13.6 Hz, 1H), 4.02 (q, J=7.5 Hz, 2H), 2.82 (s, 3H), 1.22 (t, J=7.5 Hz, 3H).

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.63 min, 97% homogeneity index.

LCMS: Anal. Calcd. for C$_{17}$H$_{14}$Cl$_2$N$_6$O$_2$ 404.06 found: 405.15 (M+H)$^+$.

Example 54-55

Step 10. Ethyl 6-(aminomethyl)-5-(2,4-dichlorophenyl)-7-methylimidazo[1,2-a]pyrimidine-2-carboxylate a nd Ethyl 6-(aminomethyl)-5-(2,4-dichlorophenyl)-7-methylimidazo[1,2-a]lpyrimidine-3-carboxylate

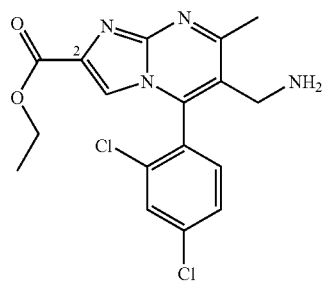

-continued

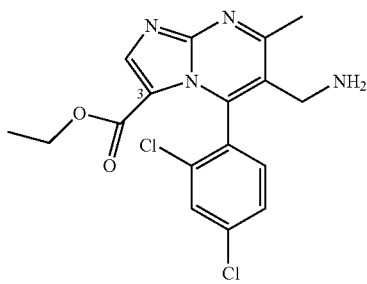

To a stirred solution of ethyl 6-(azidomethyl)-5-(2,4-dichlorophenyl)-7-methylimidazo[1,2-a]pyrimidine-2-carboxylate (450 mg, 1.12 mmol) in THF (10 mL) and H$_2$O (0.5 mL) was added PPh$_3$ polymer bound (3 mmol/g, 750 mg, 2.25 mmol). The reaction was heated to 50° C. for 24 h. The reaction was filtered and concentrated to give crude ethyl 6-(aminomethyl)-5-(2,4-dichlorophenyl)-7-methylimidazo[1,2-a]pyrimidine-2-carboxylate (315 mg, 74% crude yield) as a yellow oil. A part (115 mg) was purified by reverse phase preparatory HPLC (MeOH—H$_2$O-TFA system) to give ethyl 6-(aminomethyl)-5-(2,4-dichlorophenyl)-7-methylimidazo[1,2-a]pyrimidine-2-carboxylate, TFA salt (100 mg) as a white solid.

$^1$H NMR (400 MHz, CD$_3$OD) δ 7.94 (d, J=1.8 Hz, 1H), 7.75 (dd, J=1.8, 8.3 Hz, 1H), 7.64 (s, 1H), 7.63 (d, J=8.3 Hz, 1H), 4.36 (q, J=7.0 Hz, 2H), 4.18 (d, J=14.9 Hz, 1H), 4.02 (d, J=14.9 Hz, 1H), 2.83 (s, 3H), 1.35 (t, J=7.0 Hz, 3H).

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=2.01 min, 97% homogeneity index.

LCMS: Anal. Calcd. for C$_{17}$H$_{16}$Cl$_2$N$_4$O$_2$ 378.07 found: 379.04 (M+H)$^+$.

HRMS: Anal. Calcd. for C$_{17}$H$_{17}$Cl$_2$N$_4$O$_2$ 379.0729 found: 379.0736 (M+H)$^+$.

These same procedures were followed to prepare ethyl 6-(aminomethyl)-5-(2,4-dichlorophenyl)-7-methylimidazo[1,2-a]pyrimidine-3-carboxylate (Example 55).

$^1$H NMR (400 MHz, CD$_3$OD) δ 8.35 (s, 1H), 7.79 (d, J=2.2 Hz, 1H), 7.60 (dd, J=2.2, 8.4 Hz, 1H), 7.49 (d, J=8.4 Hz, 1H), 4.20 (d, J=15.0 Hz, 1H), 4.01 (d, J=15.0 Hz, 1H), 4.01 (q, J=7.0 Hz, 2H), 2.86 (s, 3H), 1.19 (t, J=7.0 Hz, 3H).

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=1.90 min, 99% homogeneity index.

LCMS: Anal. Calcd. for C$_{17}$H$_{16}$Cl$_2$N$_4$O$_2$ 378.07; found: 379.22 (M+H)$^+$.

HRMS: Anal. Calcd. for C$_{17}$H$_{17}$Cl$_2$N$_4$O$_2$ 379.0729; found: 379.0736 (M+H)$^+$.

Example 56 and 57

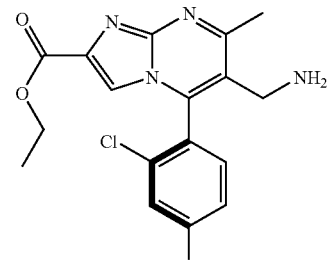

(−)-isomer

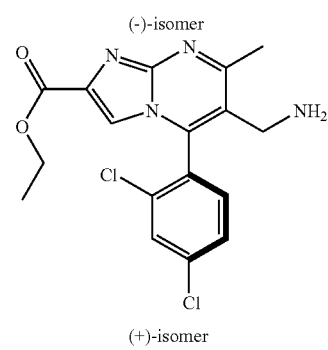

(+)-isomer 6-(Aminomethyl)-5-(2,4-dichlorophenyl)-7-methylimidazo[1,2-a]pyrimidine-2-carboxylate exist as a 1:1 mixture of two stable atropisomers. These two isomers can be separated by chiral HPLC Chiralcel OJ 4.6×250, 15% B isocratic over 20 minutes, A=heptane, B=MeOH-EtOH (1:1) with 0.1% DEA. For fast eluting isomer (the − isomer): t$_R$=10.6 min. For slower eluting isomer (the + isomer): t$_R$=12.7 min.

50 mg of 6-(aminomethyl)-5-(2,4-dichlorophenyl)-7-methylimidazo[1,2-a]pyrimidine-2-carboxylate were separated on a chiral OJ column using the above conditions to obtain (−)-6-(aminomethyl)-5-(2,4-dichlorophenyl)-7-methylimidazo[1,2-a]pyrimidine-2-carboxylate (15 mg, 86.5% ee) [α]$^{24.6}_D$−25.8° (c 3.15, MeOH) and (+)-6-(aminomethyl)-5-(2,4-dichlorophenyl)-7-methylimidazo[1,2-a]pyrimidine-2-carboxylate (17 mg, 88.5% ee) [α]$^{24.9}_D$+24.9° (c 3.11, MeOH).

The absolute stereochemistry was determined by single crystal X-ray analysis for an intermediate five steps before.

Example 58

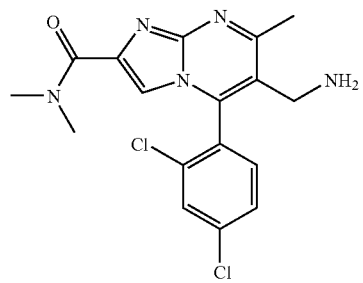

Example 58

Step 1-2. 6-((tert-Butoxycarbonyl)methyl)-5-(2,4-dichlorophenyl)-7-methylimidazo[1,2-a]pyrimidine-2-carboxylic acid

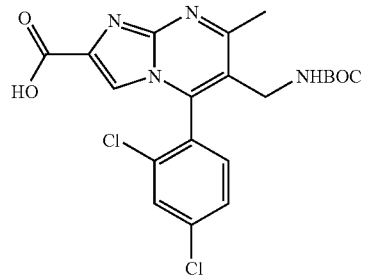

To a stirred solution of ethyl 6-(aminomethyl)-5-(2,4-dichlorophenyl)-7-methylimidazo[1,2-a]pyrimidine-2-carboxylate (Example 54, Step 10, 200 mg, 0.53 mmol) in THF (5 mL) at room temperature was added (BOC)$_2$O (1.0 M in THF, 1.05 mL, 1.05 mmol) and Et$_3$N (0.37 mL, 2.65 mmol). After 2 h, the reaction was concentrated under reduced pressure and diluted with EtOAc. The organic layer was washed with NH$_4$Cl and brine prior to drying over anhydrous MgSO$_4$. Filtration, concentration under reduced pressure and purification by silica gel chromatography gave ethyl 6-((tert-butoxycarbonyl)methyl)-5-(2,4-dichlorophenyl)-7-methylimidazo[1,2-a]pyrimidine-2-carboxylate (100 mg, 40%) as a white solid.

$^1$H NMR (400 MHz, CDCl$_3$) δ 7.68 (d, J=2.2 Hz, 1H), 7.57 (dd, J=2.2, 8.3 Hz, 1H), 7.51 (d, J=8.3 Hz, 1H), 7.36 (s, 1H), 4.74 (br s, 1H), 4.39 (q, J=7.0 Hz, 2H), 4.19 (m, 2H), 2.77 (s, 3H), 1.40 (s, 9H), 1.26 (t, J=7.0 Hz, 3H).

To a stirred solution of ethyl 6-((tert-butoxycarbonyl)methyl)-5-(2,4-dichlorophenyl)-7-methylimidazo[1,2-a]pyrimidine-2-carboxylate (100 mg, 021 mmol) in THF (2 mL) and H$_2$O (0.5 mL) at room temperature was added LiOH.H$_2$O (18 mg, 0.42 mmol). After 16 h, the reaction was concentrated under reduced pressure and diluted with EtOAc. The organic layer was washed with 1N HCl and brine prior to drying over anhydrous MgSO$_4$. Filtration, concentration under reduced pressure gave 6-((tert-butoxycarbonyl)methyl)-5-(2,4-dichlorophenyl)-7-methylimidazo[1,2-a]pyrimidine-2-carboxylic acid (95 mg, 100%) as a light yellow solid.

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.16 min, 95% homogeneity index.

LCMS: Anal. Calcd. for C$_{20}$H$_{21}$Cl$_2$N$_4$O$_4$ 451.09; found: 451.05 (M+H)$^+$.

Example 58

Step 1-2. 6-(Aminomethyl)-5-(2,4-dichlorophenyl)-N,N,7-trimethylimidazo[1,2-a]pyrimidine-2-carboxamide

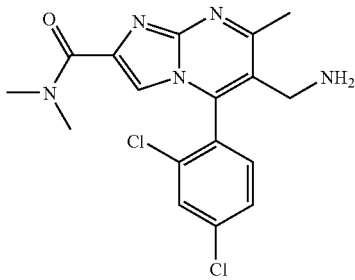

To a stirred solution of 6-((tert-butoxycarbonyl)methyl)-5-(2,4-dichlorophenyl)-7-methylimidazo[1,2-a]pyrimidine-2-carboxylic acid (20 mg, 0.04 mmol) in THF (2 mL) was added Me$_2$NH (2 N in THF, 0.04 mL, 0.08 mmol), HOAt (9 mg, 0.07 mmol), EDC (13 mg, 0.07 mmol) and $^i$Pr$_2$NEt (15 µL, 0.09 mmol). The reaction was kept at room temperature for 2 h and was concentrated under reduced pressure. The residue was diluted with EtOAc and the organic layer was washed with 1N HCl, 1N NaOH and brine prior to drying over anhydrous MgSO$_4$. Filtration and concentration under reduced pressure afforded tert-butyl (5-(2,4-dichlorophenyl)-2-(dimethylcarbamoyl)-7-methylimidazo[1,2-a]pyrimidin-6-yl)methylcarbamate (20 mg, 100% crude yield).

The same product can be prepared by an alternative method as described below:

To a stirred solution of 6-((tert-butoxycarbonyl)methyl)-5-(2,4-dichlorophenyl)-7-methylimidazo[1,2-a]pyrimidine-2-carboxylic acid (20 mg, 0.04 mmol) in THF (2 mL) was added (COCl)$_2$ (2.0 M in CH$_2$Cl$_2$, 0.04 mL, 0.08 mmol) and DMF (1 µL). After 1 h, the reaction was concentrated under reduced pressure and dissolved in THF (2 mL). To this solution was added Me$_2$NH (2 N in THF, 0.04 mL, 0.08 mmol) and Et$_3$N (0.03 mL, 0.2 mmol). After 3 h, the reaction was concentrated under reduced pressure. The residue was diluted with EtOAc and the organic layer was washed with 1N HCl, 1N NaOH and brine prior to drying over anhydrous MgSO$_4$. Filtration and concentration under reduced pressure afforded tert-butyl (5-(2,4-dichlorophenyl)-2-(dimethylcarbamoyl)-7-methylimidazo[1,2-a]pyrimidin-6-yl)methylcarbamate (20 mg, 100% crude yield).

To a stirred solution of tert-butyl (5-(2,4-dichlorophenyl)-2-(dimethylcarbamoyl)-7-methylimidazo[1,2-a]pyrimidin-6-yl)methylcarbamate (20 mg crude) in CH$_2$Cl$_2$ (2 mL) was added TFA (0.1 mL). After 2 hr, the reaction was concentrated under reduced pressure and purified by revere phase preparative HPLC to obtain 6-(aminomethyl)-5-(2,4-dichlorophenyl)-N,N,7-trimethylimidazo[1,2-a]pyrimidine-2-carboxamide, TFA salt (7 mg, 33%) as a white solid.

$^1$H NMR (400 MHz, CD$_3$OD) δ 7.94 (d, J=2.2 Hz, 1H), 7.74 (dd, J=2.2, 7.9 Hz, 1H), 7.59 (d, J=7.9 Hz, 1H), 7.46 (s, 1H), 4.16 (d, J=14.9 Hz, 1H), 4.02 (d, J=14.9 Hz, 1H), 3.37 (s, 3H), 3.10 (s, 3H), 2.82 (s, 3H).

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=2.19 min, 97% homogeneity index.

LCMS: Anal. Calcd. for $C_{17}H_{18}Cl_2N_5O$ 378.09; found: 378.03 (M+H)$^+$.

HRMS: Anal. Calcd. for $C_{17}H_{18}Cl_2N_5O$ 378.0888; found: 378.0900 (M+H)$^+$.

Examples 59 to 142

Using the same methods for preparation of Example 58, the following compounds were prepared as TFA or di-TFA salts:

Example 59 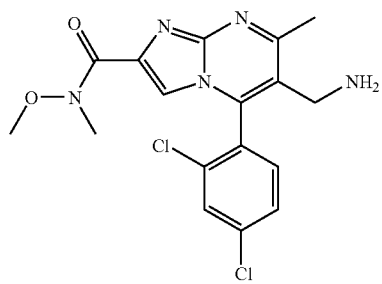

$t_R$ = 2.24 min (96%)
LCMS: Anal. Calcd. for $C_{17}H_{17}Cl_2N_5O_2$ 393.08; found: 393.98 (M + H)$^+$
HRMS: Anal. Calcd. for $C_{17}H_{18}Cl_2N_5O_2$ 394.0838; found: 394.0847 (M + H)$^+$ Example 60 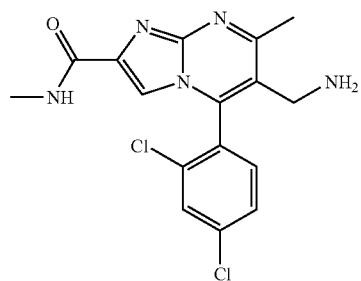

$t_R$ = 2.14 min (95%)
LCMS: Anal. Calcd. for $C_{16}H_{15}Cl_2N_5O$ 363.07; found: 363.97 (M + H)$^+$
HRMS: Anal. Calcd. for $C_{16}H_{16}Cl_2N_5O$ 364.0732; found: 364.0734 (M + H)$^+$ Example 61 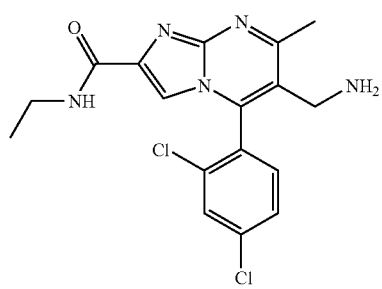

$t_R$ = 2.47 (100%)
LCMS: Anal. Calcd. for $C_{17}H_{17}Cl_2N_5O$ 377.08; found: 378.02 (M + H)$^+$
HRMS: Anal. Calcd. for $C_{17}H_{18}Cl_2N_5O$ 378.0888; found: 378.0884 (M + H)$^+$ Example 62 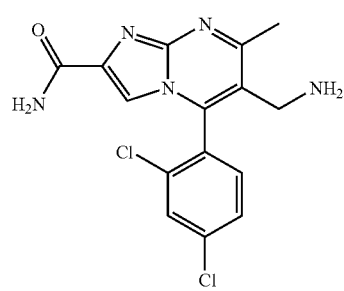

$t_R$ = 1.15 min (98%)
LCMS: Anal. Calcd. for $C_{15}H_{13}Cl_2N_5O$ 349.05; found: 350.00 (M + H)$^+$
HRMS: Anal. Calcd. for $C_{15}H_{14}Cl_2N_5O$ 350.0575; found: 350.0565 (M + H)$^+$ Example 63 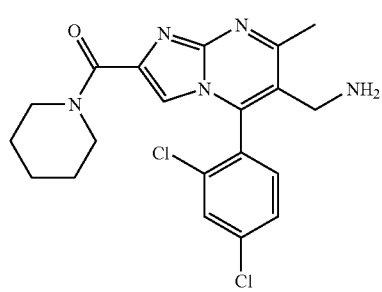

$t_R$ = 2.07 min (98%)
LCMS: Anal. Calcd. for $C_{20}H_{21}Cl_2N_5O$ 417.11; found: 418.07 (M + H)$^+$
HRMS: Anal. Calcd. for $C_{20}H_{22}Cl_2N_5O$ 418.1201; found: 418.1208 (M + H)$^+$ -continued Example 64 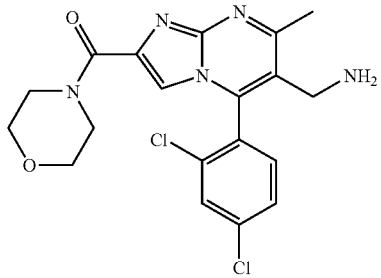

$t_R$ = 1.52 min (99%)
LCMS: Anal. Calcd. for $C_{19}H_{19}Cl_2N_5O_2$
419.09; found: 420.06 (M + H)$^+$
HRMS: Anal. Calcd. for $C_{19}H_{20}Cl_2N_5O_2$
420.0994; found: 420.1006 (M + H)$^+$ Example 65 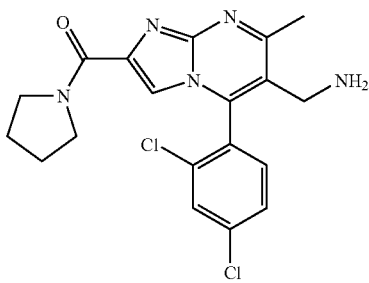

$t_R$ = 1.80 (100%)
LCMS: Anal. Calcd. for $C_{19}H_{19}Cl_2N_5O$
403.10; found: 404.05 (M + H)$^+$
HRMS: Anal. Calcd. for $C_{19}H_{20}Cl_2N_5O$
404.1045; found: 404.1026 (M + H)$^+$ Example 66 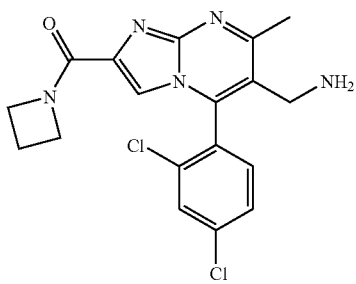

$t_R$ = 1.60 min (100%)
LCMS: Anal. Calcd. for $C_{18}H_{17}Cl_2N_5O$
389.08; found: 390.02 (M + H)$^+$
HRMS: Anal. Calcd. for $C_{18}H_{18}Cl_2N_5O$
390.0888; found: 390.0882 (M + H)$^+$ Example 67 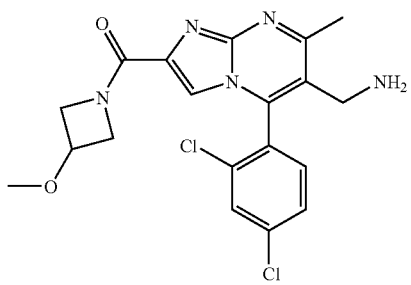

$t_R$ = 1.64 min (100%)
LCMS: Anal. Calcd. for $C_{19}H_{19}Cl_2N_5O_2$
419.09; found: 420.07 (M + H)$^+$
HRMS: Anal. Calcd. for $C_{19}H_{20}Cl_2N_5O_2$
420.0994; found: 420.1006 (M + H)$^+$ Example 68 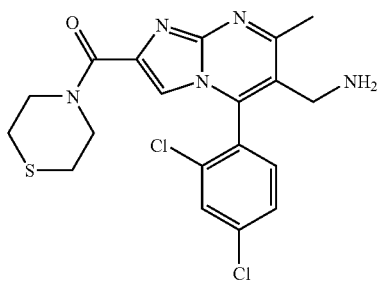

$t_R$ = 2.76 min (97%)
LCMS: Anal. Calcd. for $C_{19}H_{19}Cl_2N_5OS$
435.07; found: 436.04 (M + H)$^+$
HRMS: Anal. Calcd. for $C_{19}H_{20}Cl_2N_5OS$
436.0766; found: 436.0774 (M + H)$^+$ -continued

| Example 69 | 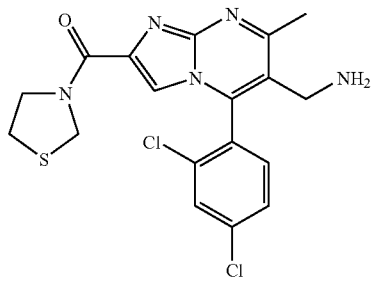 | $t_R$ = 1.90 min (96%)<br>LCMS: Anal. Calcd. for $C_{18}H_{17}Cl_2N_5OS$ 421.05; found: 422.02 $(M + H)^+$<br>HRMS: Anal. Calcd. for $C_{18}H_{18}Cl_2N_5OS$ 422.0609; found: 422.0629 $(M + H)^+$ |
|---|---|---|
| Example 70 | 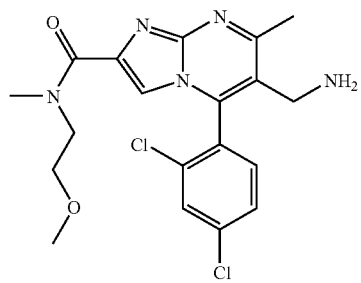 | $t_R$ = 1.59 min (99%)<br>LCMS: Anal. Calcd. for $C_{19}H_{21}Cl_2N_5O_2$ 421.11; found: 422.07 $(M + H)^+$<br>HRMS: Anal. Calcd. for $C_{19}H_{22}Cl_2N_5O_2$ 422.1151; found: 422.1159 $(M + H)^+$ |
| Example 71 | 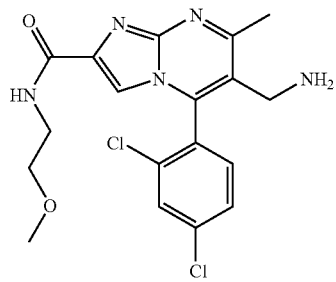 | $t_R$ = 1.61 min (100%)<br>LCMS: Anal. Calcd. for $C_{18}H_{19}Cl_2N_5O_2$ 407.09; found: 408.06 $(M + H)^+$<br>HRMS: Anal. Calcd. for $C_{18}H_{19}Cl_2N_5O_2$ 408.0994; found: 408.0999 $(M + H)^+$ |
| Example 72 | 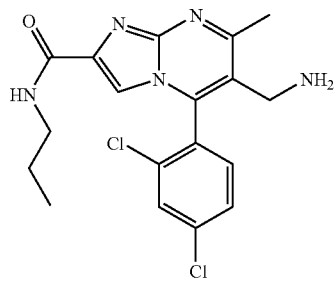 | $t_R$ = 2.83 min (97%)<br>LCMS: Anal. Calcd. for $C_{18}H_{19}Cl_2N_5O$ 391.10 found: 392.10 $(M + H)^+$ |
| Example 73 | 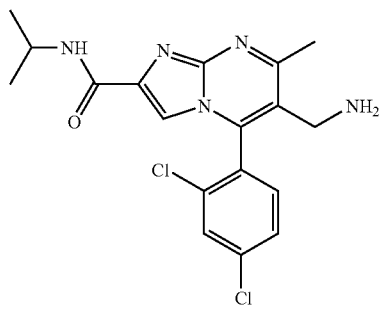 | $t_R$ = 2.81 min (95%)<br>LCMS: Anal. Calcd. for $C_{18}H_{19}Cl_2N_5O$ 391.10 found: 392.10 $(M + H)^+$ |

-continued
| Example 74 | 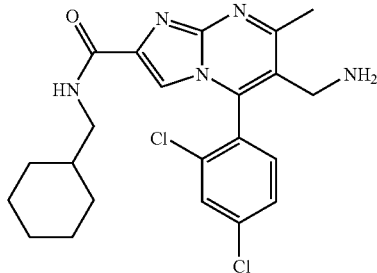 | $t_R$ = 3.56 min (95%)<br>LCMS: Anal. Calcd. for $C_{22}H_{25}Cl_2N_5O$<br>445.14 found: 446.20 $(M + H)^+$ |
| --- | --- | --- |
| Example 75 | 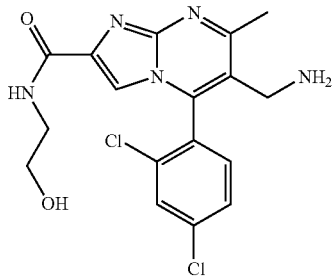 | $t_R$ = 2.20 min (95%)<br>LCMS: Anal. Calcd. for $C_{17}H_{17}Cl_2N_5O_2$<br>393.08 found: 394.10 $(M + H)^+$ |
| Example 76 | 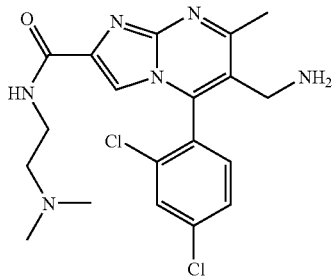 | $t_R$ = 2.16 min (98%)<br>LCMS: Anal. Calcd. for $C_{19}H_{22}Cl_2N_6O$<br>420.12 found: 421.10 $(M + H)^+$ |
| Example 77 | 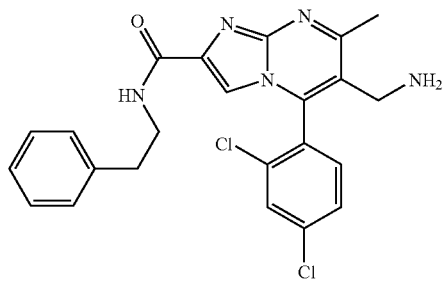 | $t_R$ = 3.29 (94%)<br>LCMS: Anal. Calcd. for $C_{23}H_{21}Cl_2N_5O$<br>453.11 found: 454.10 $(M + H)^+$ |
| Example 78 | 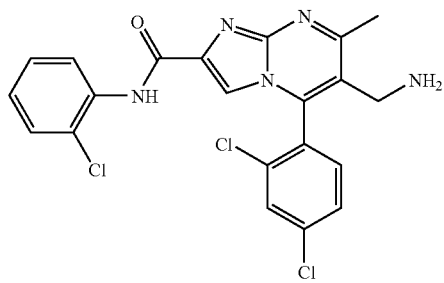 | $t_R$ = 3.61 min (90%)<br>LCMS: Anal. Calcd. for $C_{21}H_{16}C_{13}N_5O$<br>459.04 found: 460.00 $(M + H)^+$ |

-continued
| Example 79 | 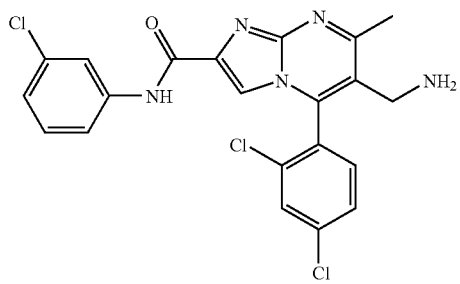 | $t_R$ = 3.66 min (100%)<br>LCMS: Anal. Calcd. for $C_{21}H_{16}Cl_3N_5O$<br>459.04 found: 460.10 $(M + H)^+$ |
|---|---|---|
| Example 80 | 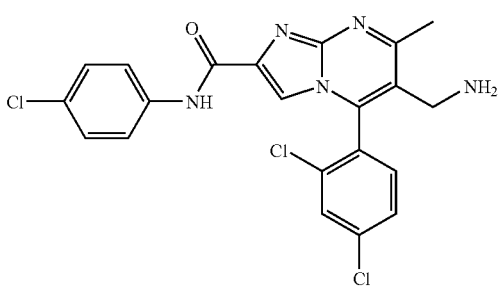 | $t_R$ = 3.64 min (100%)<br>LCMS: Anal. Calcd. for $C_{21}H_{16}Cl_3N_5O$<br>459.04 found: 460.10 $(M + H)^+$ |
| Example 81 | 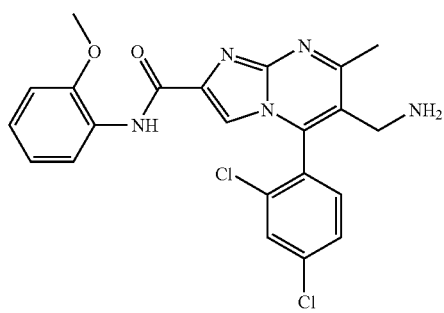 | $t_R$ = 3.48 min (100%)<br>LCMS: Anal. Calcd. for $C_{22}H_{19}Cl_2N_5O_2$<br>455.09 found: 456.10 $(M + H)^+$ |
| Example 82 | 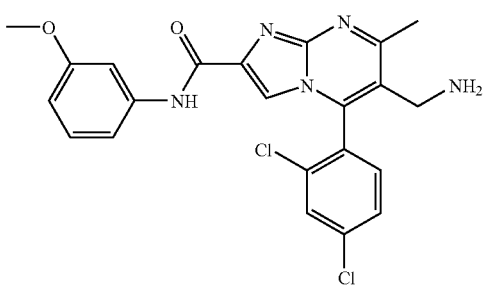 | $t_R$ = 3.33 min (96%)<br>LCMS: Anal. Calcd. for $C_{22}H_{19}Cl_2N_5O_2$<br>455.09 found: 456.10 $(M + H)^+$ |
| Example 83 | 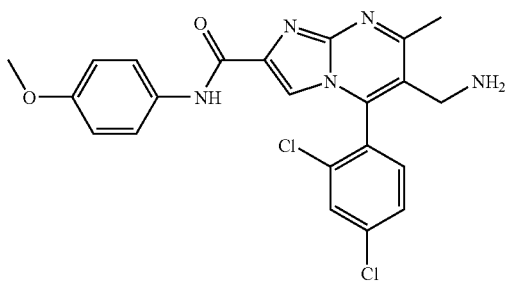 | $t_R$ = 3.25 min (97%)<br>LCMS: Anal. Calcd. for $C_{22}H_{19}Cl_2N_5O_2$<br>455.09 found: 456.10 $(M + H)^+$ |

| | | |
|---|---|---|
| Example 84 | 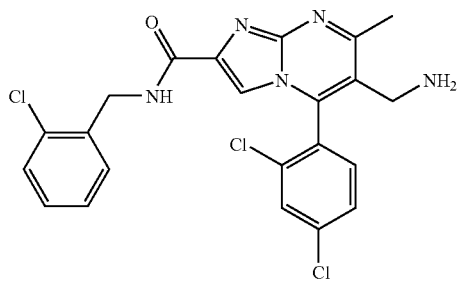 | $t_R$ = 3.36 min (95%)<br>LCMS: Anal. Calcd. for $C_{22}H_{18}Cl_3N_5O$<br>473.06 found: 474.10 $(M + H)^+$ |
| Example 85 | 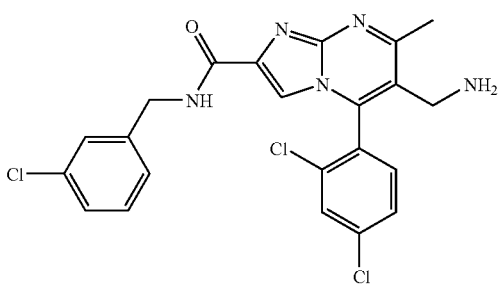 | $t_R$ = 3.42 min (100%)<br>LCMS: Anal. Calcd. for $C_{22}H_{18}Cl_3N_5O$<br>473.06 found: 474.10 $(M + H)^+$ |
| Example 86 | 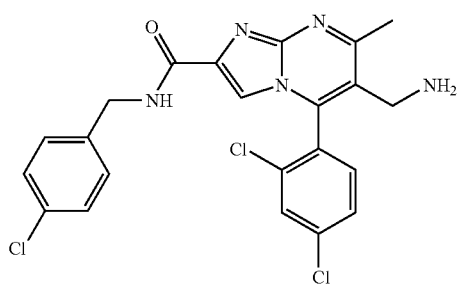 | $t_R$ = 3.42 min (100%)<br>LCMS: Anal. Calcd. for $C_{22}H_{18}Cl_3N_5O$<br>473.06 found: 474.10 $(M + H)^+$ |
| Example 87 | 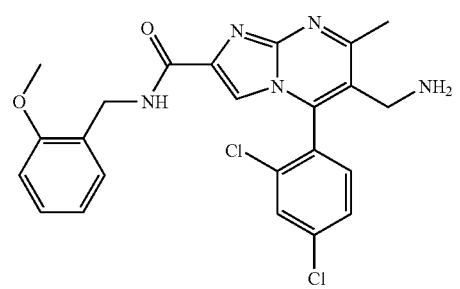 | $t_R$ = 3.24 min (100%)<br>LCMS: Anal. Calcd. for $C_{23}H_{21}Cl_2N_5O_2$<br>469.11 found: 470.10 $(M + H)^+$ |
| Example 88 | 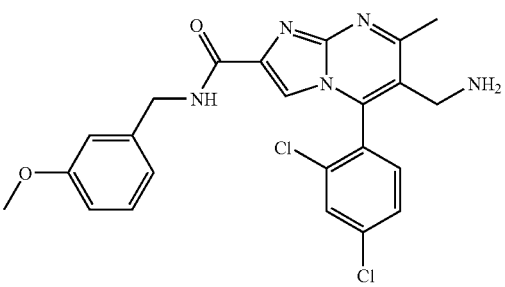 | $t_R$ = 3.15 min (100%)<br>LCMS: Anal. Calcd. for $C_{23}H_{21}Cl_2N_5O_2$<br>469.11 found: 470.10 $(M + H)^+$ |

-continued
Example 89 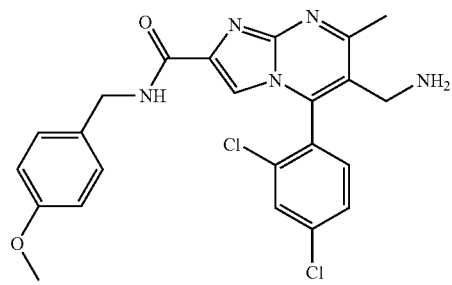
$t_R$ = 3.12 min (100%)
LCMS: Anal. Calcd. for $C_{23}H_{21}Cl_2N_5O_2$
469.11 found: 470.10 $(M + H)^+$
Example 90 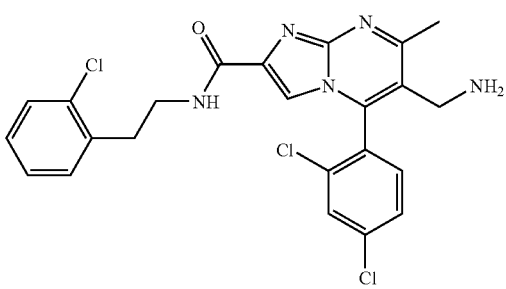
$t_R$ = 3.48 min (98%)
LCMS: Anal. Calcd. for $C_{23}H_{20}Cl_3N_5O$
487.07 found: 488.10 $(M + H)^+$
Example 91 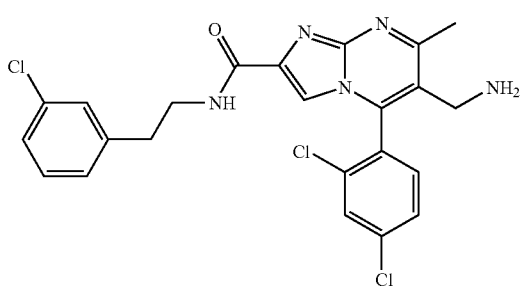
$t_R$ = 3.52 min (100%)
LCMS: Anal. Calcd. for $C_{23}H_{20}Cl_3N_5O$
487.07 found: 488.10 $(M + H)^+$
Example 92 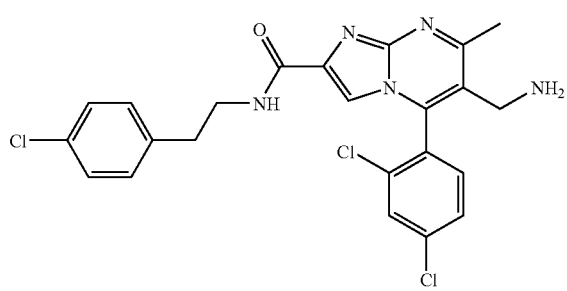
$t_R$ = 3.53 min (98%)
LCMS: Anal. Calcd. for $C_{23}H_{20}Cl_3N_5O$
487.07 found: 488.10 $(M + H)^+$
Example 93 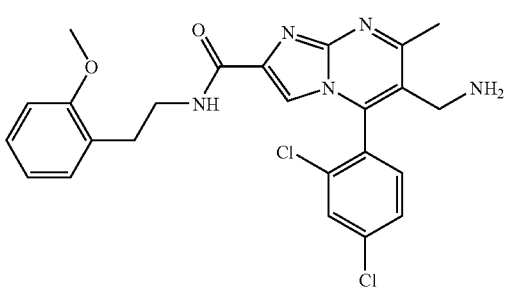
$t_R$ = 3.36 min (94%)
LCMS: Anal. Calcd. for $C_{24}H_{23}Cl_2N_5O_2$
483.12 found: 484.10 $(M + H)^+$ -continued
Example 94 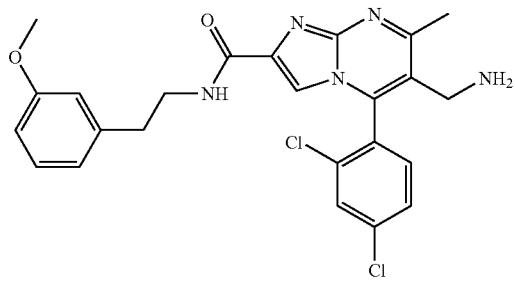 $t_R$ = 3.27 min (97%)
LCMS: Anal. Calcd. for $C_{24}H_{23}Cl_2N_5O_2$
483.12 found: 484.10 $(M + H)^+$
Example 95 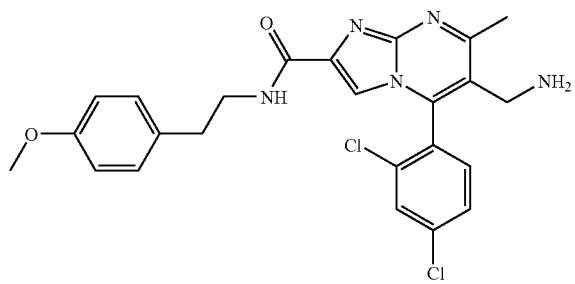 $t_R$ = 3.25 min (100%)
LCMS: Anal. Calcd. for $C_{24}H_{23}Cl_2N_5O_2$
483.12 found: 484.10 $(M + H)^+$
Example 96 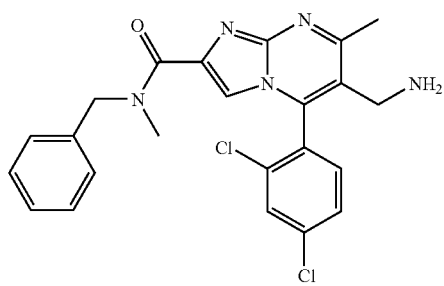 $t_R$ = 3.18 min (97%)
LCMS: Anal. Calcd. for $C_{23}H_{21}Cl_2N_5O$
453.11 found: 454.10 $(M + H)^+$
Example 97 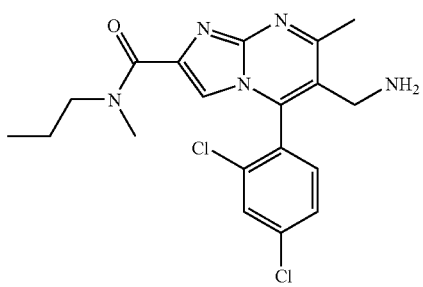 $t_R$ = 2.87 min (95%)
LCMS: Anal. Calcd. for $C_{19}H_{21}Cl_2N_5O$
405.11 found: 406.10 $(M + H)^+$
Example 98 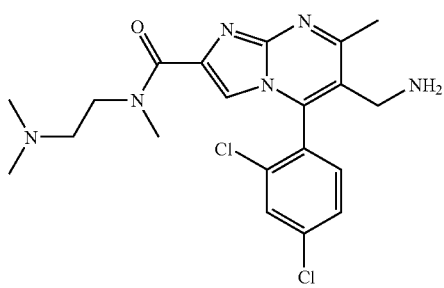 $t_R$ = 2.09 min (98%)
LCMS: Anal. Calcd. for $C_{20}H_{24}Cl_2N_6O$
434.14 found: 435.10 $(M + H)^+$

| | | |
|---|---|---|
| Example 99 | 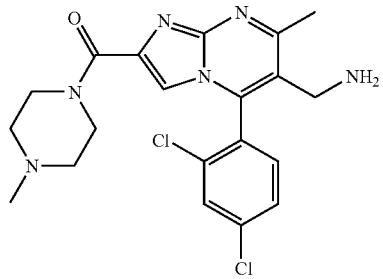 | $t_R$ = 2.42 min (100%)<br>LCMS: Anal. Calcd. for $C_{20}H_{22}Cl_2N_6O$<br>432.12 found: 433.10 $(M + H)^+$ |
| Example 100 | 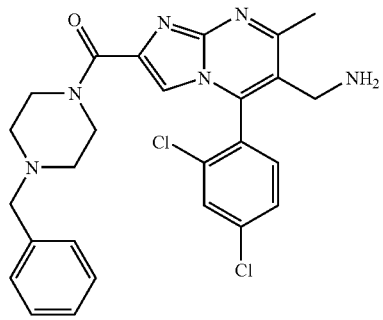 | $t_R$ = 3.36 min (98%)<br>LCMS: Anal. Calcd. for $C_{26}H_{26}Cl_2N_6O$<br>508.15 found: 509.20 $(M + H)^+$ |
| Example 101 | 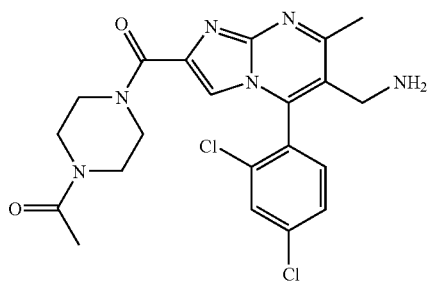 | $t_R$ = 2.28 min (98%)<br>LCMS: Anal. Calcd. for $C_{21}H_{22}Cl_2N_6O_2$<br>460.12 found: 461.10 $(M + H)^+$ |
| Example 102 | 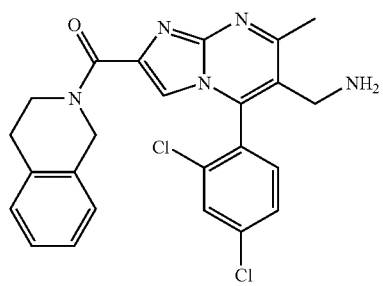 | $t_R$ = 3.36 min (100%)<br>LCMS: Anal. Calcd. for $C_{24}H_{21}Cl_2N_5O$<br>465.11 found: 466.10 $(M + H)^+$ |
| Example 103 | 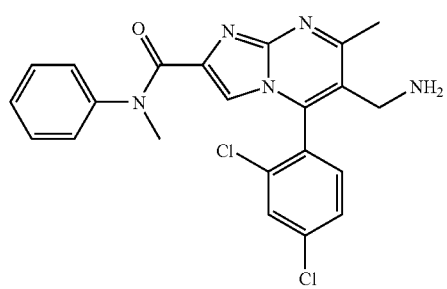 | $t_R$ = 2.86 min (90%)<br>LCMS: Anal Calcd. for $C_{22}H_{19}Cl_2N_5O$<br>439.10 found: 440.10 $(M + H)^+$ |

-continued
Example 104 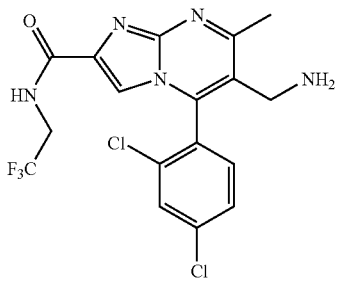 $t_R$ = 2.86 min (95%)
LCMS: Anal. Calcd. for $C_{17}H_{14}Cl_2F_3N_5O$
431.05 found: 432.10 $(M + H)^+$
Example 105 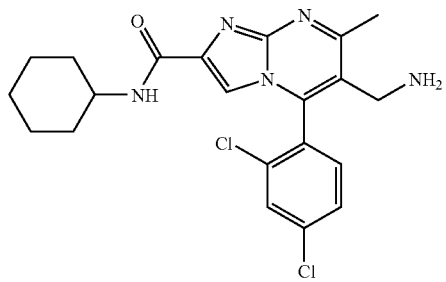 $t_R$ = 3.34 min (98%)
LCMS: Anal. Calcd. for $C_{21}H_{23}Cl_2N_5O$
431.13 found: 432.10 $(M + H)^+$
Example 106 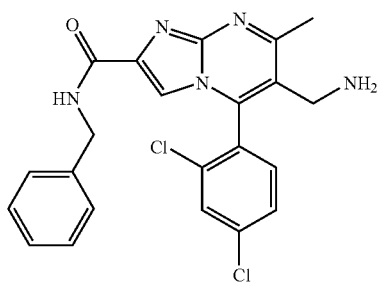 $t_R$ = 4.14 min (97%)
LCMS: Anal. Calcd. for $C_{22}H_{19}Cl_2N_5O$
439.10 found: 440.10 $(M + H)^+$
Example 107 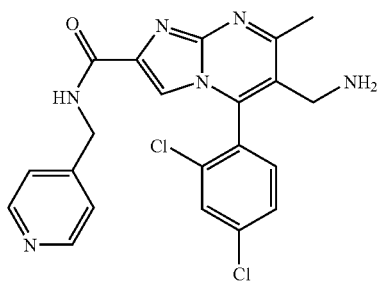 $t_R$ = 2.46 min (98%)
LCMS: Anal. Calcd. for $C_{21}H_{18}Cl_2N_6O$
440.09 found: 441.10 $(M + H)^+$
Example 108 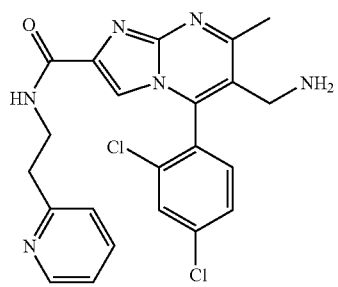 $t_R$ = 2.75 min (96%)
LCMS: Anal. Calcd. for $C_{22}H_{20}Cl_2N_6O$
454.11 found: 455.10 $(M + H)^+$

| | | |
|---|---|---|
| Example 109 | 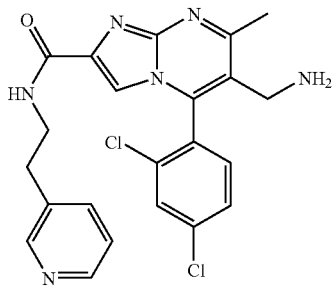 | $t_R$ = 2.70 min (98%)<br>LCMS: Anal. Calcd. for $C_{22}H_{20}Cl_2N_6O$<br>454.11 found: 455.10 $(M + H)^+$ |
| Example 110 | 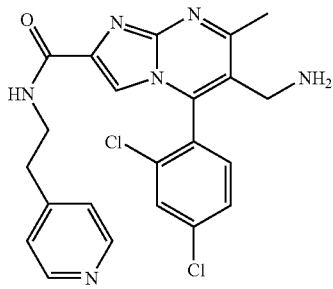 | $t_R$ = 2.68 min (98%)<br>LCMS: Anal. Calcd. for $C_{22}H_{20}Cl_2N_6O$<br>454.11 found: 455.10 $(M + H)^+$ |
| Example 111 | 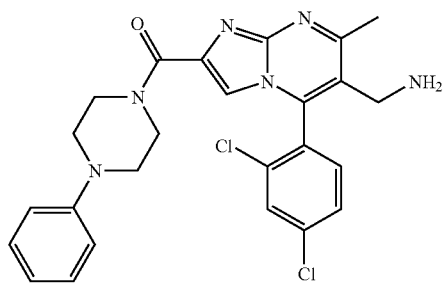 | $t_R$ = 3.36 min (96%)<br>LCMS: Anal. Calcd. for $C_{25}H_{24}Cl_2N_6O$<br>494.14 found: 495.10 $(M + H)^+$ |
| Example 112 | 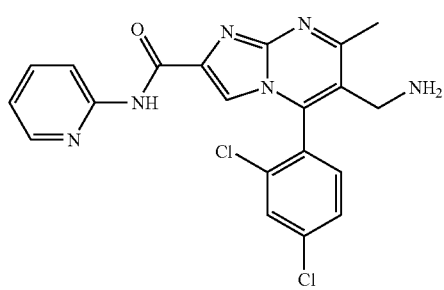 | $t_R$ = 3.11 min (95%)<br>LCMS: Anal. Calcd. for $C_{20}H_{16}Cl_2N_6O$<br>426.08 found: 427.10 $(M + H)^+$ |
| Example 113 | 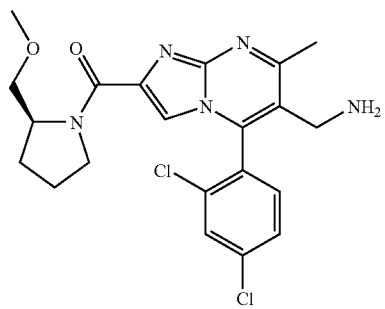 | $t_R$ = 2.20 min (100%)<br>LCMS: Anal. Calcd. for $C_{21}H_{23}Cl_2N_5O_2$<br>447.12 found: 448.10 $(M + H)^+$ |

-continued

| | | |
|---|---|---|
| Example 114 | 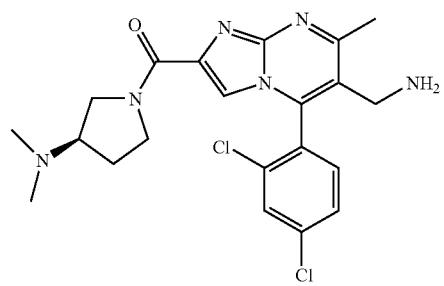 | $t_R$ = 1.16 min (100%)<br>LCMS: Anal. Calcd. for $C_{21}H_{24}Cl_2N_6O$<br>446.14 found: 447.10 $(M + H)^+$ |
| Example 115 | 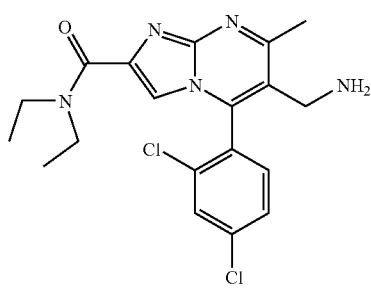 | $t_R$ = 2.24 min (100%)<br>LCMS: Anal. Calcd. for $C_{19}H_{21}Cl_2N_5O$<br>405.11 found: 406.10 $(M + H)^+$ |
| Example 116 | 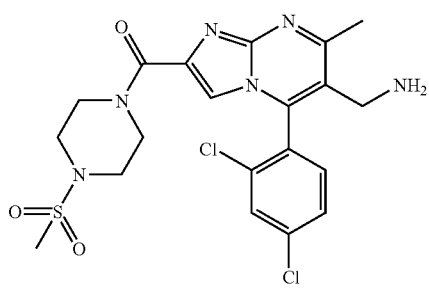 | $t_R$ = 1.79 min (97%)<br>LCMS: Anal. Calcd. for $C_{20}H_{22}Cl_2N_6O_3S$<br>496.09 found: 497.10 $(M + H)^+$ |
| Example 117 | 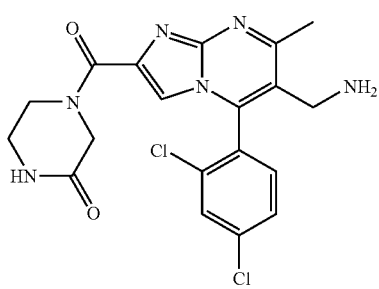 | $t_R$ = 1.43 min (94%)<br>LCMS: Anal. Calcd. for $C_{19}H_{18}Cl_2N_6O_2$<br>432.09 found: 433.00 $(M + H)^+$ |
| Example 118 | 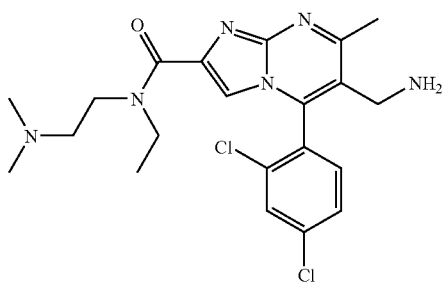 | $t_R$ = 1.43 min (93%)<br>LCMS: Anal. Calcd. for $C_{21}H_{26}Cl_2N_6O$<br>448.15 found: 449.10 $(M + H)^+$ |

-continued
| | | |
|---|---|---|
| Example 119 | 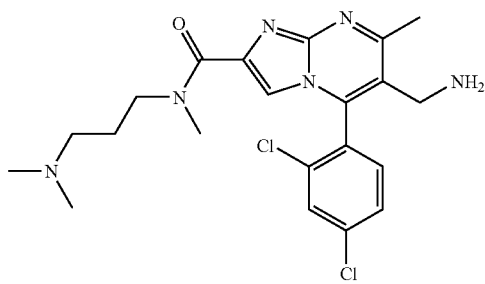 | $t_R$ = 1.34 min (95%)<br>LCMS: Anal. Calcd. for $C_{21}H_{26}Cl_2N_6O$<br>448.15 found: 449.10 $(M + H)^+$ |
| Example 120 | 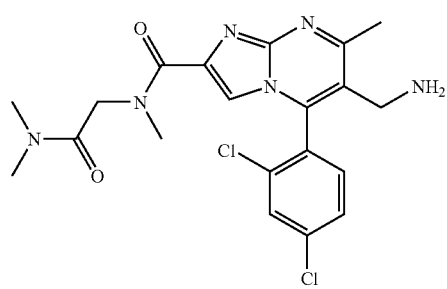 | $t_R$ = 1.55 min (93%)<br>LCMS: Anal. Calcd. for $C_{20}H_{22}Cl_2N_6O_2$<br>448.12 found: 449.14 $(M + H)^+$ |
| Example 121 | 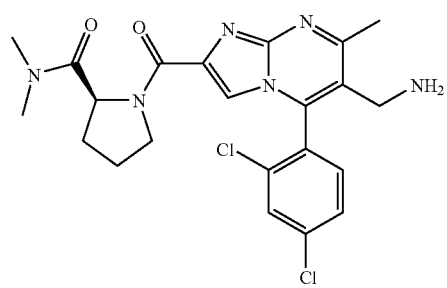 | $t_R$ = 1.83 min (100%)<br>LCMS: Anal. Calcd. for $C_{22}H_{24}Cl_2N_6O_2$<br>474.13 found: 475.20 $(M + H)^+$ |
| Example 122 | 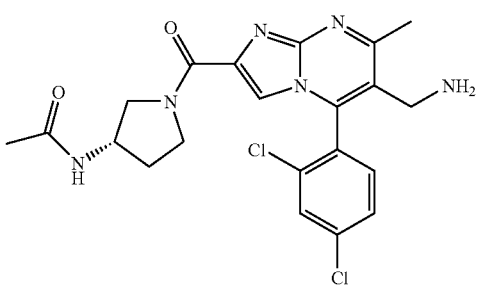 | $t_R$ = 1.57 min (100%)<br>LCMS: Anal. Calcd. for $C_{21}H_{22}Cl_2N_6O_2$<br>460.12 found: 461.20 $(M + H)^+$ |
| Example 123 | 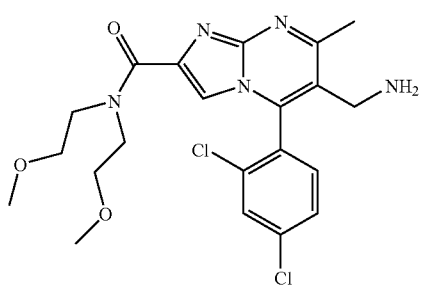 | $t_R$ = 2.05 min (88%)<br>LCMS: Anal. Calcd. for $C_{21}H_{25}Cl_2N_5O_3$<br>465.13 found: 466.20 $(M + H)^+$ |

-continued
Example 124 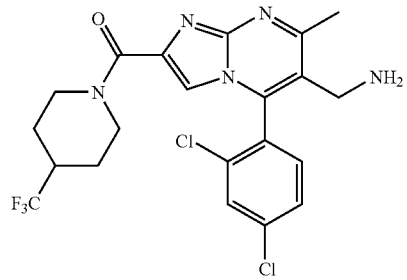
$t_R$ = 2.65 min (98%)
LCMS: Anal. Calcd. for $C_{21}H_{20}Cl_2F_3N_5O$
485.10 found: 486.10 (M + H)$^+$
Example 125 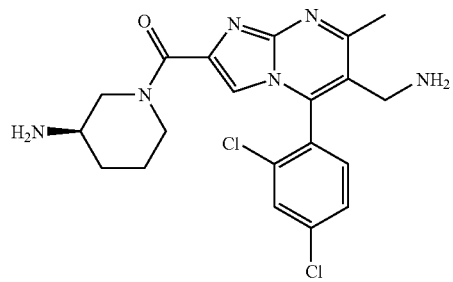
$t_R$ = 1.33 min (96%)
LCMS: Anal. Calcd. for $C_{20}H_{22}Cl_2N_6O$
432.12 found: 433.10 (M + H)$^+$
Example 126 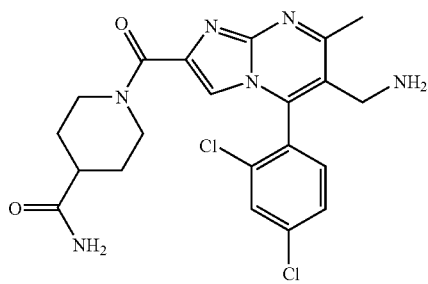
$t_R$ = 1.49 min (90%)
LCMS: Anal. Calcd. for $C_{21}H_{22}Cl_2N_6O_2$
460.12 found: 461.10 (M + H)$^+$
Example 127 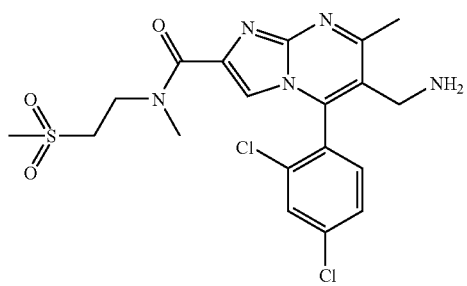
$t_R$ = 1.54 min (100%)
LCMS: Anal. Calcd. for $C_{19}H_{21}Cl_2N_5O_3S$
469.07 found: 470.10 (M + H)$^+$
Example 128 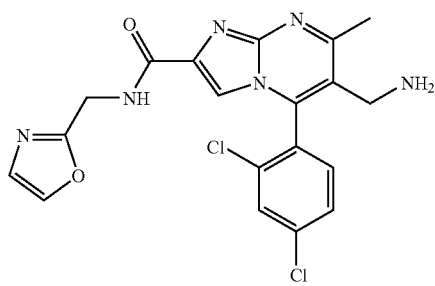
$t_R$ = 1.82 min (89%)
LCMS: Anal. Calcd. for $C_{19}H_{16}Cl_2N_6O_2$
430.07 found: 431.00 (M + H)$^+$

| | | |
|---|---|---|
| Example 129 | 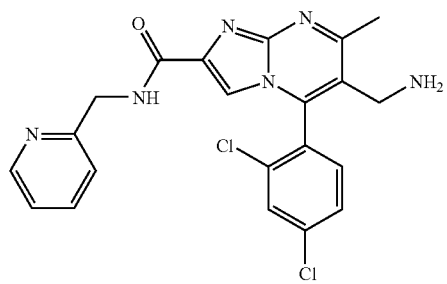 | $t_R$ = 1.34 min (100%)<br>LCMS: Anal. Calcd. for $C_{21}H_{18}Cl_2N_6O$<br>440.09 found: 441.10 (M + H)$^+$ |
| Example 130 | 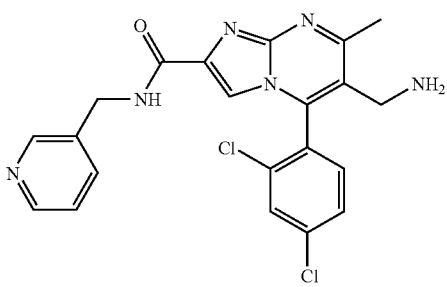 | $t_R$ = 1.34 min (100%)<br>LCMS: Anal. Calcd. for $C_{21}H_{18}Cl_2N_6O$<br>440.09 found: 441.10 (M + H)$^+$ |
| Example 131 | 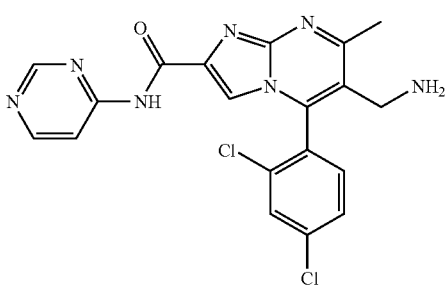 | $t_R$ = 2.98 min (100%)<br>LCMS: Anal. Calcd. for $C_{19}H_{15}Cl_2N_7O$<br>427.07 found: 428.10 (M + H)$^+$ |
| Example 132 | 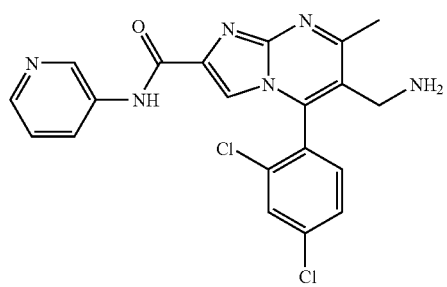 | $t_R$ = 1.62 min (100%)<br>LCMS: Anal. Calcd. for $C_{20}H_{16}Cl_2N_6O$<br>426.08 found: 427.00 (M + H)$^+$ |
| Example 133 | 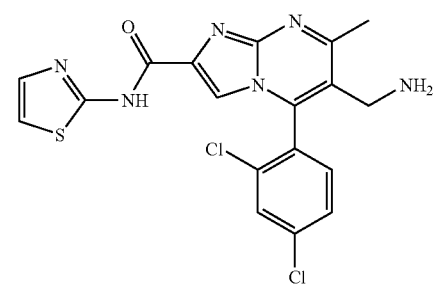 | $t_R$ = 2.40 min (100%)<br>LCMS: Anal. Calcd. for $C_{18}H_{14}Cl_2N_6OS$<br>432.03 found: 433.00 (M + H)$^+$ |

| | | |
|---|---|---|
| Example 134 | 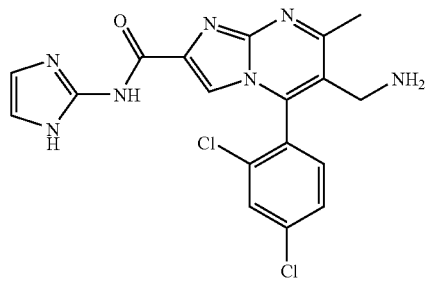 | $t_R$ = 1.53 min (90%)<br>LCMS: Anal. Calcd. for $C_{18}H_{15}Cl_2N_7O$<br>415.07 found: 416.00 $(M + H)^+$ |
| Example 135 | 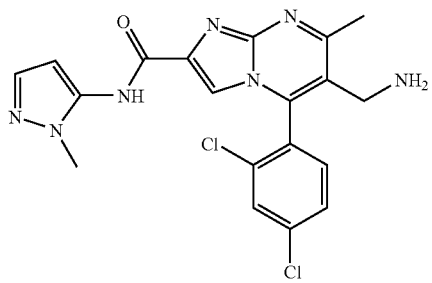 | $t_R$ = 2.05 min (97%)<br>LCMS: Anal. Calcd. for $C_{19}H_{17}Cl_2N_7O$<br>429.09 found: 430.10 $(M + H)^+$ |
| Example 136 | 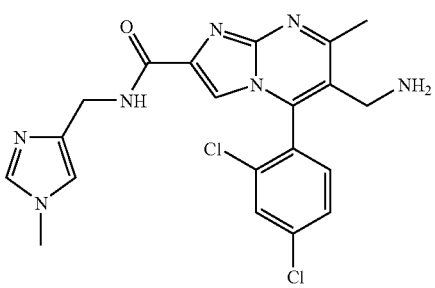 | $t_R$ = 1.30 min (98%)<br>LCMS: Anal. Calcd. for $C_{20}H_{19}Cl_2N_7O$<br>443.10 found: 444.10 $(M + H)^+$ |
| Example 137 | 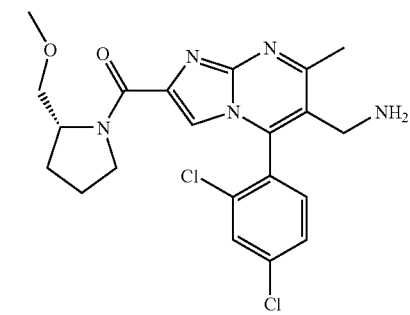 | $t_R$ = 2.20 min (100%)<br>LCMS: Anal. Calcd. for $C_{21}H_{23}Cl_2N_5O_2$<br>447.12 found: 448.10 $(M + H)^+$ |
| Example 138 | 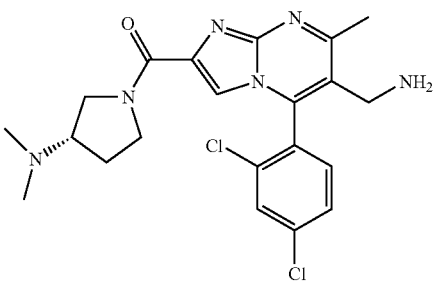 | $t_R$ = 1.16 min (98%)<br>LCMS: Anal. Calcd. for $C_{21}H_{24}Cl_2N_6O$<br>446.14 found: 447.10 $(M + H)^+$ |

-continued

| | | |
|---|---|---|
| Example 139 | 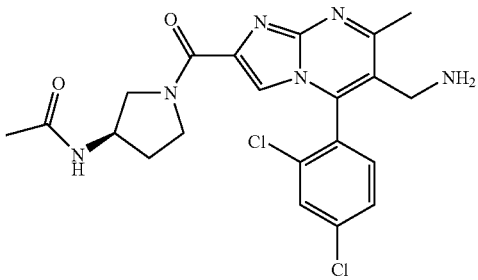 | $t_R$ = 1.58 min (98%)<br>LCMS: Anal. Calcd. for $C_{21}H_{22}Cl_2N_6O_2$<br>460.12 found: 461.20 (M + H)$^+$ |
| Example 140 | 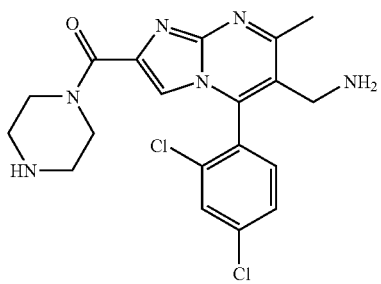 | $t_R$ = 1.95 min (90%)<br>LCMS: Anal. Calcd. for $C_{19}H_{20}Cl_2N_6O$<br>418.11 found: 419.20 (M + H)$^+$ |
| Example 141 | 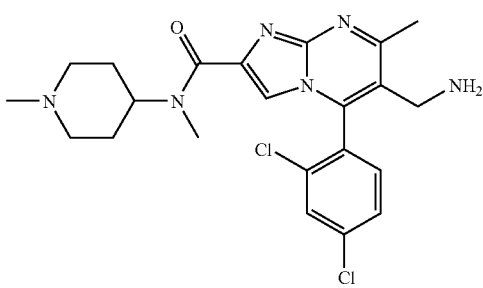 | $t_R$ = 2.18 min (90%)<br>LCMS: Anal. Calcd. for $C_{22}H_{26}Cl_2N_6O$<br>460.15 found: 461.30 (M + H)$^+$ |
| Example 142 | 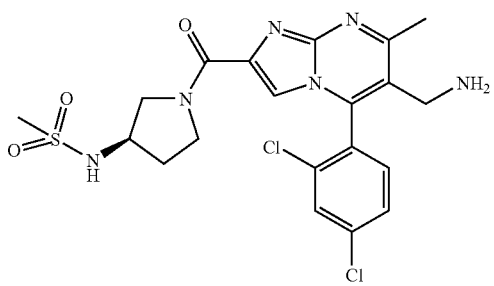 | $t_R$ = 1.63 min (97%)<br>LCMS: Anal. Calcd. for $C_{20}H_{22}Cl_2N_6O_3S$<br>496.09 found: 497.20 (M + H)$^+$ |

Example 143

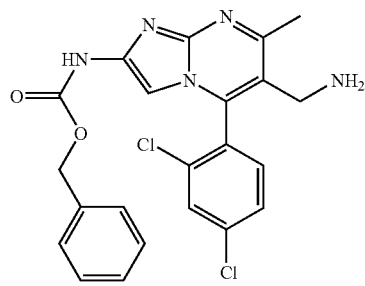

To a stirred solution of 6-((tert-butoxycarbonyl)methyl)-5-(2,4-dichlorophenyl)-7-methylimidazo[1,2-a]pyrimidine-2-carboxylic acid (Example 58, Step 2, 30 mg, 0.07 mmol) in PhCH$_3$ (3 mL) was added DPPA (19 μL, 0.09 mmol), PhCH$_2$OH (17 μL, 0.17 mmol) and Et$_3$N (12 μL, 0.09 mmol). The reaction was heated to 100° C. for 16 h and was concentrated under reduced pressure. The resulting residue was diluted with EtOAc and extracted with satd aq NH$_4$Cl, NaHCO$_3$ and brine prior to drying over anhydrous MgSO$_4$. Filtration, concentration under reduced pressure and purification by silica gel chromatography afforded benzyl 6-((tert-butoxycarbonyl)methyl)-5-(2,4-dichlorophenyl)-7-methylimidazo[1,2-a]pyrimidine-2-carbamate (20 mg, 32%).

$^1$H NMR (400 MHz, CDCl$_3$) δ 7.67 (d, J=1.8 Hz, 1H), 7.53 (dd, J=1.8, 7.9 Hz, 1H), 7.32-7.48 (m, 7H), 5.40 (d, J=12.3 Hz, 1H), 5.36 (d, J=12.3 Hz, 1H), 5.17 (s, 1H), 4.66 (br s, 1H), 4.11 (m, 2H), 2.73 (s, 3H), 1.41 (s, 9H).

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=4.40 min, 95% homogeneity index.

LCMS: Anal. Calcd. for $C_{27}H_{27}Cl_2N_5O_4$ 555.14; found: 556.18 (M+H)$^+$.

LCMS: Anal. Calcd. for $C_{22}H_{19}Cl_2N_5O_2$ 455.09; found: 456.08 (M+H)$^+$.

Examples 144 to 146

Using the same methods for preparation of Example 143, the following compounds were prepared as TFA or di-TFA salts:

Example 144
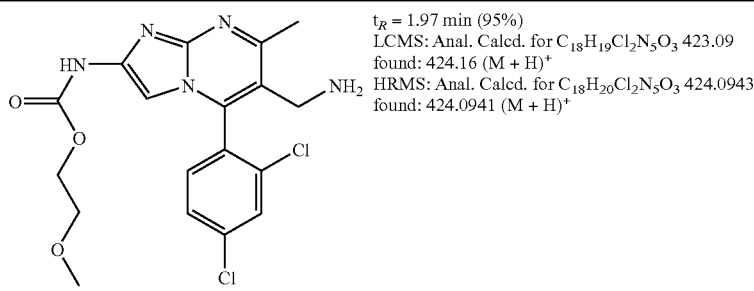
$t_R$ = 1.97 min (95%)
LCMS: Anal. Calcd. for $C_{18}H_{19}Cl_2N_5O_3$ 423.09 found: 424.16 (M + H)$^+$
HRMS: Anal. Calcd. for $C_{18}H_{20}Cl_2N_5O_3$ 424.0943 found: 424.0941 (M + H)$^+$ Example 145
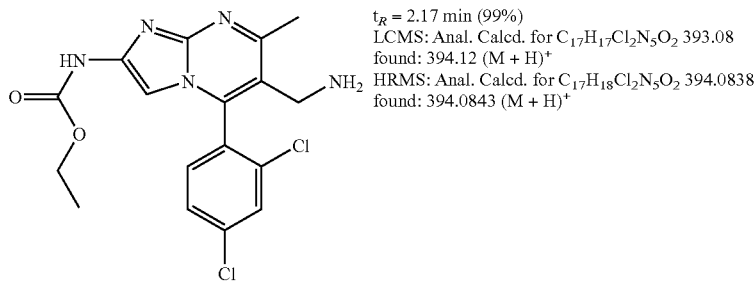
$t_R$ = 2.17 min (99%)
LCMS: Anal. Calcd. for $C_{17}H_{17}Cl_2N_5O_2$ 393.08 found: 394.12 (M + H)$^+$
HRMS: Anal. Calcd. for $C_{17}H_{18}Cl_2N_5O_2$ 394.0838 found: 394.0843 (M + H)$^+$ Example 146
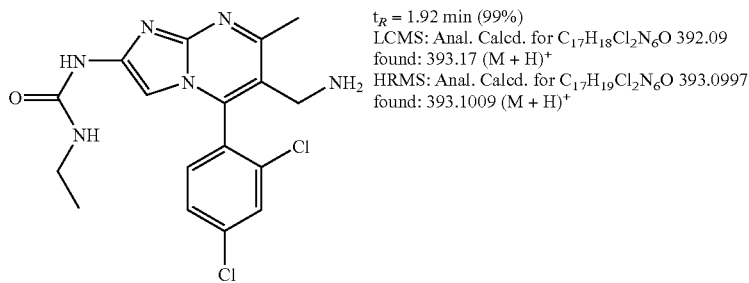
$t_R$ = 1.92 min (99%)
LCMS: Anal. Calcd. for $C_{17}H_{18}Cl_2N_6O$ 392.09 found: 393.17 (M + H)$^+$
HRMS: Anal. Calcd. for $C_{17}H_{19}Cl_2N_6O$ 393.0997 found: 393.1009 (M + H)$^+$ To a stirred solution of benzyl 6-((tert-butoxycarbonyl)methyl)-5-(2,4-dichlorophenyl)-7-methylimidazo[1,2-a]pyrimidine-2-carbamate (10 mg, 0.02 mmol) in CH$_2$Cl$_2$ (3 mL) was added TFA (0.1 mL). After 2 h, the reaction was concentrated under reduced pressure and purified by revere phase preparative HPLC to obtain benzyl 6-(aminomethyl)-5-(2,4-dichlorophenyl)-7-methylimidazo[1,2-a]pyrimidin-2-ylcarbamate, TFA salt (5 mg, 50%) as a white solid.

$^1$H NMR (400 MHz, CD$_3$OD) δ 7.91 (d, J=2.2 Hz, 1H), 7.71 (dd, J=2.2, 8.4 Hz, 1H), 7.67 (s, 1H), 7.60 (d, J=8.4 Hz, 1H), 7.31-7.46 (m, 5H), 5.38 (d, J=12.3 Hz, 1H), 5.34 (d, J=12.3 Hz, 1H), 4.17 (d, J=14.9 Hz, 1H), 4.01 (d, J=14.9 Hz, 1H), 2.82 (s, 3H).

HPLC-MS Phenomenex LUNA C-18 4.6×50 mm, 0 to 100% B over 4 minutes, 1 minutes hold time, A=90% water, 10% methanol, 0.1% TFA, B=10% 5 water, 90% methanol, 0.1% TFA, RT=2.67 min, 99% homogeneity index.

Example 147

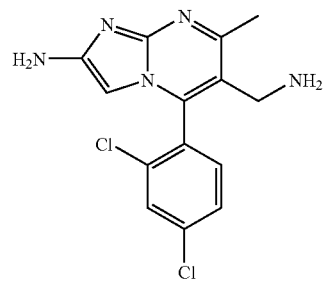

Example 147

Step 1. Trimethylsilylethyl 6-((tert-butoxycarbonyl)methyl)-5-(2,4-dichlorophenyl)-7-methylimidazo[1,2-a]pyrimidine-2-carbamate

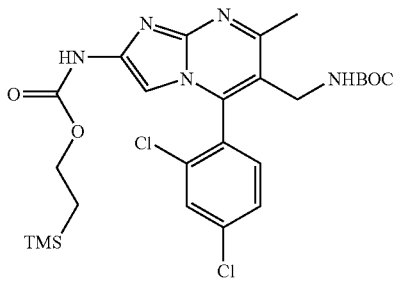

To a stirred solution of 6-((tert-butoxycarbonyl)methyl)-5-(2,4-dichlorophenyl)-7-methylimidazo[1,2-a]pyrimidine-2-carboxylic acid (Example 58, Step 2, 45 mg, 0.1 mmol) in PhCH₃ (3 mL) was added DPPA (43 μL, 0.2 mmol), TMSCH₂CH₂OH (71 μL, 0.5 mmol) and Et₃N (31 μL, 0.22 mmol). The reaction was heated to 65° C. for 16 h and was concentrated under reduced pressure. The resulting residue was diluted with EtOAc and extracted with satd aq NH₄Cl, NaHCO₃ and brine prior to drying over anhydrous MgSO₄. Filtration, concentration under reduced pressure and purification by silica gel chromatography afforded trimethylsilylethyl 6-((tert-butoxycarbonyl)methyl)-5-(2,4-dichlorophenyl)-7-methylimidazo[1,2-a]pyrimidine-2-carbamate (14 mg, 25%).

$^1$H NMR (400 MHz, CDCl₃) δ 8.25 (br s, 1H), 7.61 (d, J=2.2 Hz, 1H), 7.47 (dd, J=2.2, 8.0 Hz, 1H), 7.37 (d, J=8.0 Hz, 1H), 6.96 (s, 1H), 5.18 (br s, 1H), 4.20 (m, 2H), 4.04 (m, 2H), 2.55 (s, 3H), 1.38 (s, 9H), 1.01 (m, 2H).

Example 147

Step 2-3. 6-(Aminomethyl)-5-(2,4-dichlorophenyl)-7-methylimidazo[1,2-a]pyrimidin-2-amine

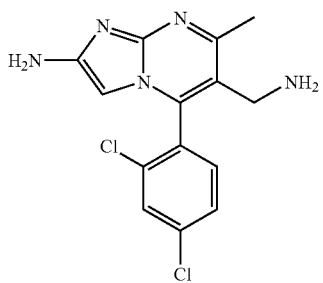

To a stirred solution of trimethylsilylethyl 6-((tert-butoxycarbonyl)methyl)-5-(2,4-dichlorophenyl)-7-methylimidazo[1,2-a]pyrimidine-2-carbamate (12 mg, 0.02 mmol) in THF (2 mL) was added TBAF (1.0 M in THF, 0.03 mL, 0.03 mmol). After 2 h, the reaction was concentrated and diluted with EtOAc. The organic layer was extracted with NH4Cl and brine prior to drying over anhydrous MgSO₄. Filtration, concentration under reduced pressure gave tert-butyl 2-amino-5-(2,4-dichlorophenyl)-7-methylimidazo[1,2-a]pyrimidin-6-ylcarbamate (10 mg, 100% crude yield).

To a stirred solution of tert-butyl 2-amino-5-(2,4-dichlorophenyl)-7-methylimidazo[1,2-a]pyrimidin-6-ylcarbamate (10 mg crude, 0.02 mmol) in CH₂Cl₂ (2 mL) was added TFA (0.1 mL). After 2 h, the reaction was concentrated under reduced pressure and purified by revere phase preparative HPLC to obtain 6-(aminomethyl)-5-(2,4-dichlorophenyl)-7-methylimidazo[1,2-a]pyrimidin-2-amine, TFA salt (3.3 mg, 28%) as a yellow solid.

$^1$H NMR (400 MHz, CD₃OD) δ 7.95 (d, J=2.2 Hz, 1H), 7.75 (dd, J=2.2, 8.4 Hz, 1H), 7.63 (d, J=8.4 Hz, 1H), 4.18 (d, J=14.9 Hz, 1H), 4.00 (d, J=14.9 Hz, 1H), 2.86 (s, 3H).

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=0.85 min, 95% homogeneity index.

LCMS: Anal. Calcd. for C₁₄H₁₃Cl₂N₅ 321.05; found: 322.08 (M+H)⁺.

Example 148

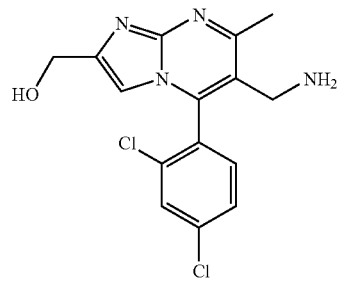

To a stirred solution of 6-((tert-butoxycarbonyl)methyl)-5-(2,4-dichlorophenyl)-7-methylimidazo[1,2-a]pyrimidine-2-carboxylic acid (Example 58, Step 2, 24 mg, 0.05 mmol) in THF (3 mL) at room temperature was added ClCOOEt (8 μL, 0.08 mmol) and Et₃N (12 μL, 0.08 mmol). After 1.5 h, the reaction was filtered to remove the insolubles and to the filtrate at 0° C. was added NaBH₄ (4 mg, 0.10 mmol) in H₂O (0.3 mL). After 30 min, the reaction was quenched with satd aq NH₄Cl and diluted with EtOAc. The organic layer was washed with satd aq NH₄Cl and brine prior to drying over MgSO₄. Filtration and concentration under reduced pressure afforded the crude tert-butyl (5-(2,4-dichlorophenyl)-2-(hydroxymethyl)-7-methylimidazo[1,2-a]pyrimidin-6-yl)methylcarbamate (24 mg, 100% crude yield) which was moved on to next step without further purification.

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=2.67 min, 90% homogeneity index.

LCMS: Anal. Calcd. for C₂₀H₂₂Cl₂N₄O₃ 436.1 1; found: 436.97 (M+H)⁺.

To a stirred solution of tert-butyl (5-(2,4-dichlorophenyl)-2-(hydroxymethyl)-7-methylimidazo[1,2-a]pyrimnidin-6-yl)methylcarbamate (24 mg crude) in CH₂Cl₂ (2 mL) was added TFA (0.1 mL). After 2 h, the reaction was concentrated under reduced pressure and purified by revere phase preparative HPLC to obtain (6-(aminomethyl)-5-(2,4-dichlorophenyl)-7-methylimidazo[1,2-a]pyrimidin-2-yl)methanol, TFA salt (10 mg, 42%) as a white solid.

¹H NMR (400 MHz, CD₃OD) δ 7.98 (d, J=2.2 Hz, 1H), 7.57 (dd, J=2.2, 8.4 Hz, 1H), 7.61 (d, J=8.4 Hz, 1H), 4.89 (br s, 2H), 4.21 (d, J=14.9 Hz, 1H), 4.06 (d, J=14.9 Hz, 1H), 2.89 (s, 3H).

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=1.00 min, 100% homogeneity index.

LCMS: Anal. Calcd. for $C_{15}H_{14}Cl_2N_4O$ 336.05; found: 337.02 $(M+H)^+$.

Example 149

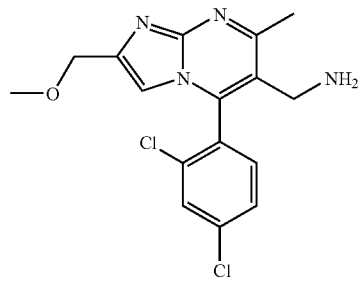

To a stirred solution of tert-butyl (5-(2,4-dichlorophenyl)-2-(hydroxymethyl)-7-methylimidazo[1,2-a]pyrimidin-6-yl)methylcarbamate (intermediate for Example 148, 15 mg, 0.03 mmol) in CH₂Cl₂ (3 mL) at room temperature was added MsCl (4 μL, 0.05 mmol) and Et₃N (10 μL, 0.07 mmol). After 16 h, HPLC-MS analysis showed the formation of a mixture of corresponding mesylate and chloride. The reaction was concentrated under reduced pressure and diluted with EtOAc. The organic layer was washed with satd aq NH₄Cl and brine prior to drying over MgSO₄. Filtration and concentration under reduced pressure afforded the crude mixture of mesylate and chloride (~15 mg).

The crude mixture of mesylate and chloride (~15 mg) was dissolved in MeOH (4 mL) and the reaction was heated to 50° C. for 16 h. The reaction was concentrated under reduced pressure and dissolved in CH₂Cl₂ (2 mL). TFA (0.1 mL) was added and after 2 h, the reaction was concentrated under reduced pressure and purified by revere phase preparative HPLC to obtain (5-(2,4-dichlorophenyl)-2-(methoxymethyl)-7-methylimidazo[1,2-a]pyrimidin-6-yl)methanamine, TFA salt (6 mg, 50%) as a white solid.

¹H NMR (400 MHz, CD₃OD) δ 7.96 (d, J=1.8 Hz, 1H), 7.76 (dd, J=1.8, 8.4 Hz, 1H), 7.63 (d, J=8.4 Hz, 1H), 7.45 (s, 1H), 4.60 (s, 2H), 4.22 (d, J=15.0 Hz, 1H), 4.07 (d, J=15.0 Hz, 1H), 3.42 (s, 3H), 2.90 (s, 3H).

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=1.06 min, 96% homogeneity index.

LCMS: Anal. Calcd. for $C_{16}H_{16}Cl_2N_4O$ 350.07; found: 351.04 $(M+H)^+$.

HRMS: Anal. Calcd. for $C_{16}H_{17}Cl_2N_4O$ 351.0779; found: 351.0771 $(M+H)^+$.

Example 150

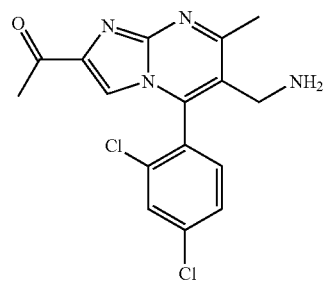

To a stirred solution of tert-butyl (5-(2,4-dichlorophenyl)-2-(methoxy(methyl)carbamoyl)-7-methylimidazo[1,2-a]pyrimidin-6-yl)methylcarbamate (intermediate for Example 59, 15 mg, 0.03 mmol) in THF (1 mL) at 0° C. was added MeMgBr (3M in THF, 0.05 mL, 0.15 mmol). After 30 min, the reaction was quenched with satd aq NH₄Cl and diluted with EtOAc. The organic layer was washed with satd aq NH₄Cl and brine prior to drying over MgSO₄. Filtration, concentration under reduced pressure and purification by silica gel chromatography afforded tert-butyl (2-acetyl-5-(2,4-dichlorophenyl)-7-methylimidazo[1,2-a]pyrimidin-6-yl)methylcarbamate (10 mg, 73%) as a white solid.

¹H NMR (400 MHz, CDCl₃) δ 7.69 (d, J=1.8 hz, 1H), 7.54 (dd, J=1.8, 8.4 Hz, 1H), 7.36 (s, 1H), 7.32 (d, J=8.4 Hz, 1H), 4.52 (br s, 1H), 4.10-4.29 (m, 2H), 2.80 (s, 3H), 2.73 (s, 3H), 1.41 (s, 9H).

LCMS: Anal. Calcd. for $C_{21}H_{22}Cl_2N_4O_3$ 448.1 1; found: 449.12 $(M+H)^+$.

To a stirred solution of tert-butyl (2-acetyl-5-(2,4-dichlorophenyl)-7-methylimidazo[1,2-a]pyrimidin-6-yl)methylcarbamate (5 mg, 0.01 mmol) in CH₂Cl₂ (2 mL) was added TFA (0.1 mL). After 2 h, the reaction was concentrated under reduced pressure and purified by revere phase preparative HPLC to obtain 1-(6-(aminomethyl)-5-(2,4-dichlorophenyl)-7-methylimidazo[1,2-a]pyrimidin-2-yl)ethanone, TFA salt (2 mg, 40%) as a white solid.

¹H NMR (400 MHz, CD₃OD) δ 7.96 (d, J=2.2 Hz, 1H), 7.77 (s, 1H), 7.74 (dd, J=2.2, 8.4 Hz, 1H), 7.61 (d, J=8.4 Hz, 1H), 4.17 (d, J=14.9 Hz, 1H), 4.01 (d, J=14.9 Hz, 1H), 2.81 (s, 3H), 2.59 (s, 3H).

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=1.47 min, 97% homogeneity index.

LCMS: Anal. Calcd. for $C_{16}H_{14}Cl_2N_4O$ 348.05; found: 349.03 $(M+H)^+$.

HRMS: Anal. Calcd. for $C_{16}H_{15}Cl_2N_4O$ 349.0623; found: 349.0627 (M+H)+.

Example 151

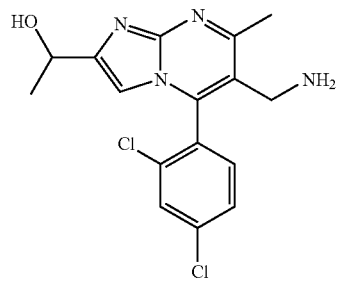

To a stirred solution of tert-butyl (2-acetyl-5-(2,4-dichlorophenyl)-7-methylimidazo[1,2-a]pyrimidin-6-yl)methylcarbamate (intermediate for Example 150, 5 mg, 0.01 mmol) in THF (2 mL) and $H_2O$ (0.3 mL) at room temperature was added $NaBH_4$ (2 mg, 0.05 mmol). After 30 min, the reaction was concentrated under reduced pressure and diluted with EtOAc. The organic layer was washed with satd aq $NH_4Cl$ and brine prior to drying over $MgSO_4$. Filtration, concentration under reduced pressure and purification by silica gel chromatography afforded crude tert-butyl (5-(2,4-dichlorophenyl)-2-(1-hydroxyethyl)-7-methylimidazo[1,2-a]pyrimidin-6-yl)methylcarbamate (5 mg, 100% crude yield).

To a stirred solution of tert-butyl (5-(2,4-dichlorophenyl)-2-(1-hydroxyethyl)-7-methylimidazo[1,2-a]pyrimidin-6-yl)methylcarbamate (5 mg) in $CH_2Cl_2$ (2 mL) was added TFA (0.1 mL). After 2 h, the reaction was concentrated under reduced pressure and purified by revere phase preparative HPLC to obtain 1-(6-(aminomethyl)-5-(2,4-dichlorophenyl)-7-methylimidazo[1,2-a]pyrimidin-2-yl)ethanol, TFA salt (2 mg, 38%) as a white solid.

$^1$H NMR (400 MHz, $CD_3OD$) δ 7.97 (d, J=2.2 Hz, 1H), 7.76 (dd, J=2.2, 8.3 Hz, 1H), 7.64 (d, J=8.3 Hz, 1H), 7.38 (s, 1H), 5.03 (m, 1H), 4.24 (d, J=15.0 Hz, 1H), 4.08 (d, J=15.0 Hz, 1H), 2.92 (s, 3H), 1.55 (d, J=6.6 Hz, 3H).

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=1.16 min, 95% homogeneity index.

LCMS: Anal. Calcd. for $C_{16}H_{16}Cl_2N_4O$ 350.07; found: 351.01 (M+H)+.

HRMS: Anal. Calcd. for $C_{16}H_{17}Cl_2N_4O$ 351.0779; found: 351.0772 (M+H)+.

Example 152

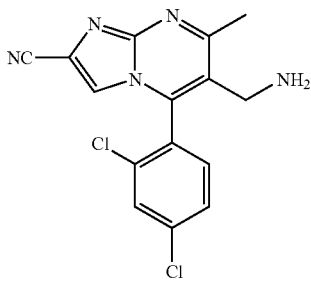

Example 152

Step 1. tert-Butyl (2-cyano-5-(2,4-dichlorophenyl)-7-methylimidazo[1,2-a]pyrimidin-6-yl)methylcarbamate

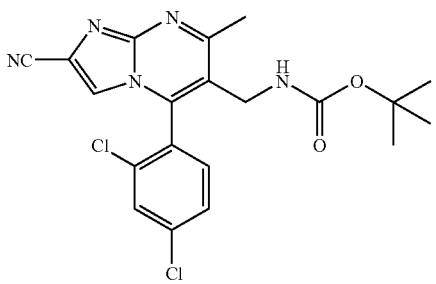

To a stirred solution of tert-butyl (2-carbamoyl-5-(2,4-dichlorophenyl)-7-methylimidazo[1,2-a]pyrimidin-6-yl)methylcarbamate (Example 58, Step 2, 30 mg, 0.07 mmol) in dioxane (1.5 mL) was added pyridine (10.5 mg, 0.13 mmol) and TFAA (15.4 mg, 0.07 mmol). The reaction was kept at room temperature for 16 and additional pyridine (10.5 mg, 0.13 mmol) and TFAA (15.4 mg, 0.07 mmol) were added. After 5 h, the reaction was quenched by $H_2O$ and diluted with EtOAc. The organic layer was washed with satd aq $NH_4Cl$ and brine prior to drying over $MgSO_4$. Filtration, concentration under reduced pressure and purification by silica gel chromatography afforded tert-butyl (2-cyano-5-(2,4-dichlorophenyl)-7-methylimidazo[1,2-a]pyrimidin-6-yl)methylcarbamate (20 mg, 69% yield).

Example 152

Step 2. 6-(Aminomethyl)-5-(2,4-dichlorophenyl)-7-methylimidazo[1,2-a]pyrimidine-2-carbonitrile

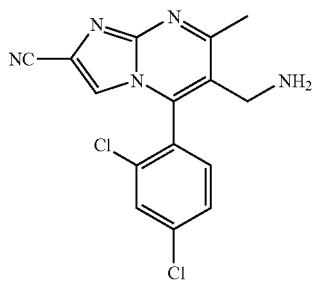

To a stirred solution of tert-butyl (2-cyano-5-(2,4-dichlorophenyl)-7-methylimidazo[1,2-a]pyrimidin-6-yl)methylcarbamate (10 mg, 0.02 mmol) in CH$_2$Cl$_2$ (2 mL) was added TFA (0.1 mL). After 2 h, the reaction was concentrated under reduced pressure and purified by revere phase preparative HPLC to obtain 6-(aminomethyl)-5-(2,4-dichlorophenyl)-7-methylimidazo[1,2-a]pyrimidine-2-carbonitrile, TFA salt (5 mg, 48%) as a white solid.

$^1$H NMR (400 MHz, CD$_3$OD) δ 7.97 (s, 1H), 7.93 (d, J=2.2 Hz, 1H), 7.73 (dd, J=2.2, 8.4 Hz, 1H), 7.58 (d, J=8.4 Hz, 1H), 4.15 (d, J=14.9 Hz, 1H), 4.01 (d, J=14.9 Hz, 1H), 2.83 (s, 3H).

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=1.49 min, 100% homogeneity index.

LCMS: Anal. Calcd. for C$_{15}$H$_{11}$Cl$_2$N$_5$ 331.04; found: 332.02 (M+H)$^+$.

HRMS: Anal. Calcd. for C$_{15}$H$_{12}$Cl$_2$N$_5$ 332.0457; found: 332.0470 (M+H)$^+$.

Example 153

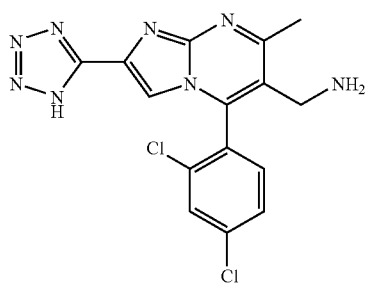

To a stirred solution of tert-butyl (2-cyano-5-(2,4-dichlorophenyl)-7-methylimidazo[1,2-a]pyrimidin-6-yl)methylcarbamate (intermediate for Example 152, 27 mg, 0.06 mmol) in DMF (2 mL) was added NaN$_3$ (6 mg, 0.09 mmol) and NH$_4$Cl (5 mg, 0.09 mmol). After heating to 100° C. for 24 h, the reaction was diluted with EtOAc. The organic layer was washed with satd aq NH$_4$Cl and brine prior to drying over MgSO$_4$. Filtration, concentration under reduced pressure and purification by silica gel chromatography afforded crude tert-butyl (5-(2,4-dichlorophenyl)-7-methyl-2-(1H-tetrazol-5-yl)imidazo[1,2-a]pyrimidin-6-yl)methylcarbamate (20 mg).

To a stirred solution of tert-butyl (5-(2,4-dichlorophenyl)-7-methyl-2-(1H-tetrazol-5-yl)imidazo[1,2-a]pyrimidin-6-yl)methylcarbamate (20 mg) in CH$_2$Cl$_2$ (2 mL) was added TFA (0.2 mL). After 2 h, the reaction was concentrated under reduced pressure and purified by revere phase preparative HPLC to obtain (5-(2,4-dichlorophenyl)-7-methyl-2-(1H-tetrazol-5-yl)imidazo[1,2-a]pyrimidin-6-yl)methanamine, TFA salt (6 mg, 20%) as a light yellow solid.

$^1$H NMR (400 MHz, CD$_3$OD) δ 7.97 (d, J=2.2 Hz, 1H), 7.80 (s, 1H), 7.78 (dd, J=2.2, 8.4 Hz, 1H), 7.66 (d, J=8.4 Hz, 1H), 4.21 (d, J=15.0 Hz, 1H), 4.05 (d, J=15.0 Hz, 1H), 2.86 (s, 3H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=1.82 min, 97% homogeneity index.

LCMS: Anal. Calcd. for C$_{15}$H$_{12}$Cl$_2$N$_8$ 374.06; found: 375.05 (M+H)$^+$.

HRMS: Anal. Calcd. for C$_{15}$H$_{12}$Cl$_2$N$_8$ 375.0640; found: 375.0638 (M+H)$^+$.

Example 154

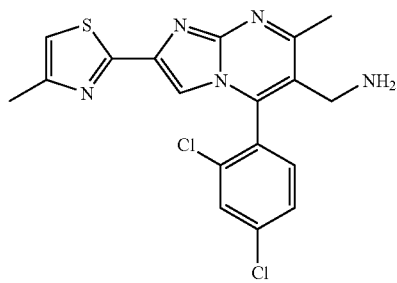

Example 154

Step 1. tert-Butyl (2-carbamothioyl-5-(2,4-dichlorophenyl)-7-methylimidazo[1,2-a]pyrimidin-6-yl)methylcarbamate

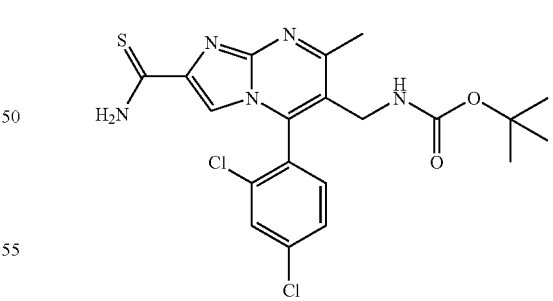

To a stirred solution of tert-butyl (2-carbamoyl-5-(2,4-dichlorophenyl)-7-methylimidazo[1,2-a]pyrimidin-6-yl)methylcarbamate (intermediate for Example 62, 150 mg, 0.33 mmol) in THF (10 mL) was added Lawesson's reagent (202 mg, 0.50 mmol). After heating to 65° C. for 20 h, the reaction mixture was poured into H$_2$O (5 mL). The resulting mixture was extracted with EtOAc and the organic layer was washed with satd aq NH$_4$Cl and brine prior to drying over MgSO$_4$. Filtration, concentration under reduced pressure afforded crude tert-butyl (2-carbamothioyl-5-(2,4-dichlorophenyl)-7-methylimidazo[1,2-a]pyrimidin-6-yl)methylcarbamate (339 mg, 100% crude yield) as a yellow oil.

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.62 min, 85% homogeneity index.

LCMS: Anal. Calcd. for $C_{20}H_{21}Cl_2N_5O_2S$ 465.08; found: 466.15 $(M+H)^+$.

Example 154

Step 2. (5-(2,4-Dichlorophenyl)-7-methyl-2-(4-methylthiazol-2-yl)imidazo[1,2-a]pyrimidin-6-yl)methanamine

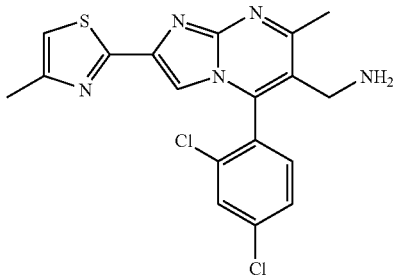

To a stirred solution of crude tert-butyl (2-carbamothioyl-5-(2,4-dichlorophenyl)-7-methylimidazo[1,2-a]pyrimidin-6-yl)methylcarbamate (155 mg, 0.33 mmol) in EtOH (10 mL) was added chloroacetone (62 mg, 0.67 mmol). After heating to 70° C. for 24 h, the reaction was concentrated and purified by preparatory HPLC to afforded (5-(2,4-dichlorophenyl)-7-methyl-2-(4-methylthiazol-2-yl)imidazo[1,2-a]pyrimidin-6-yl)methanamine, TFA salt (25 mg, 20%) as a white solid.

$^1$H NMR (400 MHz, CD$_3$OD) δ 7.98 (d, J=1.8 Hz, 1H), 7.76 (dd, J=1.8, 8.4 Hz, 1H), 7.65 (d, J=8.4 Hz, 1H), 7.64 (s, 1H), 7.25 (s, 1H), 4.19 (d, J=15.0 Hz, 1H), 4.00 (d, J=15.0 Hz, 1H), 2.83 (s, 3H), 2.43 (s, 3H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=2.31 min, 98% homogeneity index.

LCMS: Anal. Calcd. for $C_{18}H_{15}Cl_2N_5S$ 403.04; found: 404.18 $(M+H)^+$.

HRMS: Anal. Calcd. for $C_{18}H_{16}Cl_2N_5$ 404.0503; found: 404.0508 $(M+H)^+$.

Example 155

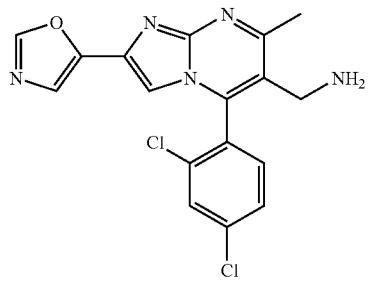

Example 155

Step 1. 6-(tert-Butoxycarbonyl)-5-(2,4-dichlorophenyl)-7-methylimidazo[1,2-a]pyrimidine-2-carboxylic acid

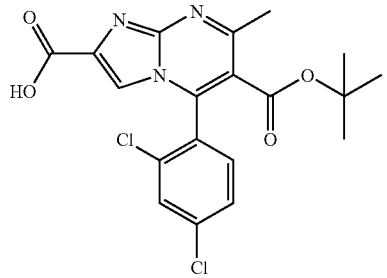

To a stirred solution of 6-tert-butyl 2-ethyl 5-(2,4-dichlorophenyl)-7-methylimidazo[1,2-a]pyrimidine-2,6-dicarboxylate (Example 54, Step 4, 3 g, 6.66 mmol) in THF (6 mL) and MeOH (2 mL) was added LiOH.H$_2$O (0.42 g, 9.99 mmol) in H$_2$O (2 mL). After 1 h, the reaction was quenched by 1N HCl till pH to 2. The organic volatiles were removed under reduced pressure and the residue was dissolved in EtOAc. The organic layer was washed with satd aq NH$_4$Cl and brine prior to drying over MgSO$_4$. Filtration, concentration under reduced pressure and recrystallization from 1:2 EtOAc/hexanes afforded 6-(tert-butoxycarbonyl)-5-(2,4-dichlorophenyl)-7-methylimidazo[1,2-a]pyrimidine-2-carboxylic acid (2.78 g, 90%) as a cream solid.

$^1$H NMR (400 MHz, CDCl$_3$) δ 7.69 (d, J=1.8 Hz, 1H), 7.61 (s, 1H), 7.52 (dd, J=1.8, 8.4 Hz, 1H), 7.35 (d, J=8.4 Hz, 1H), 2.80 (s, 3H), 1.29 (s, 9H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.59 min, 100% homogeneity index.

Example 155

Step 2. tert-Butyl 5-(2,4-dichlorophenyl)-2-(hydroxymethyl)-7-methylimidazo[1,2-a]pyrimidine-6-carboxylate

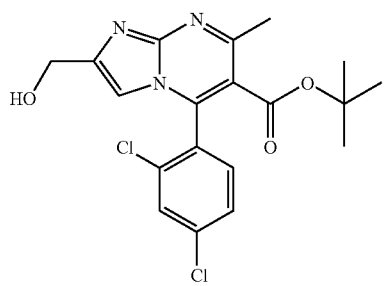

To a stirred solution of 6-(tert-butoxycarbonyl)-5-(2,4-dichlorophenyl)-7-methylimidazo[1,2-a]pyrimidine-2-carboxylic acid (400 mg, 0.95 mmol) in THF (6 mL) at room temperature was added ClCOOEt (0.14 mL, 1.42 mmol) and Et$_3$N (0.26 mL, 1.9 mmol). After 1.5 h, the reaction was filtered to remove the insolubles and to the filtrate at 0° C. was added NaBH₄ (72 mg, 1.9 mmol) in H₂O (0.2 mL). After 30 min, the reaction was quenched with 1N HCl and diluted with EtOAc. The organic layer was washed with satd aq NH₄Cl and brine prior to drying over MgSO₄. Filtration and concentration under reduced pressure afforded the crude tert-butyl 5-(2,4-dichlorophenyl)-2-(hydroxymethyl)-7-methylimidazo[1,2-a]pyrimidine-6-carboxylate (400 mg, 100% crude yield) which was moved on to next step without further purification.

Example 155

Step 3. tert-Butyl 5-(2,4-dichlorophenyl)-2-formyl-7-methylimidazo[1,2-a]pyrimidine-6-carboxylate

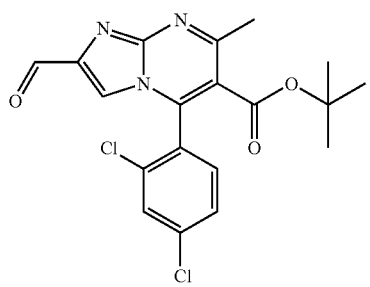

To a stirred solution of crude tert-butyl 5-(2,4-dichlorophenyl)-2-(hydroxymethyl)-7-methylimidazo[1,2-a]pyrimidine-6-carboxylate (400 mg) in CH₂Cl₂ (6 mL) was added Dess-Martin periodinane (605 mg, 1.43 mmol). After 2 h, the reaction was concentrated under reduced pressure and diluted with EtOAc. The organic layer was washed with satd aq NaHCO₃ and brine prior to drying over MgSO₄. Filtration, concentration under reduced pressure and purification by silica gel chromatography afforded tert-butyl 5-(2,4-dichlorophenyl)-2-formyl-7-methylimidazo[1,2-a]pyrimidine-6-carboxylate (90 mg, 41% for the two steps) as a light yellow solid.

¹H NMR (400 MHz, CDCl₃) δ 10.15 (s, 1H), 7.68 (d, J=2.2 Hz, 1H), 7.52 (s, 1H), 7.51 (dd, J=2.2, 8.4 Hz, 1H), 7.34 (d, J=8.4 Hz, 1H), 2.79 (s, 3H), 1.29 (s, 9H).

Example 155

Step 4. tert-Butyl 5-(2,4-dichlorophenyl)-7-methyl-2-(oxazol-5-yl)imidazo[1,2-a]pyrimidine-6-carboxylate

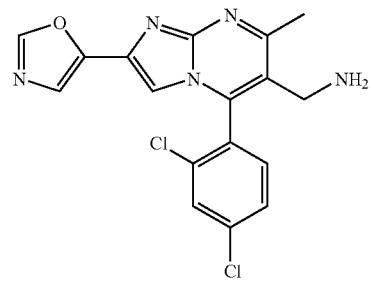

To a stirred solution of tert-butyl 5-(2,4-dichlorophenyl)-2-formyl-7-methylimidazo[1,2-a]pyrimidine-6-carboxylate (90 mg, 0.22 mmol) in MeOH (4 mL) was added tosyl methyl isocyanide (52 mg, 0.27 mmol) and K₂CO₃ (61 mg, 0.44 mmol). After heating to 60° C. for 30 min, the reaction was concentrated under reduced pressure and purified by silica gel chromatography to provide tert-butyl 5-(2,4-dichlorophenyl)-7-methyl-2-(oxazol-5-yl)imidazo[1,2-a]pyrimidine-6-carboxylate (65 mg, 66%) as a light yellow solid.

¹H NMR (400 MHz, CDCl₃) δ 7.88 (s, 1H), 7.70 (d, J=1.8 Hz, 1H), 7.66 (s, 1H), 7.52 (dd, J=1.8, 8.4 Hz, 1H), 7.37 (d, J=8.4 Hz, 1H), 7.17 (s, 1H), 2.77 (s, 3H), 1.29 (s, 9H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.74 min, 95% homogeneity index.

LCMS: Anal. Calcd. for $C_{21}H_{18}Cl_2N_4O_3$ 444.08; found: 445.10 (M+H)⁺.

Example 155

Step 5-10. (5-(2,4-Dichlorophenyl)-7-methyl-2-(oxazol-5-yl)imidazo[1,2-a]pyrimidin-6-yl)methanamine

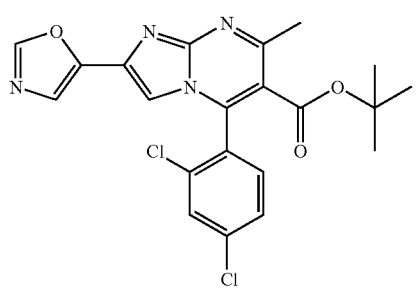

Starting from tert-butyl 5-(2,4-dichlorophenyl)-7-methyl-2-(oxazol-5-yl)imidazo[1,2-a]pyrimidine-6-carboxylate, (5-(2,4-dichlorophenyl)-7-methyl-2-(oxazol-5-yl)imidazo[1,2-a]pyrimidin-6-yl)methanamine, TFA salt was prepared using the same methods described in Example 54.

¹H NMR (400 MHz, CD₃OD) δ 8.27 (s, 1H), 7.95 (d, J=1.8 Hz, 1H), 7.75 (dd, J=1.8, 8.4 Hz, 1H), 7.65 (d, J=8.4 Hz, 1H), 7.60 (s, 1H), 7.51 (s, 1H), 4.19 (d, J=15.0 Hz, 1H), 4.01 (d, J=15.0 Hz, 1H), 2.86 (s, 3H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=1.62 min, 100% homogeneity index.

LCMS: Anal. Calcd. for $C_{17}H_{13}Cl_2N_5O$ 373.05; found: 374.12 (M+H)⁺.

HRMS: Anal. Calcd. for $C_{17}H_{14}Cl_2N_5O$ 374.0573; found: 374.0573 (M+H)+.

Example 156

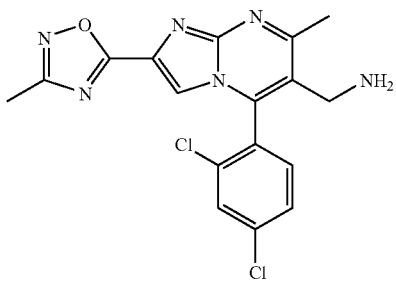

Example 156

Step 1. tert-Butyl 2-carbamoyl-5-(2,4-dichlorophenyl)-7-methylimidazo[1,2-a]pyrimidine-6-carboxylate

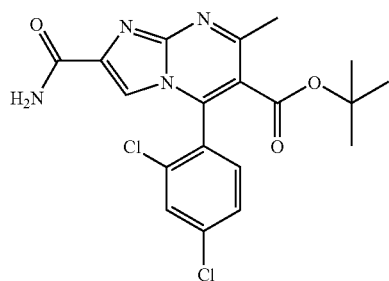

To a stirred solution of 6-(tert-butoxycarbonyl)-5-(2,4-dichlorophenyl)-7-methylimidazo[1,2-a]pyrimidine-2-carboxylic acid (Example 155, Step 1, 500 mg, 1.18 mmol) in THF (10 mL) at room temperature was added PyBOP (787 mg, 1.78 mmol), HOBt (240 mg, 1.18 mmol), NH$_4$Cl (95 mg, 1.78 mmol) and $^i$Pr$_2$NEt (0.4 mL, 2.37 mmol). After 24 h, the reaction was concentrated under reduced pressure and diluted with EtOAc. The organic layer was washed with 1N HCl, 1N NaOH and brine prior to drying over anhydrous MgSO$_4$. Filtration, concentration under reduced pressure and purification by silica gel chromatography afforded tert-butyl 2-carbamoyl-5-(2,4-dichlorophenyl)-7-methylimidazo[1,2-a]pyrimidine-6-carboxylate (560 mg, 100%) as a light yellow solid.

LCMS: Anal. Calcd. for $C_{19}H_{18}Cl_2N_4O_3$ 420.08; found: 421.15 (M+H)+.

Example 156

Step 2. tert-Butyl 5-(2,4-dichlorophenyl)-7-methyl-2-(3-methyl-1,2,4-oxadiazol-5-yl)imidazo[1,2-a]pyrimidine-6-carboxylate

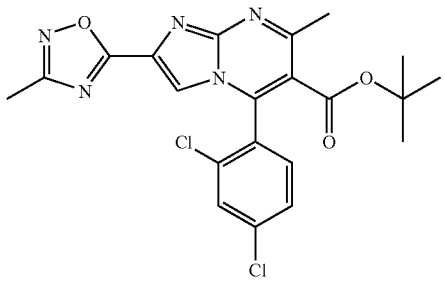

To a stirred solution of tert-butyl 2-carbamoyl-5-(2,4-dichlorophenyl)-7-methylimidazo[1,2-a]pyrimidine-6-carboxylate (60 mg, 0.14 mmol) in PhCH$_3$ (3 mL) was added DMA-DMA (70 μL, 0.43 mmol). The reaction was heated to 90° C. for 2 h and was concentrated to afford the crude ester as a black oil. This crude product was dissolved in dioxane (2 mL) and AcOH (2 mL) and NH$_2$OH.HCl (15 mg, 0.21 mmol) was added followed by NaOH (2N solution, 0.1 mL, 0.2 mmol). After heating to 90° C. for 2 h, the reaction was concentrated under reduced pressure and diluted with EtOAc. The organic layer was washed with H$_2$O and brine prior to drying over anhydrous MgSO$_4$. Filtration, concentration under reduced pressure and purification by silica gel chromatography afforded tert-butyl 5-(2,4-dichlorophenyl)-7-methyl-2-(3-methyl-1,2,4-oxadiazol-5-yl)imidazo[1,2-a]pyrimidine-6-carboxylate (38 mg, 58%) as a yellow solid.

$^1$H NMR (400 MHz, CDCl$_3$) δ 7.68 (d, J=1.8 Hz, 1H), 7.66 (s, 1H), 7.51 (dd, J=1.8, 8.2 Hz, 1H), 7.38 (d, J=8.2 Hz, 1H), 2.79 (s, 3H), 2.45 (s, 3H), 1.30 (s, 9H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.82 min, 95% homogeneity index.

LCMS: Anal. Calcd. for $C_{21}H_{19}Cl_2N_5O_3$ 459.09; found: 460.18 (M+H)+.

Example 156

Step 4-9. (5-(2,4-Dichlorophenyl)-7-methyl-2-(3-methyl-1,2,4-oxadiazol-5-yl)imidazo[1,2-a]pyrimidin-6-yl)methanamine

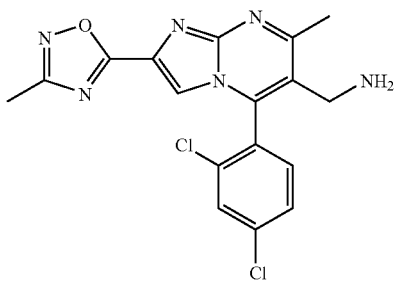

Starting from tert-butyl 5-(2,4-dichlorophenyl)-7-methyl-2-(3-methyl-1,2,4-oxadiazol-5-yl)imidazo[1,2-a]pyrimidine-6-carboxylate, (5-(2,4-dichlorophenyl)-7-methyl-2-(3-methyl-1,2,4-oxadiazol-5-yl)imidazo[1,2-a]pyrimidin-6-yl)methanamine, TFA salt was prepared using the same methods described in Example 54.

$^1$H NMR (400 MHz, CD$_3$OD) δ 7.96 (d, J=1.8 Hz, 1H), 7.90 (s, 1H), 7.76 (dd, J=1.8, 8.3 Hz, 1H), 7.64 (d, J=8.3 Hz, 1H), 4.18 (d, J=14.9 Hz, 1H), 4.04 (d, J=14.9 Hz, 1H), 2.86 (s, 3H), 2.42 (s, 3H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=2.20 min, 100% homogeneity index.

LCMS: Anal. Calcd. for C$_{17}$H$_{14}$Cl$_2$N$_6$O 388.06; found: 389.10 (M+H)$^+$.

HRMS: Anal. Calcd. for C$_{17}$H$_{15}$Cl$_2$N$_6$O 389.0673; found: 389.0673 (M+H)$^+$.

Example 157

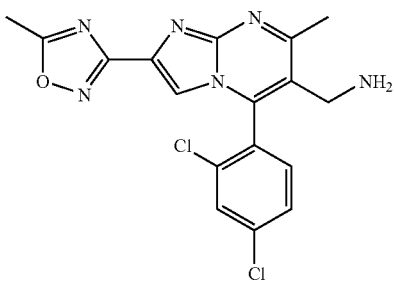

Example 157

Step 1. tert-Butyl 2-cyano-5-(2,4-dichlorophenyl)-7-methylimidazo[1,2-a]pyrimidine-6-carboxylate

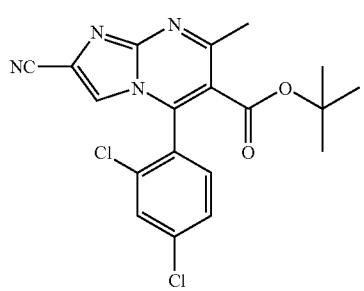

To a stirred solution of tert-butyl 2-carbamoyl-5-(2,4-dichlorophenyl)-7-methylimidazo[1,2-a]pyrimidine-6-carboxylate (Example 156, Step 1, 50 mg, 0.12 mmol) in CH$_2$Cl$_2$ (3 mL) was added TFAA (50 mg, 0.24 mmol) and Et$_3$N (33 μL, 0.24 mmol). After 2 h, the reaction was extracted with H$_2$O and brine prior to drying over anhydrous MgSO$_4$. Filtration, concentration under reduced pressure afforded tert-butyl 2-cyano-5-(2,4-dichlorophenyl)-7-methylimidazo[1,2-a]pyrimidine-6-carboxylate (50 mg, 95% pure) as a yellow oil.

Example 157

Step 2. tert-Butyl 5-(2,4-dichlorophenyl)-7-methyl-2-(5-methyl-1,2,4-oxadiazol-3-yl)imidazo[1,2-a]pyrimidine-6-carboxylate

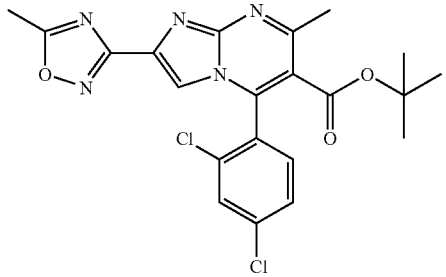

To a stirred solution of tert-butyl 2-cyano-5-(2,4-dichlorophenyl)-7-methylimidazo[1,2-a]pyrimidine-6-carboxylate (50 mg, 0.12 mmol) in EtOH (3 mL) was added NH$_2$OH.HCl (10 mg, 0.12 mmol) and KOH (8.5 mg, 0.12 mmol). After heating to 70° C. for 6 h, the reaction was concentrated under reduced pressure. The resulting residue was suspended in H$_2$O and filtered to collect the desired product as a yellow solid (53 mg). This product was dissolved in PhCH$_3$ (3 mL) and DMA-DMA (0.2 mL) was added. The reaction was heated to 90° C. for 2 h and was concentrated and purified by silica gel chromatography to give tert-butyl 5-(2,4-dichlorophenyl)-7-methyl-2-(5-methyl-1,2,4-oxadiazol-3-yl)imidazo[1,2-a]pyrimidine-6-carboxylate (46 mg, 68% for three steps) as a light yellow solid.

$^1$H NMR (400 MHz, CDCl$_3$) δ 7.67 (d, J=1.8 Hz, 1H), 7.54 (s, 1H), 7.52 (dd, J=1.8, 8.4 Hz, 1H), 7.38 (d, J=8.4 Hz, 1H), 2.78 (s, 3H), 2.65 (s, 3H), 1.28 (s, 9H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.70 min, 95% homogeneity index.

LCMS: Anal. Calcd. for C$_{21}$H$_{19}$Cl$_2$N$_5$O$_3$ 459.09; found: 460.20 (M+H)$^+$.

Example 157

Step 3-8. (5-(2,4-Dichlorophenyl)-7-methyl-2-(5-methyl-1,2,4-oxadiazol-3-yl)imnidazo[1,2-a]pyrimidin-6-yl)methanamine

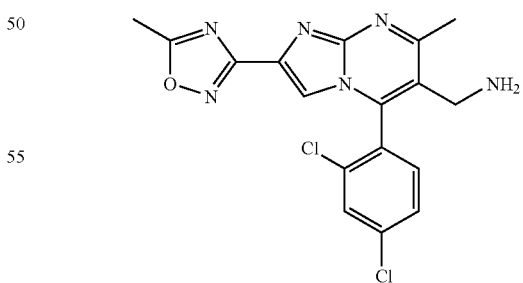

Starting from tert-butyl 5-(2,4-dichlorophenyl)-7-methyl-2-(5-methyl-1,2,4-oxadiazol-3-yl)imidazo[1,2-a]pyrimidine-6-carboxylate, (5-(2,4-dichlorophenyl)-7-methyl-2-(5-methyl-1,2,4-oxadiazol-3-yl)imidazo[1,2-a]pyrimidin-6-yl)methanamine, TFA salt was prepared using the same methods described in Example 54.

$^1$H NMR (400 MHz, CD$_3$OD) δ 7.95 (d, J=1.8 Hz, 1H), 7.74 (dd, J=1.8, 8.4 Hz, 1H), 7.67 (d, J=8.4 Hz, 1H), 7.65 (s, 1H), 4.21 (d, J=15.0 Hz, 1H), 4.04 (d, J=15.0 Hz, 1H), 2.84 (s, 3H), 2.63 (s, 3H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=1.83 min, 100% homogeneity index.

LCMS: Anal. Calcd. for C$_{17}$H$_{14}$Cl$_2$N$_6$O 388.06; found: 389.14 (M+H)$^+$.

HRMS: Anal. Calcd. for C$_{17}$H$_{15}$Cl$_2$N$_6$O 389.0673; found: 389.0670 (M+H)$^+$.

Example 158

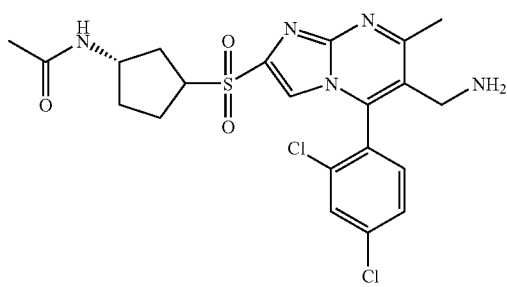

Example 158

Step 1. 2-Amino-1H-imidazole4-sulfonic acid

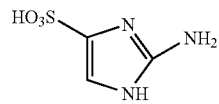

2-Amino-1H-imidazole-4-sulfonic acid was prepared according to J. B. Ekeley; J. M. Fulmer *J. Am. Chem. Soc.,* 1930, 52, 2026-2028.

Example 158

Step 2. 2-(2,4-Dichlorobenzylidene)-3-oxobutanamide

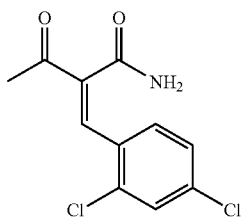

A suspension of acetoacetamide (5.05 g, 50 mmol), 2,4-di-chlorobenzaldehyde (9.20 g, 52 mmole), piperidine (170 mg, 2 mmol) and acetic acid (120 mg, 2 mmol) in isopropanol (50 mL) was stirred at room temperature for 14 h. The precipitation was collected and rinsed with an additional isopropanol (20 mL). After drying in vacuo, 2-(2,4-dichlorobenzylidene)-3-oxobutanamide was obtained as a white solid (6.3g, 49%).

$^1$H NMR (500 MHz, d$^6$-DMSO) δ 7.90 (s, 1H), 7.77 (d, J=1.7 Hz, 1H), 7.73 (d, J=8.3 Hz, 1H), 7.61 (s, 1H), 7.57 (s, 1H), 7.53 (dd, J=1.9, 8.2 Hz, 1H), 2.38 (s, 3H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=1.68 min, 100% purity.

LCMS: Anal. Calcd. for C$_{11}$H$_9$Cl$_2$NO$_2$ 257.0; found: 257.9 (M+H)$^+$.

Example 158

Step 3. 6-Carbamoyl-5-(2,4-dichlorophenyl)-7-methyl-5,8-dihydroimidazo[1,2-a]pyrimidine-2-sulfonic acid

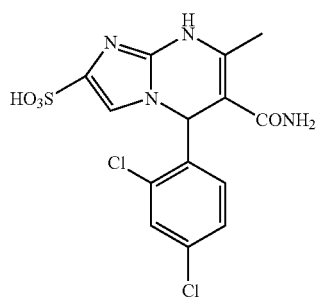

A suspension of 2-amino-1H-imidazole-4-sulfonic acid (82 mg, 0.5 mmol) and 2-(2,4-dichlorobenzylidene)-3-oxobutanamide (125 mg, 0.5 mmol) in 3:1 EtOH/H$_2$O (2 mL) was heated to 80° C. for 14 h. After removal of solvent, the residue was dissolved in 1N NaOH and extracted with EtOAc (5 mL×2). The aqueous solution was then acidified with conc. HCl to pH=1. The precipitation which had formed was collected and further washed with H$_2$O. After drying in vacuo, 6-carbamoyl-5-(2,4-dichlorophenyl)-7-methyl-5,8-dihydroimidazo[1,2-a]pyrimidine-2-sulfonic acid was obtained a yellow solid (97 mg, 48%).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=0.97 min.

LCMS: Anal. Calcd. for C$_{14}$H$_{12}$Cl$_2$N$_4$O$_4$S 402.0; found: 403.1 (M+H)$^+$.

Example 158

Step 4. 6-Carbamoyl-5-(2,4-dichlorophenyl)-7-methylimidazo[1,2-a]pyrimidine-2-sulfonic acid

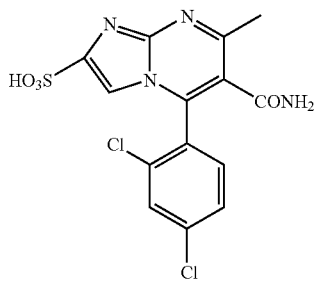

A suspension of 6-carbamoyl-5-(2,4-dichlorophenyl)-7-methyl-5,8-dihydroimidazo[1,2-a]pyrimidine-2-sulfonic acid (90 mg, 0.23 mmol) and MnO$_2$ (110 mg, 1.27 mmol) in dioxane (2 mL) was heated to 80° C. for 24 h. HPLC analysis indicated 50% conversion, and additional MnO$_2$ (200 mg) was added and heating was continued for additional 48 h. After removal of catalyst and solvent, 6-carbamoyl-5-(2,4-dichlorophenyl)-7-methylimidazo[1,2-a]pyrimidine-2-sulfonic acid was obtained as a brown solid ~90% pure (75mg, 82%). The crude product was used for the subsequent reaction without further purification.

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=1.11 min, 90% homogeneity index.

LCMS: Anal. Calcd. for $C_{14}H_{10}Cl_2N_4O_4S$ 400.0; found: 401.0 (M+H)$^+$.

Example 158

Step 5. 5-(4-Chloro-2-methylphenyl)-6-cyano-7-methylimidazo[1,2-a]pyrimidine-2-sulfonyl chloride

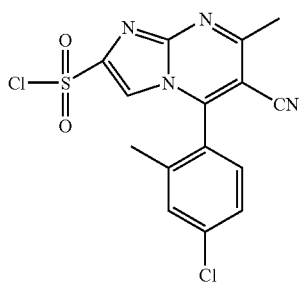

A solution of 6-carbamoyl-5-(2,4-dichlorophenyl)-7-methylimidazo[1,2-a]pyrimidine-2-sulfonic acid (75 mg, 0.18 mmol) in POCl$_3$ (2 mL) was heated to 100° C. for 14 h. After concentration, the residue was dissolved in CH$_2$Cl$_2$ (10 mL) in the presence of satd aq NaHCO$_3$ (10 mL) and stirred for 10 min. The organic layer was collected, washed with brine and dried over MgSO$_4$. Filtration, concentration under reduced pressure and purification by silica gel chromatography (0-60% hexanes in EtOAc over 20 min) to obtain 5-(4-chloro-2-methylphenyl)-6-cyano-7-methylimidazo[1,2-a]pyrimidine-2-sulfonyl chloride as yellow oil (34 mg, 45%).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.25 min.

LCMS: Anal. Calcd. for $C_{14}H_7Cl_3N_4O_2S$ 399.9; found: 401.0 (M+H)$^+$.

Example 158

Step 6. (S)—N-(1-(6-Cyano-5-(2,4-dichlorophenyl)-7-methylimidazo[1,2-a]pyrimidin-2-ylsulfonyl)pyrrolidin-3-yl)acetamide

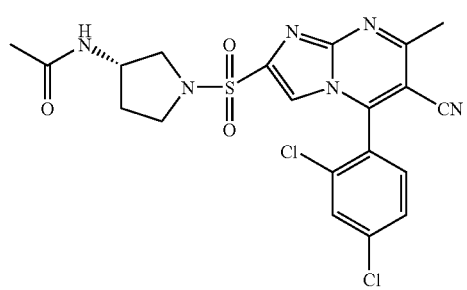

To a stirred solution of 5-(4-chloro-2-methylphenyl)-6-cyano-7-methylimidazo[1,2-a]pyrimidine-2-sulfonyl chloride (34 mg, 0.09 mmol) in CH$_2$Cl$_2$ (2 mL) was added (S)—N-(pyrrolidin-3-yl) acetamide (16.3 mg, 0.13 mol) and Et$_3$N (20 mg, 0.2 mmol). After 14 h, the reaction was extracted with 1N HCl (2 mL×2) before drying over MgSO$_4$. Filtration and concentration under reduced pressure afforded (S)—N-(1-(6-cyano-5-(2,4-dichlorophenyl)-7-methylimidazo[1,2-a]pyrimidin-2-ylsulfonyl)pyrrolidin-3-yl)acetamide as a white solid (34 mg, 81%). This crude product was used directly for the subsequent reaction without further purification.

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=2.88 min, 97% homogeneity index.

LCMS: Anal. Calcd. for $C_{20}H_{18}Cl_2N_6O_3S$ 492.1; found: 493.1 (M+H)$^+$.

Example 158

Step 7. (S)—N-(1-(6-(Aminomethyl)-5-(2,4-dichlorophenyl)-7-methylinmidazo[1,2-a]pyrimidin-2-ylsulfonyl)pyrrolidin-3-yl)acetamide

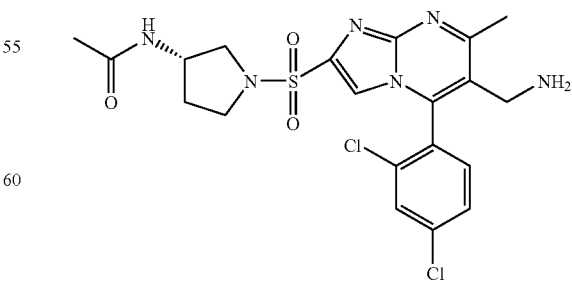

To a stirred suspension of (S)—N-(1-(6-cyano-5-(2,4-dichlorophenyl)-7-methylimidazo[1,2-a]pyrimidin-2-ylsulfonyl)pyrrolidin-3-yl)acetamide (20 mg, 0.04 mmol) in NH$_3$/MeOH (2N solution, 2 mL) was added NH$_4$CO$_2$ (54 mg, 1 mmol) and RaNi (250 mg suspended in H$_2$O). The insolubles were filtered off after 1 h and the resulting residue was purified by reverse phase HPLC to obtain (S)—N-(1-(6-(Aminomethyl)-5-(2,4-dichlorophenyl)-7-methylimidazo[1,2-a]pyrimidin-2-ylsulfonyl)pyrrolidin-3-yl)acetamide, TFA salt (11 mg, 45%) as a white solid.

$^1$H NMR (500 MHz, CD$_3$OD) δ 7.95 (S, 1 H), 7.72-7.77 (d, 1 H), 7.59-7.65 (m, 2 H), 4.11-4.23 (d, 1 H), 3.99-4.08 (d, 1H), 3.48-3.63 (m, 3H), 2.84 (s, 3 H), 1.99-2.13 (m, 2 H), 1.87-1.89 (d, 3H), 1.78-1.85 (m, 1H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=1.84 min, 97% homogeneity index.

LCMS: Anal. Calcd. for C$_{20}$H$_{22}$Cl$_2$N$_6$O$_3$S 496.09; found: 497.24 (M+H)$^+$.

Examples 159 to 161

Using the same methods for preparation of Example 158, the following compounds were prepared as TFA or di-TFA salts:

Example 162

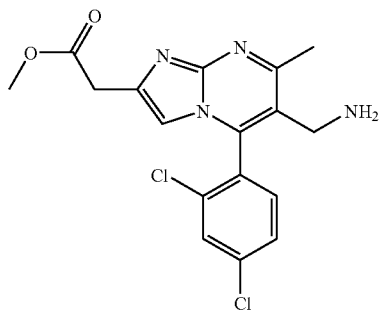

| Example 159 | 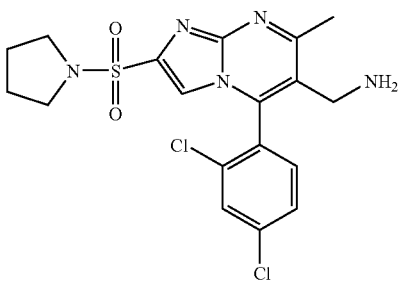 | $t_R$ = 2.78 min (97%)<br>LCMS: Anal. Calcd. for C$_{18}$H$_{19}$Cl$_2$N$_5$O$_2$S 439.06<br>found: 440.20 (M + H)$^+$ |
| --- | --- | --- |
| Example 160 | 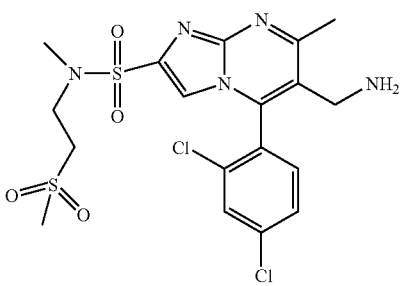 | $t_R$ = 2.36 min (99%)<br>LCMS: Anal. Calcd. for C$_{18}$H$_{21}$Cl$_2$N$_5$O$_4$S$_2$ 505.04<br>found: 506.10 (M + H)$^+$ |
| Example 161 | 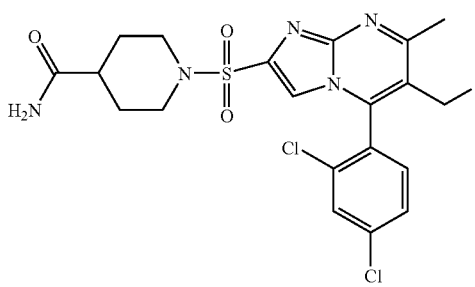 | $t_R$ = 1.87 min (98%)<br>LCMS: Anal. Calcd. for C$_{20}$H$_{22}$Cl$_2$N$_6$O$_3$S 496.09<br>found: 497.10 (M + H)$^+$<br>HRMS: Anal. Calcd. for C$_{20}$H$_{22}$Cl$_2$N$_6$O$_3$S 497.0924<br>found: 497.0936 (M + H)$^+$ |

Example 162

Step 1. Methyl 2-(2-amino-1H-imidazol-4-yl)acetate

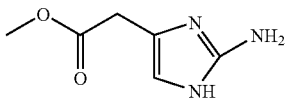

Methyl 2-(2-amino-1H-imidazol-4-yl)acetate was synthesized according to M. J. Bouchet; A. Rendon; C. G. Wermuth; M. Goelcdner; C. Hirth *J. Med. Chem.* 1987, 30, 2222-2227.

Example 162

Step 2. Methyl 2-(6-carbamoyl-5-(2,4-dichlorophenyl)-7-methyl-5,8-dihydroimidazo[1,2-a]pyrimidin-2-yl)acetate

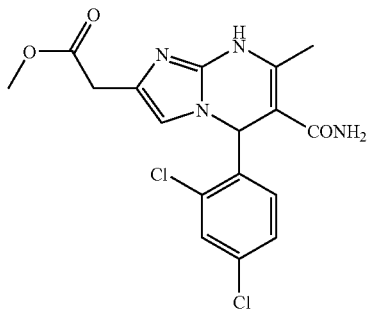

A mixture of methyl 2-(2-amino-1H-imidazol-4-yl)acetate (986 mg, 6.4 mmol) and 2-(2,4-dichlorobenzylidene)-3-oxobutanamide (Example 158, Step 2, 1.64 g, 6.4 mmol) in isopropyl alcohol (40 mL) was placed as a slurry in a 100° C. oil bath. The mixture became a clear solution within 2 min and a precipitate formed during heating for 14.5 h. Upon cooling to room temperature, the tan solids were isolated by filtration with hexanes wash (2×15 mL) to provide methyl 2-(6-carbamoyl-5-(2,4-dichlorophenyl)-7-methyl-5,8-dihydroimidazo[1,2-a]pyrimidin-2-yl)acetate (1.14 g, 45%) as a tan solid.

$^1$H NMR (500 MHz, d$^6$-DMSO) δ 9.70 (s, 1H), 7.58 (s, 1H), 7.40 (d, J=8.5 Hz, 1H), 7.36 (d, J=8.2 Hz, 1H), 6.93 (br s, 2H), 6.55 (s, 1H), 6.40 (s, 1H), 3.54 (s, 3H), 3.34 (m, 2H), 2.16 (s, 3H).

HPLC Phenomenex Luna, 5u, 4.6×50 mm, detection at 220 nm, flow rate 4 mL/min, 0 to 100% B over 4 minutes, 1 minute hold time, A=90% water, 10% methanol, 0.2% H$_3$PO$_4$, B=10% water, 90% methanol, 0.2% H$_3$PO$_4$, t$_R$=1.73 min, 100% purity.

LCMS: Anal. Calcd. for C$_{17}$H$_{16}$Cl$_2$N$_4$O$_3$: 394.06; found: 395.2 (M+H)$^+$.

Example 162

Step 3. Methyl 2-(6-carbamoyl-5-(2,4-dichlorophenyl)-7-methylimidazo[1,2-a]pyrimidin-2-yl)acetate

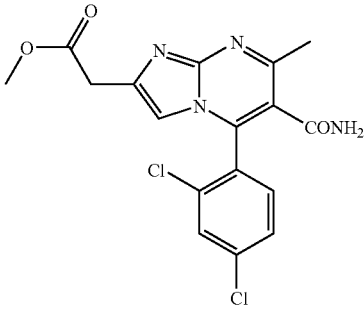

To a slurry of methyl 2-(6-carbamoyl-5-(2,4-dichlorophenyl)-7-methyl-5,8-dihydroimidazo[1,2-a]pyrimidin-2-yl)acetate (1.05 g, 2.66 mmol) in THF (30 mL was added 2,3-dichloro-5,6-dicyano-1,4-benzoquinone (604 mg, 2.66 mmol). After 30 min, CH$_2$Cl$_2$ (100 mL) and satd aq NaHCO$_3$ (50 mL) were added. The layers were separated, the aqueous layer extracted with an additional 50 mL of CH$_2$Cl$_2$, and the combined CH$_2$Cl$_2$ extracts were washed with satd aq NaHCO$_3$ (3×50 mL). The organic solution was dried with MgSO$_4$, filtered, and concentrated under reduced pressure to yield methyl 2-(6-carbamoyl-5-(2,4-dichlorophenyl)-7-methylimidazo[1,2-a]pyrimidin-2-yl)acetate (816 mg, 2.08 mmol, 78%) as a pale grey-green solid contaminated with 11% (by HPLC analysis) of the starting material. This material was used without further purification.

$^1$H NMR (500 MHz, d$^6$-DMSO) δ 7.87 (s, 1H), 7.82 (s, 1H), 7.62 (br s, 2H), 7.57 (d, J=8.3 Hz, 1 Hz), 7.05 (s, 1H), 3.68 (s, 2H), 3.50 (s, 3H), 2.50 (s, 3H).

HPLC Phenomenex Luna, 5u, 4.6×50 mm, detection at 220 nm, flow rate 4 mL/min, 0 to 100% B over 4 minutes, 1 minute hold time, A=90% water, 10% methanol, 0.2% H$_3$PO$_4$, B=10% water, 90% methanol, 0.2% H$_3$PO$_4$, t$_R$=1.71 min, 89% purity.

LCMS: Anal. Calcd. for C$_{17}$H$_{14}$Cl$_2$N$_4$O$_3$: 392.04; found: 393.2 (M+H)$^+$.

Example 162

Step 4. Methyl 2-(6-cyano-5-(2,4-dichlorophenyl)-7-methylimidazo[1,2-a]pyrimidin-2-yl)acetate

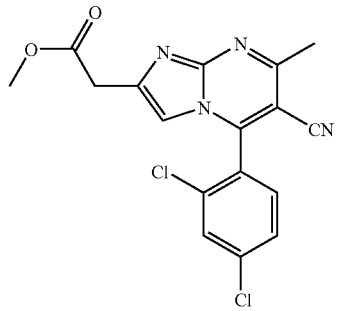

To a suspension of methyl 2-(6-carbamoyl-5-(2,4-dichlorophenyl)-7-methylimidazo[1,2-a]pyrimidin-2-yl)acetate (766 mg, 1.95 mmol) in $CH_2Cl_2$ (20 mL) was added $Et_3N$ (592 mg, 5.85 mmol) and trifluoroacetic anhydride (819 mg, 3.90 mmol). The reaction mixture became a dark brown-green solution within 2 min. Satd aq NH4Cl (20 mL) was added after 30 min. The organic layer was washed with 20 mL each of satd aq $NaHCO_3$ and water, followed by drying with $MgSO_4$, filtration, and concentration under reduced pressure. The residue was purified by silica gel chromatography eluting product through a 40 mm i.d. by 150 mm column with 1.5% MeOH in $CH_2Cl_2$. Concentration of the fractions containing product gave methyl 2-(6-cyano-5-(2,4-dichlorophenyl)-7-methylimidazo[1,2-a]pyrimidin-2-yl)acetate (583 mg, 80%) as a yellow foam.

$^1$H NMR (500 MHz, $CDCl_3$) δ 7.64 (s, 1H), 7.49 (d, J=8.3 Hz, 1H), 7.41 (d, J=8.2 Hz, 1H), 7.11 (s, 1H), 3.83 (s, 2H), 3.65 (s, 3H), 2.79 (s, 3H).

HPLC Phenomenex Luna, 5u, 4.6×50 mm, detection at 220 nm, flow rate 4 mL/min, 0 to 100% B over 4 minutes, 1 minute hold time, A=90% water, 10% methanol, 0.2% $H_3PO_4$, B=10% water, 90% methanol, 0.2% $H_3PO_4$, $t_R$=3.08 min, >99% purity.

LCMS: Anal. Calcd. for $C_{17}H_{12}Cl_2N_4O_2$: 374.03; found: 375.1 $(M+H)^+$.

Example 162

Step 5. Methyl 2-(6-(aminomethyl)-5-(2,4-dichlorophenyl)-7-methylimidazo[1,2-a]pyrimidin-2-yl) acetate

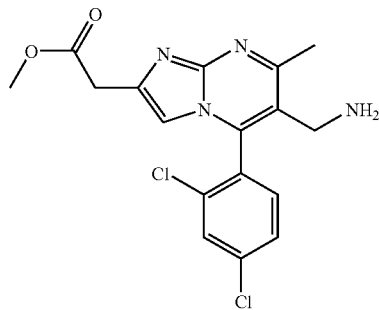

To a solution of methyl 2-(6-cyano-5-(2,4-dichlorophenyl)-7-methylimidazo[1,2-a]pyrimidin-2-yl)acetate (50 mg, 0.13 mmol) in MeOH (1 mL) in a thick-walled pressure tube with Teflon cap was added Aldrich grade 2400 Raney nickel (570 mg as a damp slurry in water) followed by hydrazine hydrate (92.7 mg, 1.85 mmol) and the tube quickly capped. After 15 h, the vessel was vented and analysis by HPLC indicated 50% product.

To a second solution of methyl 2-(6-cyano-5-(2,4-dichlorophenyl)-7-methylimidazo[1,2-a]pyrimidin-2-yl)acetate (50 mg, 0.13 mmol) in methanol (1 mL) was added Aldrich grade 2400 Raney nickel (353 mg as a damp slurry in water) and the reaction placed under an atmosphere of $H_2$ using a balloon. After 15 h, the reaction was vented and analysis by HPLC indicated 59% product.

The supernatants from the two reactions were combined and passed through a plug of Celite (30 mm i.d.×30 mm) eluting with 30 mL of methanol. Concentration under reduced pressure provided an oil which was purified using a UCT 2.5 gram C-18 cartridge (#CEC-18) eluting product with 3-9% methanol in 0.1% aqueous TFA. Fractions containing product were concentrated to give methyl 2-(6-(aminomethyl)-5-(2,4-dichlorophenyl)-7-methylimidazo[1,2-a]pyrimidin-2-yl)acetate, TFA salt (31 mg, 24%) as a sticky tan foam.

HPLC Phenomenex Luna, 5u, 4.6×50 mm, detection at 220 nm, flow rate 4 mL/min, 0 to 100% B over 4 minutes, 1 minute hold time, A=90% water, 10% methanol, 0.2% $H_3PO_4$, B=10% water, 90% methanol, 0.2% $H_3PO_4$, $t_R$=1.21 min, 98% purity.

LCMS: Anal. Calcd. for $C_{17}H_{16}Cl_2N_4O_2$: 378.07; found: 379.20 $(M+H)^+$.

HRMS: Anal. Calcd. for $C_{17}H_{17}Cl_2N_4O_2$ 379.0729 found: 379.0734 $(M+H)^+$.

Example 163

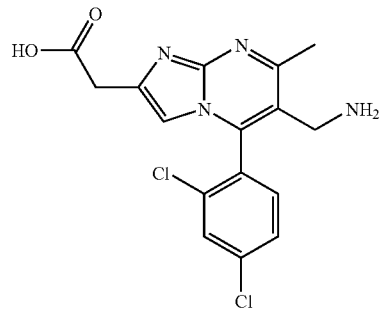

Example 163

2-(6-(Aminomethyl)-5-(2,4-dichlorophenyl)-7-methylimidazo[1,2-a]pyrimidin-2-yl)acetic acid

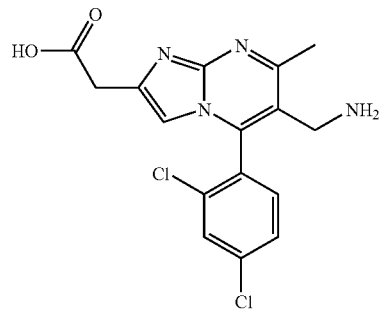

To a solution of methyl 2-(6-(aminomethyl)-5-(2,4-dichlorophenyl)-7-methylimidazo[1,2-a]pyrimidin-2-yl)acetate (18 mg, 0.04 mmol) in THF (0.1 mL) was added LiOH (2.0 M in $H_2O$, 0.37 mL, 0.74 mmol). After 30 min, TFA (60 µL) was added followed by water (1 mL). The mixture was eluted through a UCT 2.5 gram C-18 cartridge (#CEC-18) with water and fractions containing product were combined and concentrated to provide 2-(6-(aminomethyl)-5-(2,4-dichlorophenyl)-7-methylimidazo[1,2-a]pyrimidin-2-yl)acetic acid, TFA salt (4 mg, 23%) as a colorless oil.

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, $t_R$=1.32 min, 98% purity.

LCMS: Anal. Calcd. for $C_{16}H_{14}Cl_2N_4O_2$: 364.05; found: 365.2 (M+H)$^+$.

Example 164

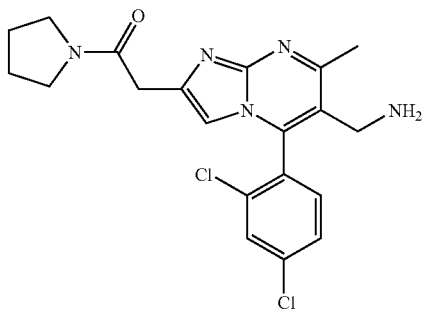

Example 164

Step 1. 2-(6-Cyano-5-(2,4-dichlorophenyl)-7-methylimidazo[1,2-a]pyrimidin-2-yl)acetic acid

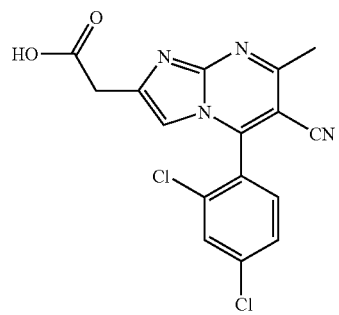

To a solution of methyl 2-(6-cyano-5-(2,4-dichlorophenyl)-7-methylimidazo[1,2-a]pyrimidin-2-yl)acetate (Example 162, Step 4, 260 mg, 0.7 mmol) in THF (1.4 mL) was added LiOH (2.0 M in H$_2$O, 7 mL, 14 mmol). After 18 min, the clear brown reaction was adjusted to pH 2 using hydrochloric acid (2 N in H$_2$O, 2.35 mL, 4.7 mmol). The solution became less dark and a precipitate formed. The mixture was extracted with EtOAc (3×7 mL), the combined organic extracts were back-washed with 5 mL water, and then dried with MgSO$_4$. Filtration and concentration provided 2-(6-cyano-5-(2,4-dichlorophenyl)-7-methylimidazo[1,2-a]pyrimidin-2-yl)acetic acid (239 mg, 95%) as a yellow-brown foam.

$^1$H NMR (500 MHz, CDCl$_3$) δ 7.63 (s, 1H), 7.49 (d, J=8.2 Hz, 1H), 7.42 (d, J=8.3 Hz, 1H), 7.10 (s, 1H), 3.88 (d, J=17.6 Hz, 1H), 3.83 (d, J=18.1 Hz, 1H), 2.79 (s, 3H).

HPLC Phenomenex Luna, 5u, 4.6×50 mm, detection at 220 nm, flow rate 4 mL/min, 0 to 100% B over 4 minutes, 1 minute hold time, A=90% water, 10% methanol, 0.2% H$_3$PO$_4$, B=10% water, 90% methanol, 0.2% H$_3$PO$_4$, $t_R$=2.88 min, 100% purity.

LCMS: Anal. Calcd. for $C_{16}H_{10}Cl_2N_4O_2$: 360.02; found: 361.2 (M+H)$^+$.

Example 164

Step 2. 5-(2,4-Dichlorophenyl)-7-methyl-2-(2-oxo-2-(pyrrolidin-1-yl)ethyl)imidazo[1,2-a]pyrimidine-6-carbonitrile

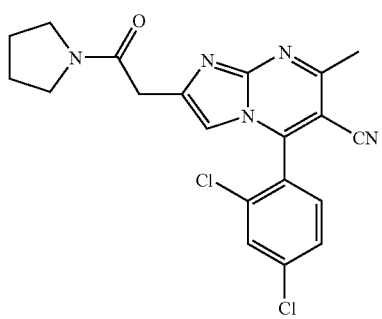

To a solution of 2-(6-cyano-5-(2,4-dichlorophenyl)-7-methylimidazo[1,2-a]pyrimidin-2-yl)acetic acid (72 mg, 0.2 mmol) in CH$_3$CN (0.7 mL) were added HOAT (41 mg, 0.3 mmol) and EDC (77 mg, 0.4 mmol). After one min all of the solids had dissolved to produce a clear tan to brown solution. At 5 min, pyrrolidine (14.5 mg, 0.2 mmol) was added. At 20 min from the addition of pyrrolidine, the reaction was quenched with EtOAc (3 mL) and then washed with satd aq NaHCO$_3$ (2×3 mL), satd aq NH$_4$Cl (2×3 mL), and water (3 mL). The organic layer was dried with MgSO$_4$, filtered, and concentrated to yield 5-(2,4-dichlorophenyl)-7-methyl-2-(2-oxo-2-(pyrrolidin-1-yl)ethyl)imidazo[1,2-a]pyrimidine-6-carbonitrile (46 mg, 56%) as a yellow-brown oil.

$^1$H NMR (500 MHz, CDCl$_3$) δ 7.62 (s, 1H), 7.47 (d, J=8.2 Hz, 1H), 7.39 (d, J=8.3 Hz, 1H), 7.22 (s, 1H), 3.83 (d, J=15.9 Hz, 1H), 3.76 (d, J=16.0 Hz, 1H), 3.63 (m, 1H), 3.55 (m, 1H), 3.38 (dd, J=5.5, 7.2 Hz, 2H), 2.78 (s, 3H) 1.91 (m, 2H), 1.79 (m, 2H).

HPLC Phenomenex Luna, 5u, 4.6×50 mm, detection at 220 nm, flow rate 4 mL/min, 0 to 100% B over 4 minutes, 1 minute hold time, A=90% water, 10% methanol, 0.2% H$_3$PO$_4$, B=10% water, 90% methanol, 0.2% H$_3$PO$_4$, $t_R$=3.05 min, >98% purity.

LCMS: Anal. Calcd. for $C_{20}H_{17}Cl_2N_5O$: 413.08; found: 414.2 (M+H)$^+$.

Example 164

Step 3. 2-(6-Aminomethyl)-5-(2,4-dichlorophenyl)-7-methylimidazo[1,2-a]pyrimidin-2-yl)-1-(pyrrolidin-1-yl)ethanone

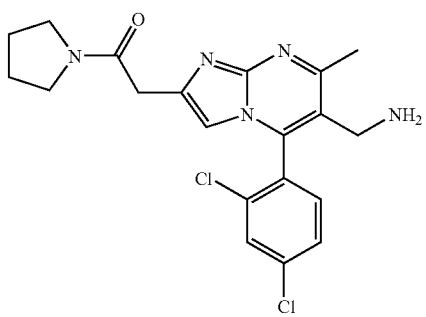

To a solution of 5-(2,4-dichlorophenyl)-7-methyl-2-(2-oxo-2-(pyrrolidin-1-yl)ethyl)imidazo[1,2-a]pyrimidine-6-carbonitrile (46 mg, 0.11 mmol) in methanol (1 mL) was added Aldrich grade 2400 Raney nickel (348 mg as a damp slurry in water) and the reaction placed under an atmosphere of $H_2$ using a balloon. After 5.5 h, the $H_2$ was removed and the supernatant passed through a 15 mm i.d.×15 mm Celite plug eluting with MeOH (7 mL). This material was concentrated to an oil and purified by passage through a UCT 2.5 gram C-18 cartridge (#CEC-18) eluting product with 4-20% MeOH in 0.1% aqueous TFA. Fractions containing product were concentrated to provide 2-(6-Aminomethyl)-5-(2,4-dichlorophenyl)-7-methylimidazo[1,2-a]pyrimidin-2-yl)-1-(pyrrolidin-1-yl)ethanone, TFA salt (26 mg, 44%) as a tan foam.

$^1$H NMR (500 MHz, CD$_3$OD) δ 7.95 (s, 1 H), 7.76 (d, J=8.3 Hz, 1H), 7.66 (d, J=8.2 Hz, 1H), 7.44 (bs, 1H), 4.27 (d, J=14.9, 2H), 4.09 (d, J=14.9, 2H), 3.99 (br s, 2H), 3.58 (br s, 2H), 3.44 (br s, 2H), 2.93 (br s, 3H), 2.03 (br s, 2H), 1.91 (br s, 2H).

HPLC Phenomenex Luna, 5u, 4.6×50 mm, detection at 220 nm, flow rate 4 mL/min, 0 to 100% B over 4 minutes, 1 minute hold time, A=90% water, 10% methanol, 0.2% $H_3PO_4$, B=10% water, 90% methanol, 0.2% $H_3PO_4$, $t_R$=1.27 min, 98% purity.

LCMS: Anal. Calcd. for $C_{20}H_{21}Cl_2N_5O$: 417.11; found: 418.20 (M+H)$^+$.

Example 165 and 166

Using the same methods described for synthesis of Example 164, the following compounds were prepared as TFA salts:

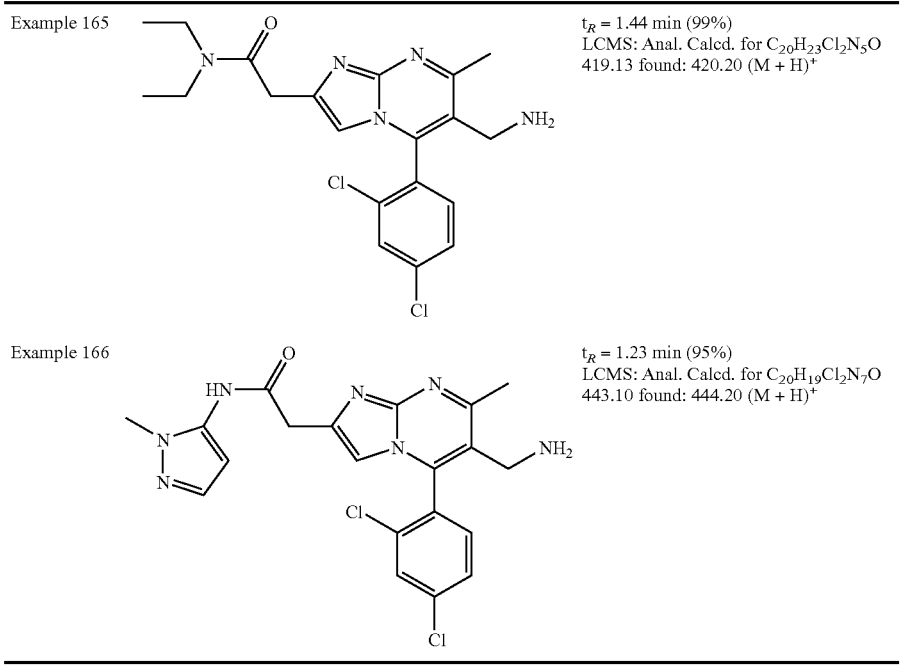

Example 165: $t_R$ = 1.44 min (99%)
LCMS: Anal. Calcd. for $C_{20}H_{23}Cl_2N_5O$ 419.13 found: 420.20 (M + H)$^+$ Example 166: $t_R$ = 1.23 min (95%)
LCMS: Anal. Calcd. for $C_{20}H_{19}Cl_2N_7O$ 443.10 found: 444.20 (M + H)$^+$

Example 167

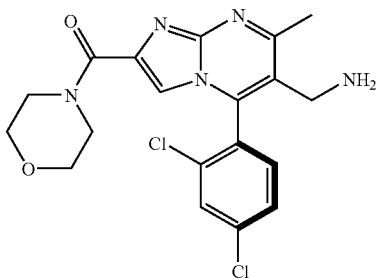

Example 167

Step 1. (−) and (+)-Ethyl 6-(azidomethyl)-5-(2,4-dichlorophenyl)-7-methylimidazo[1,2-a]pyrimidine-2-carboxylate

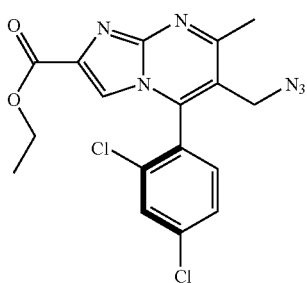
(−)-isomer

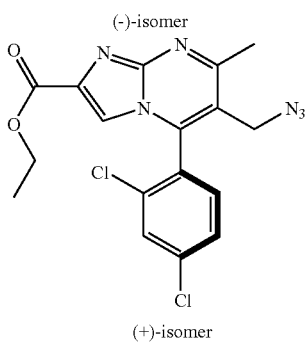
(+)-isomer

Ethyl 6-(azidomethyl)-5-(2,4-dichlorophenyl)-7-methylimidazo[1,2-a]pyrimidine-2-carboxylate (Example 54, Step 9) exists as a 1:1 mixture of two stable atropisomers. Ten grams of the racemate were separated by supercritical fluid chromatography on Chiralpak OF, 250×20 mm, 10 micron, at 35° C., 50 mL/min, mobile Phase: $CO_2$/MeOH/DEA: 65/35/0.1, injection Volume: 3.5 mL of 33 mg/mL sample solution, detector wavelength: 220 nm to obtain (−)-ethyl 6-(azidomethyl)-5-(2,4-dichlorophenyl)-7-methylimidazo[1,2-a]pyrimidine-2-carboxylate (5 g, 50%) and (+)-ethyl 6-(azidomethyl)-5-(2,4-dichlorophenyl)-7-methylimidazo[1,2-a]pyrimidine-2-carboxylate (5 g, 50%), both as white solid.

For the (−)-isomer: HPLC Chiralpak OF, 4.6×250 mm, 10 micron, isocratic $CO_2$/MeOH/DEA: 60/40/0.1 over 25 min, 2.0 mL/min, $t_R$=10.91 min, 100% homogeneity index, >99.9% enantimeric excess.

For the (+)-isomer: HPLC Chiralpak OF, 4.6×250 mm, 10 micron, isocratic $CO_2$/MeOH/DEA: 60/40/0.1 over 25 min, 2.0 mL/min, $t_R$=17.94 min, 100% homogeneity index, >99.9% enantimeric excess.

The absolute stereochemistry was determined by single crystal X-ray analysis for an intermediate four steps before.

Example 167

Step 2. (+)-6-(Azidomethyl)-5-(2,4-dichlorophenyl)-7-methylimidazo[1,2-a]pyrimidine-2-carboxylic acid

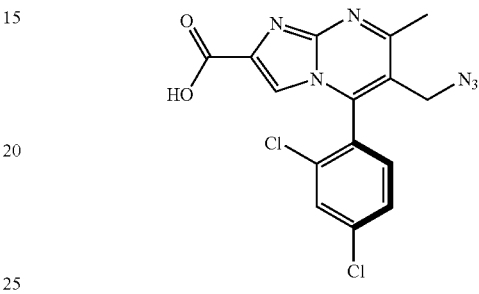

To a stirred solution of (+)-ethyl 6-(azidomethyl)-5-(2,4-dichlorophenyl)-7-methylimidazo[1,2-a]pyrimidine-2-carboxylate (1 g, 2.47 mmol) in THF (20 mL) and $H_2O$ (2 mL) was added $LiOH \cdot H_2O$ (155 mg, 3.70 mmol). After heating to 50° C. for 16 h, the reaction was concentrated under reduced pressure and diluted with EtOAc. The aqueous layer was acidified by 1N HCl to pH=1. The organic layer was washed with satd aq $NH_4Cl$ and brine before drying over $MgSO_4$. Filtration, concentration under reduced pressure provided (+)-6-(azidomethyl)-5-(2,4-dichlorophenyl)-7-methylimidazo[1,2-a]pyrimidine-2-carboxylic acid (874 mg, 94%) as a white solid.

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.20 min, 99% homogeneity index.

Example 167

Step 3. (+)-(6-(Azidomethyl)-5-(2,4-dichlorophenyl)-7-methylimidazo[1,2-a]pyrimidin-2-yl)(morpholino)methanone

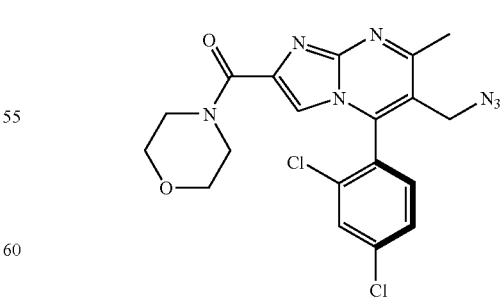

To a stirred solution of (+)-6-(azidomethyl)-5-(2,4-dichlorophenyl)-7-methylimidazo[1,2-a]pyrimidine-2-carboxylic acid (150 mg, 0.40 mmol) in THF (10 mL) was added morpholine (52 mg, 0.60 mmol), HOAt (81 mg, 0.60 mmol), EDC (114 mg, 0.60 mmol) and $^i$Pr$_2$NEt (103 mg, 0.80 mmol). The reaction was kept at room temperature for 2 h and was concentrated under reduced pressure. The residue was diluted with EtOAc and the organic layer was washed with 1N HCl, 1N NaOH and brine prior to drying over anhydrous MgSO$_4$. Filtration and concentration under reduced pressure afforded (+)-(6-(azidomethyl)-5-(2,4-dichlorophenyl)-7-methylimidazo[1,2-a]pyrimidin-2-yl)(morpholino)methanone (177 mg, 100% crude yield) as a clear glass.

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.34 min, 93% homogeneity index.

LCMS: Anal. Calcd. for C$_{19}$H$_{17}$Cl$_2$N$_7$O$_2$ 445.08; found: 446.20 (M+H)$^+$.

Example 167

Step 3. (+)-(6-(Aminomethyl)-5-(2,4-dichlorophenyl)-7-methylimidazo[1,2-a]pyrimidin-2-yl)(morpholino)methanone

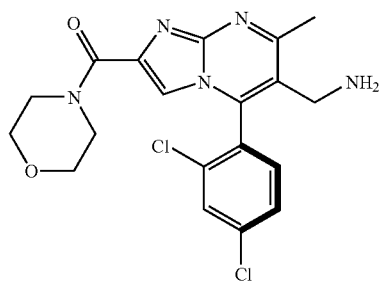

To a stirred solution of (+)-(6-(azidomethyl)-5-(2,4-dichlorophenyl)-7-methylimidazo[1,2-a]pyrimidin-2-yl)(morpholino)methanone (177 mg, 0.40 mmol) in THF (8 mL) and H$_2$O (0.8 mL) was added PPh$_3$ polymer bound (3 mmol/g, 199 mg, 0.60 mmol). The reaction was heated to 50° C. for 24 h. The reaction was filtered, concentrated under reduced pressure and purified by reverse phase HPLC (TFA containing solvents were used) to give (+)-(6-(aminomethyl)-5-(2,4-dichlorophenyl)-7-methylimidazo[1,2-a]pyrimidin-2-yl)(morpholino)methanone, TFA salt (58 mg, 27% yield) as a white solid.

[α]$^{24.3}_D$+54.12° (c 2.62, MeOH). $^1$H NMR (400 MHz, CD$_3$OD) δ 7.92 (d, J=2.2 Hz, 1H), 7.73 (dd, J=2.2, 8.4 Hz, 1H), 7.62 (d, J=8.4 Hz, 1H), 7.55 (s, 1H), 4.19 (d, J=15.0 Hz, 1H), 4.01 (d, J=15.0 Hz, 1H), 4.01 (br s, 2H), 3.73 (br s, 6H), 2.86 (s, 3H).

HPLC-MS Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=2.26 min, 99% homogeneity index.

LCMS: Anal. Calcd. for C$_{19}$H$_{19}$Cl$_2$N$_5$O$_2$ 419.09 found: 420.19 (M+H)$^+$.

HRMS: Anal. Calcd. for C$_{19}$H$_{20}$Cl$_2$N$_5$O$_2$ 420.0994 found: 420.0985 (M+H)$^+$.

Examples 168 to 197

Using the same methods for preparation of Example 167, the following compounds were prepared as TFA or di-TFA salts:

Example 168

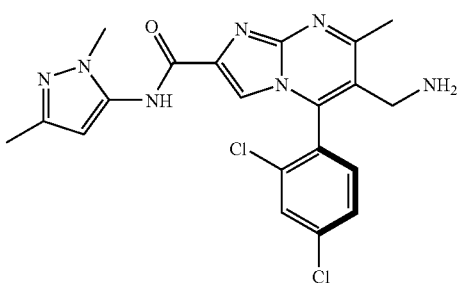

t$_R$ = 2.75 min (99%)
LCMS: Anal. Calcd. for C$_{20}$H$_{19}$Cl$_2$N$_7$O 443.10 found: 444.21 (M + H)$^+$
HRMS: Anal. Calcd. for C$_{20}$H$_{20}$Cl$_2$N$_7$O 444.1106 found: 444.1128 (M + H)$^+$ Example 169

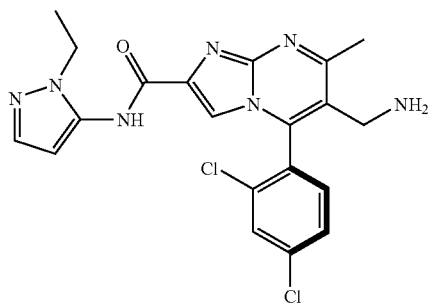

t$_R$ = 1.95 min (99%)
LCMS: Anal. Calcd. for C$_{20}$H$_{19}$Cl$_2$N$_7$O 443.10 found: 444.21 (M + H)$^+$
HRMS: Anal. Calcd. for C$_{20}$H$_{20}$Cl$_2$N$_7$O 444.1106 found: 444.1126 (M + H)$^+$

| | | |
|---|---|---|
| Example 170 | 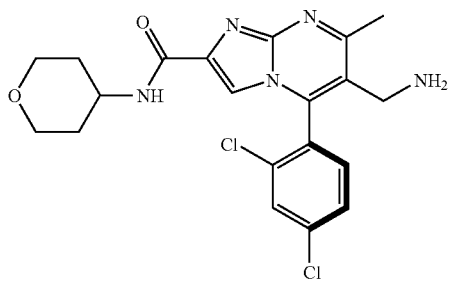 | $t_R$ = 1.82 min (99%)<br>LCMS: Anal. Calcd. for $C_{20}H_{21}Cl_2N_5O_2$<br>433.11 found: 434.22 (M + H)$^+$ |
| Example 171 | 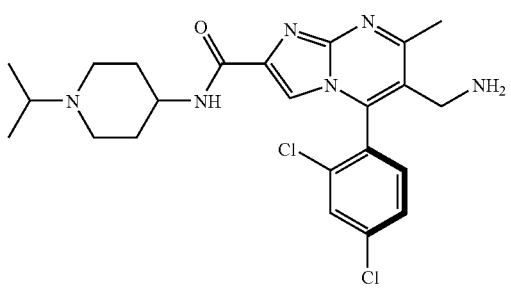 | $t_R$ = 1.07 min (98%)<br>LCMS: Anal. Calcd. for $C_{23}H_{28}Cl_2N_6O$<br>474.17 found: 475.32 (M + H)$^+$<br>HRMS: Anal. Calcd. for $C_{23}H_{29}Cl_2N_6O$<br>475.1780 found: 475.1791 (M + H)$^+$ |
| Example 172 | 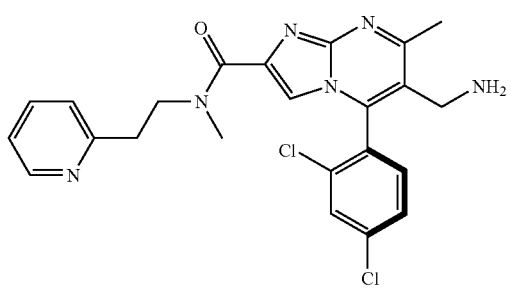 | $t_R$ = =1.01 min (99%)<br>LCMS: Anal. Calcd. for $C_{23}H_{22}Cl_2N_6O$<br>468.12 found: 469.20 (M + H)$^+$<br>HRMS: Anal. Calcd. for $C_{23}H_{23}Cl_2N_6O$<br>469.1310 found: 469.1307 (M + H)$^+$ |
| Example 173 | 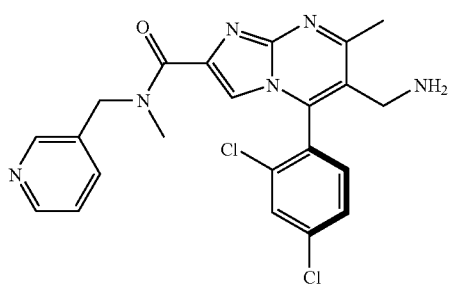 | $t_R$ = 0.92 min (98%)<br>LCMS: Anal. Calcd. for $C_{22}H_{20}Cl_2N_6O$<br>454.11 found: 455.36 (M + H)$^+$<br>HRMS: Anal. Calcd. for $C_{22}H_{21}Cl_2N_6O$<br>455.1154 found: 455.1136 (M + H)$^+$ |
| Example 174 | 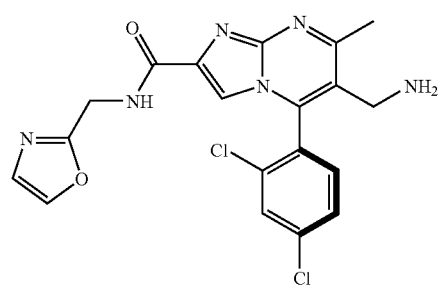 | $t_R$ = 1.62 min (98%)<br>LCMS: Anal. Calcd. for $C_{19}H_{16}Cl_2N_6O_2$<br>430.07 found: 431.31 (M + H)$^+$<br>HRMS: Anal. Calcd. for $C_{19}H_{17}Cl_2N_6O_2$<br>431.0789 found: 431.0794 (M + H)$^+$ |

| | | |
|---|---|---|
| Example 175 | 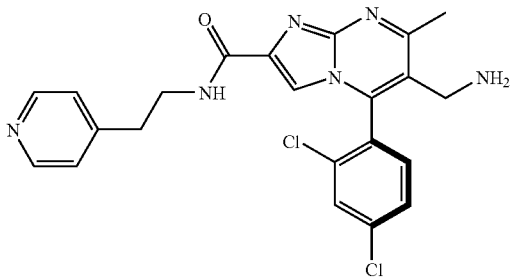 | $t_R$ = 0.96 min (97%)<br>LCMS: Anal. Calcd. for $C_{22}H_{20}Cl_2N_6O$<br>454.11 found: 455.36 $(M + H)^+$<br>HRMS: Anal. Calcd. for $C_{22}H_{21}Cl_2N_6O$<br>455.1154 found: 455.1168 $(M + H)^+$ |
| Example 176 | 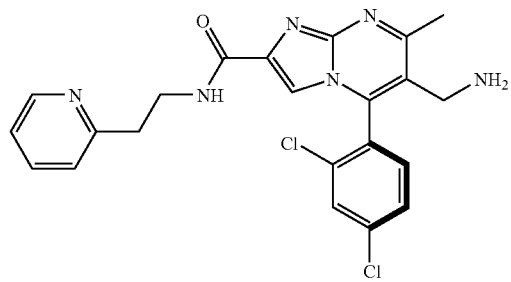 | $t_R$ = 0.95 min (96%)<br>LCMS: Anal. Calcd. for $C_{22}H_{20}Cl_2N_6O$<br>454.11 found: 455.34 $(M + H)^+$<br>HRMS: Anal. Calcd. for $C_{22}H_{21}Cl_2N_6O$<br>455.1154 found: 455.1145 $(M + H)^+$ |
| Example 177 | 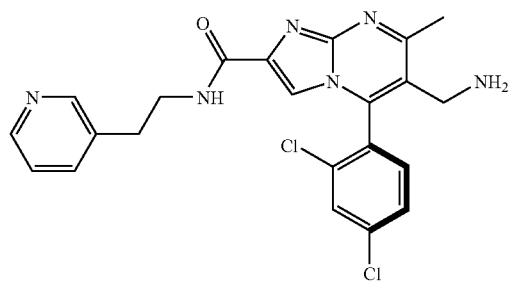 | $t_R$ = 0.97 min (98%)<br>LCMS: Anal. Calcd. for $C_{22}H_{20}Cl_2N_6O$<br>454.11 found: 455.32 $(M + H)^+$<br>HRMS: Anal. Calcd. for $C_{22}H_{21}Cl_2N_6O$<br>455.1154 found: 455.1167 $(M + H)^+$ |
| Example 178 | 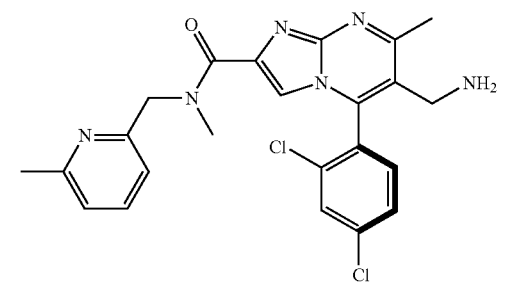 | $t_R$ = 1.00 min (99%)<br>LCMS: Anal. Calcd. for $C_{23}H_{22}Cl_2N_6O$<br>468.12 found: 469.33 $(M + H)^+$<br>HRMS: Anal. Calcd. for $C_{23}H_{22}Cl_2N_6O$<br>469.1310 found: 469.1322 $(M + H)^+$ |
| Example 179 | 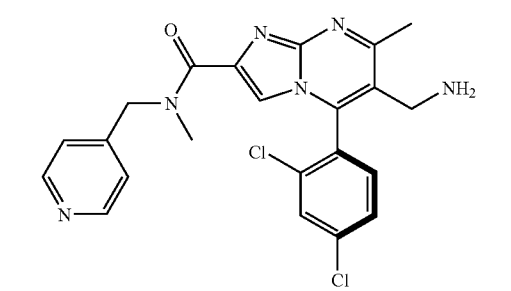 | $t_R$ = 0.79 min (99%)<br>LCMS: Anal. Calcd. for $C_{22}H_{20}Cl_2N_6O$<br>454.11 found: 455.33 $(M + H)^+$<br>HRMS: Anal. Calcd. for $C_{22}H_{21}Cl_2N_6O$<br>455.1154 found: 455.1167 $(M + H)^+$ |

-continued

Example 180 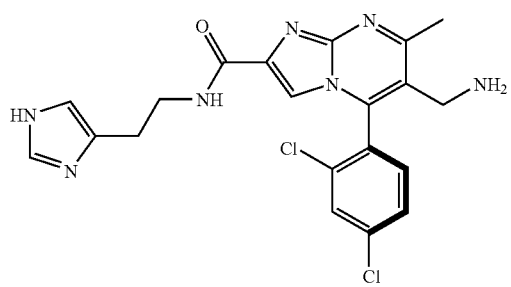
$t_R$ = 1.48 min (95%)
LCMS: Anal. Calcd. for $C_{20}H_{19}Cl_2N_7O$
443.10 found: 444.30 (M + H)$^+$
HRMS: Anal. Calcd. for $C_{20}H_{20}Cl_2N_7O$
444.1106 found: 444.1123 (M + H)$^+$ Example 181 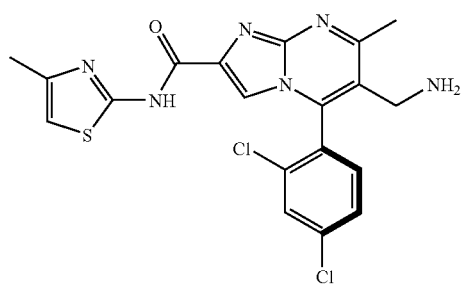
$t_R$ = 2.71 min (95%)
LCMS: Anal. Calcd. for $C_{19}H_{16}Cl_2N_6OS$
446.05 found: 447.22 (M + H)$^+$
HRMS: Anal. Calcd. for $C_{19}H_{17}Cl_2N_6OS$
447.0562 found: 447.0571 (M + H)$^+$ Example 182 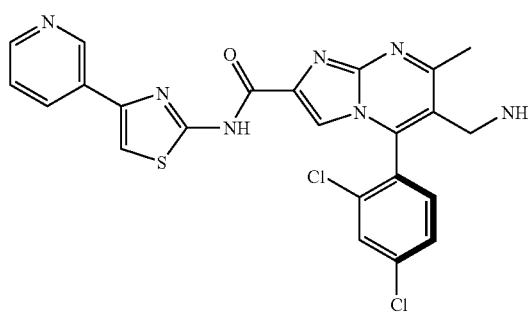
$t_R$ = 1.83 min (95%)
LCMS: Anal. Calcd. for $C_{23}H_{17}Cl_2N_7OS$
509.06 found: 510.29 (M + H)$^+$
HRMS: Anal. Calcd. for $C_{23}H_{18}Cl_2N_7OS$
510.0671 found: 510.0686 (M + H)$^+$ Example 183 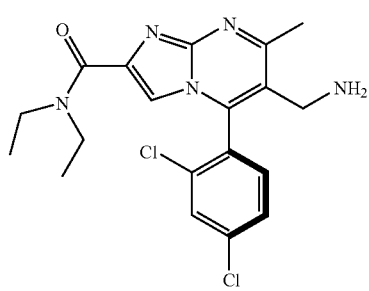
$t_R$ = 1.98 min (95%)
LCMS: Anal. Calcd. for $C_{19}H_{21}Cl_2N_5O$
405.11 found: 406.35 (M + H)$^+$
HRMS: Anal. Calcd. for $C_{19}H_{22}Cl_2N_5O$
406.1201 found: 406.1208 (M + H)$^+$ Example 184 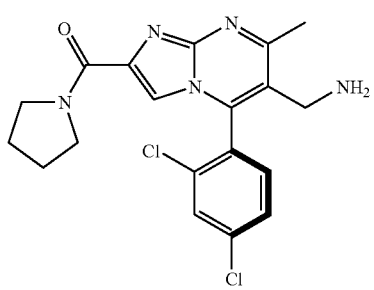
$t_R$ = 2.53 min (97%)
LCMS: Anal. Calcd. for $C_{19}H_{19}Cl_2N_5O_2$
403.10 found: 404.33 (M + H)$^+$
HRMS: Anal. Calcd. for $C_{19}H_{20}Cl_2N_5O_2$
404.1045 found: 404.1036 (M + H)$^+$ -continued

| Example 185 | 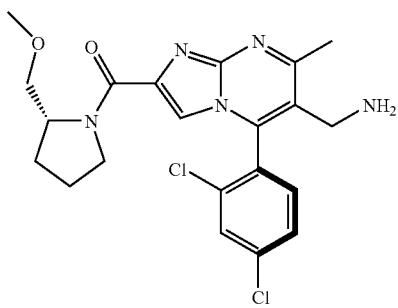 | $t_R$ = 2.76 min (95%)<br>LCMS: Anal. Calcd. for $C_{21}H_{23}Cl_2N_5O_2$<br>447.12 found: 448.36 (M + H)$^+$<br>HRMS: Anal. Calcd. for $C_{21}H_{24}Cl_2N_5O_2$<br>448.1307 found: 448.1316 (M + H)$^+$ |
|---|---|---|
| Example 186 | 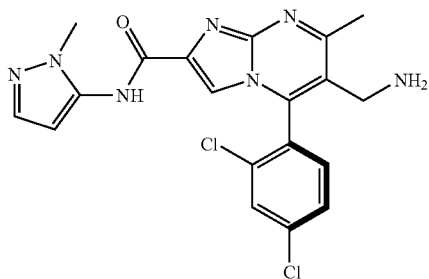 | $t_R$ = =1.87 min (95%)<br>LCMS: Anal. Calcd. for $C_{19}H_{17}Cl_2N_7O$<br>429.09 found: 430.33 (M + H)$^+$<br>HRMS: Anal. Calcd. for $C_{19}H_{18}Cl_2N_7O$<br>430.0950 found: 430.0966 (M + H)$^+$ |
| Example 187 | 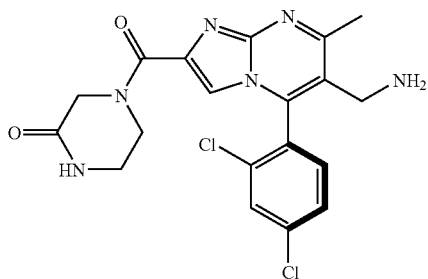 | $t_R$ = 1.19 min (95%)<br>LCMS: Anal. Calcd. for $C_{19}H_{18}Cl_2N_6O_2$<br>432.09 found: 433.33 (M + H)$^+$<br>HRMS: Anal. Calcd. for $C_{19}H_{19}Cl_2N_6O_2$<br>433.0947 found: 433.0945 (M + H)$^+$ |
| Example 188 | 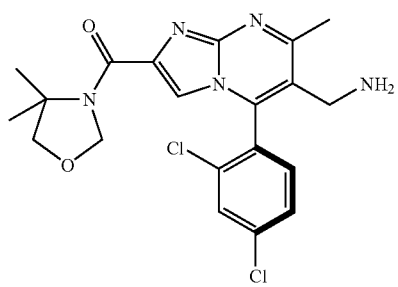 | $t_R$ = 2.13 min (95%)<br>LCMS: Anal. Calcd. for $C_{20}H_{21}Cl_2N_5O_2$<br>433.11 found: 434.31 (M + H)$^+$<br>HRMS: Anal. Calcd. for $C_{20}H_{22}Cl_2N_5O_2$<br>434.1151 found: 434.1163 (M + H)$^+$ |
| Example 189 | 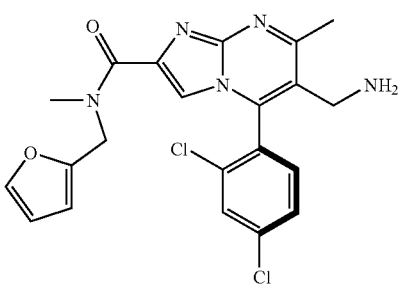 | $t_R$ = 2.09 min (98%)<br>LCMS: Anal. Calcd. for $C_{21}H_{19}Cl_2N_5O_2$<br>443.09 found: 444.30 (M + H)$^+$<br>HRMS: Anal. Calcd. for $C_{21}H_{20}Cl_2N_5O_2$<br>444.0994 found: 444.0987 (M + H)$^+$ |

| | | |
|---|---|---|
| Example 190 | 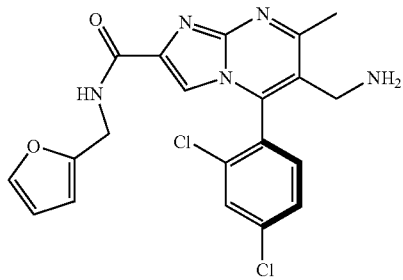 | $t_R$ = 2.03 min (98%)<br>LCMS: Anal. Calcd. for $C_{20}H_{17}Cl_2N_5O_2$<br>429.08 found: 430.30 (M + H)$^+$<br>HRMS: Anal. Calcd. for $C_{20}H_{18}Cl_2N_5O_2$<br>430.0838 found: 430.0822 (M + H)$^+$ |
| Example 191 | 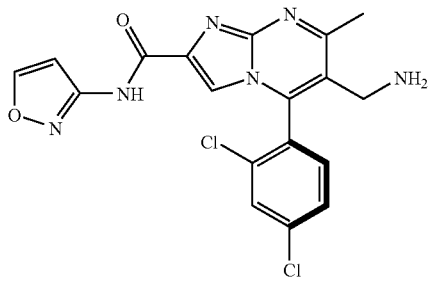 | $t_R$ = 1.88 min (98%)<br>LCMS: Anal. Calcd. for $C_{18}H_{14}Cl_2N_6O_2$<br>416.06 found: 417.27 (M + H)$^+$<br>HRMS: Anal. Calcd. for $C_{18}H_{15}Cl_2N_6O_2$<br>417.0634 found: 417.0643 (M + H)$^+$ |
| Example 192 | 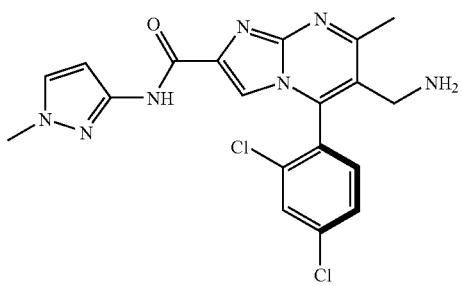 | $t_R$ = 1.88 min (96%)<br>LCMS: Anal. Calcd. for $C_{19}H_{17}Cl_2N_7O$<br>429.09 found: 430.29 (M + H)$^+$<br>HRMS: Anal. Calcd. for $C_{19}H_{18}Cl_2N_7O$<br>430.0950 found: 430.0960 (M + H)$^+$ |
| Example 193 | 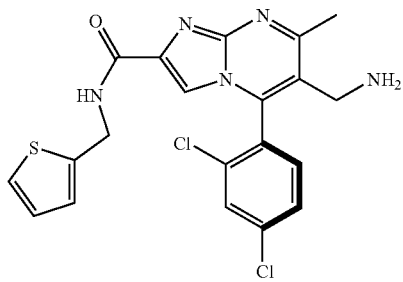 | $t_R$ = 2.24 min (98%)<br>LCMS: Anal. Calcd. for $C_{20}H_{17}Cl_2N_5OS$<br>445.05 found: 446.26 (M + H)$^+$<br>HRMS: Anal. Calcd. for $C_{20}H_{18}Cl_2N_5OS$<br>446.0609 found: 446.0625 (M + H)$^+$ |
| Example 194 | 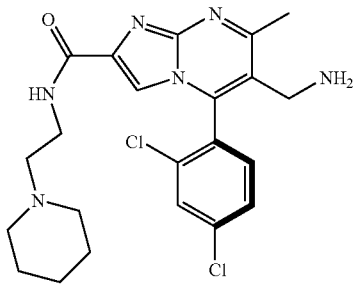 | $t_R$ = 0.94 min (94%)<br>LCMS: Anal. Calcd. for $C_{22}H_{26}Cl_2N_6O$<br>460.15 found: 461.38 (M + H)$^+$<br>HRMS: Anal. Calcd. for $C_{22}H_{27}Cl_2N_6O$<br>461.1640 found: 461.1640 (M + H)$^+$ |

| | | |
|---|---|---|
| Example 195 | 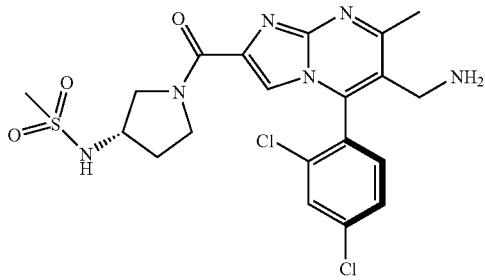 | $t_R$ = 1.53 min (99%)<br>LCMS: Anal. Calcd. for $C_{20}H_{22}Cl_2N_6O_3S$<br>496.1 found: 497.2 $(M + H)^+$ |
| Example 196 | 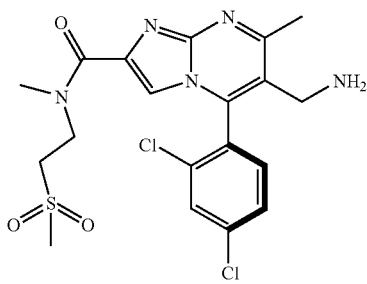 | $t_R$ = 2.20 min (99%)<br>LCMS: Anal. Calcd. for $C_{19}H_{21}Cl_2N_5O_3S$<br>469.07 found: 470.20 $(M + H)^+$ |
| Example 197 | 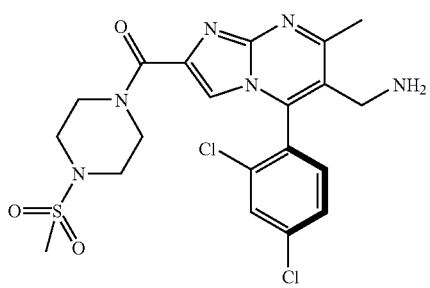 | $t_R$ = 2.42 min (100%)<br>LCMS: Anal. Calcd. for $C_{20}H_{22}Cl_2N_6O_3S$<br>496.09 found: 497.20 $(M + H)^+$ |

We claim:
1. A compound selected from the group consisting of:
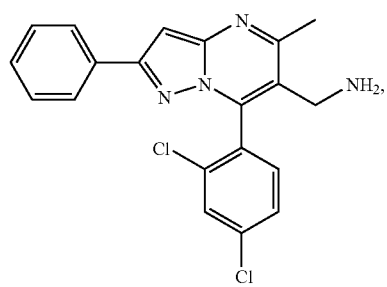
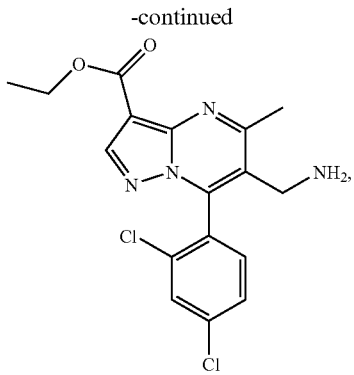
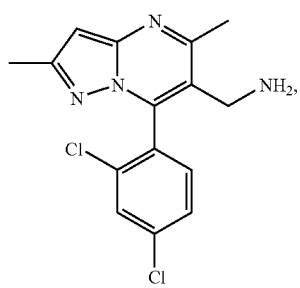
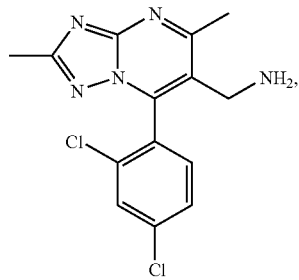
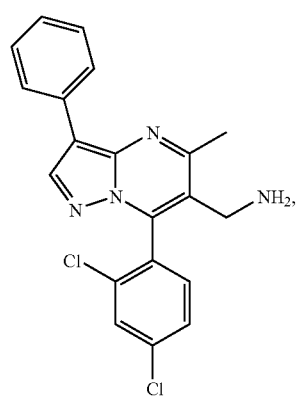
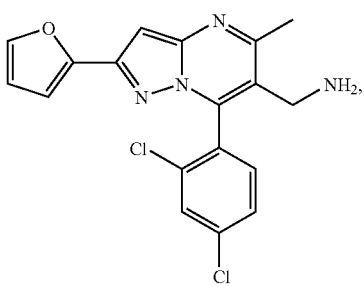

-continued
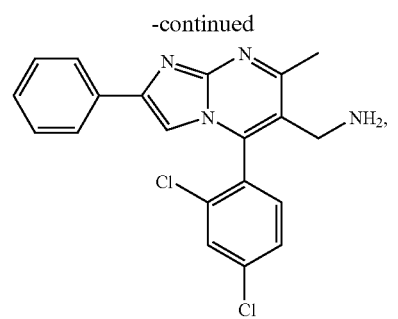
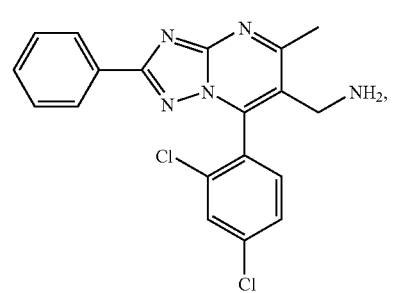
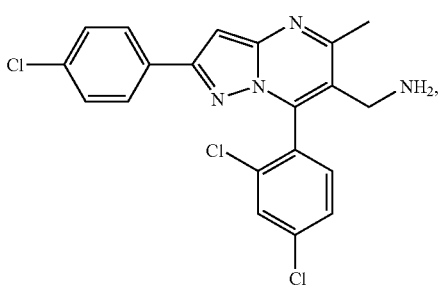
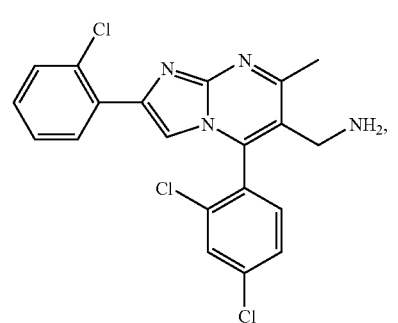
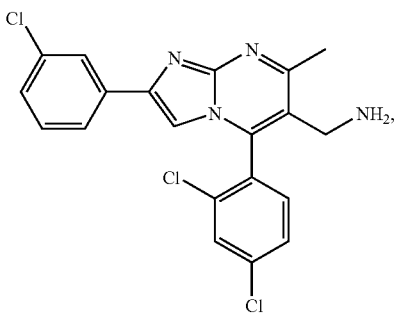
-continued
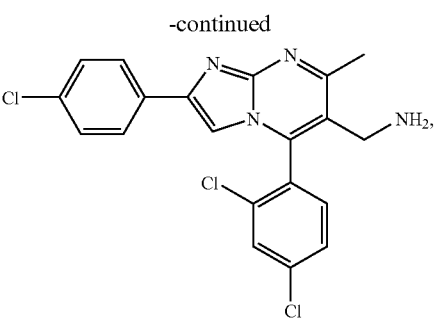
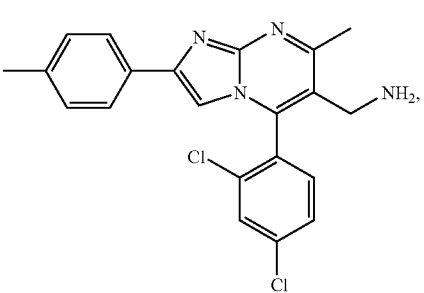
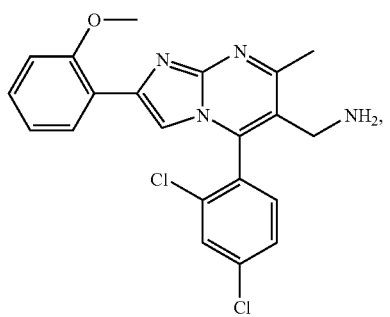
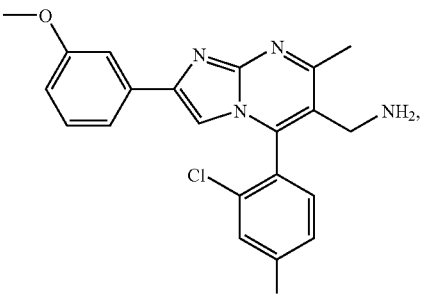
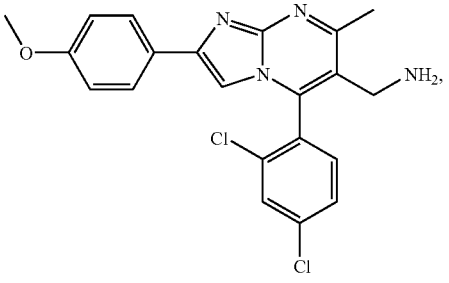

195
-continued
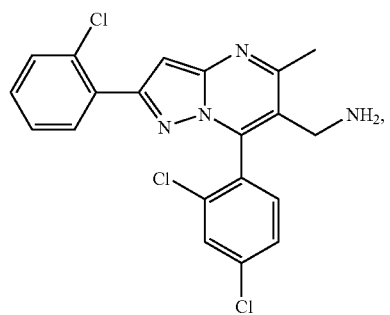
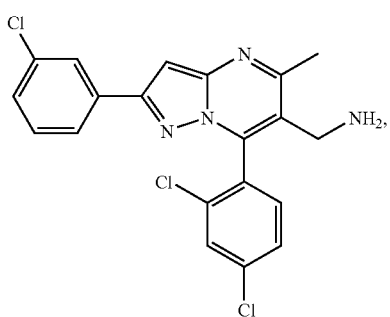
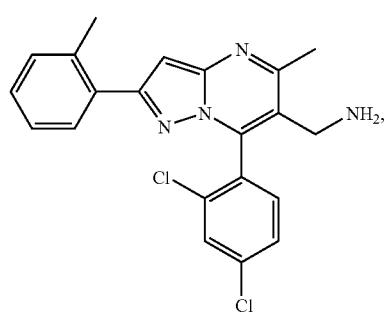
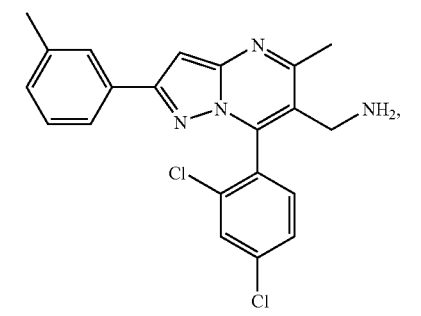
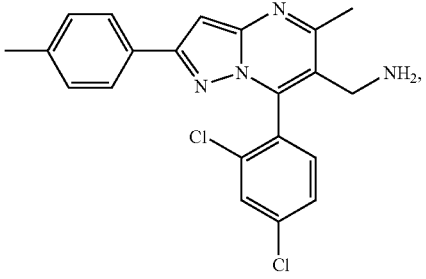
196
-continued
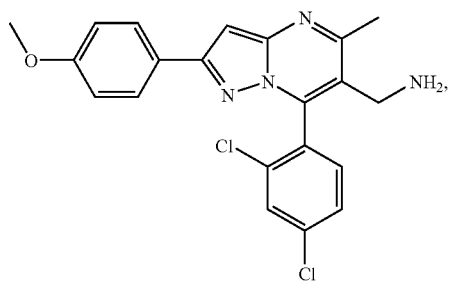
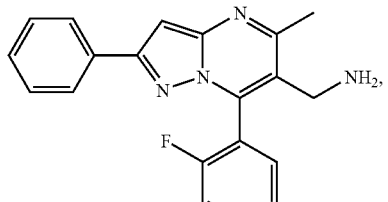
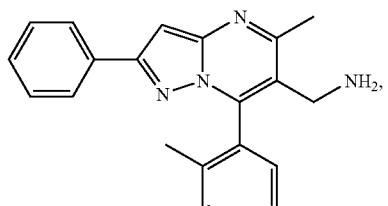
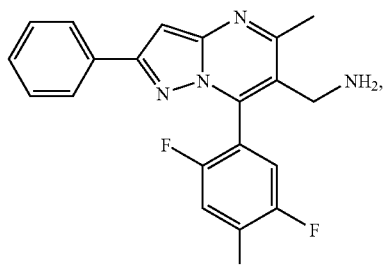
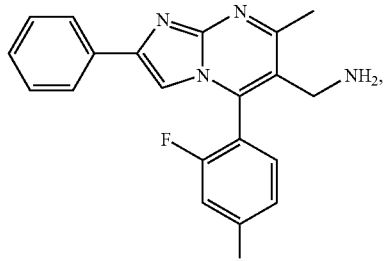
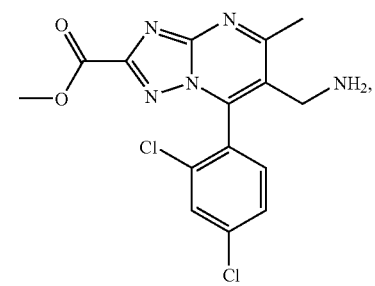

-continued
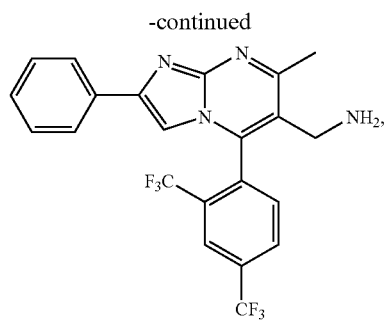
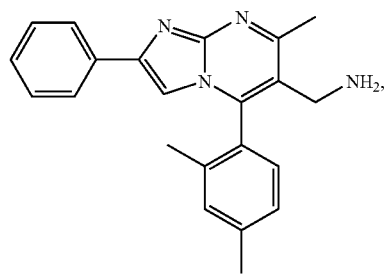
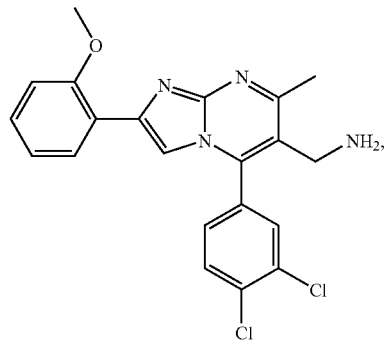
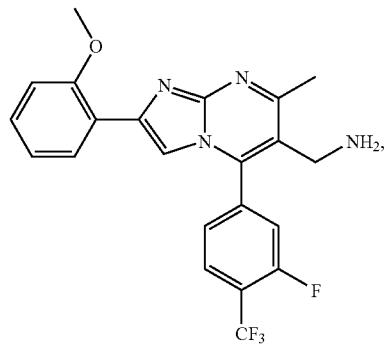
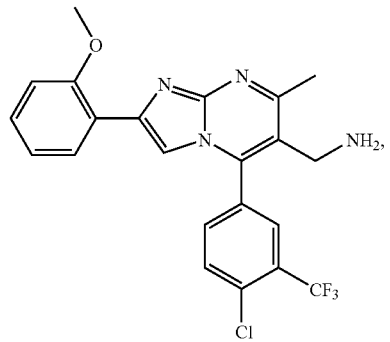
-continued
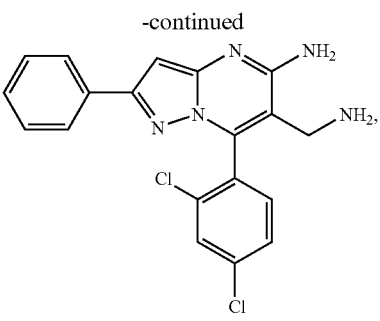
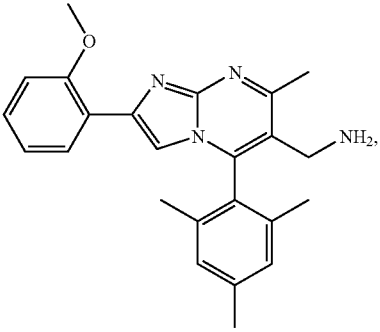
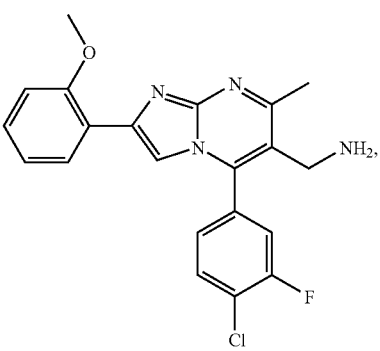
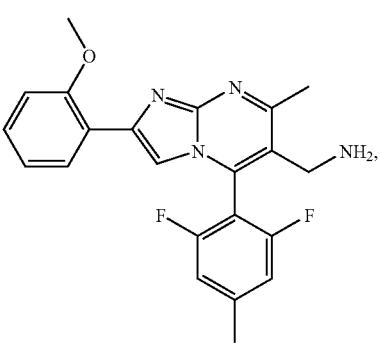
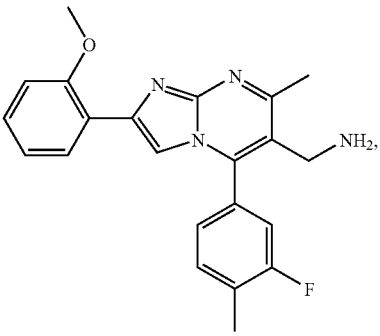

-continued
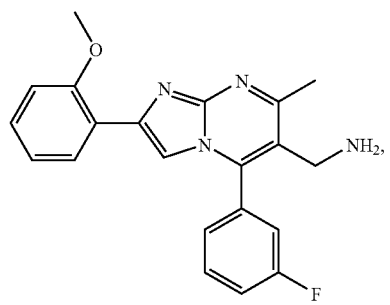
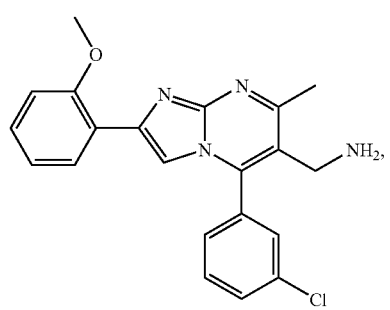
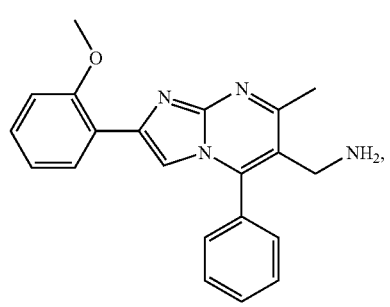
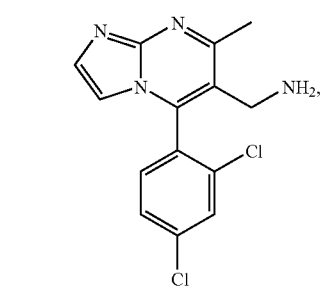
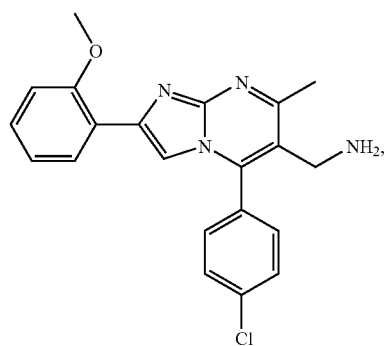
-continued
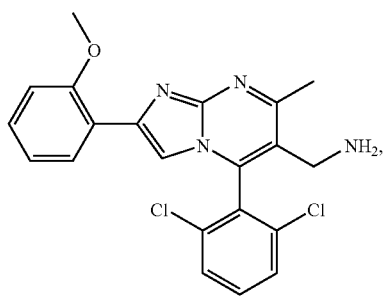
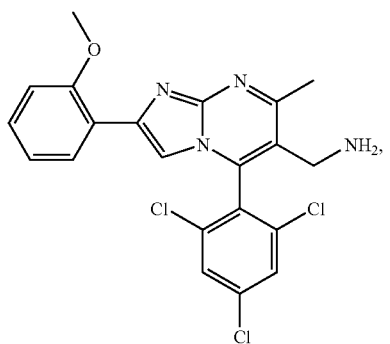
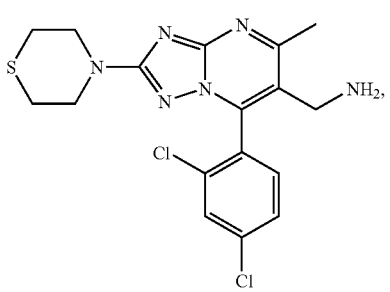
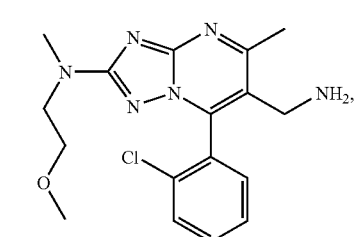
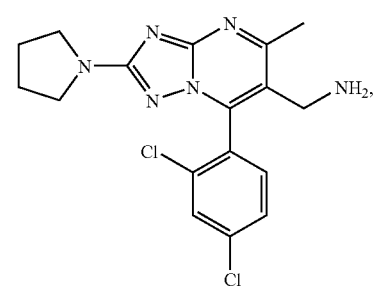

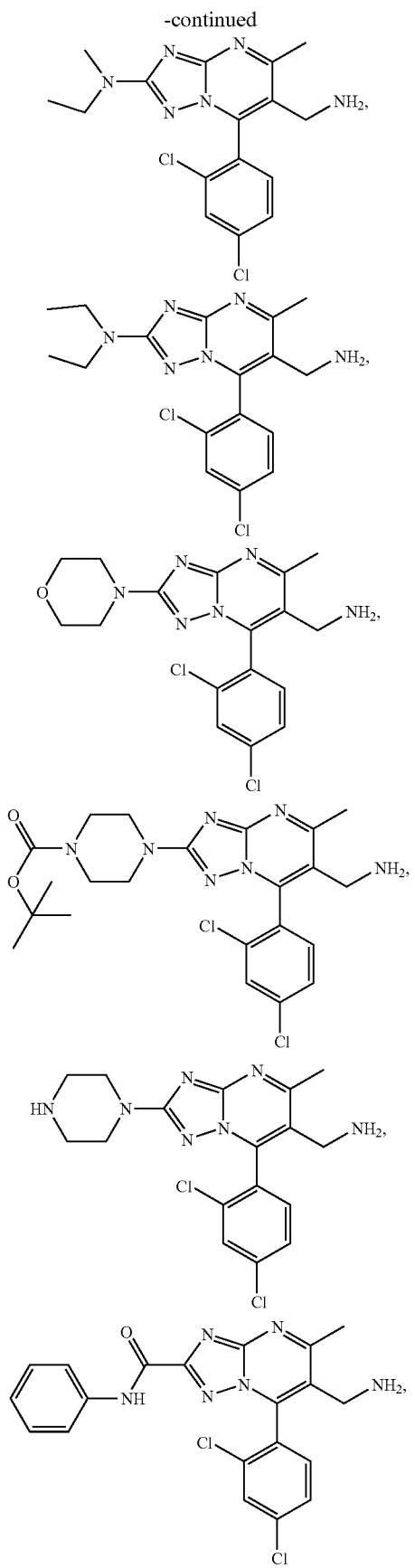

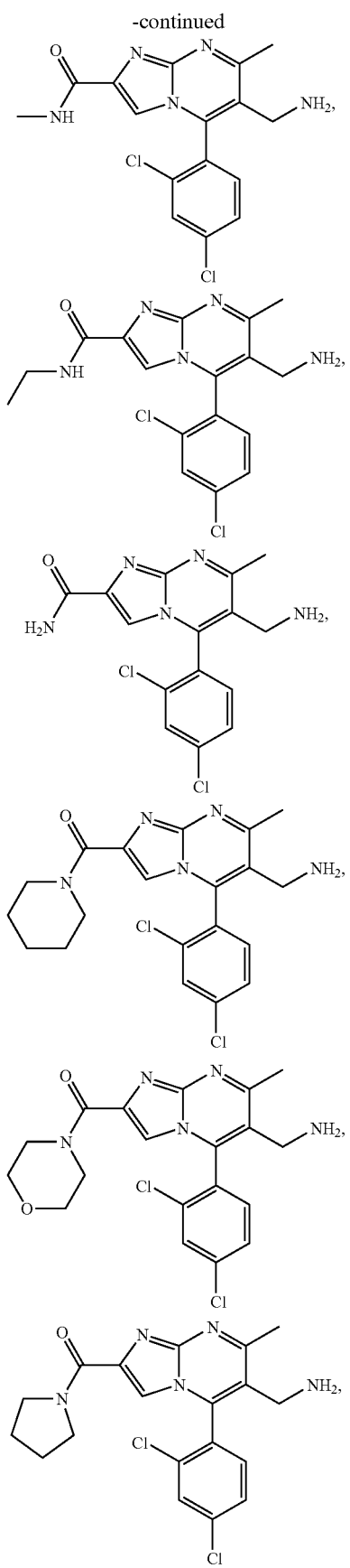

-continued
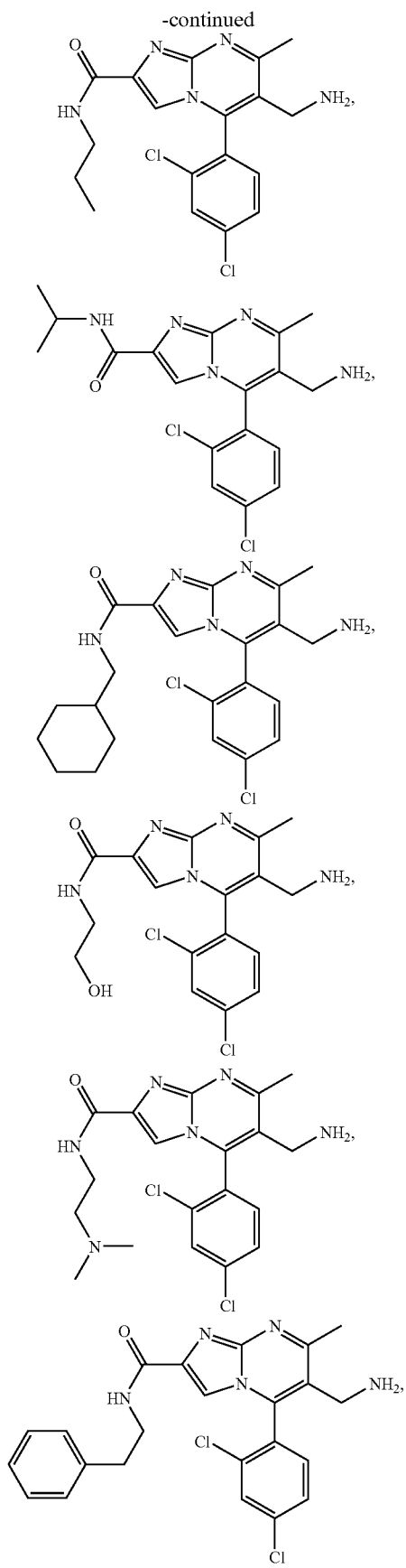
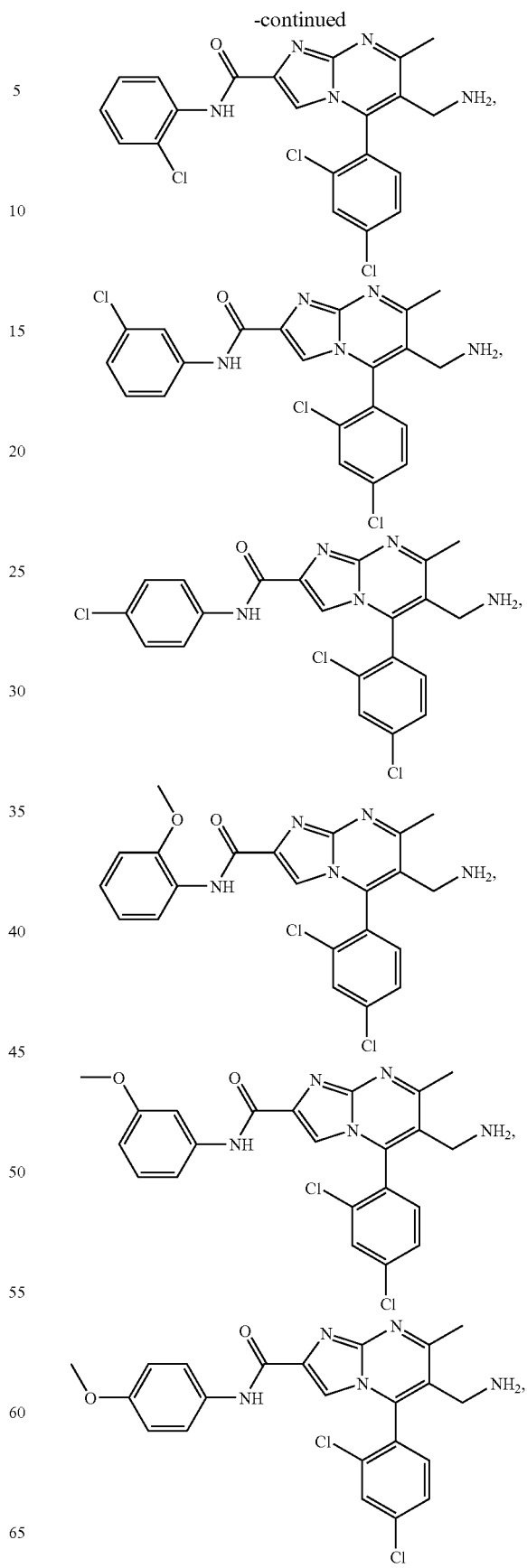

-continued
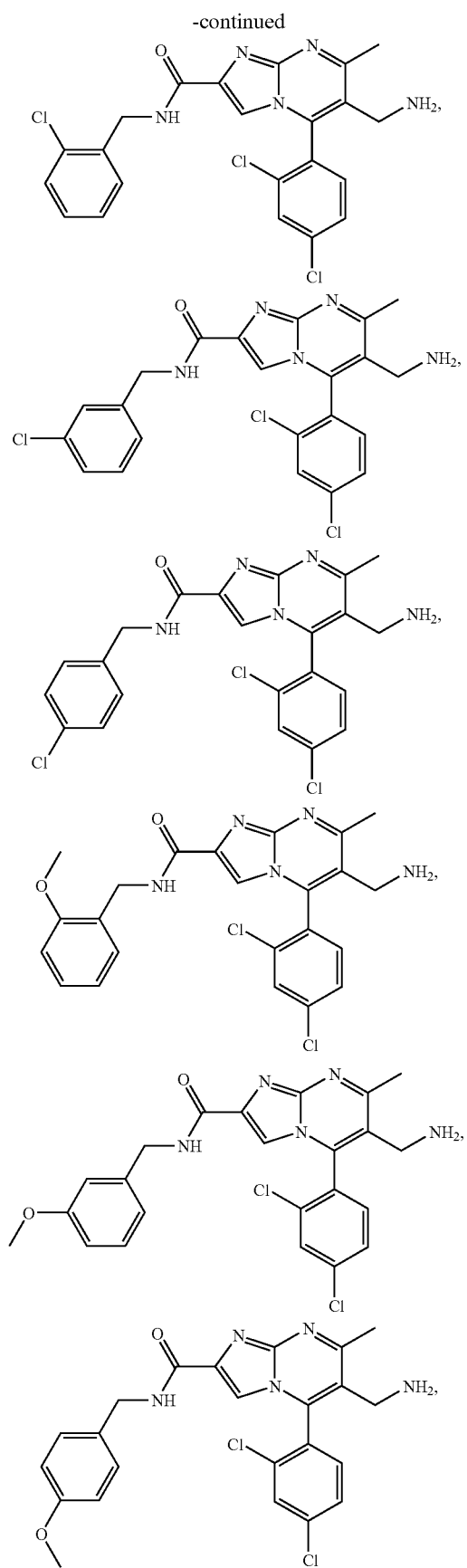
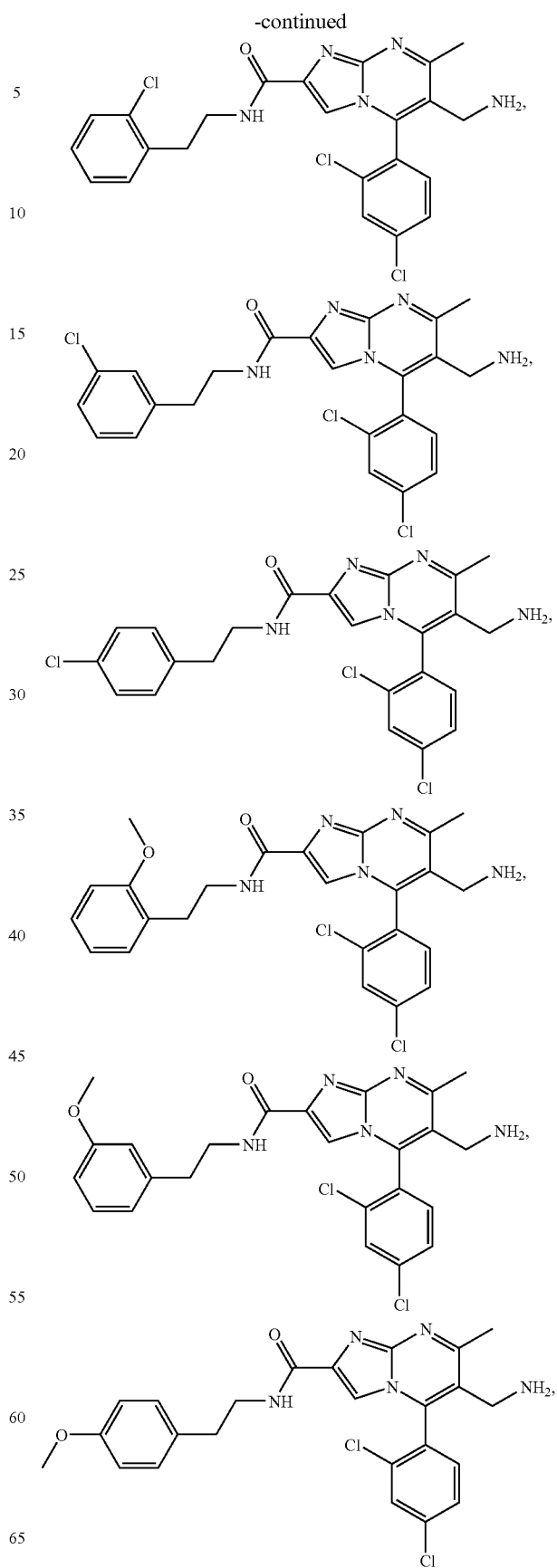

-continued
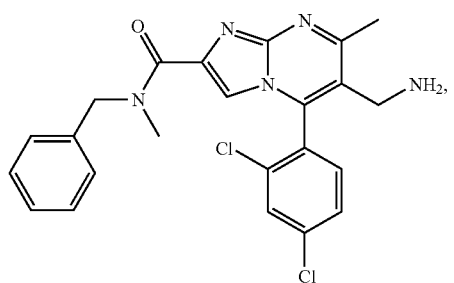
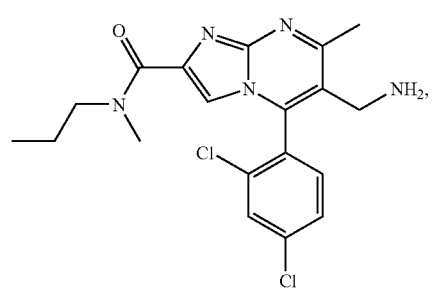
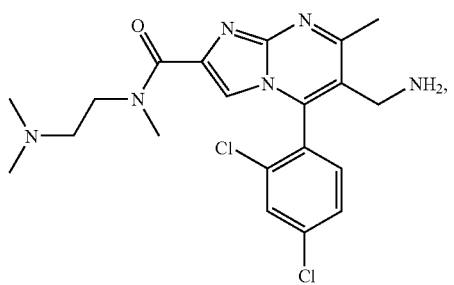
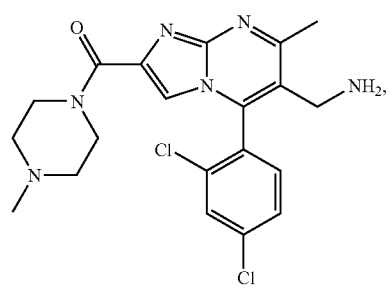
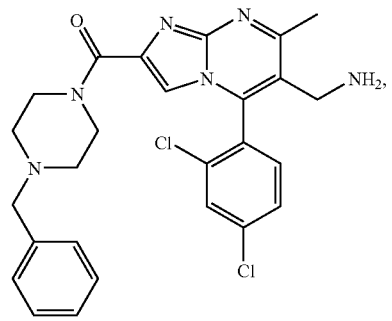
-continued
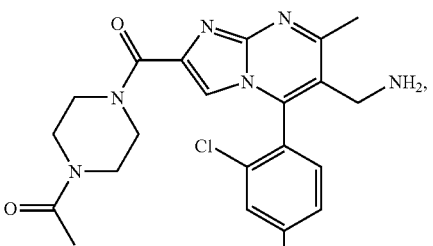
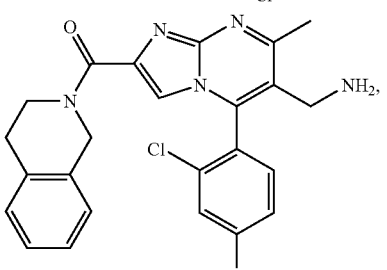
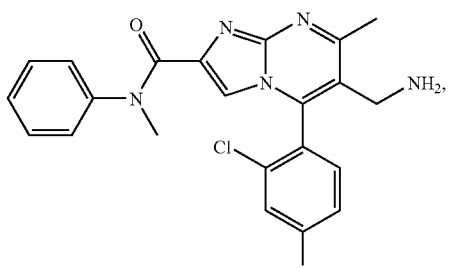
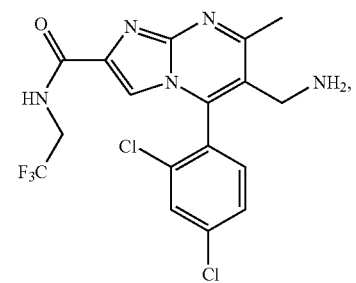
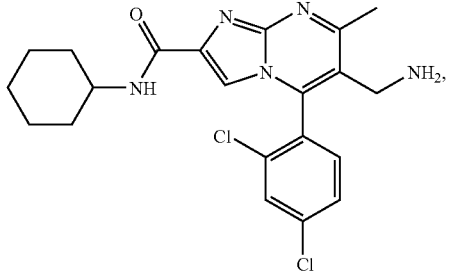
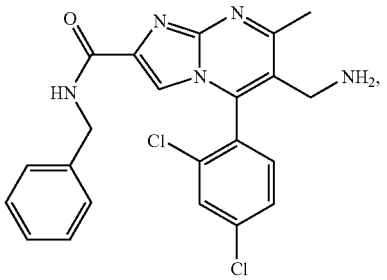

-continued
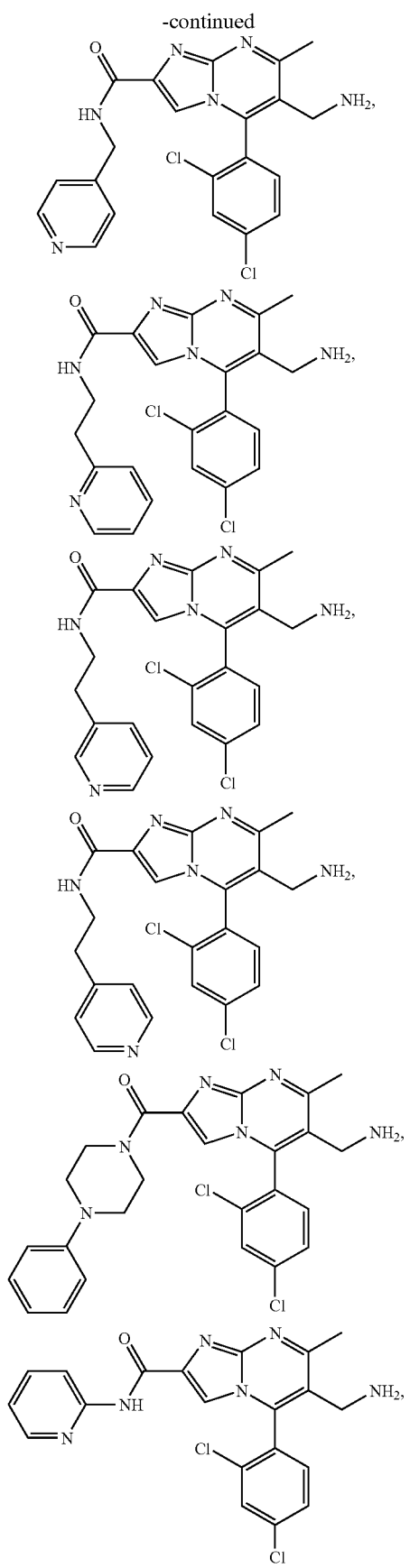
-continued
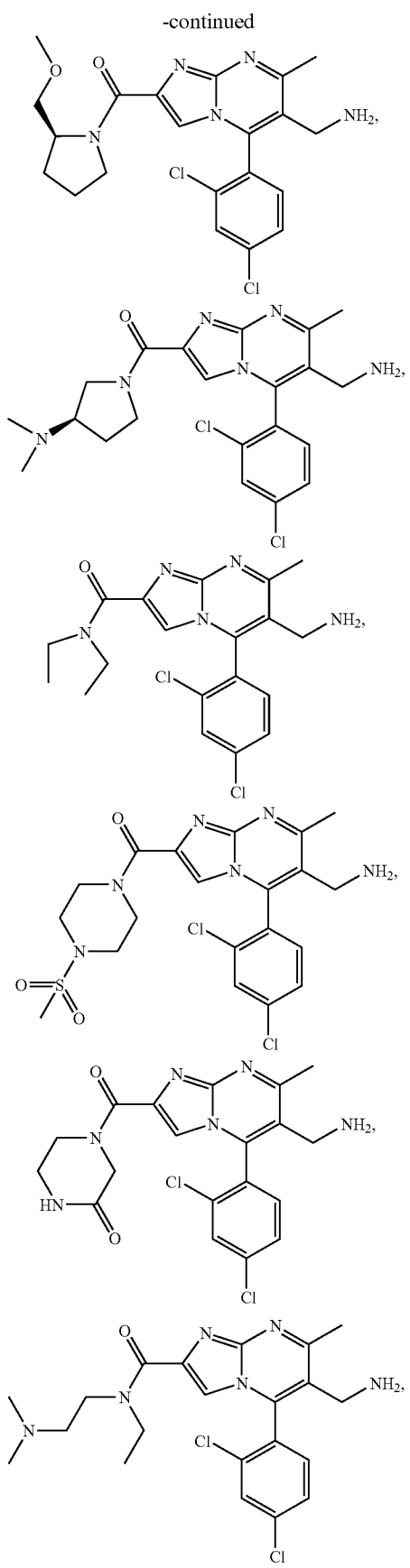

213
-continued
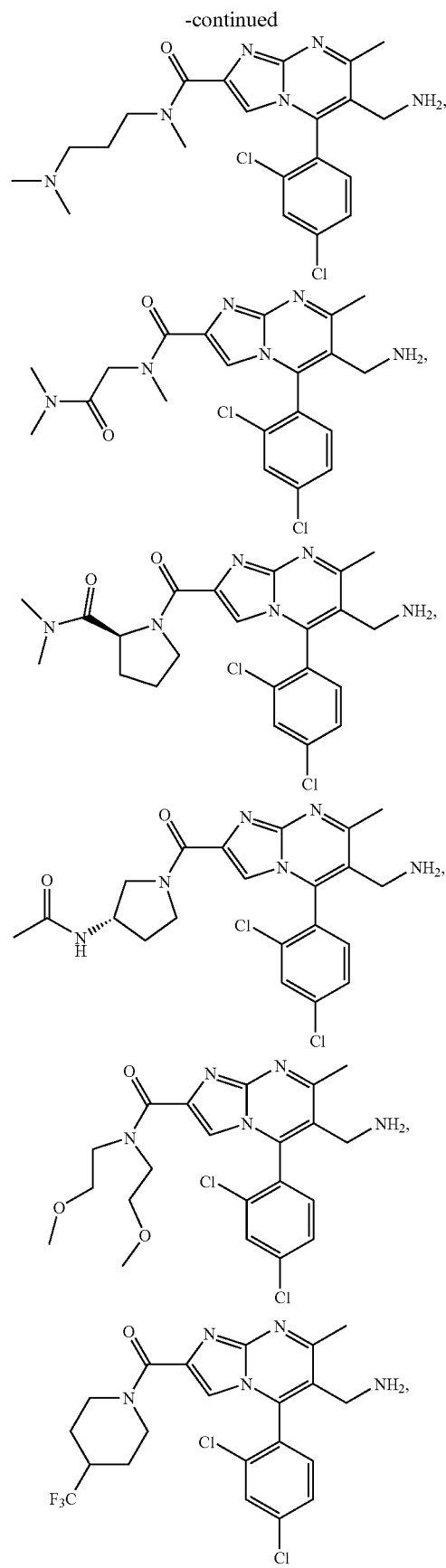
214
-continued
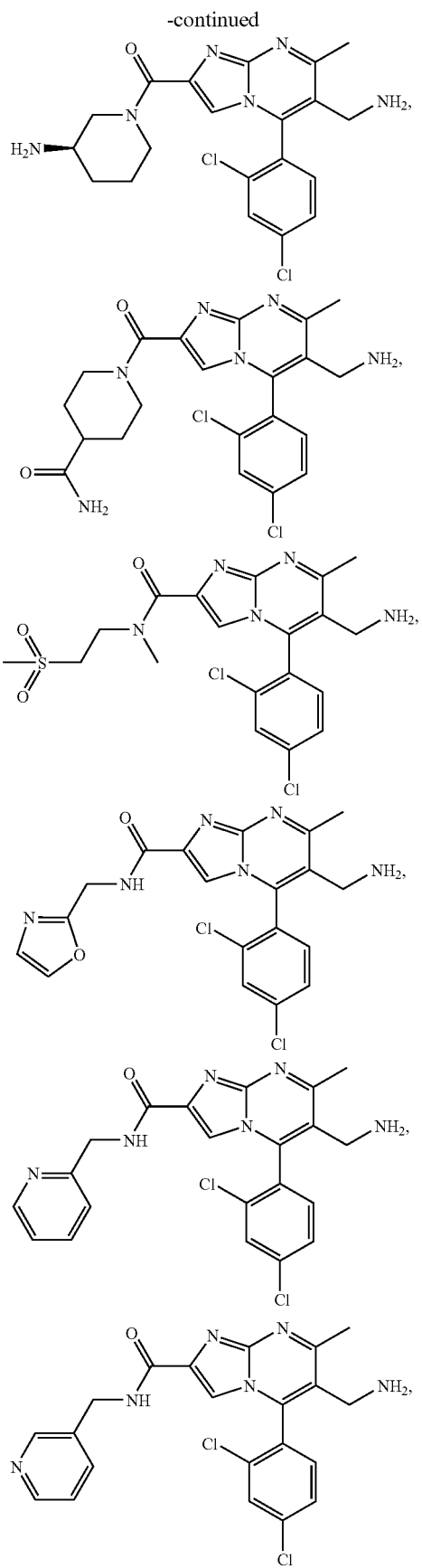

215
-continued
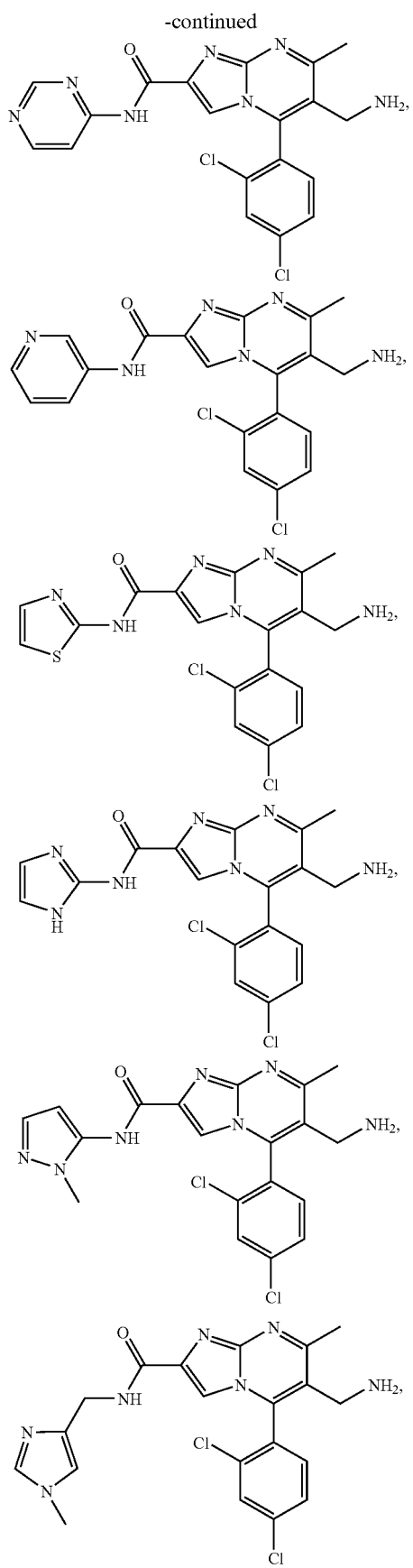
216
-continued
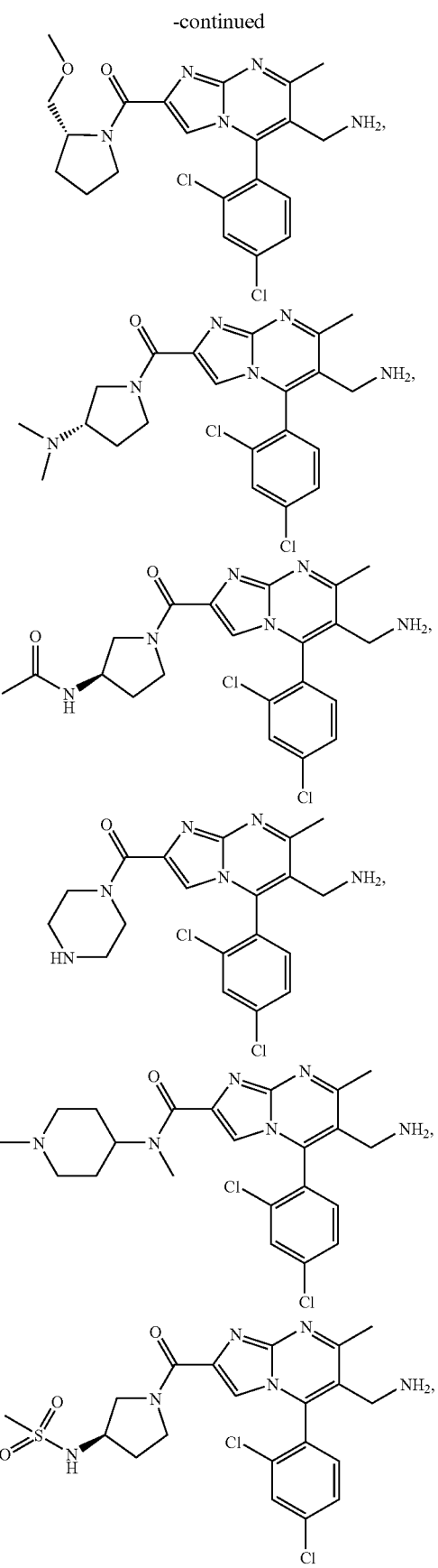

-continued
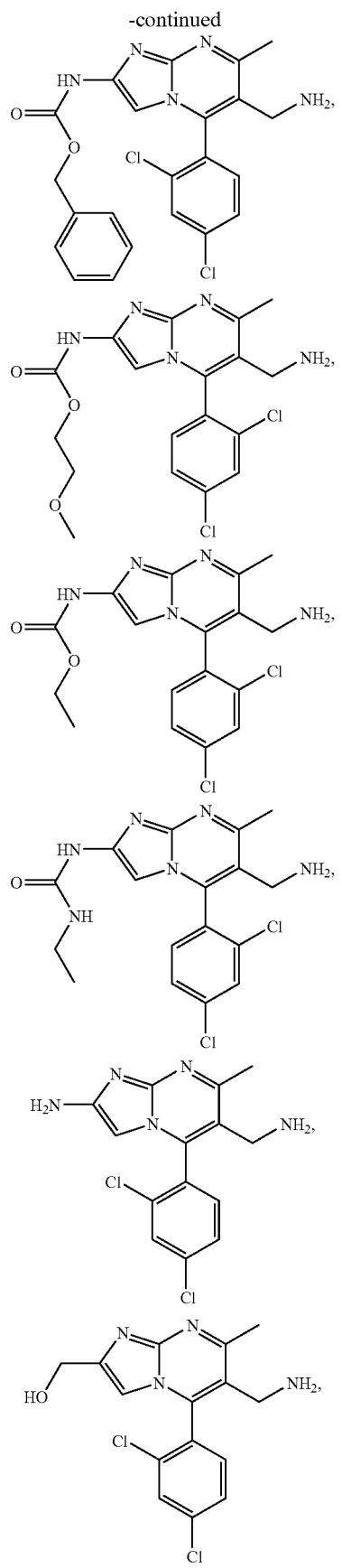
-continued
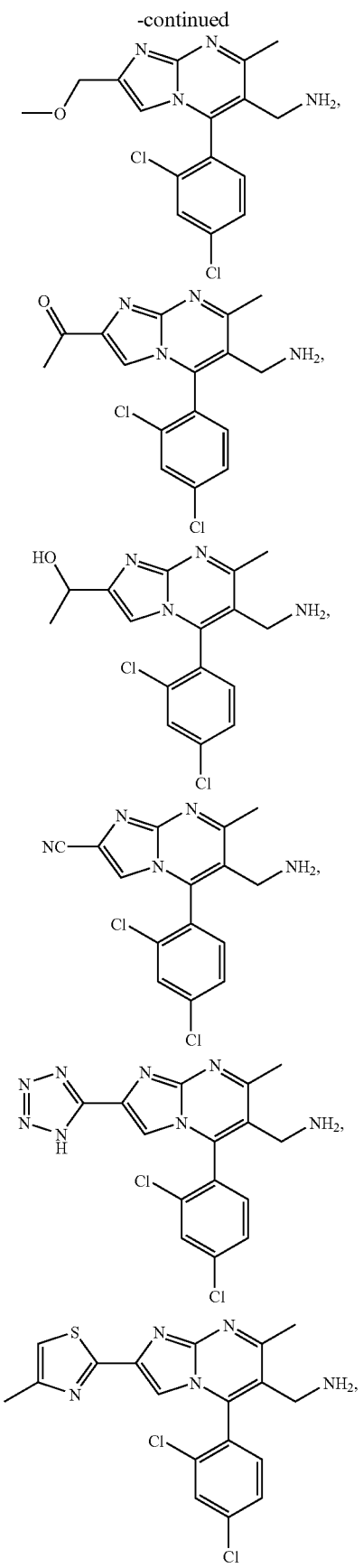

219
-continued
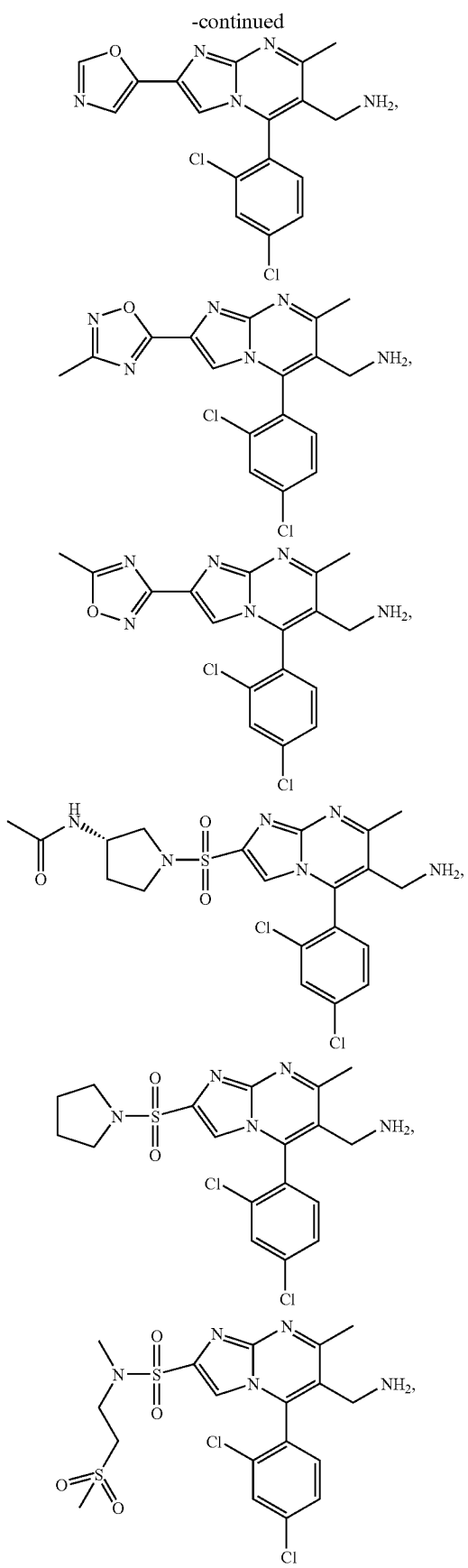
220
-continued
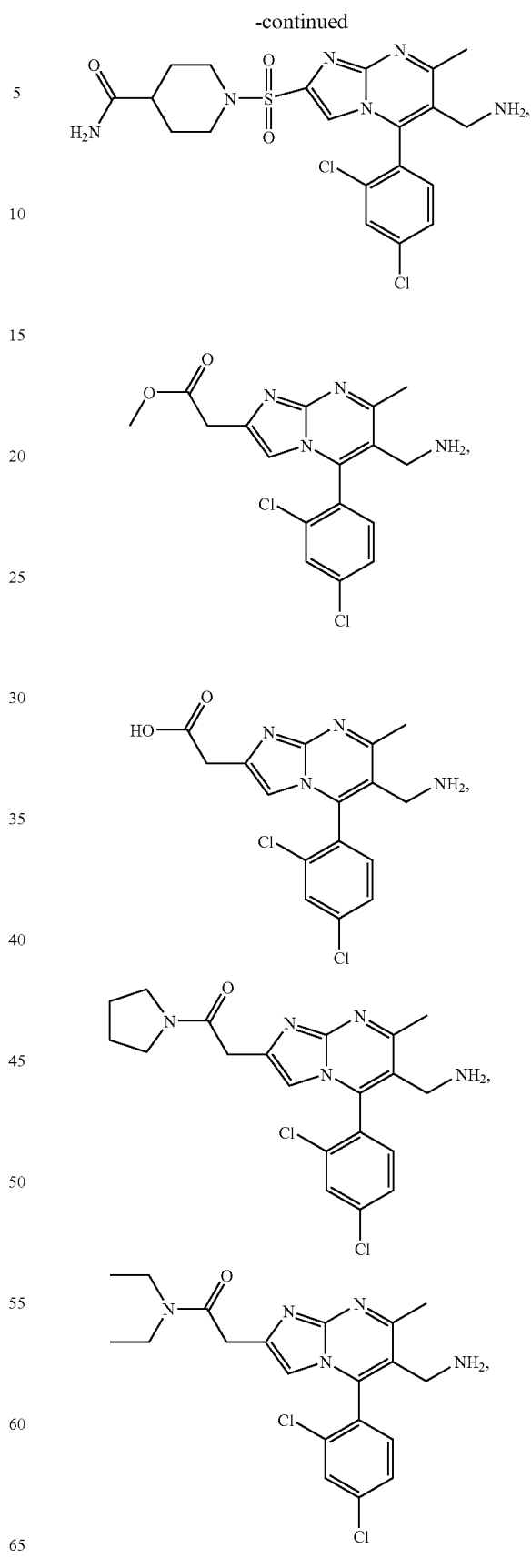

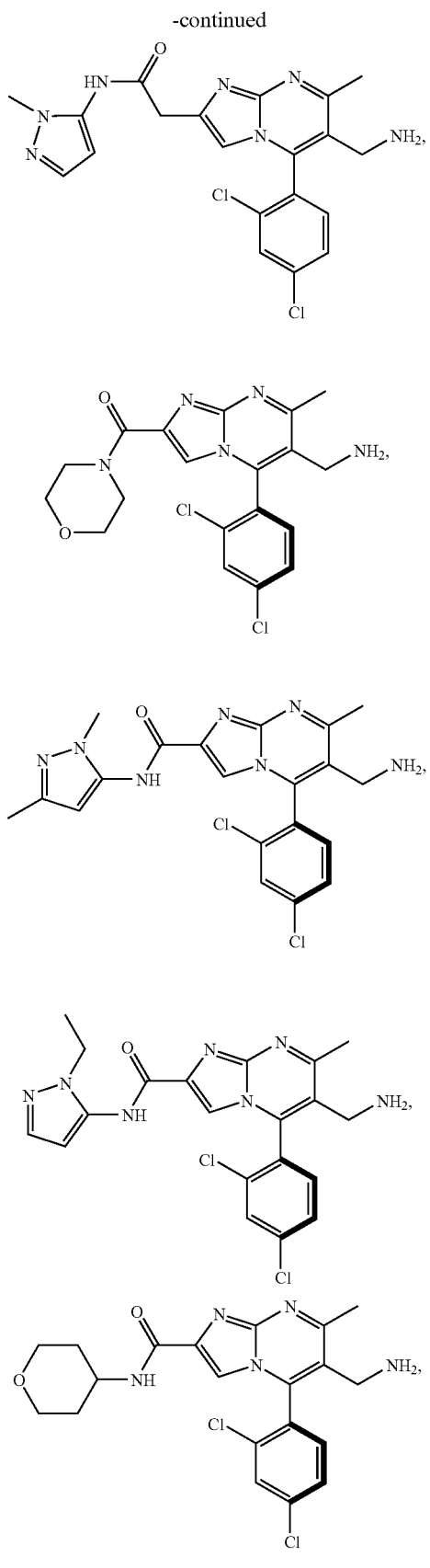
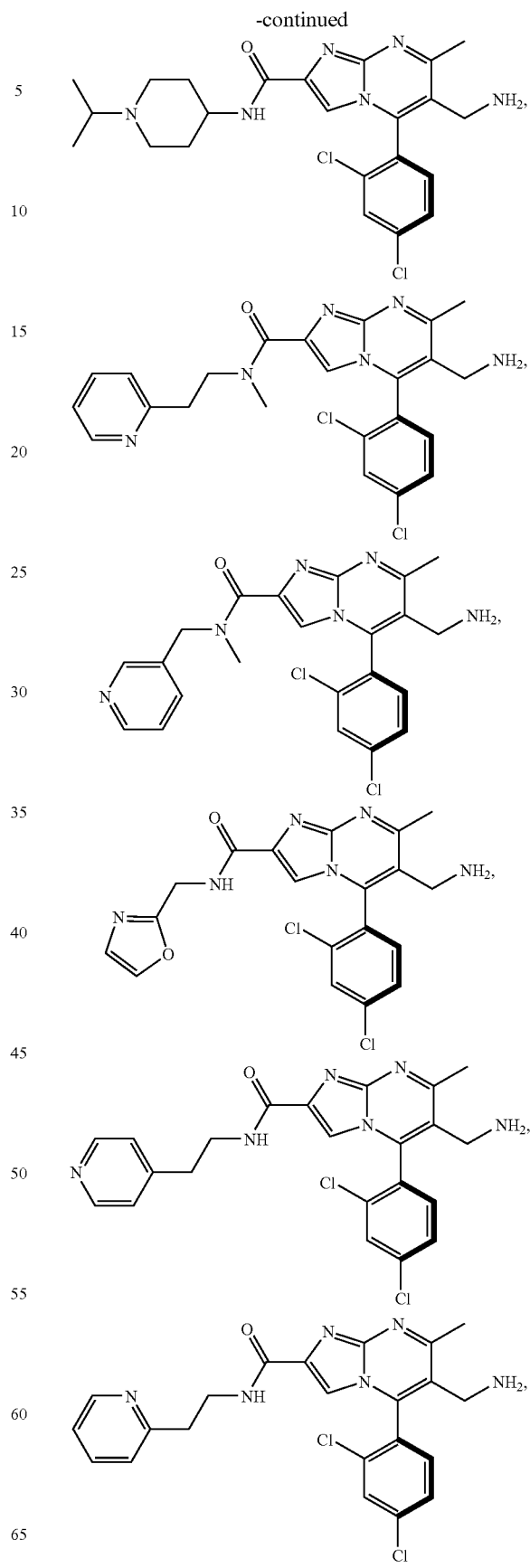

223
-continued
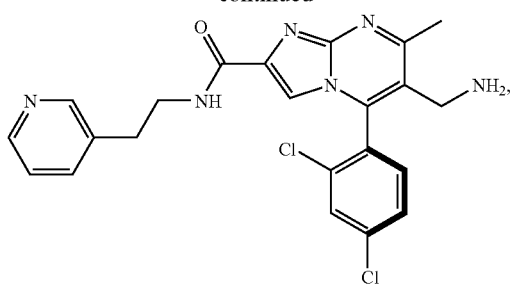
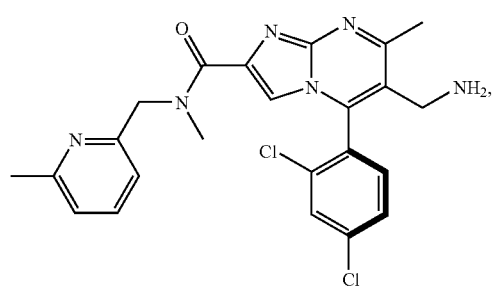
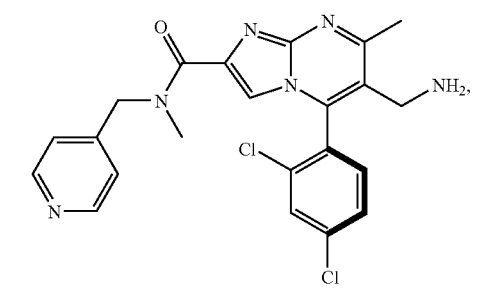
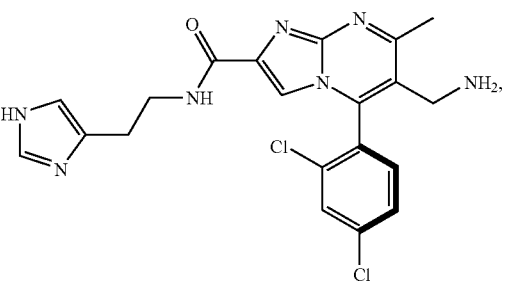
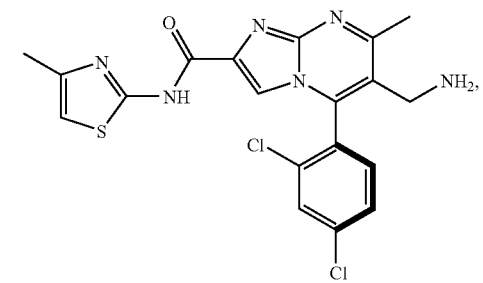
224
-continued
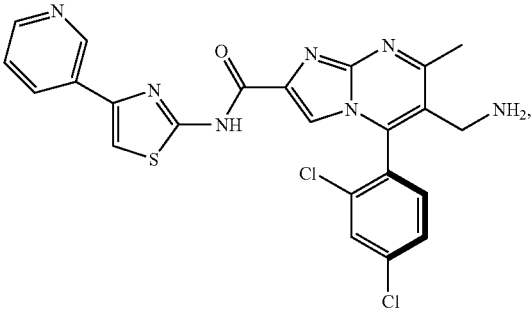
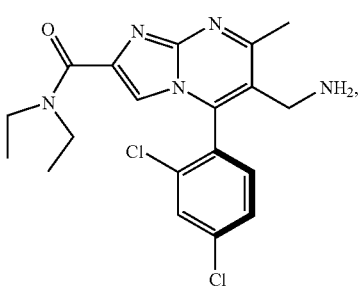
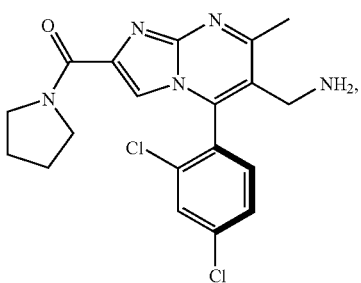
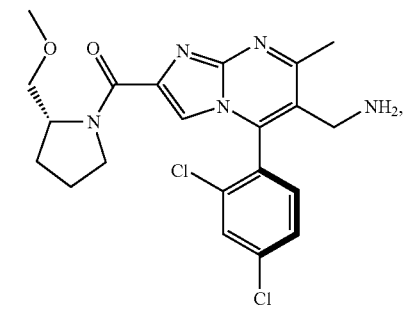
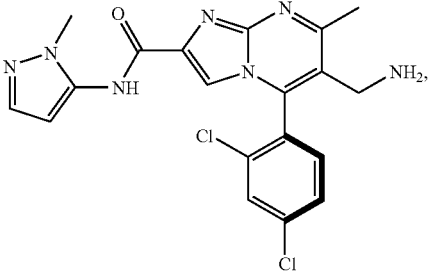

-continued

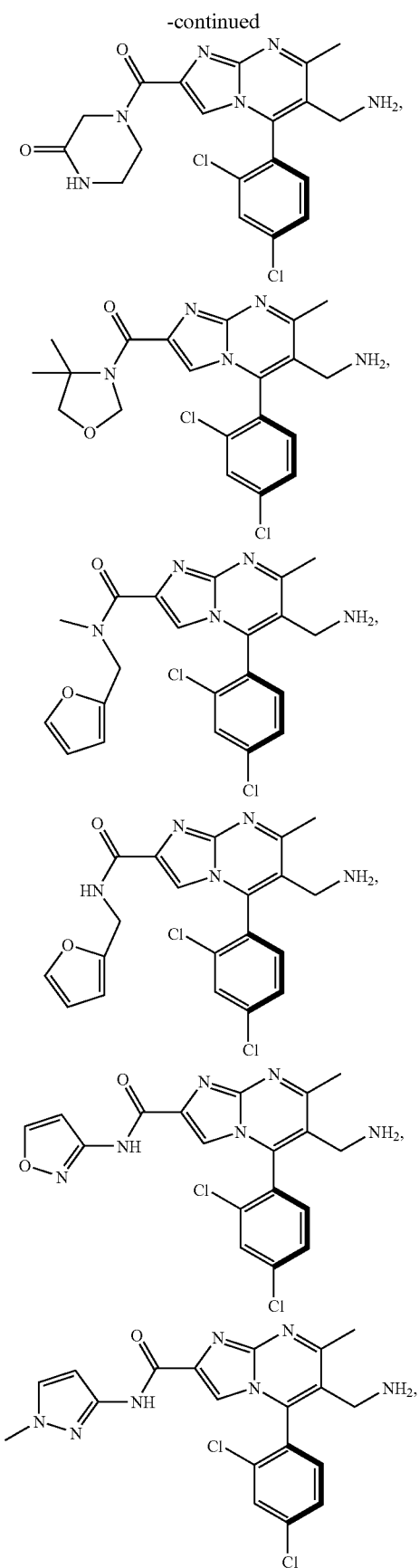

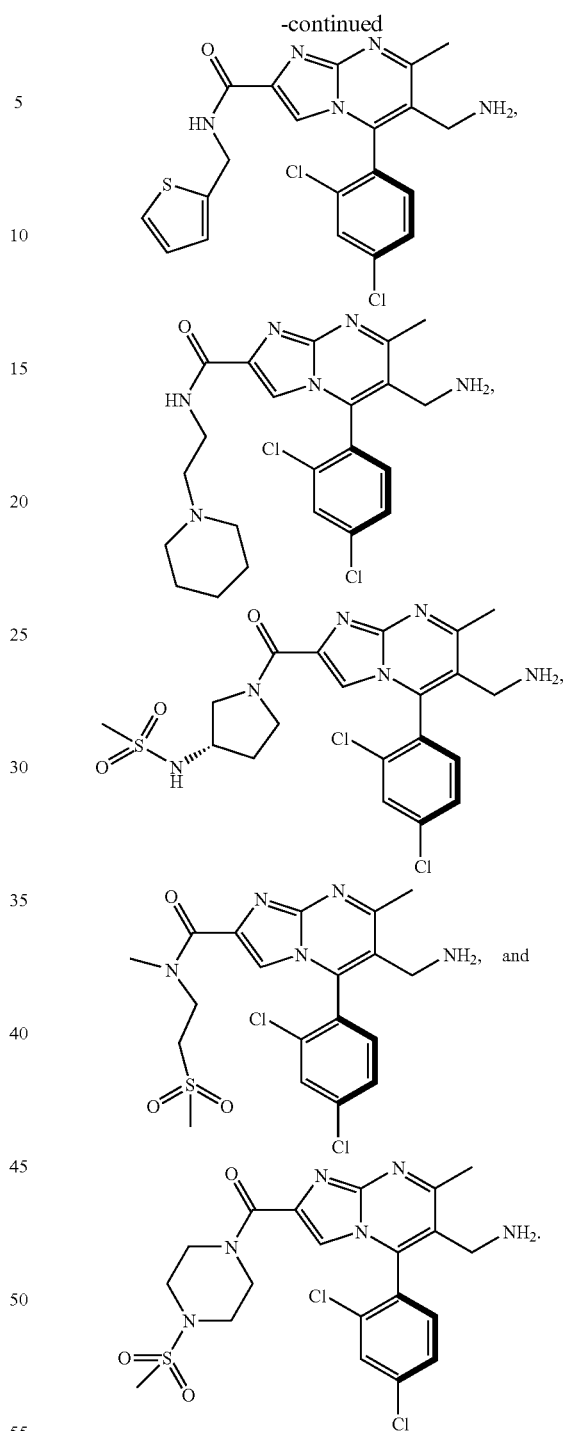

and
or a pharmaceutically acceptable salt and/or stereoisomer thereof.

2. A pharmaceutical composition comprising a compound as defined in claim 1 and a pharmaceutically acceptable carrier therefor.

3. A method for treating or delaying the progression or onset of Type II diabetes, which comprises administering to a mammalian species in need of treatment a therapeutically effective amount of a compound as defined in claim 1.

* * * * *

UNITED STATES PATENT AND TRADEMARK OFFICE
CERTIFICATE OF CORRECTION

| | | |
|---|---|---|
| PATENT NO. | : 7,635,699 B2 | Page 1 of 1 |
| APPLICATION NO. | : 11/314470 | |
| DATED | : December 22, 2009 | |
| INVENTOR(S) | : Meng et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 471 days.

Signed and Sealed this

Second Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,635,699 B2 | Page 1 of 1 |
| APPLICATION NO. | : 11/314470 | |
| DATED | : December 22, 2009 | |
| INVENTOR(S) | : Wei Meng et al. | |

It is certified that error appears in the above-identified patent and that said Letters Patent is hereby corrected as shown below:

On the Title Page:

Item (75), Inventors, change "Cherry Hill, NJ" to -- North Grafton, MA --.

In the Claims:

Claim 1:

Column 226, line 48, delete ".".

Column 226, lines 56 and 57, above "or", delete "and".

Signed and Sealed this
Third Day of January, 2012

David J. Kappos
*Director of the United States Patent and Trademark Office*